US012653896B2

(12) United States Patent
Owen et al.

(10) Patent No.: US 12,653,896 B2
(45) Date of Patent: Jun. 16, 2026

(54) TARGETED DENDRIMER CONJUGATES

(71) Applicant: Starpharma Pty Ltd, Preston (AU)

(72) Inventors: David Owen, Preston (AU); Sammi Tsegay, Preston (AU); Sudhir Shengule, Preston (AU); Pauline Reitano, Preston (AU); Christopher Porter, Preston (AU); Angus Johnston, Preston (AU); Daniel Yuen, Preston (AU)

(73) Assignee: Starpharma Pty Ltd, Preston (AU)

( * ) Notice: Subject to any disclaimer, the term of this patent is extended or adjusted under 35 U.S.C. 154(b) by 1089 days.

(21) Appl. No.: 17/637,924

(22) PCT Filed: Aug. 28, 2020

(86) PCT No.: PCT/AU2020/050910
§ 371 (c)(1),
(2) Date: Feb. 24, 2022

(87) PCT Pub. No.: WO2021/035310
PCT Pub. Date: Mar. 4, 2021

(65) Prior Publication Data

US 2022/0288216 A1 Sep. 15, 2022

(30) Foreign Application Priority Data

Aug. 28, 2019 (AU) ................................ 2019903152

(51) Int. Cl.
*A61K 47/56* (2017.01)
*A61K 47/10* (2017.01)
(Continued)

(52) U.S. Cl.
CPC .............. *A61K 47/56* (2017.08); *A61K 47/10* (2013.01); *A61K 47/641* (2017.08); (Continued)

(58) Field of Classification Search
None
See application file for complete search history.

(56) References Cited

U.S. PATENT DOCUMENTS

| | | | |
|---|---|---|---|
| 7,993,650 | B2 | 8/2011 | Carlsson |
| 2010/0278750 | A1 | 11/2010 | Krippner et al. |
| 2011/0028695 | A1 | 2/2011 | Revets |

FOREIGN PATENT DOCUMENTS

| | | | |
|---|---|---|---|
| EP | 2215125 | A1 | 8/2010 |
| JP | 2010-523595 | A | 7/2010 |

(Continued)

OTHER PUBLICATIONS

Mehta, D. et al. (2018), Mol. Pharmaceutics, vol. 15, pp. 4568-4576 (Year: 2018).*

(Continued)

*Primary Examiner* — Karl J Puttlitz

(74) *Attorney, Agent, or Firm* — McCarter & English, LLP

(57) ABSTRACT

Provided herein are dendrimer-targeting agent conjugates comprising a dendrimer, the dendrimer comprising a core unit and lysine or lysine analogue building units, a HER2 targeting agent which is a peptidic moiety having a molecular weight of up to about 80 kDa and comprising an antigen-binding site, which is covalently linked by a spacer group, and a therapeutic agent which is covalently linked to a surface building unit of the dendrimer. Also provided herein are compositions comprising the conjugates, and therapeutic methods using the conjugates, particularly for treating cancer.

15 Claims, 24 Drawing Sheets

Specification includes a Sequence Listing.

Compound 74 Compound 75 Compound 76

(51) Int. Cl.
*A61K 47/64* (2017.01)
*A61K 47/68* (2017.01)
*A61P 35/00* (2006.01)

(52) U.S. Cl.
CPC ...... *A61K 47/6849* (2017.08); *A61K 47/6855* (2017.08); *A61K 47/6885* (2017.08); *A61P 35/00* (2018.01)

(56) References Cited

FOREIGN PATENT DOCUMENTS

| | | | | |
|---|---|---|---|---|
| WO | 2007/048190 | A1 | 5/2007 | |
| WO | 2007/082331 | A1 | 7/2007 | |
| WO | 2008/017122 | A1 | 2/2008 | |
| WO | 2008/017125 | A1 | 2/2008 | |
| WO | 2008/124639 | A2 | 10/2008 | |
| WO | WO-2012167309 | A1 * | 12/2012 | ............ A61K 31/00 |
| WO | 2014/026286 | A1 | 2/2014 | |
| WO | 2015/035446 | A1 | 3/2015 | |
| WO | 2015/184510 | A1 | 12/2015 | |
| WO | 2020/014750 | A1 | 1/2020 | |
| WO | 2020/102852 | A1 | 5/2020 | |
| WO | 2020/107078 | A1 | 6/2020 | |

OTHER PUBLICATIONS

Lee et al., Mol Cells. May 16, 2019;42(5):386-396 (Year: 2019).*
Abbasi et al., Dendrimers: synthesis, applications, and properties. Nanoscale Res Lett. May 21, 2014;9(1):247, 10 pages.
Reshadmanesh et al., Evaluation of cellular and transcriptional targeting of breast cancer stem cells via anti-HER2 nanobody conjugated PAMAM dendrimers. Artif Cells Nanomed Biotechnol. 2018;46(sup3):S105-S115.
European Office Action for Application No. 20859417.6, dated Sep. 1, 2023, 13 pages.
Abdollahpour-Alitappeh et al., Monomethyl auristatin E Exhibits Potent Cytotoxic Activity against Human Cancer Cell Lines SKBR3 and HEK293. Novelty in Medicine. 2017;4:145-51.
Arbabi-Ghahroudi, Camelid Single-Domain Antibodies: Historical Perspective and Future Outlook. Front Immunol. Nov. 20, 2017;8:1589. 8 pages.
Arezumand et al., Nanobodies as Novel Agents for Targeting Angiogenesis in Solid Cancers. Front Immunol. Dec. 8, 2017;8:1746, 13 pages.
Bargh et al., Cleavable linkers in antibody-drug conjugates. Chem Soc Rev. Aug. 12, 2019;48(16):4361-4374.
Blackman et al., Tetrazine ligation: fast bioconjugation based on inverse-electron-demand Diels-Alder reactivity. J Am Chem Soc. Oct. 15, 2008;130(41):13518-9.
Chang, ADCs with high ADR, high targeting valence, and product homogeneity. Immunwork. slideshow, 32 pages, (2019).
Chatterjee et al., A versatile platform for single- and multiple-unnatural amino acid mutagenesis in *Escherichia coli*. Biochemistry. Mar. 12, 2013;52(10):1828-37.
Dal Corso et al., Fast Cyclization of a Proline-Derived Self-Immolative Spacer Improves the Efficacy of Carbamate Prodrugs. Angew Chem Int Ed Engl. Mar. 2, 2020;59(10):4176-4181.
Dal Corso et al., Protease-Cleavable Linkers Modulate the Anti-cancer Activity of Noninternalizing Antibody-Drug Conjugates. Bioconjug Chem. Jul. 19, 2017;28(7):1826-1833.
Ducry, Antibody-Drug Conjugates. Methods in Molecular Biology 1045. Humana Press. 315 pages, (2013).
Eglezos, Dendrimers in Drug Delivery, Starpharma's DEP™ technology. PODD Slideshow, 15 pages, Oct. 14, 2014.
Hussack et al., Isolation and characterization of camelid single-domain antibodies against HER2. BMC Res Notes. Dec. 5, 2018;11(1):866, 5 pages.
Ma et al., Targeted delivery of polyamidoamine-paclitaxel conjugate functionalized with anti-human epidermal growth factor receptor 2 trastuzumab. Int J Nanomedicine. Mar. 18, 2015;10:2173-90.
Mehta et al., Reducing Dendrimer Generation and PEG Chain Length Increases Drug Release and Promotes Anticancer Activity of PEGylated Polylysine Dendrimers Conjugated with Doxorubicin via a Cathepsin-Cleavable Peptide Linker. Mol Pharm. Oct. 1, 2018;15(10):4568-4576.
Miyano et al., Anionic amino acid dendrimer-trastuzumab conjugates for specific internalization in HER2-positive cancer cells. Mol Pharm. Aug. 2, 2010;7(4):1318-27.
Oroudjev et al., Maytansinoid-antibody conjugates induce mitotic arrest by suppressing microtubule dynamic instability. Mol Cancer Ther. Oct. 2010;9(10):2700-13.
Pohlmann et al., Resistance to Trastuzumab in Breast Cancer. Clin Cancer Res. Dec. 15, 2009;15(24):7479-7491.
Pruszynski et al., Targeting breast carcinoma with radioiodinated anti-HER2 Nanobody. Nucl Med Biol. Jan. 2013;40(1):52-9.
Rostami et al., Peptide-conjugated PEGylated PAMAM as a highly affinitive nanocarrier towards HER2-overexpressing cancer cells. RSC Advances. 2016;6:107337-107343.
Shukla et al., HER2 specific tumor targeting with dendrimer conjugated anti-HER2 mAb. Bioconjug Chem. Sep.-Oct. 2006;17(5):1109-15.
Vaneycken et al., Preclinical screening of anti-HER2 nanobodies for molecular imaging of breast cancer. FASEB J. Jul. 2011;25(7):2433-46.
Verel et al., 89Zr immuno-PET: comprehensive procedures for the production of 89Zr-labeled monoclonal antibodies. J Nucl Med. Aug. 2003;44(8):1271-81.
Wu et al., A Single Domain-Based Anti-Her2 Antibody Has Potent Antitumor Activities. Transl Oncol. Apr. 2018;11 (2):366-373.
International Search Report and Written Opinion for Application No. PCT/AU2020/050910, dated Nov. 9, 2020, 12 pages.
Japanese Office Action for Application No. 2022-513525, dated Jul. 2, 2024, 9 pages.

* cited by examiner

Compound 74 Compound 75 Compound 76

| Organs | Time / days | Dendrimer / organ ratio value | | | | | | | | | | | | |
|---|---|---|---|---|---|---|---|---|---|---|---|---|---|---|
| | | *NB (16 kDa)* | *G2 (10.2 kDa)* | *G2 + NB (25.7 kDa)* | *G3-P412 (9.6 kDa)* | *G3-P412 + NB (25.1 kDa)* | *G3-P1K (16.4 kDa)* | *G3-P1K + NB (31.9 kDa)* | *G4 (27.9 kDa)* | *G4 + NB (43.4 kDa)* | *(G4 + NB) + 10 x NB (43.4 kDa)* | *G4 + 2-4 NB (multi NB) (60.3 kDa)* | *G5 (51.4kDa)* | *G5 + NB (66.8 kDa)* |
| | | *104* | *99* | *86* | *100* | *88* | *101* | *87* | *102* | *90* | *90* | *91* | *103* | *92* |
| *Tumour:Blood* | 2 | 17.17 | 1.02 | 13.04 | 1.70 | 24.30 | 0.91 | 4.87 | 1.66 | 3.87 | 3.58 | 4.43 | 0.69 | 7.14 |
| | 9 | 1.24 | 6.57 | 10.58 | 0.74 | 1.67 | 7.76 | 25.86 | 21.92 | 56.95 | 32.30 | 12.62 | 13.68 | 325.01 |
| *Tumour:Liver* | 2 | 4.51 | 0.20 | 0.94 | 0.04 | 0.31 | 0.28 | 0.96 | 0.67 | 2.09 | 1.78 | 1.19 | 0.75 | 1.63 |
| | 9 | 1.36 | 0.11 | 0.28 | 0.01 | 0.05 | 0.15 | 0.71 | 0.29 | 0.66 | 0.52 | 0.27 | 0.37 | 1.09 |
| *Tumour:Spleen* | 2 | 2.56 | 0.29 | 1.09 | 0.13 | 1.16 | 0.33 | 1.12 | 0.35 | 1.41 | 0.95 | 0.83 | 0.29 | 1.12 |
| | 9 | 0.10 | 0.11 | 0.23 | 0.01 | 0.05 | 0.04 | 0.25 | 0.05 | 0.21 | 0.16 | 0.07 | 0.07 | 0.09 |
| *Tumour:Kidneys* | 2 | 0.01 | 0.73 | 0.10 | 0.06 | 0.03 | 0.69 | 0.24 | 2.05 | 5.21 | 3.87 | 3.40 | 2.22 | 7.15 |
| | 9 | 0.00 | 0.82 | 0.06 | 0.05 | 0.01 | 0.51 | 1.15 | 2.03 | 2.99 | 3.07 | 1.43 | 2.29 | 6.36 |

Fig. 21

| | | Dendrimer / %Injected Dose.gram$^{-1}$ | | | | | | | | | | | | |
|---|---|---|---|---|---|---|---|---|---|---|---|---|---|---|
| Organ | Time / days | NB (16 kDa) | G2 (10.2 kDa) | G2 + NB (25.7 kDa) | G3-P412 (9.6 kDa) | G3-P412 + NB (25.1 kDa) | G3-P1K (16.4 kDa) | G3-P1K + NB (31.9 kDa) | G4 (27.9 kDa) | G4 + NB (43.4 kDa) | (G4 + NB) + 10 x NB (43.4 kDa) | G4 + 2-4 NB (multi NB) (60.3 kDa) | G5 (51.4kDa) | G5 + NB (66.8 kDa) |
| Compound | | 104 | 99 | 86 | 100 | 88 | 101 | 87 | 102 | 90 | 90 | 91 | 103 | 92 |
| Tumour | 2 | 1.05 | 1.74 | 2.70 | 0.71 | 2.28 | 2.67 | 4.78 | 3.96 | 12.53 | 12.64 | 7.85 | 4.04 | 11.96 |
| | 9 | 0.31 | 0.78 | 1.06 | 0.25 | 0.31 | 1.53 | 4.56 | 1.72 | 4.15 | 4.55 | 2.70 | 3.31 | 8.18 |
| Liver | 2 | 0.23 | 8.70 | 3.06 | 18.25 | 7.82 | 9.62 | 5.22 | 5.85 | 6.05 | 7.34 | 6.73 | 5.48 | 7.29 |
| | 9 | 0.23 | 7.18 | 3.71 | 20.85 | 6.02 | 10.10 | 6.44 | 5.85 | 7.34 | 8.72 | 10.23 | 9.59 | 7.56 |
| Spleen | 2 | 0.53 | 5.83 | 2.96 | 5.51 | 2.14 | 8.12 | 4.27 | 11.13 | 8.98 | 13.06 | 9.46 | 16.45 | 10.65 |
| | 9 | 0.00 | 7.38 | 4.47 | 35.24 | 6.88 | 47.73 | 18.02 | 34.23 | 21.52 | 30.23 | 37.09 | 45.59 | 87.39 |
| Kidneys | 2 | 109.01 | 2.36 | 28.56 | 11.23 | 79.08 | 4.05 | 20.07 | 1.93 | 2.47 | 3.29 | 2.33 | 1.87 | 1.66 |
| | 9 | 62.22 | 0.93 | 17.03 | 5.36 | 55.61 | 3.11 | 4.06 | 0.85 | 1.44 | 1.57 | 1.91 | 1.43 | 1.29 |
| Heart | 2 | 0.10 | 1.42 | 0.61 | 1.39 | 0.49 | 1.91 | 1.29 | 1.53 | 2.62 | 3.18 | 1.98 | 3.08 | 3.33 |
| | 9 | 0.00 | 0.64 | 0.52 | 0.92 | 0.28 | 1.23 | 0.81 | 1.11 | 1.36 | 1.35 | 1.72 | 1.83 | 1.99 |
| Lungs | 2 | 0.11 | 1.25 | 0.54 | 4.95 | 0.58 | 4.36 | 2.31 | 1.39 | 2.82 | 2.80 | 1.72 | 2.71 | 2.86 |
| | 9 | 0.00 | 0.44 | 0.38 | 2.78 | 0.55 | 3.55 | 1.33 | 1.06 | 1.32 | 1.24 | 1.38 | 1.12 | 1.43 |
| Bone | 2 | 0.26 | 1.04 | 0.63 | 0.98 | 0.63 | 0.93 | 1.75 | 1.31 | 2.17 | 3.03 | 2.27 | 1.70 | 8.07 |
| | 9 | 0.00 | 0.28 | 0.34 | 0.58 | -0.53 | 0.79 | 0.54 | 1.54 | 1.78 | 1.78 | 3.77 | 1.30 | 2.72 |
| Blood | 2 | 0.08 | 1.67 | 0.22 | 0.42 | 0.09 | 3.05 | 1.03 | 2.37 | 3.40 | 3.51 | 1.81 | 5.97 | 2.75 |
| | 9 | 0.00 | 0.00 | -0.26 | -0.45 | -0.29 | -0.20 | -0.18 | 0.08 | -0.19 | -0.21 | -0.22 | 0.04 | 0.00 |
| GI Tract | 2 | 0.04 | 0.87 | 0.37 | 1.17 | 0.34 | 1.01 | 0.67 | 0.68 | 1.04 | 1.35 | 0.96 | 0.85 | 0.89 |
| | 9 | 0.11 | 0.31 | 0.32 | 0.80 | 0.29 | 0.77 | 0.52 | 0.37 | 0.46 | 0.57 | 0.64 | 0.63 | 0.62 |
| Tail | 2 | 0.07 | 1.78 | 0.71 | 2.36 | 0.69 | 1.14 | 0.71 | 0.93 | 2.26 | 2.14 | 0.90 | 1.47 | 1.47 |
| | 9 | 0.03 | 2.56 | 1.76 | 0.58 | 1.50 | 0.99 | 1.32 | 2.53 | 1.12 | 1.29 | 1.03 | 1.03 | 1.14 |

Fig. 22

TARGETED DENDRIMER CONJUGATES

CROSS-REFERENCE TO RELATED APPLICATIONS

This application is a U.S. national stage application, filed under 35 U.S.C. § 371 (c), of International Application No. PCT/AU2020/050910, filed on Aug. 28, 2020, which claims priority to Australian Patent Application No. 2019903152, filed on Aug. 28, 2019. The entire contents of each of the aforementioned applications are incorporated herein by reference.

FIELD

The present disclosure generally to therapies useful for targeting cancers in which HER2 is overexpressed. More specifically, the disclosure relates to the targeted delivery of therapeutic agent moieties, by means of a dendrimer-targeting moiety conjugate which comprises a HER2 antibody fragment or mimetic, and a therapeutic agent moiety such as a residue of an ultracytotoxic agent.

BACKGROUND

According to the WHO, cancer is the second leading cause of death worldwide, being responsible for an estimated 9.6 million deaths in 2018. The most common forms of cancer are lung, breast, colorectal, prostate, skin cancer and stomach cancer.

There have been many efforts to develop effective oncology therapies. However, the challenge of finding a new therapy which has sufficient potency at the target, appropriate pharmacokinetic properties such that it can be delivered to the site of action, and sufficient duration of action, together with a good safety profile, is extremely difficult, time-consuming and costly.

The development of monoclonal antibody therapies, such as trastuzumab (Herceptin®) and rituximab (Mabthera®) constitutes one type of approach which has had notable success. For example, Herceptin® was approved in 1998, and is used for the therapy of HER2-overexpressing breast and gastric cancers. The antibody works by binding to the HER2/ERBB2 receptor which is over-expressed in some forms of cancer, and blocking signals that stimulate cancer cell growth. There are however drawbacks with Herceptin®. For example, known side effects include heart muscle damage and heart failure. Herceptin® is also not fully effective, even in the subset of patients whose cancers are HER2 positive, and several mechanisms for resistance have been proposed (Pohlmann, Mayer and Mernaugh, 2009).

Another, contrasting, approach for therapy involves the use of cytotoxic agents which are active against rapidly dividing cells. A long-established example is cisplatin, which is used for the treatment of various cancers, including ovarian cancer, bladder cancer, testicular cancer and squamous cell carcinoma. A further group of cytotoxic agents are the ultracytotoxics, including auristatins such as monomethyl auristatin E (MMAE), which are extremely potent agents but which can simultaneously cause severe toxicity and damaging side effects to some patients. As a consequence, such ultracytotoxic agents cannot safely be administered to a patient as chemotherapeutic agents in their own right. Research has been carried out to identify means of utilising such ultracytotoxic agents, leading to the development of antibody drug conjugates such as brentuximab vedotin (Adcetris®), which contains MMAE conjugated to brentuximab (a CD30 antibody) through a linear linker, and which is approved for the therapy of Hodgkin lymphoma and anaplastic large cell lymphoma.

Many drug candidates fail in clinical trials due to a poor therapeutic index, i.e., the ratio of therapeutic effect to toxicity. Some of the reasons underlying these failures include lack of potency, lack of specificity, poor drug absorption/bioavailability, inability to control biodistribution, rapid metabolism and clearance, and instability on storage. Indeed, there is a balance to strike in achieving the necessary therapeutic cytotoxicity to kill cancer cells, and mitigating the detrimental toxicity and side effects to levels that may be tolerated by the patient.

Various approaches have been investigated to try and improve the therapeutic efficacy of compounds with suboptimal properties. For example, for compounds which are rapidly cleared, sustained release formulations may be developed. One such example in the field of chemotherapeutics is the product Onivyde®, a liposomal formulation of the active ingredient irinotecan which has a greatly reduced rate of elimination from plasma compared with a conventional formulation (Messerer et al., 2004). Other technologies include the use of depot injection formulations (e.g., Lupron Depot®). Dendrimer technologies have also been investigated in an attempt to improve properties of pharmaceutically active agents and circumvent formulation difficulties, for example WO2012/167309 describes the provision of drug-dendrimer conjugates, particularly containing the poorly soluble pharmaceutical agent docetaxel.

Despite these and other advances in the art, there remains a need to develop further therapies which are safe and efficacious at treating diseases such as cancers.

Any discussion of documents, acts, materials, devices, articles or the like which has been included in the present specification is not to be taken as an admission that any or all of these matters form part of the prior art base or were common general knowledge in the field relevant to the present disclosure.

SUMMARY

In a first aspect, there is provided dendrimer-targeting agent conjugate, comprising:

a) a dendrimer comprising
   i) a core unit (C); and
   ii) building units (BU), each building unit being a lysine residue or an analogue thereof;
   wherein the core unit is covalently attached to at least two building units via amide linkages, each amide linkage being formed between a nitrogen atom present in the core unit and a carbon atom of an acyl group present in a building unit;
b) a HER2 targeting agent which is a peptidic moiety having a molecular weight of up to about 80 kDa and comprising an antigen-binding site, which is covalently linked to the dendrimer by a spacer group;
c) a therapeutic agent which is covalently linked to a surface building unit of the dendrimer; and
d) a hydrophilic polymeric group that is covalently linked to surface building units of the dendrimer.

In some embodiments, the peptidic moiety is selected from: a heavy chain antibody, Fab, Fv, scFv or a single domain antibody. In some embodiments, the peptidic moiety comprises or consists of a heavy chain variable ($V_H$) domain. In some embodiments, the peptidic moiety comprises or consists of a light chain variable ($V_L$) domain.

In some embodiments, the targeting agent has a molecular weight of about 5 kDa to about 30 kDa. In some embodiments, the targeting agent has a molecular weight of about 5 kDa to about 18 kDa. In some embodiments, the targeting agent has a molecular weight of about 5 kDa to about 15 kDa. In some embodiments, the targeting agent has a molecular weight of about 10 kDa to about 16 kDa. In some embodiments, the targeting agent has a molecular weight of about 14 kDa to about 18 kDa.

In some embodiments, the targeting agent comprises less than 120 amino acid residues.

In some embodiments, the targeting agent comprises or consists of any of the amino acid sequences as defined herein.

In some embodiments, one targeting agent is covalently linked to the dendrimer. In some embodiments, more than one targeting agent is covalently linked to the dendrimer.

In some embodiments, the targeting agent precursor comprises an unnatural amino acid residue, the unnatural amino acid residue having a side-chain including a reactive functional group. In some embodiments, the unnatural amino acid residue is a residue of,

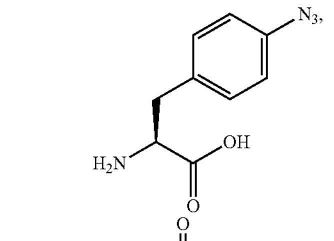

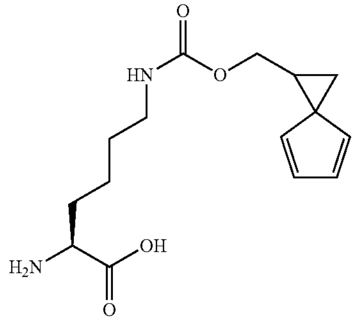

, or

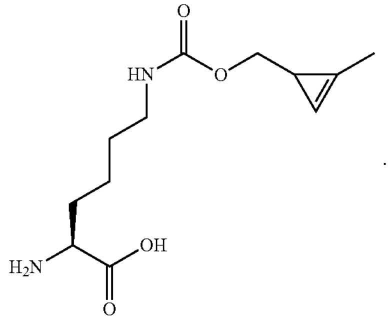

In some embodiments, the targeting agent is covalently linked to the spacer group via the C-terminus of the targeting moiety.

In some embodiments, the spacer group precursor comprises a reactive functional group which is an alkyne group. In some embodiments, the alkyne group is a dibenzocyclooctyne group.

In some embodiments, the spacer group is covalently attached to a surface building unit of the dendrimer. In some embodiments, the spacer group is covalently attached to the core unit.

In some embodiments, the covalent linkage between the targeting agent and the spacer group has been formed by reaction between complementary reactive functional groups present on a targeting agent precursor and a spacer group precursor. In some embodiments, the spacer group comprises an alkene group.

In some embodiments, the therapeutic agent is a chemotherapeutic agent. In some embodiments, the therapeutic agent is a cytotoxic agent. In some embodiments, the therapeutic agent is an ultracytotoxic agent. In some embodiments, the therapeutic agent is an auristatin or a maytansinoid. In some embodiments, the therapeutic agent is monomethyl auristatin E. In some embodiments, the therapeutic agent is monomethyl auristatin F. In some embodiments, the therapeutic agent is SN-38. In some embodiments, the therapeutic agent is cabazitaxel.

In some embodiments, the therapeutic agent is covalently linked to a surface building unit of the dendrimer via a linker. In some embodiments, the therapeutic agent is covalently linked to a surface building unit of the dendrimer via a cleavable linker. In some embodiments, the cleavable linker comprises a Val-Cit-PAB group.

In some embodiments, the conjugate comprises a hydrophilic polymeric group covalently linked to surface building units of the dendrimer. In some embodiments, the hydrophilic polymeric group is a PEG group, which is covalently linked to surface building units of the dendrimer. In some embodiments, the PEG groups have an average molecular weight in the range of from about 500 to about 2500 g/mole.

In some embodiments, the spacer group comprises a PEG group.

In some embodiments, the core unit comprises the structure:

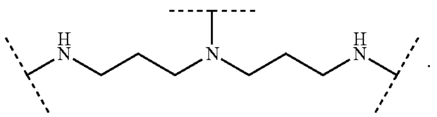

In some embodiments, the core unit comprises the structure:

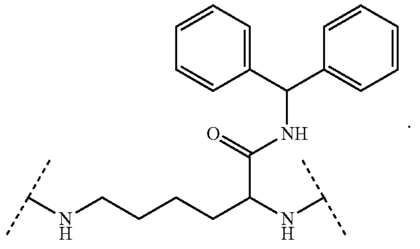

In some embodiments, the core unit is BHALys.

In some embodiments, the dendrimer has from one to five generations of building units. In some embodiments, the dendrimer has three to five generations of building units. In some embodiments, the dendrimer has three generations of building units. In some embodiments, the dendrimer has four generations of building units. In some embodiments, the dendrimer has five generations of building units.

In some embodiments, the building units are each:

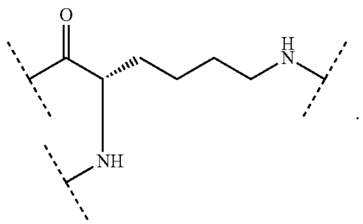

In some embodiments, the conjugate is for administration in combination with a further active agent.

In some embodiments, the conjugate is internalised within a HER2-expressing cell.

In some embodiments, administration of the conjugate results in reduced side effects in comparison to administration of an equivalent dose of free therapeutic agent.

In some embodiments, administration of the conjugate provides for at least a 50% reduction in the maximum plasma concentration of released therapeutic agent in comparison to administration of an equivalent dose of free therapeutic agent.

In a second aspect, there is provided a composition comprising a plurality of conjugates as defined herein.

In a third aspect, there is provided a pharmaceutical composition, comprising:

i) a conjugate as described herein; and ii) a pharmaceutically acceptable excipient.

In some embodiments, the composition is formulated for parenteral delivery.

In some embodiments, the conjugate or composition is for use in the treatment of cancer.

In a fourth aspect, there is provided a method of treating cancer comprising administering to a subject in need thereof a therapeutically effective amount of the conjugate or composition as described herein.

In a fifth aspect, there is provide the use of the conjugate or composition as described herein, in the manufacture of a medicament for the treatment of cancer.

In some embodiments, the cancer is ovarian cancer, breast cancer, stomach cancer, uterine cancer, or another cancer characterised by abnormal expression of the ERBB2 gene.

In a sixth aspect, there is provided, a method of killing a HER2-expressing cell, comprising: contacting a conjugate as defined herein with a HER2-expressing cell such that the conjugate is internalised within the cell, whereby the therapeutic agent kills the HER2-expressing cell.

It will be appreciated that further aspects, embodiments, and examples, are described herein, which may include one or more of the embodiments or features as described above.

BRIEF DESCRIPTION OF THE DRAWINGS

FIG. 21 shows a table providing the tumour:organ ratio of ex vivo signal of injected zirconium dose per gram for compounds of the present disclosure at days 2 and 9.

FIG. 22 shows a table providing the percentage injected zirconium dose per gram in ex vivo tumour and organs for compounds of the present disclosure at days 2 and 9.

KEY TO THE SEQUENCE LISTING

Figure 1:
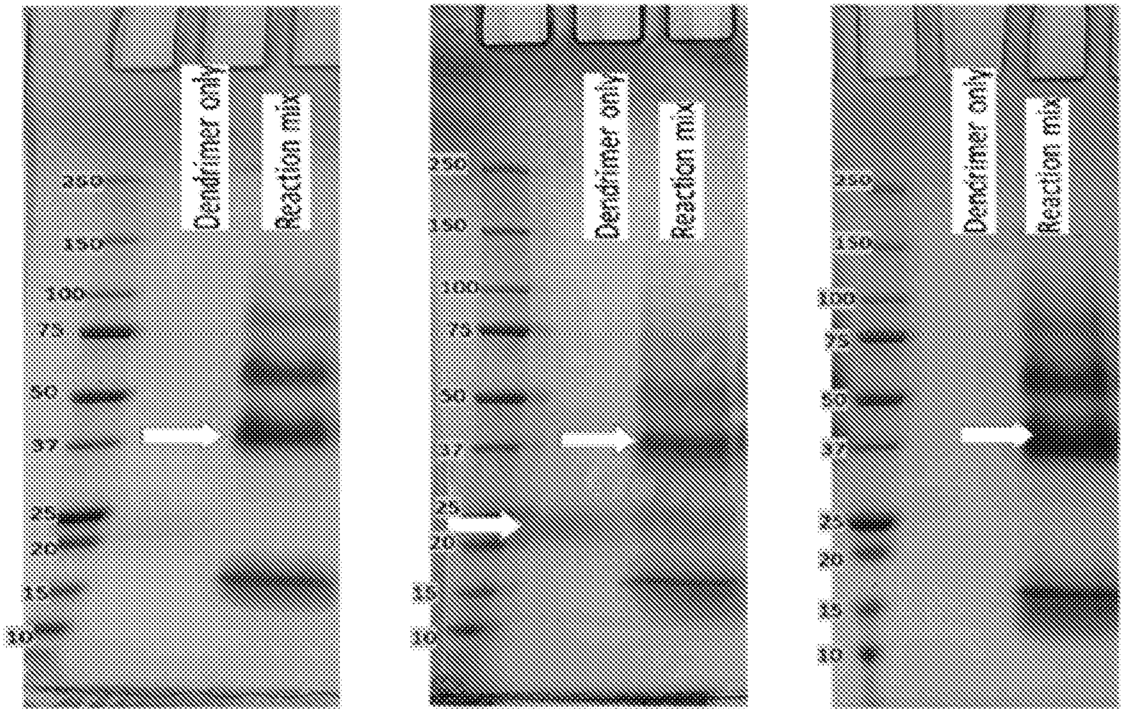
FIG. 1 shows SDS Page analysis of compounds 74, 75 and 76 stained with Coomassie blue.

SEQ ID NO. 1: 2D3 nanobody.

SEQ ID NO. 2: 2D3 nanobody with N-terminal tag, TEV, C-terminal azide.

SEQ ID NO. 3: 2D3 nanobody with C-terminal tag, TEV, azide.

DETAILED DESCRIPTION

General Definitions

Unless specifically defined otherwise, all technical and scientific terms used herein shall be taken to have the same meaning as commonly understood by one of ordinary skill in the art (e.g., chemistry, biochemistry, medicinal chemistry, polymer chemistry, and the like).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. As used herein, the term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

As used herein, the terms "a", "an" and "the" include both singular and plural aspects, unless the context clearly indicates otherwise.

As used herein, the term "subject" refers to any organism that is susceptible to a HER2 (human epidermal growth factor receptor 2) associated disease or condition. In one embodiment, the subject can be an animal. In one example, the subject is a mammal. In one embodiment, the subject is human. In one embodiment, the subject is a non-human animal. In one embodiment, the subject has cancer. In one embodiment, the subject has a HER2 positive cancer.

As used herein, the term "treating" includes alleviation of symptoms associated with a specific disorder or condition. For example, as used herein, the term "treating cancer" includes alleviating symptoms associated with cancer. In one embodiment, the term "treating cancer" refers to a reduction in cancerous tumour size. In one embodiment, the term "treating cancer" refers to a reduction in invasiveness of a cancer. In one embodiment, the term "treating cancer" refers to an increase in progression-free survival. As used herein, the term "progression-free survival" refers to the length of time during and after the treatment of cancer that a patient lives with the disease, i.e., cancer, but does not have a recurrence or increase in symptoms of the disease.

As used herein, the term "prevention" includes prophylaxis of the specific disorder or condition. For example, as used herein, the term "preventing cancer" refers to preventing the onset or duration of the symptoms associated with cancer. In one embodiment, the term "preventing cancer" refers to slowing or halting the progression of the cancer. In one embodiment, the term "preventing cancer" refers to slowing or preventing metastasis.

The term "therapeutically effective amount", as used herein, refers to a conjugate containing a therapeutic agent being administered in an amount sufficient to alleviate or prevent to some extent one or more of the symptoms of the disorder or condition being treated. The result can be the reduction and/or alleviation of the signs, symptoms, or causes of a disease or condition, or any other desired alteration of a biological system. In one embodiment, the term "therapeutically effective amount" refers to a conjugate being administered in an amount sufficient to result in a reduction in cancerous tumour size. In one embodiment, the term "therapeutically effective amount" refers to a conjugate being administered in an amount sufficient to result in an increase in progression-free survival. The term, an "effective amount", as used herein, refers to an amount of a conjugate effective to achieve a desired pharmacologic effect or therapeutic improvement without undue adverse side effects or to achieve a desired pharmacologic effect or therapeutic improvement with a reduced side effect profile. Therapeutically effective amounts may for example be determined by routine experimentation, including but not limited to a dose escalation clinical trial. The term "therapeutically effective amount" includes, for example, a prophylactically effective amount. In one embodiment, a prophylactically effective amount is an amount sufficient to prevent metastasis. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. An appropriate "effective amount" in any individual case may be determined by one of ordinary skill in the art using routine experimentation.

As used herein, the term "attached" refers to a connection between chemical components by way of covalent bonding. The term "covalent bonding" is used interchangeably with the term "covalent attachment".

Dendrimer

In a first aspect there is provided dendrimer-targeting agent conjugate, comprising:

a) a dendrimer comprising
   i) a core unit (C); and
   ii) building units (BU), each building unit being a lysine residue or an analogue thereof;
   wherein the core unit is covalently attached to at least two building units via amide linkages, each amide linkage being formed between a nitrogen atom present in the core unit and a carbon atom of an acyl group present in a building unit;
b) a HER2 targeting agent which is a peptidic moiety having a molecular weight of up to about 80 kDa and comprising an antigen-binding site, which is covalently linked to the dendrimer by a spacer group;
c) a therapeutic agent which is covalently linked to a surface building unit of the dendrimer; and
d) a hydrophilic polymeric group that is covalently linked to surface building units of the dendrimer.

Dendrimeric conjugates have been demonstrated to be highly effective anti-cancer agents in in vitro and in vivo tests, and demonstrate improved effects relative to Herceptin® and Kadcycla® (a HER2-emtansine antibody-drug conjugate) in experimental studies. In contrast to Herceptin® itself, the conjugates are rapidly internalised into HER2-overexpressing cancer cells. It is anticipated that the fast internalisation properties assist in delivering a high proportion of the therapeutic agent administered via the conjugates to the desired site of action. The ability to deliver the therapeutic moiety specifically to the target cell, where it is rapidly internalised, assists in reducing unwanted side effects (i.e., toxicity) associated with exposure of other non-cancerous cells to cytotoxic agents. Such an approach is particularly advantageous in the instance of the delivery of cytotoxic therapeutic moieties (e.g., ultracytotoxic therapeutic moieties), in which their free circulation in blood plasma can have toxic effects.

As used herein, the term "dendrimer" refers to a molecule containing a core and dendrons attached to the core. Each dendron is made up of generations of branched building units resulting in a branched structure with increasing number of branches with each generation of building units. A "conjugate" may include pharmaceutically acceptable salts or solvates as defined herein.

As used herein, the term "building unit" refers to a branched molecule which is a lysine residue or an analogue thereof having three functional groups, one (e.g. derived from a carboxylic acid group) for attachment to the core or a previous generation of building units and at least two functional groups (e.g. derived from amine for attachment to the next generation of building units or forming the surface of the dendrimer molecule).

The skilled person will appreciate that the conjugates may be produced in a variety of forms, including salt forms (e.g. where there are ionisable groups present in the conjugate), as well as different solvates, for example. It will be understood that the present disclosure relates to all such forms of the dendrimer-targeting moiety conjugates.

Suitable salts of the conjugates include those formed with organic or inorganic acids or bases. As used herein, the phrase "pharmaceutically acceptable salt" refers to pharmaceutically acceptable organic or inorganic salts. Exemplary acid addition salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Exemplary base addition salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. It will also be appreciated that non-pharmaceutically acceptable salts also fall within the scope of the present disclosure since these may be useful as intermediates in the preparation of pharmaceutically acceptable salts or may be useful during storage or transport.

Those skilled in the art of organic and/or medicinal chemistry will appreciate that many organic compounds can form complexes with solvents in which they are reacted or from which they are precipitated or crystallized. These complexes are known as "solvates". For example, a complex with water is known as a "hydrate". As used herein, the phrase "pharmaceutically acceptable solvate" or "solvate" refer to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine.

Core Unit

The core unit (C) of the dendrimer is covalently attached to building units via amide linkages, each amide linkage being formed between a nitrogen atom present in the core unit and the carbon atom of an acyl group present in a building unit. Accordingly, the core unit may for example be formed from a core unit precursor comprising amino groups. Any suitable amino-containing molecule may be used as the core unit precursor.

Typically, the core unit provides additional functionality to the nitrogen atoms used for covalent attachment of building units, for example it may comprise a functional group for attachment of the targeting moiety through the spacer group. In other words, the HER2 targeting agent is typically covalently linked to the core unit of the dendrimer by the spacer group. In some embodiments, the core unit is derivable from a precursor having three reactive nitrogen atoms, two of which may be used for attachment of building units, and one of which may be used for attachment of a spacer group.

In some embodiments, the core unit has the structure:

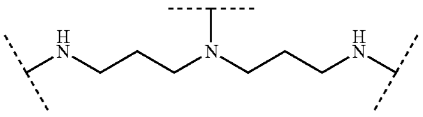

.

In some embodiments, the core unit is a lysine molecule with three attachment points, having the structure:

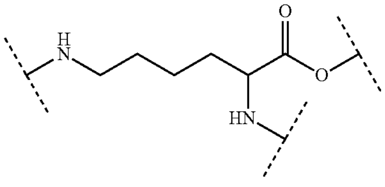

.

In some embodiments, the core unit is derivable from a precursor having two reactive nitrogen atoms, which may be used for attachment of building units. For example, in some embodiments, the core unit may be derivable from ethylenediamine, 1,4-diaminobutane or 1,6-diaminohexane. In some embodiments, the core unit has the structure:

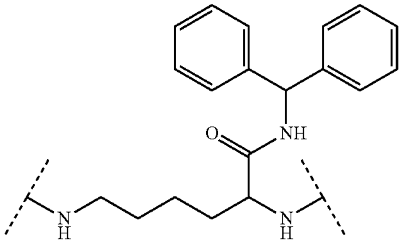

, i.e., whereby the core unit comprises a lysine residue in which the acid moiety has been capped with a benzhydrylamine (BHA-Lys) to form the corresponding amide, and may, for example, be formed from a core unit precursor:

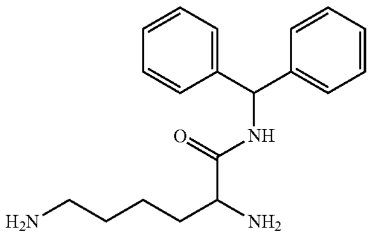 [SMILES: NCCCCC(N)C(=O)NC(c1ccccc1)c1ccccc1]

having two reactive (amino) nitrogens.

Where a core unit precursor with only two reactive nitrogen atoms is used, such as BHA-Lys, the two amino groups are typically functionalised with building units, and the spacer group (and thus the targeting agent) is typically attached via a surface building unit. The present dendrimer-targeting agent conjugates allow for multiple terminal groups, to be presented on the surface of the dendrimer-targeting agent conjugates in a controlled manner. In particular, where lysine building units are used, the placement of the targeting agent and/or hydrophilic polymeric group and/or therapeutic agent on alpha or epsilon nitrogen atoms of the building units can be predetermined as described below. In some preferred embodiments, the hydrophilic polymeric groups, therapeutic agents, and targeting agents are provided on the surface of the dendrimer via attachment through the building units. In other words, in those embodiments, the core unit does not provide an attachment point for the targeting agent other than via the building units. It will be understood that, in such embodiments, any functional groups present in the core unit which are not used for covalent attachment to a building unit will either be unreacted (i.e. unreactive in the conditions to which the conjugate has been exposed), or will have been capped with a suitable capping group to prevent further reaction. An example of such a core unit is the BHA-Lys group discussed above.

Building Units

The building units (BU) are lysine residues or analogues thereof, and may be formed from suitable building unit precursors, e.g. lysine or lysine analogues containing appropriate protecting groups. Lysine analogues have two amino nitrogen atoms for bonding to a subsequent generation of building units and an acyl group for bonding to a previous generation of building units or a core unit. Examples of suitable building units include

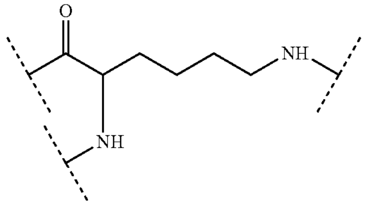

,

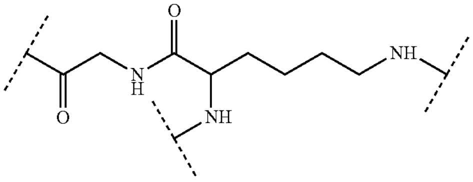

,

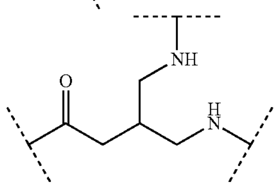

,

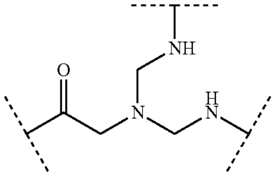

, and

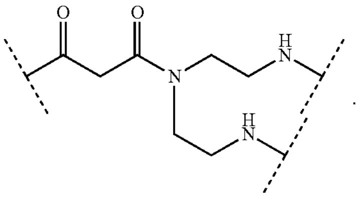

.

wherein the acyl group of each building unit provides a covalent attachment point for attachment to the core or to a previous generation building unit; and wherein each nitrogen atom provides a covalent attachment point for covalent attachment to a subsequent generation building unit, or a terminal group such as a linked therapeutic agent.

In some preferred embodiments, the building units are each:

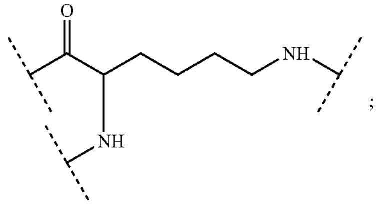

wherein the acyl group of each building unit provides a covalent attachment point for attachment to the core unit or to a previous generation building unit; and wherein each nitrogen atom provides a covalent attachment point for covalent attachment to a subsequent generation building unit, or a terminal group such as a linked therapeutic agent.

In some preferred embodiments, the building units are each:

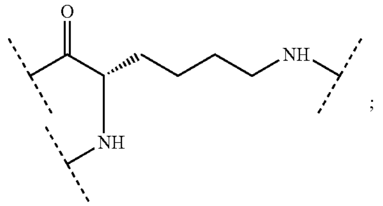

wherein the acyl group of each building unit provides a covalent attachment point for attachment to the core or to a previous generation building unit; and wherein each nitrogen atom provides a covalent attachment point for covalent attachment to a subsequent generation building unit, or a terminal group such as a linked therapeutic agent.

The outermost generation of building units ($BU_{outer}$) may be formed by lysine or lysine analogue building units as used in the other generations of building units (BU) as described above. The outermost generation of building units ($BU_{outer}$) is the generation of building units that is outermost from the core unit of the dendrimer, i.e., no further generations of building units are attached to the outermost generation of building units ($BU_{outer}$).

It will be appreciated that the dendrons of the dendrimer may, for example, be synthesised to the required number of generations through the attachment of building units (BU) accordingly. In some embodiments each generation of building units (BU) may be formed of the same building unit, for example all of the generations of building units may be lysine building units. In some other embodiments, one or more generations of building units may be formed of different building units to other generations of building units.

The dendrimer moiety typically has from one to five generations of building units. In some embodiments, the dendrimer is a one generation building unit dendrimer. In some embodiments, the dendrimer is a two generation building unit dendrimer. In some embodiments, the dendrimer is a three generation building unit dendrimer. In some embodiments, the dendrimer is a four generation building unit dendrimer. In some embodiments, the dendrimer is a five generation building unit dendrimer. For example, a three generation building unit dendrimer is a dendrimer having a structure which includes three building units which are covalently linked to each another, for example in the case where the building units are lysines, and it may comprise the substructure:

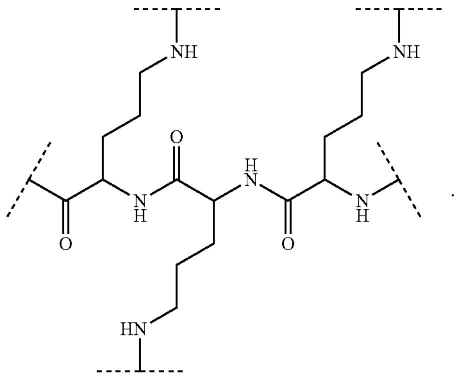

In some embodiments, the dendrimer has complete generations of building units. For example, a three generation dendrimer has three complete generations of building units. With a core having two reactive amine groups, such a three generation dendrimer will comprise 14 building units (i.e. core unit+2 BU+4 BU+8 BU). However, it will be appreciated that, due to the nature of the synthetic process for producing the dendrimers, one or more reactions carried out to produce the dendrimers may not go fully to completion. Accordingly, in some embodiments, the dendrimer may comprise incomplete generations of building units. For example, a population of dendrimers may be obtained, in which the dendrimers have a distribution of numbers of building units per dendrimer. In some embodiments, a population of dendrimers is obtained which has a mean number of building units per dendrimer of at least 8, or at least 9, or at least 10, or at least 11, or at least 12, or at least 13. In some embodiments, a population of dendrimers is obtained in which at least 60%, at least 70%, at least 80%, at least 90% or at least 95% of the dendrimers have 10 or more building units. In some embodiments, a population of dendrimers is obtained in which at least 60%, at least 70%, at least 80%, at least 90% or at least 95% of the dendrimers have 12 or more building units.

In some embodiments, each generation of building units in each dendron (X) may be represented by the formula $[BU]_2^{(b-1)}$, wherein b is the generation number. A dendron (X) having three complete generations of building units is represented as $[BU]_1$-$[BU]_2$-$[BU]_4$.

Targeting Agent

A dendrimer-targeting agent conjugate as described herein comprises a HER2 targeting agent, i.e. the targeting agent is capable of binding to human epidermal growth factor receptor 2 (HER2, also known as ERBB2; Gene ID No. 2064, NCBI). The HER2 targeting agents as described herein are useful for targeting of the disclosed dendrimer conjugates to tumours and cancer cells.

The targeting agent comprises a peptidic moiety having a molecular weight of up to about 80 kDa and comprises an antigen-binding site that specifically binds and/or has an affinity for the molecule (i.e. HER2). The interaction may occur through any type of bonding or association including for example covalent, ionic and hydrogen bonding, Van der Waals forces.

In an embodiment, the HER2 targeting agent as described herein has a molecular weight of about 3 kDa to about 80 kDa, or about 3 kDa to about 60 kDa, or about 3 kDa to about 50 kDa, or about 3 kDa to about 40 kDa, or about 3 kDa to about 30 kDa, or about 3 kDa to about 20 kDa, or about 3 kDa to about 15 kDa, or about 3 kDa to about 13 kDa, or about 5 kDa to about 15 kDa, or about 5 kDa to about 12 kDa, or about 5 kDa to about 10 kDA.

In an embodiment, the HER2 targeting agent has a molecular weight of about 3 kDa to about 80 kDa. In an embodiment, the HER2 targeting agent has a molecular weight of about 3 kDa to about 60 kDa. In an embodiment, the HER2 targeting agent has a molecular weight of about 3 kDa to about 50 kDa. In an embodiment, the HER2 targeting agent has a molecular weight of about 3 kDa to about 40 kDa. In an embodiment, the HER2 targeting agent has a molecular weight of about 3 kDa to about 30 kDa. In an embodiment, the HER2 targeting agent has a molecular weight of about 3 kDa to about 20 kDa. In an embodiment, the HER2 targeting agent has a molecular weight of about 3 kDa to about 15 kDa. In an embodiment, the HER2 targeting agent has a molecular weight of about 3 kDa to about 13 kDa. In an embodiment, the HER2 targeting agent has a molecular weight of about 5 kDa to about 15 kDa. In an embodiment, the HER2 targeting agent has a molecular weight of about 5 kDa to about 12 kDa. In an embodiment, the HER2 targeting agent has a molecular weight of about 5 kDa to about 10 kDa.

As described herein "kDA" or "kilodalton" refers to a unit of molecular mass consisting of 1000 daltons.

In some embodiments, the targeting agent is an antibody fragment. As used herein, the term "antibody fragment" shall be taken to mean a portion of or a fragment of an antibody capable of specifically binding to an antigen, including for example, a $F_V$, $V_H$, $V_L$ or a variable region as defined herein. This term shall be understood to encompass fragments directly derived from an antibody as well as proteins produced using recombinant means. In an embodiment, the antibody fragment is selected from a Fab, Fv, scFv, heavy chain antibody, domain antibody, heavy chain antibody, diabody or triabody.

As used herein, the term "Fv" shall be taken to mean any protein, whether comprised of multiple polypeptides or a single polypeptide (scFV), in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. In an embodiment, an Fv of the disclosure (as well as any protein of the disclosure) may have multiple antigen binding sites which may or may not bind the same antigen. This term shall be understood to encompass fragments directly derived from an antibody as well as proteins produced using recombinant means. In some examples, the $V_H$ is not linked to a heavy chain constant domain CH1 and/or the $V_L$ is not linked to a light chain constant domain (CL), e.g., a domain antibody. Exemplary Fv containing polypeptides or proteins include a Fab fragment, a Fab' fragment, a F(ab') fragment, a scFv, a diabody, a triabody, A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A Fab fragment generally comprises or consists of a $V_H$ and $C_H1$ and a $V_L$ and CL. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

In some embodiments, the antibody fragment is selected from: a heavy chain antibody, Fab, Fv, scFv or a single domain antibody.

As used herein, the "single-domain antibodies (sdAbs)", also referred to as a "domain antibodies (dAb)" or "nanobodies" comprises a single variable region of a heavy chain $V_H$ or light chain $V_L$. In an embodiment, the variable region is camelid-derived. In an embodiment, the variable region is derived from sharks. In an embodiment, the $V_H$ is a camelid-derived $V_H$.

In some embodiments, the targeting agent is a single domain antibody. In some embodiments, the targeting agent is a VH single domain antibody. In some embodiments, the targeting agent is a VL single domain antibody.

In an embodiment, the single domain antibody comprises a single domain amino acid sequence as described in for example, EP2215125A1, US20110028695, Hussack et al. (2018) or. Arezumand et al. (2017). In an embodiment, the single domain antibody comprises a single domain amino acid sequence as described US20110028695. In some embodiments, the single domain antibody is a nanobody described in Vaneycken et al. (Vaneycken et al., (2011)). In some embodiments, the single domain antibody is 2Rs15d (Vaneycken et al., (2011)). In some embodiments, the single domain antibody is 2Rb17c (Vaneycken et al., (2011)). In some embodiments, the single domain antibody is 1R59b (Vaneycken et al., (2011)). In some embodiments, the single domain antibody is 2R5a (Vaneycken et al., (2011)). In some embodiments, the single domain antibody is 1R136d (Vaneycken et al., (2011)). In some embodiments, the single domain antibody is 1R143c (Vaneycken et al., (2011)). In some embodiments, the single domain antibody is C3 (Wu et al., (2018)). In some embodiments, the single domain antibody is 5F7GGC (Pruszynski et al., (2013)) In an embodiment, the single domain antibody is 5F7 comprising the amino acid sequence having at least 95%, at least 96%, at least 97%, at least 98%, at least 99%, or 100% homology to that shown in US20110028695.

In an embodiment, the single domain antibody comprises a single domain amino acid sequence as disclosed in Example 7. In an embodiment, the single domain antibody is 2D3 comprising the amino acid sequence as shown in SEQ ID NO: 1986 of US20110028695.

In an embodiment, the single domain antibody comprises the amino acid sequence

```
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSS.
```

In some embodiments, the targeting agent does not compete for HER2 binding with trastuzumab and/or pertuzumab. In some embodiments, the targeting agent competes for HER2 binding with trastuzumab and/or pertuzumab. In an embodiment, the targeting agent is 2D3, and the targeting agent competes for HER2 binding with trastuzumab and/or pertuzumab. In some embodiments, the targeting agent binds to an extracellular domain of HER2. In some embodiments, the targeting agent binds to HER2 extracellular domain I, II, III, and/or IV. In one embodiment, the targeting agent binds to HER2 extracellular domain III. In some embodiments, the targeting agent binds to the dimerization arm of ErbB2. In the instance where the targeting agent binds to the dimerization arm of ErbB2, the targeting agent may compete for HER2 binding with pertuzumab. In some embodiments, the targeting agent binds to HER2 with a binding affinity of at least 1 nM, at least 2 nM, at least 5 nM, at least 10 nM, as determined by SPR studies.

In some embodiments, the HER2 targeting agent is a single domain antibody and has a molecular weight of about 4 kDa to about 80 kDa, or about 5 kDa to about 80 kDa, or about 5 kDa to about 60 kDa, or about 5 kDa to about 50 kDa, or about 5 kDa to about 40 kDa, or about 5 kDa to about 30 kDa, or about 5 kDa to about 20 kDa, or about 5 kDa to about 15 kDa, or about 5 kDa to about 12 kDa, or about 10 kDa to about 16 kDa.

In some embodiments, the HER2 targeting agent comprises less than about 500, less than about 400, less than about 300, less than about 200, less than about 150, less than about 140, less than about 130, less than about 120, less than about 110, less than about 100 amino acid residues. In some embodiments, the HER2 targeting agent comprises more than about 50, more than about 75, more than about 100, or more than about 120 amino acid residues. In some embodiments, the HER2 targeting agent comprises less than 120 amino acid residues. In some embodiments, the HER2 targeting agent comprises from about 100 to about 120 amino acid residues.

In some embodiments, the HER2 targeting agent is a mimetic of an antibody or an antibody fragment. As used herein, the term "mimetic" or "mimetics" refers to compounds that like antibodies or antibody fragments, can bind antigens, but are not structurally related to antibodies. This term shall be understood to not encompass antibodies or antibody fragments as described herein. This term shall be understood to encompass synthetic mimetics (produced in vitro) and mimetics produced using recombinant means. This term shall be understood to encompass protein mimetics.

In an embodiment, the mimetic is selected from an: affibody, aptamer, affilins, affimer, affitins, anticalins, avimers, alpha bodies, monobodies, DARPins, Fyomers, fibronectin type III-derived protein scaffold, phytocystatin-derived protein scaffold and a paratope mimetic peptide. Like antibodies, mimetics can be used as targeting moieties.

In an embodiment, the mimetic is derived from one of the following protein scaffolds: z domain of protein A, gamma-B crystallin, ubiquitin, cystatin, sac7d, triple helix, coiled coil, lipocalin, cyclotides, A domains of a membrane receptor, ankyrin repeat motif, sh3 domain of Fym, Kunits domians of a protease inhibitor, type III domain of fibronectin and IgG-like, thermostable carbohydrate binding module family 32 (CBM32) from a *Clostridium perfringens.*

In an embodiment, the mimetic is about 3 kDa to about 20 kDa, or about 4 kDa to about 18 kDa, or about 6 kDa to about 16 kDa, or about 6 kDa to about 14 kDa, or about 6 kDa to about 12 kDa, or about 6 kDa to about 10 kDa, or about 6 kDa to about 8 kDa. In an embodiment, the mimetic is about 3 kDa to about 20 kDa, In an embodiment, the mimetic is about 3 kDa to about 20 kDa. In an embodiment, the mimetic is about 4 kDa to about 18 kDa. In an embodiment, the mimetic is about 6 kDa to about 16 kDa. In an embodiment, the mimetic is about 6 kDa to about 14 kDa. In an embodiment, the mimetic is about 6 kDa to about 12 kDa. In an embodiment, the mimetic is about 6 kDa to about 10 kDa. In an embodiment, the mimetic is about 6 kDa to about 8 kDa.

In some embodiments, the targeting agent is an affibody. As used herein, the term "affibody" refers to any of a class of very small (approximately 6 kDa) polypeptide antibody mimetics based on a three alpha helix bundle domain of about 58 amino acids in length known as a "Z domain". Typically, the scaffold for affibodies is based on a modified version of the B-domain of Protein A. Affibodies are characterized by very high stability (withstanding temperatures as high as 90° C. and target affinities ranging from nanomolar to picomolar. See, e.g., Nord et al. (1995), Protein Eng., 8:601-608. Examples of known affibodies include, for example, affibodies against HER2 (e.g., the Anti-HER2 Affibody®, AFFIBODY AB, Bromma, Sweden; U.S. Pat. No. 7,993,650).

In some embodiments, the targeting agent is an affibody and has a molecular weight in the range of about 3 kDa to about 10 kDa, or about 3 kDa to about 8 kDa, or about 4 kDa to about 8 kDa, or about 4 kDa to about 7 kDa, or about 5 kDa to about 7 kDa, or about 6 kDa.

In some embodiments, the targeting agent is an affibody and has fewer than 80 amino acid residues, or fewer than 70 amino acid residues, or fewer than 65 amino acid residues, or fewer than 60 amino acid residues. In some embodiments, the targeting agent is made up of from 40 to 80 amino acid residues, or from 50 to 70 amino acid residues, or from 55 to 65 amino acid residues, or from 56 to 60 amino acid residues, or about 58 amino acid residues.

For the purposes for the present disclosure, the term "antibody" comprises four chain protein comprising e.g., two light chains and two heavy chains including recombinant or modified antibodies (e.g., chimeric antibodies, humanized antibodies, primatized antibodies, de-immunized antibodies and half antibodies, bispecific antibodies) capable of specifically binding to one or a few closely related antigens by virtue of a Fv. An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50-70 kDa) covalently linked and two light chains (~23 kDa each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region (VH or VL wherein each are ~110 amino acids in length) and one or more constant domains at the C-terminus. The constant domain of the light chain (CL which is ~110 amino acids in length) is aligned with and disulfide bonded to the first constant domain of the heavy chain (CH which is –330-440 amino acids in length). The light chain variable region is aligned with the variable region of the heavy chain. The antibody heavy chain can comprise 2 or more additional CH domains (such as, CH2, CH3 and the like) and can comprise a hinge region between the CH1 and CH2 constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a human antibody or a deimmunized or germlined version thereof, or an affinity matured version thereof.

The terms "full-length antibody," or "whole antibody" are used interchangeably to refer to an antibody in its substantially intact form, as opposed to an antigen binding fragment of an antibody. Specifically, whole antibodies include those with heavy and light chains including a constant region. The constant region may be wild-type sequence constant regions (e.g., human wild-type sequence constant regions) or amino acid sequence variants thereof.

As used herein, the term "variable region" refers to the portions of the light and/or heavy chains of an antibody as defined herein or of a heavy chain only antibody (e.g., camelid antibodies or cartilaginous fish immunoglobulin new antigen receptors (IgNARs)) that is capable of specifically binding to an antigen and includes amino acid sequences of complementary determining regions "CDRs"; i.e., CDR1, CDR2, and CDR3, and framework regions "FRs". FR are those variable region residues other than the CDR residues. For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. Each complementarity determining region may comprise amino acid residues from a "complementarity determining region" as defined by Kabat et al., (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991). The present disclosure is not limited to FRs and CDRs as defined by the Kabat numbering system, but includes all numbering systems, including the canonical numbering system or of Chothia and Lesk (1987); Chothia et al. (1989); and/or Al-Lazikani et al., (1997); the numbering system of Honnegher and Plukthun (2001); the IMGT system discussed in Giudicelli et al., (1997); or the Enhanced Chothia Numbering Scheme (http://www.bioinfo.org.uk/mdex.html). In one example, the CDRs and/or FRs are defined according to the Kabat numbering system, e.g., as depicted in FIGS. 9A-9D in bold text. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., 1995 established that the five C-terminal amino acids of heavy chain CDR2 and/or the four N-terminal amino acids of light chain CDR1 are not generally involved in antigen binding. In one example, the CDRs and/or FRs are defined according to the Chothia numbering system, e.g., as depicted in FIGS. 9A-9D in underlined text.

As used herein, the term "Kabat numbering system" refers to the scheme for numbering antibody variable regions and identifying CDRs (hypervariable regions) as set out in Kabat (Kabat et al., 1987 and/or 1991).

As used herein, the term "Chothia numbering system" refers to the scheme for numbering antibody variable regions and identifying CDRs (structural loops) as set out in of Chothia and Lesk (Chothia and Lesk, 1987) or Al-Lazikani (Al-Lazikani et al., 1997).

As used herein, the term "antigen binding domain" shall be taken to mean the region of a compound that is capable of specifically binding to an antigen (e.g. HER2). In an embodiment, the compound is a protein. In an embodiment, the protein is an antibody or fragment thereof. In an embodiment, the antibody fragment comprises one or more of an $F_V$, $V_H$, or $V_L$ as described herein.

As used herein, the term "binds" or "binding" in reference to the interaction of a protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds", "binds specifically" or similar phrases shall be taken to mean a protein of the disclosure reacts or associates more frequently, more rapidly, with greater duration and/or with greater affinity with a particular antigen (such as HER2) or cell expressing same than it does with alternative antigens or cells. For example, a protein that specifically binds to an antigen binds that antigen with greater affinity (e.g., 20 fold or 40 fold or 60 fold or 80 fold to 100 fold or 150 fold or 200 fold greater affinity), avidity, more readily, and/or with greater duration than it binds to other antigens. It is also understood by reading this definition that, for example, a protein that specifically binds to a first antigen may or may not specifically bind to a second antigen. As such "specific binding" does not necessarily require exclusive binding or non-detectable binding of another antigen, this is meant by the term "selective binding".

In some embodiments, one targeting agent is covalently linked to the dendrimer. In some embodiments, more than one targeting agent is covalently linked to the dendrimer. In some embodiments, two targeting agents are covalently linked to the dendrimer. In some embodiments, three targeting agents are covalently linked to the dendrimer. In some embodiments, four targeting agents are covalently linked to the dendrimer.

The targeting agent is attached to the remainder of the conjugate via the spacer. In some embodiments, the covalent attachment, or linkage between the targeting agent and the spacer group has been formed by a reaction between complementary reactive functional groups present on a targeting agent precursor and a spacer group precursor which, depending on the process used to prepare the conjugate, spacer group precursor may or may not be attached to the remainder of the conjugate at the time it is reacted with the HER2 targeting moiety precursor.

In some embodiments, the targeting agent is covalently linked to the spacer group via the C-terminus of the targeting moiety.

The covalent attachment site of the targeting agent precursor can for example be cysteine, lysine, N-terminal amines, tyrosine, carbohydrates, non-natural amino acids, or transaminase (e.g., transglutaminase or sortase A) or recognition sequences. Binding sites for covalent attachment to proteins are known in the art, (for example, Milla P. et al., 2012). In silico crystal structure prediction may be used to identify positions within the targeting agent polypeptide sequence to locate the covalent attachment site that is structurally appropriate for conjugation (e.g., away from paratopes, CDRs, features critical for correct folding and conformation, and/or residues with highly charged, polar, or bulky side groups). From these candidate positions, empirical screening may be performed to determine substitution sites that best conserve function while permitting robust conjugation. In an embodiment, the 2D3 position is selected from the group consisting of positions 13, 16, 42, and 126 (c-terminus). In some embodiments, the targeting agent precursor comprises an unnatural amino acid residue for attachment to the spacer. The unnatural amino acid residue may have a side chain that has a reactive functional group that is complementary to the reactive functional group of the spacer group precursor. In some embodiments, the unnatural amino acid residue is one containing an azide group, e.g. it may be a 4-azidophenylalanine residue, e.g.

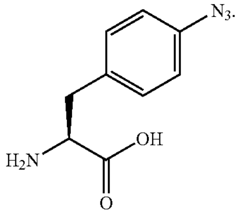 [SMILES: [N-]=[N+]=Nc1ccc(C[C@H](N)C(=O)O)cc1]

Azide groups are capable of undergoing cycloaddition reactions with alkyne groups which may be present in a spacer precursor group. In some embodiments, the unnatural amino acid is a diene-containing amino acid, e.g a spirocyclopentadiene-containing amino acid such as:

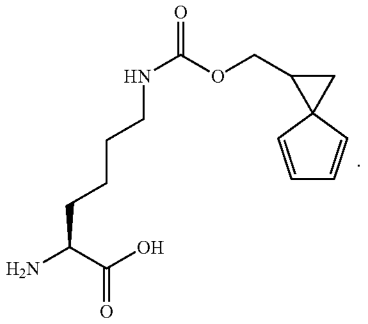 [SMILES: N[C@@H](CCCCNC(=O)OCC1CC12C=CC=C2)C(=O)O]

Diene groups are capable of undergoing cycloaddition (e.g. Diels-Alder) reactions with alkene groups, such as those present on maleimide. Further examples of unnatural amino acids which may be used for attachment to the spacer include those containing a carbonyl group, such as a ketone, and those containing a methylcyclopropylene group. Additional examples of unnatural amino acids include:

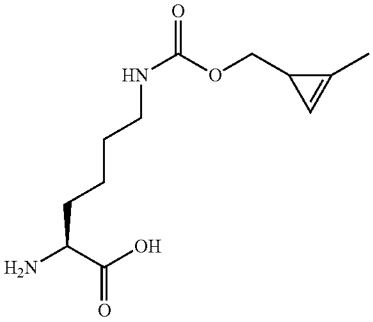
,

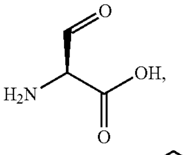

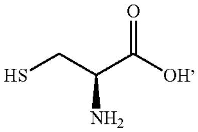

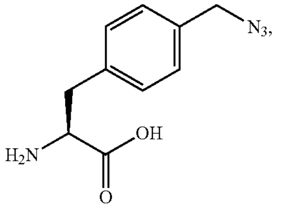
and

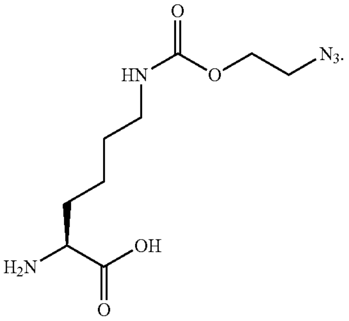

In some embodiments, the targeting agent comprises or consists of any of the amino acid sequences as defined herein.

Spacer Group

As used herein, the term "spacer group" refers to a chemical entity which serves to attach the targeting agent to the dendrimer. That is, a spacer group joins (e.g., through covalent attachment) the targeting agent to the dendrimer. The spacer group is intended to position the targeting agent such that it is capable of binding to the HER2 receptor without undue deleterious interference from other constituents of the dendrimer.

As discussed above, the targeting agent may for example be covalently attached to the dendrimer through the core of the dendrimer. In some embodiments, the spacer group is covalently attached to the core unit. In some embodiments, the targeting agent is covalently attached to the dendrimer through the core of the dendrimer. That is, the targeting agent, such as an antibody fragment, is covalently attached to the core of the dendrimer by the spacer group. Covalent attachment of a targeting agent to a dendrimer via a spacer attached to the core of the dendrimer may be beneficial if the dendrimer is sterically crowded, wherein the spacer group may be of sufficient length to protrude beyond the surface of the dendrimer, to allow for in vivo binding of the targeting agent to its receptor or similar.

In some other embodiments, the targeting agent is covalently attached to the dendrimer via a surface building unit of the dendrimer. In some embodiments, the spacer group is covalently attached to a surface building unit. For example, the targeting agent may be linked to a surface nitrogen of a lysine residue via a spacer group, for example by means of an amide bond formed between an amine group of a lysine residue, and a carboxylic acid group present on an intermediate comprising the targeting agent and spacer group. In one embodiment, the targeting agent is covalently attached to a surface nitrogen of a lysine residue via a spacer group, whereby the amide bond is formed between an amine group of a lysine residue and a carboxylic acid group present on an intermediate comprising the targeting agent and spacer group Exemplary spacer groups include polyethylene glycol (PEG), polypropylene glycol, polyaryls, peptides, amino acids, alkyl and alkenyl chains, and saccharides (mono, oligo and poly), or residues thereof. In some embodiments, the spacer group comprises a PEG chain, such as from 2 to 60 ethyleneoxy repeat units, for example from 2 to 20 or 20 to 48 repeat units. In one embodiment, the PEG is from 8 to 36 repeat units. In a further embodiment, the PEG is 12, 16, 20, 24 or 36 repeat units.

In some embodiments, the spacer group comprises multiple PEG groups interspersed with other functional groups. For example, the spacer group may comprise PEG groups linked via, e.g. amide groups or other functional groups useful for connecting parts of the spacer group.

For attachment of the spacer group to the targeting agent and/or the dendrimer, the spacer group precursor may comprise one or more reactive functional groups. In particular embodiments, the reactive functional groups comprise groups such as hydroxy, carboxy, active esters such as NHS or pentafluorophenol esters, amino, azide, maleimides (including sulfo-maleimide), dienes (such as cyclopentadienes, e.g. a spiro [2.4]hepta-4,6-diene group), tetrazine, citraconimide, alkyne-containing groups including BCN (bicycle [6.1.0]non-4-yn-9-yl), DBCO (dibenzocycloocyne-amine), activated alkenes such as methyl-cyclopropylene-containing moieties, thiol, carbonyl groups such as aldehydes and ketones, alkoxyamines, haloacetate, biotin, tetrazines, alkene-containing groups including TCO (trans-cyclooctene), methyl-cyclopropylene groups, and PTAD or other tyrosine reactive groups.

For example, in some embodiments, a spacer group intermediate may comprise two reactive groups, e.g. one at each end, which are orthogonal, i.e. at least one of the reactive groups is capable of reacting with a complementary group present on either an intermediate comprising the targeting agent, or an intermediate comprising the dendrimer, to attach the spacer group to that constituent of the conjugate, under conditions in which the other reactive group is stable and does not substantially react. This allows for the spacer to be attached (e.g., covalently attached) to either the dendrimer or the targeting agent and then subsequently, through reaction of the other reactive group with a complementary group present on the remaining constituent, in order to link the targeting agent to the dendrimer.

In some embodiments, the spacer group is attached (e.g., covalently attached) to the targeting agent by means of reaction of precursors containing alkyne and azide groups respectively (e.g. an intermediate containing the targeting group may contain an azide group, and an intermediate containing the spacer group may contain an alkyne group). Such reaction leads to formation of a triazole-containing group, e.g.:

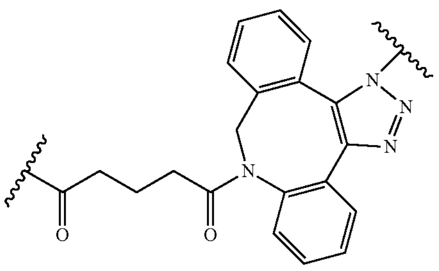
, and may be formed by reaction of precursors having the following structures:

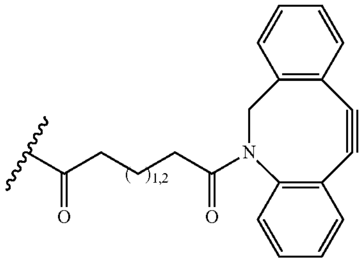
and

As another example, the spacer group may be attached via formation of a triazole-containing group, e.g.:

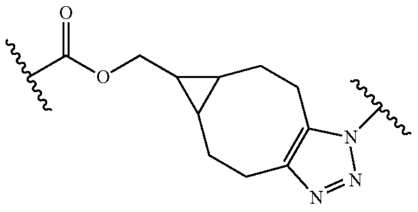 [SMILES: *C(=O)OCC1C2CCc3nnn(*)c3CCC21]

and may be formed by reaction of precursors having the following structures:

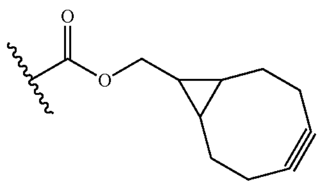
and

In some embodiments, the spacer group is attached (e.g., covalently attached) to the targeting agent by means of reaction of precursors containing alkene (e.g. strained alkenes such as trans-cyclooctene) and tetrazine groups respectively. Such reaction leads to formation of a pyridazine-containing group, with extrusion of nitrogen, e.g.:

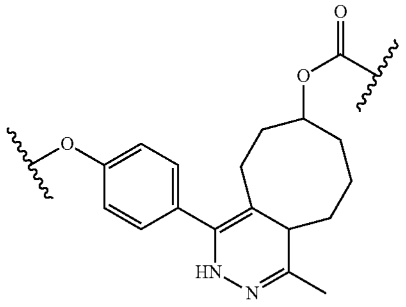 [SMILES: *Oc1ccc(C2=C3CCC(OC(*)=O)CCCC3C(C)=NN2)cc1]

and may be formed by reaction of precursors having the following structures:

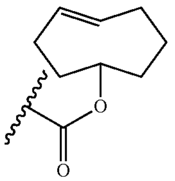

and

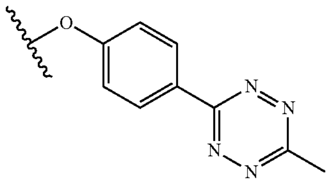

.

In some embodiments, the spacer group is attached (e.g., covalently attached) to the targeting agent by means of reaction of precursors containing alkene (e.g. strained alkenes such as methylcyclopropene) and tetrazine groups respectively. Such reaction leads to formation of a pyridazine-containing group, with extrusion of nitrogen.

For attachment (e.g., covalent attachment) of the spacer group to the dendrimer, a spacer group precursor may comprise a further functional group. For example, the spacer group precursor may comprise a carboxylic acid group which is capable of reacting with an amino group which forms part of a core unit precursor (e.g. forming an amide linkage).

In some embodiments, the spacer group is attached (e.g., covalently attached) to the dendrimer by means of reaction of precursors comprising carboxylic acid and amine groups, e.g. a spacer group intermediate may contain a carboxylic acid group which can react with an amine group present as part of or extending from the core unit, e.g. forming an amide linkage, and is attached to the targeting agent by reaction of precursors containing alkyne and azide groups respectively (e.g. an intermediate containing the targeting group may contain an azide group, and an intermediate containing the spacer group may contain an alkyne group).

As discussed above, the targeting agent precursor may comprise an unnatural amino acid residue. In some embodiments, the targeting agent comprises an unnatural amino acid residue. This unnatural amino acid residue may be, for example, any unnatural amino acid capable of presenting a reactive side-chain, wherein the reactive side-chain bears functional groups that are complementary to those functional groups present on the spacer group precursor. In such a way, it is possible for the complementary functional groups to react, and therefore for attachment of the targeting moiety precursor to the spacer group precursor to occur. In some embodiments, the unnatural amino acid residue is a 4-azidophenylalanine residue. In some embodiments, the spacer group precursor contains an alkyne group for conjugating to a targeting moiety precursor containing an unnatural amino acid residue. In some embodiments, the spacer group precursor contains an alkyne group for conjugating to a targeting agent precursor containing a 4-azidophenylalanine residue. In some embodiments, the spacer group precursor contains an alkyne group that is a dibenzylcyclooctane group for conjugating to a targeting moiety precursor containing a 4-azidophenylalanine residue. In some embodiments, one end of the spacer group is attached to the targeting moiety by cycloaddition reaction of a DBCO group with an azido moiety on a 4-phenylalanine residue which forms part of the targeting moiety, e.g. forming a triazole-containing group such as:

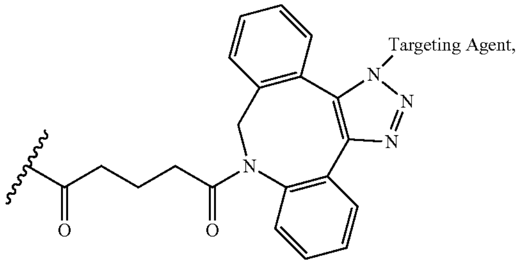

or by reaction of a BCN ((bicycle[6.1.0]non-4-yn-9-yl)) group with an azido moiety on a 4-phenylalanine residue which forms part of the targeting moiety, e.g., forming a triazole-containing group such as:

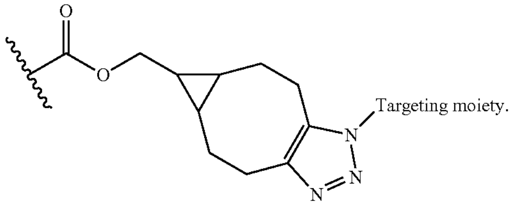

In some embodiments, one end of the spacer group is attached (e.g., covalently attached to the dendrimer by an amidation reaction between an amino group present on the core or present on a surface building unit, and between a carboxyl group present on the spacer group (e.g., by reaction of an activated ester). In some embodiments, the spacer group precursor contains a tetrazine group. In some embodiments, the spacer group precursor comprises a maleimide group, e.g. for conjugating to a diene (such as a cyclopentadiene, e.g. a spiro [2.4]hepta-4,6-diene group).

In some embodiments, the spacer group precursor contains a PEG chain with a reactive carboxyl group for joining to an amine at the core of the dendrimer and an azide group for conjugating to a targeting agent precursor containing a reactive alkyne moiety. In some embodiments, the spacer group precursor consists of a PEG chain with a reactive amine group for joining to a carboxyl group at the core of the dendrimer and an azide group for conjugating to a targeting agent precursor containing a reactive alkyne moiety. In some embodiments, the spacer group precursor consists of a PEG chain with a reactive carboxyl group for joining to an amine at the core of the dendrimer and a maleimide group for conjugating to a targeting agent precursor containing a reactive thiol moiety. In some embodiments, the spacer group precursor consists of a PEG chain with a reactive amine group for joining to a carboxyl group at the core of the dendrimer and a thiol or masked thiol group for conjugating to a targeting agent precursor containing a reactive maleimide moiety. In some embodiments, the spacer group precursor contains a PEG chain with a reactive carboxyl group for joining to an amine at the core of the dendrimer and a tetrazine group for conjugating to a targeting agent precursor containing a reactive alkene moiety. In some embodiments, the spacer group precursor contains a PEG chain with a reactive carboxyl group for joining to an amine at the core of the dendrimer and a maleimide group for conjugating to a targeting agent precursor containing a reactive diene (such as a cyclopentadiene, e.g. a spiro [2.4]hepta-4,6-diene group).

In some embodiments, the linkage of the targeting agent to the dendrimer may be accomplished through attaching (e.g., covalently attaching) a first spacer group to a targeting agent intermediate, a second spacer group to the dendrimer (e.g. to the core of the dendrimer), and then reacting together complementary functional groups present on the first and second spacer groups in order to link the targeting agent and the dendrimer. Such an approach may provide for facile connection of dendrimer to targeting agent. For example, a first spacer group intermediate may comprise a first reactive group at one end which is complementary to a reactive group on a targeting agent (e.g. an alkyne group, which is complementary with an azide group, and can react together to form a triazole group), and a second reactive group which is complementary to a reactive group on a second spacer group (e.g. a tetrazine-containing group which is complementary to reaction with a trans-cyclooctene-containing group). A second spacer group intermediate may for example comprise a third reactive group at one end which complementary to reaction with a reactive group on a dendrimer (e.g. a carboxylic acid group, which is complementary to reaction with an amine group), and a fourth reactive group at the other end which is complementary to reaction with a reactive group on the first spacer group intermediate (e.g. a trans-cyclooctene-containing group which is complementary to reaction with a tetrazine group). For example, first and spacer groups may be attached via a group produced by reaction of a trans-cyclooctene group and a tetrazine group, and comprising the structure:

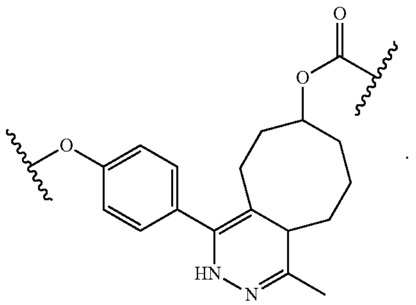 [SMILES: *Oc1ccc(C2=C3CCC(OC(*)=O)CCCC3C(C)=NN2)cc1]

In some embodiments, the targeting moiety may be linked to the dendrimer via a spacer group which is formed by reaction of an azide-moiety present on the targeting agent with an alkyne containing group at one end of a spacer group (e.g. DBCO, BCN), and by reaction of a tetrazine moiety attached to the dendrimer with a strained alkene group at the other end of the spacer group (e.g., trans cyclooctene).

The targeting agent precursor is reacted with the spacer group precursor so as to form an attachment of the targeting agent to the spacer group. Means of attaching the spacer group precursor to the targeting agent precursor are known in the art. For example, sites for covalent attachment to the targeting agent precursor include, but are not limited to, cysteine residues, lysine residues, C-terminal amino acid residues, N-terminal amines, tyrosine residues, carbohydrates, suitable non-natural amino acid residues, or transaminase or recognition sequences. Binding sites for covalent attachment to proteins, such as targeting agent precursors, are known in the art (for example, Milla P., et al., 2012). For example, the spacer group precursor may be reacted with the targeting agent precursor at the C-terminus of the targeting agent, such that the spacer group is attached to the targeting agent via the C-terminus. In some embodiments, the targeting agent is attached to the spacer group via the C-terminus of the targeting agent. In one embodiment, the targeting agent is covalently attached, or linked, to the spacer group via the C-terminus of the targeting agent.

Therapeutic Agent

As used herein, the term "therapeutic agent" refers to an agent which exerts a therapeutic effect in vivo, e.g. against HER-2 expressing cancer cells. Examples of therapeutic agents include, but are not limited to, anti-cancer agents, also referred to as chemotherapeutics, anti-neoplastic agents and cytotoxic agents. In some embodiments, the therapeutic agent is a chemotherapeutic agent. In some embodiments, the therapeutic agent is a cytotoxic agent. As used herein, the term "cytotoxic agent" refers to agents that exhibit chemotherapeutic properties. Examples of anti-cancer agents include, but are not limited to, DNA-alkylating and cross-linking agents (e.g., platinum-containing agents such as cisplatin, oxaliplatin), DNA-damaging agents such as PARP (poly ADP ribose polymerase) inhibitors (e.g. olaparib, rucaparib, niraparib, talazoparib), anti-microtubule agents (e.g., paclitaxel, docetaxel, cabazitaxel), topoisomerase inhibitors (e.g., irinotecan, topotecan, SN-38, nemorubicin), proteasome inhibitors (e.g., bortezomib), tyrosine protein kinase inhibitors (e.g., imatinib, nilotinib), EGF receptor inhibitors (e.g., gefitinib, erlotinib), cytotoxic antibiotics (e.g., anthracyclines, bleomycins), ribonucleotide reductase inhibitors (e.g., gemcitabine), antimetabolites (e.g., methotrexate, pemetrexate and anti-mitotic agents. Such anti-cancer agents may be used to treat the cancer either with curative intent (i.e., to rid the sufferer of the cancer) or else with the intent of reducing/palliating symptoms so as to provide a better quality and prolonged life for the sufferer. The anti-cancer agents may be used in conjunction with other, non-chemotherapeutic treatments of cancer (i.e., radiation therapy, surgery/biopsy).

In one embodiment, the cytotoxic agent is nemorubicin. The structure of nemorubicin is as follows:

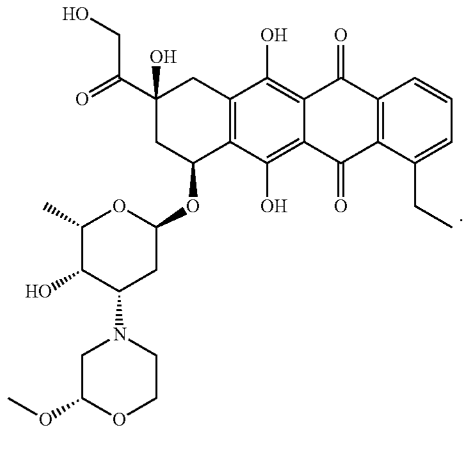 [SMILES: CCc1cccc2c1C(=O)c1c(O)c3c(c(O)c1C2=O)C[C@@](O)(C(=O)CO)C[C@@H]3O[C@H]1C[C@H](N2CCO[C@H](OC)C2)[C@H](O)[C@H](C)O1]

In one embodiment, the cytotoxic agent is cabazitaxel. The structure of cabazitaxel is as follows:

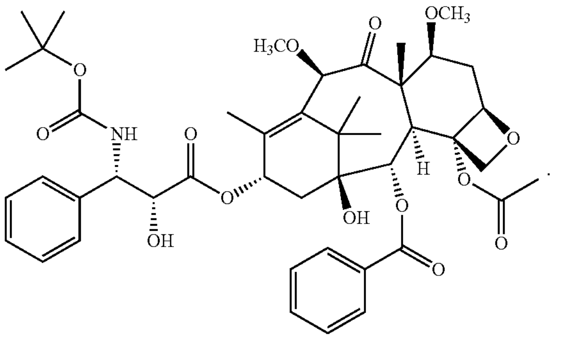 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

In one embodiment, the cytotoxic agent is docetaxel. The structure of docetaxel is as follows:

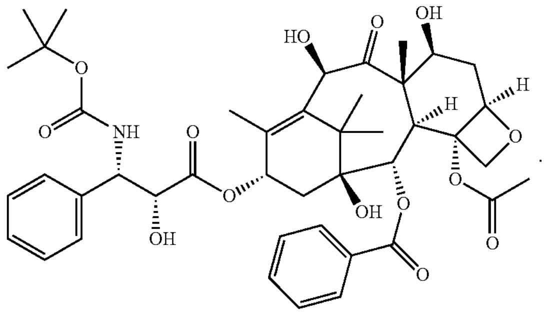

In one embodiment, the cytotoxic agent is SN-38. The structure of SN-38 is as follows:

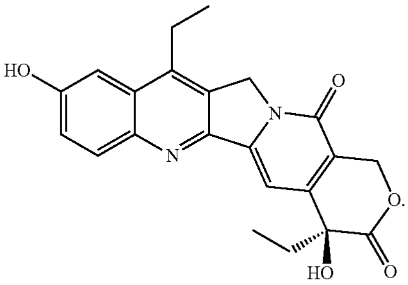 [SMILES: CCc1c2c(nc3ccc(O)cc13)-c1cc3c(c(=O)n1C2)COC(=O)[C@]3(O)CC]

In one embodiment, the cytotoxic agent is irinotecan. The structure of irinotecan is as follows:

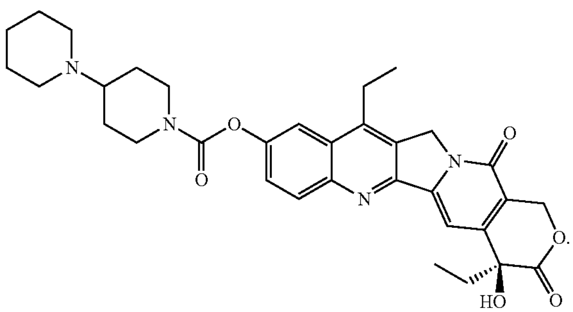 [SMILES: CCc1c2c(nc3ccc(OC(=O)N4CCC(N5CCCCC5)CC4)cc13)-c1cc3c(c(=O)n1C2)COC(=O)[C@]3(O)CC]

In one embodiment, the cytotoxic agent is topotecan. The structure of topotecan is as follows:

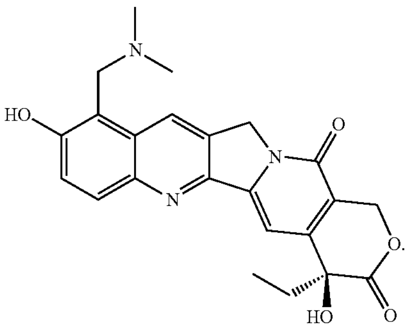 [SMILES: CC[C@@]1(O)C(=O)OCc2c1cc1n(c2=O)Cc2cc3c(CN(C)C)c(O)ccc3nc2-1]

In one embodiment, the cytotoxic agent is gemcitabine. The structure of gemcitabine is as follows.

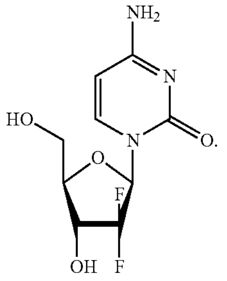

In some embodiments, the therapeutic agent is an ultra-cytotoxic agent. As used herein, the term "ultracytotoxic agent" refers to agents that exhibit highly potent chemotherapeutic properties, yet themselves are too toxic to administer alone as an anti-cancer agent. That is, an ultra-cytotoxic agent, although demonstrating chemotherapeutic properties, generally cannot be safely administered to a subject as the detrimental, toxic side-effects outweigh the chemotherapeutic benefit.

Ultracytotoxic agents include, for example, nemorubicin, the dolastatins (e.g., dolastatin-10, dolastatin-15), auristatins (e.g., monomethyl auristatin-E, monomethyl auristatin-F), maytansinoids (e.g., maytansine, mertansine/emtansine (DM1, ravtansine (DM4)), calicheamicins (e.g., calicheamicin yl), esperamicins (e.g., esperamicin A1), and pyrrolobenzodiazepines (PDB), amongst others.

In some embodiments, the therapeutic agent is an auristatin. In some embodiments, the therapeutic agent is a monomethyl auristatin. In one embodiment, the therapeutic agent is monomethyl auristatin E (MMAE). In one embodiment, the therapeutic agent is monomethyl auristatin F (MMAF). Both MMAE and MMAF are understood to inhibit cell division by blocking the polymerisation of tubulin.

The chemical structure of MMAE is as follows:

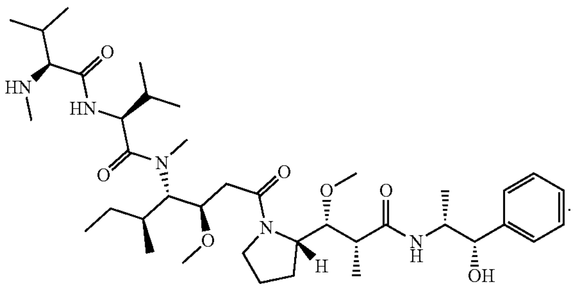 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

The chemical structure of MMAF is as follows:

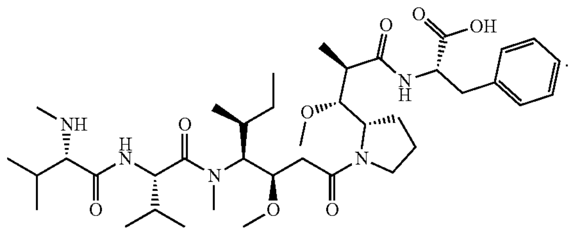 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

In some embodiments, the ultracytotoxic agent is a maytansinoid. In one embodiment, the ultracytotoxic agent is maytansine. In one embodiment, the ultracytotoxic agent is ansamitocin. In one embodiment, the ultracytotoxic agent is emtansine/mertansine (DM1). In one embodiment, the ultracytotoxic agent is ravtansine (DM4). The maytansinoids are understood to inhibit the assembly of microtubules by binding to tubulin.

The chemical structure of maytansine is as follows:

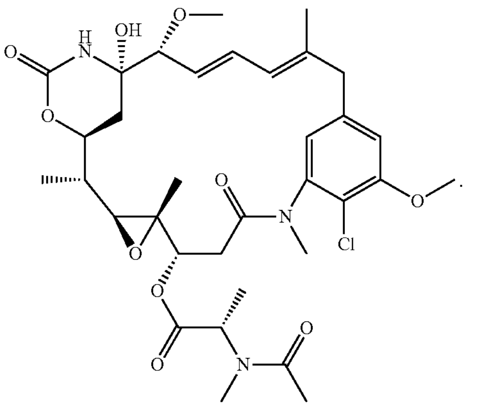 [SMILES: COc1cc2cc(c1Cl)N(C)C(=O)C[C@H](OC(=O)[C@H](C)N(C)C(C)=O)[C@]1(C)O[C@H]1[C@H](C)[C@@H]1C[C@@](O)(NC(=O)O1)[C@H](OC)/C=C/C=C(\C)C2]

The chemical structure of emtansine/mertansine is as follows:

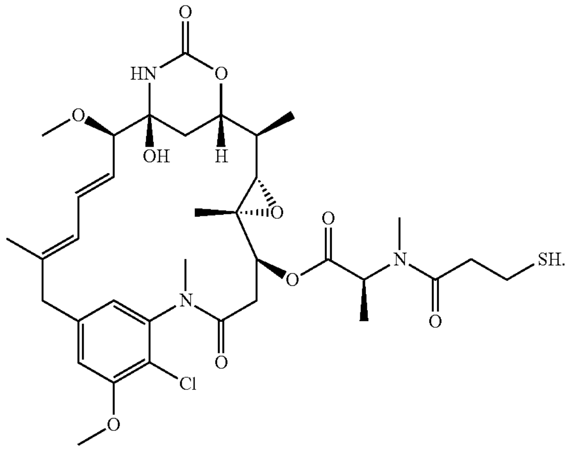

In some embodiments, the ultracytotoxic has an in vitro $IC_{50}$ against a cancer cell line (e.g. SKBR3 and/or HEK293 cells and/or MCF7 cells) which is less than 100 nM, or less than 10 nM, or less than 5 nM, or less than 3 nM, or less than 2 nM, or less than 1 nM, or less than 0.5 nM. In vitro activity of MMAE and emtansine is respectively discussed in Abdollahpour-Alitappeh et al. (2017), and Oroudjev et al. (2010).

It will be understood that the dendrimer-targeting agent conjugates may have a distribution of therapeutic agent per targeting agent. For example, it is possible that a dendrimer-targeting agent conjugate may have up to about 8 therapeutic agents per targeting agent, or even more.

From this, it will be appreciated that the therapeutic agent to targeting agent ratio (DTR) for each dendrimer-targeting agent conjugation species may vary across a population. Typically, it is desirable to produce a dendrimer-targeting agent conjugate with a high DTR. Generally, this results in a more efficacious therapy. However, a DTR that is too high, for example when the therapeutic agent is an ultracytotoxic agent, can result in undesirable toxicity.

In some embodiments, the dendrimer-targeting agent conjugate has a DTR of greater than 2. In some embodiments, the dendrimer-targeting agent conjugate has a DTR of greater than 4. In some embodiments, the dendrimer-targeting agent conjugate has a DTR of greater than 8. In some embodiments, the dendrimer-targeting agent conjugate has a DTR of greater than 14. In some embodiments, the dendrimer-targeting agent conjugate has a DTR of greater than 26.

In some embodiments, the dendrimer-targeting agent conjugate has a DTR of between about 1 and about 32. In some embodiments, the dendrimer-targeting agent conjugate has a DTR of between about 7 and about 32. In some embodiments, the dendrimer-targeting agent conjugate is a G5 dendrimer and has a DTR of between about 26 and about 32. In some embodiment, the dendrimer-targeting agent conjugate is a G4 dendrimer and has a DTR of between about 14 and about 16. In some embodiments, the dendrimer-targeting agent conjugate is a G3 dendrimer and has a DTR of between about 6 and about 8.

Where more than one targeting agent is conjugated to the dendrimer, the DTR will be reduced relative to a dendrimer-targeting agent conjugate with only targeting agent. In some embodiment, the dendrimer-targeting agent conjugate has a DTR of between about 2 and about 16. In some embodiments, the dendrimer-targeting agent conjugate has a DTR of between about 8 and about 16. In some embodiments, the dendrimer-targeting agent conjugate is a G5 dendrimer and has a DTR of between about 4 and about 16. In some embodiments, the dendrimer-targeting agent conjugate is a G5 dendrimer and has a DTR of between about 6 and about 16. In some embodiments, the dendrimer-targeting agent conjugate is a G4 dendrimer and has a DTR of between about 4 and about 8. In some embodiments, the dendrimer-targeting agent conjugate is a G4 dendrimer and has a DTR of between about 4 and about 8. In some embodiments, the dendrimer-targeting agent conjugate is a G3 dendrimer and has a DTR of between about 2 and about 4.

Owing to the ability of the dendrimer-therapeutic agent's ability to carry more than one therapeutic agent, it may be possible to obviate the need for ultracytotoxic agents. For example, the ability to target the delivery of multiple cytotoxic agents, such as, for example, docetaxel, on a single dendrimer, may be as, or more, therapeutically effective when compared to the delivery of a single ultracytotoxic agent, such as, for example, MMAE. The avoidance of ultracytotoxic agents may be an advantage.

Linker

In some embodiments, the therapeutic agent is attached to the dendrimer via a linker. The linker should preferably retain the favourable properties of the therapeutic agent, and remain substantially intact and non-toxic in systemic circulation. Linker groups can be used for example to provide suitable groups for attaching a pharmaceutically active agent to the dendrimer, for example where available functionality in the pharmaceutically active agent is not suitable for direct attachment to a building unit. Linker groups can also or instead by used to facilitate controlled release of the pharmaceutically active agent from the dendrimeric scaffold, providing a therapeutically effective concentration and desirable pharmacokinetic profile of the pharmaceutically active agent for a suitable (e.g. prolonged) period of time.

One end of the linker attaches to the therapeutic agent, and the other end of the linker attaches to the dendrimer. The point of attachment of the linker to the dendrimer may for example be to a surface building unit of the dendrimer.

A person skilled in the art will appreciate that any one of a variety of suitable linkers may be used. The linker should provide sufficient stability during systemic circulation, though allow for the rapid and efficient release of the cytotoxic drug in an active form at its site of action, e.g. once internalised into a cancer cell.

The linker may be a non-cleavable or cleavable linker. In one embodiment, the linker is a non-cleavable linker. In one embodiment, the linker is a cleavable linker. A cleavable linker, either itself or in conjunction with its linkage to the pharmaceutically active agent, comprises one or more of the following cleavable moieties: an ester group, a hydrazone group, an oxime group, an imine group or a disulphide group. In some embodiments, the linker is tumour environment cleavable, acid labile, reductive environment labile, hydrolytically labile or protease sensitive.

Chemically labile linkers include, but are not limited to, acid-labile linkers (i.e., hydrazones) and disulphide linkers. Enzymatically cleavable linkers include, but are not limited to, peptide linkers and β-glucuronide linkers. Examples of peptide linkers include, but are not limited to, Val-Ala, Val-Cit, Phe-Lys, Phe-Arg, Phe-Cit, Val-Arg, Val-Cit, Ala-Arg, and Ala-Cit. Peptide linkers, and their peptide bonds, are advantageously expected to have good serum stability, as lysosomal proteolytic enzymes have very low activities in blood. Val-Ala, Val-Cit, Phe-Lys, Phe-Arg, Phe-Cit, Val-Arg, Val-Cit, Ala-Arg, and Ala-Cit linkers are rapidly hydrolysed by Cathepsin B. In some embodiments, the linker is an enzymatically-cleavable linker. For example, in some embodiments, the linker comprises amino acid residues which are capable of recognition and cleavage by an enzyme.

In some embodiments, the linker comprises a peptide group. In some embodiments, the linker comprises a valine-citrulline-paraaminobenzyl alcohol-containing group (Val-Cit-PAB), e.g. having the structure:

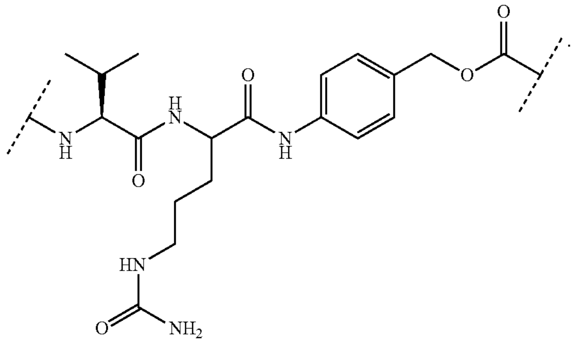

For example, the PAB group may be covalently attached to an amine group present on a therapeutic agent moiety via the carbonyl group, forming a carbamate linkage, and may be attached to an amine group present on an outer building unit via a diacyl linker which forms amide bonds with the valine amino group and the amine group present on the outer building unit.

In some embodiments, the linker comprises or consists of a glutaric acid-valine-citrulline-paraaminobenzyl alcohol group, e.g. having the structure:

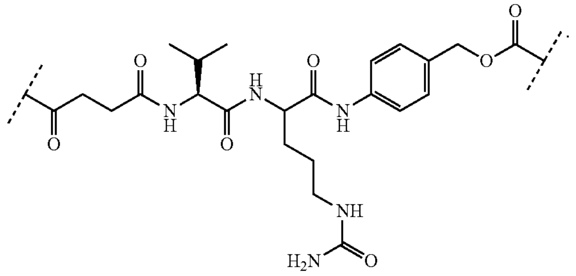

In some embodiments, the linker comprises or consists of a valine-alanine-paraaminobenzyl alcohol group, e.g., having the structure:

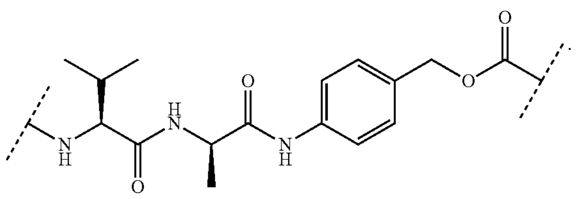

In some embodiments, the pharmaceutically active agent comprises a hydroxyl group, and the residue of the pharmaceutically active agent is attached to a linker via the oxygen atom of the hydroxyl group. This approach allows attachment to the linker via an ester group, and such ester groups have been found to be cleavable in vivo to release pharmaceutically active agent at a desirable rate.

In some embodiments, the core unit is formed from a core unit precursor comprising amino groups, the building units are lysine residues or analogues thereof, the pharmaceutically active agent comprises a hydroxyl group, the residue of the pharmaceutically active agent is attached via the oxygen atom of the hydroxyl group, and the cleavable linker is a diacyl linker, such that there is an ester linkage between the residue of the pharmaceutically active agent and the linker, and an amide linkage between the linker and a nitrogen atom present on an outermost building unit. In some embodiments, the pharmaceutically active agent comprises a hydroxyl group, the residue of the pharmaceutically active agent is attached via the oxygen atom of the hydroxyl group, and the cleavable linker is a diacyl linker group of formula:

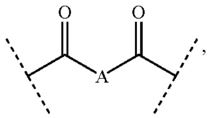
, wherein A is a $C_2$-$C_{10}$ alkylene group which is interrupted by a O, S, S—S, NH, or N(Me), or in which A is a heterocycle selected from the group consisting of tetrahydrofuran, tetrahydrothiophene, pyrrolidine, and N-methylpyrrolidine.

As used herein, the term "alkyl" refers to a monovalent straight-chain (i.e. linear) or branched saturated hydrocarbon group. In one example, an alkyl group contains from 1 to 10 carbon atoms ((i.e. $C_{1-10}$alkyl). In one example, an alkyl group contains from 1 to 6 carbon atoms (i.e. $C_{1-6}$ alkyl). Examples of alkyl groups include methyl, ethyl, propyl (e.g. n-propyl, iso-propyl), butyl (e.g. n-butyl, sec-butyl, tert-butyl), pentyl and hexyl groups.

As used herein, the term "alkylene" refers to a divalent straight-chain (i.e. linear) or branched saturated hydrocarbon group. In one example, an alkylene group contains from 2 to 10 carbon atoms ((i.e. $C_{2-10}$ alkylene). In one example, an alkylene group contains from 2 to 6 carbon atoms (i.e. $C_{2-6}$ alkylene). Examples of alkylene groups include, for example, $—CH_2CH_2—$, $—CH_2CH_2CH_2—$, $—CH_2CH(CH_3)—$, $—CH_2CH_2CH_2CH_2—$, $—CH_2CH(CH_3)CH_2—$, and the like.

Such linkers are particularly suitable for linking to therapeutic agents via a hydroxyl group present in the therapeutic agent. In such cases, the conjugate contains an ester linkage between the linker and the therapeutic agent moiety, and contains an amide linkage between the linker and the dendrimer moiety.

In some embodiments, the pharmaceutically active agent comprises a hydroxyl group, the residue of the pharmaceutically active agent is attached via the oxygen atom of the hydroxyl group, and the cleavable linker is a diacyl linker group of formula

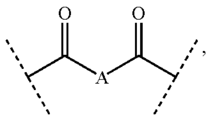
, wherein A is a $C_2$-$C_{10}$ alkylene group which is interrupted by O, S, NH, or N(Me).

In some embodiments, the pharmaceutically active agent comprises a hydroxyl group, the residue of the pharmaceutically active agent is attached via the oxygen atom of the hydroxyl group, and the diacyl linker is

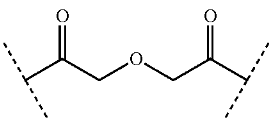
or

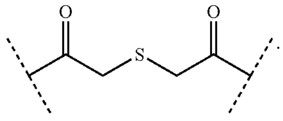
.

A specific type of cleavable linker is one which contains a disulphide moiety. Such linkers are susceptible to cleavage by glutathione. For example, a linker of this type may comprise two acyl groups linked via an alkyl chain interrupted by a disulphide moiety.

In some embodiments, the linker comprises an alkyl chain interrupted by a disulphide moiety, in which one or both of the carbon atoms which are next to the disulphide group are substituted by one or more methyl groups. For example, one of the carbon atoms next to the disulphide moiety may be substituted by a gem-dimethyl group, e.g. the linker may comprise the group:

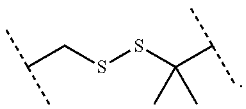
.

Another specific type of a cleavable linker is one which contains a diphosphate moiety. Such linkers are susceptible to hydrolysis by lysosomal acid pyrophosphatase and acid phosphatase enzymes. In some embodiments, the linker comprises an alkyl chain interrupted by a diphosphate moiety, also referred to as a pyrophosphate moiety:

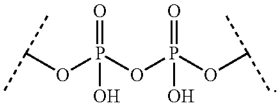
.

Another specific type of cleavable linker is one which contains a carbamate moiety. Such linkers have high hydrolytic stability prior to activation, and efficient cleavage by different intramolecular mechanisms. In some embodiments, the linker comprises an alkyl chain interrupted by a carbamate moiety:

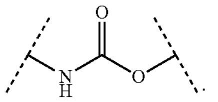

Another specific type of cleavable linker is one which contains an orthoester moiety:

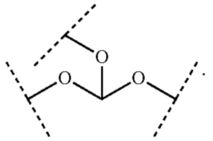

Non-cleavable linkers are linking groups which are inert or substantially inert to cleavage on exposure to in vivo conditions over the required time period. Non-cleavable linkers are not cleaved under biological conditions.

Examples include diacyl linkers bridged by an alkylene or a cycloalkylene group, e.g. a $C_{1-10}$ alkylene group or $C_{3-10}$ cycloalkylene group. Further examples of non-cleavable linkers include thioether linkers. A specific example of a non-cleavable linker is one formed by use of SMCC (succinimidyl 4-(N-maleimidomethyl)cyclohexane-1-carboxylate. SMCC can be used to react the maleimide functionality with a thiol group present on the therapeutic agent moiety, or which is attached to the therapeutic agent moiety, forming a thioether linkage. The carboxylic acid functionality can be used to react with an amino group present on an outer building unit.

In some embodiments, the linker comprises a Val-Cit-PAB group. In some embodiments, the linker comprises a Val-Arg-PAB group. In some embodiments, the linker comprises a Val-Arg-Trigger group. In some embodiments, the linker is a Val-Ala-PAB-P-Trigger group. In some embodiments, the linker is a Val-Ala-PNB-P group.

In one embodiment, the linker comprises a Val-Cit-PAB group, the therapeutic agent moiety is MMAE, and the Val-Cit-PAB group is attached to the therapeutic agent moiety as follows (i.e., Val-Cit-PAB-MMAE):

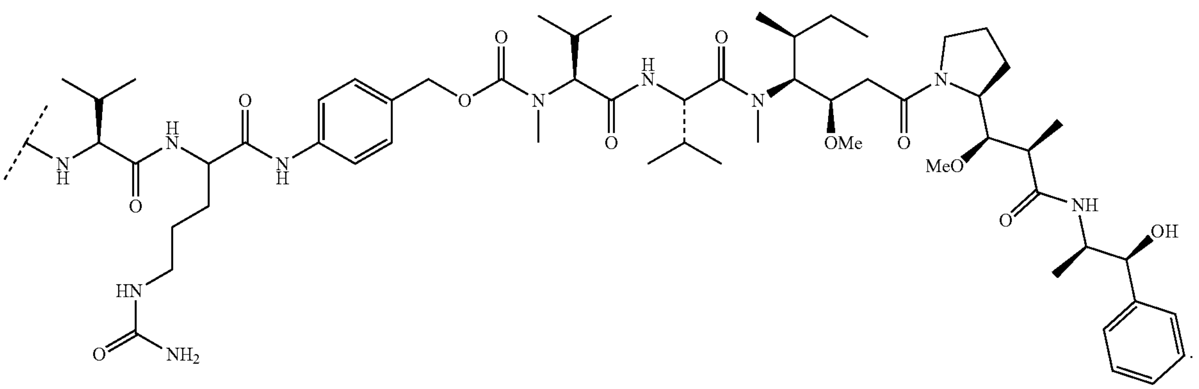

In one embodiment, the linker is a Val-Cit-PAB group, the therapeutic agent moiety is MMAF, and the Val-Cit-PAB group is attached to the therapeutic agent moiety as follows (i.e., Val-Cit-PAB-MMAF):

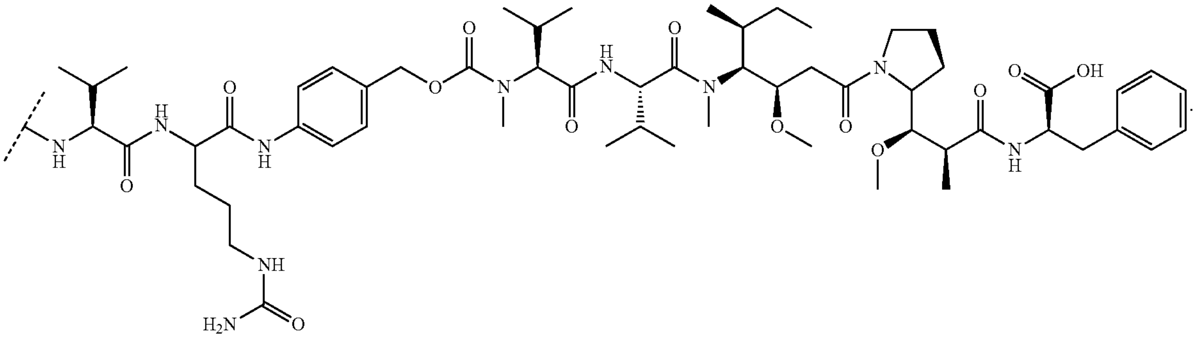

In one embodiment, the linker comprises a Glutaric acid-Val-Cit-PAB group, the therapeutic agent moiety is MMAE, and the Glutaric acid-Val-Cit-PAB group is attached to the therapeutic agent moiety as follows (i.e. Glutaric acid-Val-Cit-PAB-MMAE):

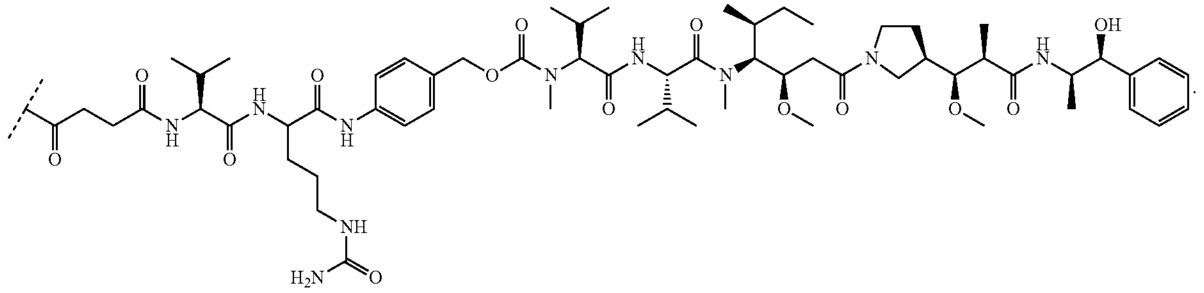

In one embodiment, the linker is a DGA (diglycolic acid) or glutaric acid group, the therapeutic agent moiety is MMAF or an ester thereof, e.g.:

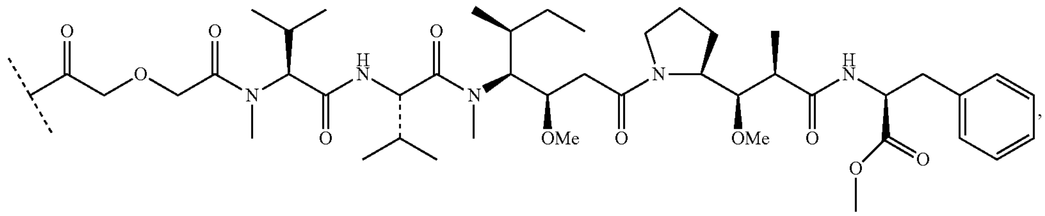

,

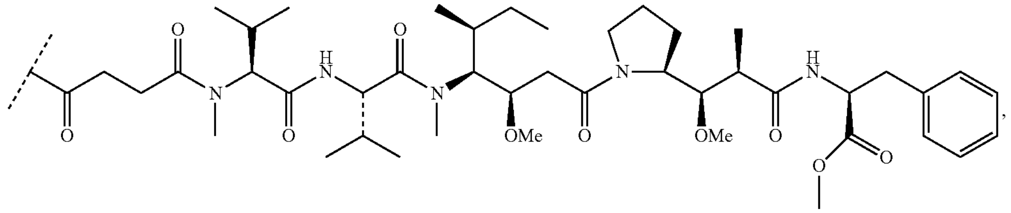

,

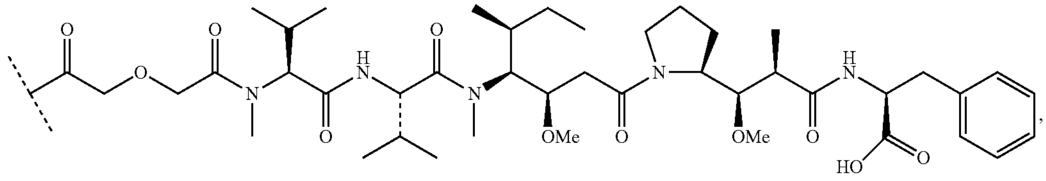

,

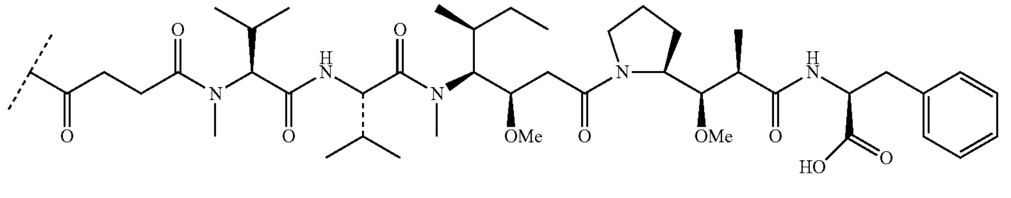

In some embodiments, the therapeutic agent is covalently linked to a surface building unit of the dendrimer through a connector group. For example, the therapeutic agent may be covalently linked to a surface building unit of the dendrimer through a connector group in addition to the linker group. The connector group allows for the therapeutic agent to be tethered at different lengths from the surface of the dendrimer. For example, a connector group may be utilised to extend the distance of the therapeutic agent from the surface of the dendrimer. This may obviate any potential issues associated with steric hindrance, which may prevent access to the cleavable linker, and may reduce the ability of the therapeutic agent to interact with the target. In some embodiments, the dendrimer-targeting agent conjugate comprises a therapeutic agent covalently linked to the surface of the dendrimer through a linker group and a connector group. In some embodiments, the order of connection is dendrimer-connector-linker-therapeutic agent. In some embodiments, the order of connection is dendrimer-linker-connector-therapeutic agent.

The connector group may comprise any chemical moiety that serves to extend the distance of the therapeutic agent from the surface of the dendrimer. In some embodiments, the connector group comprises one or more hydrophilic polymeric groups. In some embodiments, the connector group comprises between about one and about 50 hydrophilic polymeric groups. In some embodiments, the connector group comprises a PEG group. In some embodiments, the connector group comprises a PEOX group. In some embodiments, the connector group comprises a polysarcosine group. In some embodiments, the connector group comprises more than one, more than two, more than four, more than 10, more than 20, more than 30, more than 40, more than 50 PEG moieties. In some embodiments, the connector group comprises between about one and about 50 PEG moieties. In some embodiments, the connector group comprises four PEG moieties. In some embodiments, the connector group comprises 12 PEG moieties. In some embodiments, the connector group comprises 24 PEG moieties. In some embodiments, the connector group comprises 48 PEG moieties.

In some embodiments, the linker comprises a connector group, and is a $(PEG)_X$-Val-Arg-PAB-P-Trigger-moiety. X may be a number, as described above, between about one and about 50.

In one embodiment, the linker comprises a connector group, and is a $(PEG)_9$-Val-Arg-PAB-P-Trigger-NHCO moiety:

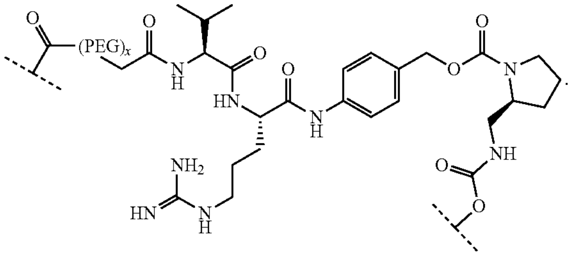

In one embodiment, the linker comprises a connector group, and is a $(PEG)_9$-Val-Arg-PAB-P-Trigger-$N(CH_3)CO$ moiety:

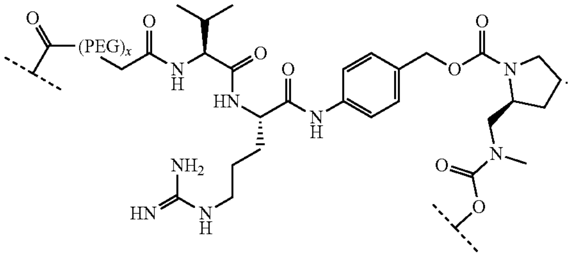

In some embodiments, the linker comprises a connector group, and is a $(PEG)_X$-O—P(O)OH—O—P(O)OH—O— moiety. Again, X may be a number, as described above, between about one and about 50.

In one embodiment, the linker comprises a connector group, and is a $(PEG)_X$-O—P(O)OH—O—P(O)OH—O— moiety:

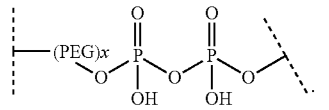

In some embodiments, the linker comprises a connector group, and is a $(PEG)_X$-Val-Ala-PAB-P-Trigger-moiety. X may be a number, as described above, between about one and about 50. In one embodiment, the linker comprises a connector group, and is a $(PEG)_9$-Val-Ala-PAB-P-Trigger-NHCO moiety.

The use of particular linkers, such as $(PEG)_X$-Val-Arg-PAB-P-Trigger- or $(PEG)_X$-O—P(O)OH—O—P(O)OH—O—, for example, may provide for release of the therapeutic agent.

In the instance of $(PEG)_X$-Val-Arg-PAB-P-Trigger-NHCO, $(PEG)_X$-Val-Arg-PAB-P-Trigger-$N(CH_3)CO$, for example, linker is initially activated by cleavage of the dipeptide portion by cellular enzymes, such as cathepsin B, which reveal the self immolative 2-(aminomethyl)pyrrolidine connector. Following intramolecular cyclisation, elimination of a hydroxyl-containing therapeutic agent occurs. Exemplary hydroxyl-containing therapeutic agents include cabazitaxel, docetaxel, and SN-38.

In the instance of a $(PEG)_X$-O—P(O)OH—O—P(O)OH—O— moiety, the linker specifically and cleanly cleaves to provide hydroxyl-containing drugs, such as cabazitaxel, docetaxel and SN-38, but also possesses the added advantage of providing drug monophosphates, which are the active species of nucleotide inhibitors such as, for example, gemcitabine.

Pharmacokinetic Modifying Groups

The conjugate comprises a plurality of hydrophilic polymer groups that are covalently linked to surface building units of the dendrimer, which can modify the pharmacokinetic properties of the conjugate. The hydrophilic polymer group, may for example, provide for improved pharmacokinetic properties.

In some embodiments, the dendrimer comprises a plurality of hydrophilic polymeric groups that are covalently linked to surface building units of the dendrimer. The term "hydrophilic polymeric group" typically refers to a polymeric group that has a solubility in water at 25° C. of at least 25 mg/ml, more preferably at least 50 mg/ml, and still more preferably at least 100 mg/ml.

In some embodiments, the hydrophilic polymeric group comprises repeating units of amino acids, alkyloxy or alkyl (acyl)amino groups. In some embodiments, the hydrophilic polymeric group comprises repeating units of amino acids, such as sarcosine. In some embodiments, the hydrophilic polymeric group comprises repeating units of alkyloxy groups (e.g. the hydrophilic polymer is a PEG group). In some embodiments the hydrophilic polymer comprises repeating units of alkyl(acyl)amino groups (e.g. the hydrophilic polymer is a PEOX group).

In some embodiments, the hydrophilic polymeric group comprises at least 10 monomer units. In some embodiments, the hydrophilic polymeric group comprises up to 100 monomer units. In some embodiments, the hydrophilic polymeric group comprises from 10 to 100, or from 10 to 50 monomer units.

In some embodiments, the hydrophilic polymeric group is a PEG group. A PEG group is a polyethylene glycol group, i.e. a group comprising repeat units of the formula $—CH_2CH_2O—$. PEG materials used to produce the dendrimer of the present disclosure typically contain a mixture of PEGs having some variance in molecular weight (i.e., +10%), and therefore, where a molecular weight is specified, it is typically an approximation of the average molecular weight of the PEG composition. For example, the term "$PEG_{\sim 2100}$" refers to polyethylene glycol having an average molecular weight of approximately 2100 Daltons, i.e. ±approximately 10% ($PEG_{1890}$ to $PEG_{2310}$). The term "$PEG_{\sim 2300}$" refers to polyethylene glycol having an average molecular weight of approximately 2300 Daltons, i.e. ±approximately 10% ($PEG_{2070}$ to $PEG_{2530}$). Three methods are commonly used to calculate MW averages: number average, weight average, and z-average molecular weights.

As used herein, the phrase "molecular weight" is intended to refer to the weight-average molecular weight which can be measured using techniques well-known in the art including, but not limited to, NMR, mass spectrometry, matrix-assisted laser desorption ionization time of flight (MALDI-TOF), gel permeation chromatography or other liquid chromatography techniques, light scattering techniques, ultracentrifugation and viscometry.

In some embodiments, the PEG groups have an average molecular weight in the range of from 500 to 2500 Daltons. In some embodiments, the PEG groups have an average molecular weight in the range of from 800 to 1200 Daltons. In some embodiments, the PEG groups have an average molecular weight in the range of from 900 to 1100 Daltons. In some embodiments, the PEG groups have an average molecular weight in the range of from 1500 to 2500 Daltons.

In some embodiments, the PEG groups have an average molecular weight in the range of from 1900 to 2300 Daltons. In some embodiments, the PEG groups have an average molecular weight in the range of from 2100 to 2500 Daltons.

In some embodiments, the PEG groups have an average molecule weight of about 1100 Daltons. In some embodiments, the PEG groups have an average molecular weight of about 2000 Daltons. In some embodiments, the PEG groups have an average molecular weight of about 800, about 900, about 1000, about 1100, about 1200, about 1300, about 1400, about 1500, about 1600, about 1700, about 1800, about 1900, about 2000, about 2100, about 2200, about 2300, about 2400 or about 2500 Daltons.

In some embodiments, the PEG group has a polydispersity index (PDI) of between about 1.00 and about 1.50, between about 1.00 and about 1.25, or between about 1.00 and about 1.10. In some embodiments, the PEG group has a polydispersity index (PDI) of about 1.05. The term "polydispersity index" refers to a measure of the distribution of molecular mass in a given polymer sample. The polydispersity index (PDI) is equal to the weight average molecular weight (Mw) divided by the number average molecular weight (Mn) and indicates the distribution of individual molecular masses in a batch of polymers. The polydispersity index (PDI) has a value equal to or greater than one, but as the polymer approaches uniform change length and average molecular weight, the polydispersity index (PDI) will be closer to one.

The PEG groups may be linear or branched. If desired, an end-capped PEG group may be used. In some embodiments, the PEG group is a methoxy-terminated PEG.

In some embodiments, the hydrophilic polymeric group is a PEOX group. In some embodiments, the dendrimer comprises a plurality of PEOX groups which are covalently linked to surface building units of the dendrimer moiety. A PEOX group is a polyethyloxazoline group, i.e. a group comprising repeat units of the formula

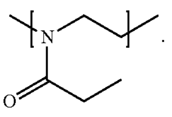

PEOX groups are so named since they can be produced by polymerisation of ethyloxazoline. PEOX materials used to produce the dendrimer of the present disclosure typically contain a mixture of PEOXs having some variance in molecular weight (i.e., +10%), and therefore, where a molecular weight is specified, it is typically an approximation of the average molecular weight of the PEOX composition. In some embodiments, the second terminal groups comprise PEOX groups having an average molecular weight of at least 750 Daltons, at least 1000 Daltons, or at least 1500 Daltons. In some embodiments, the second terminal groups comprise PEOX groups having an average molecular weight in the range of from 750 Daltons to 2500 Daltons, or from 1000 Daltons to 2000 Daltons. If desired, an end-capped PEOX group may be used. In some embodiments, the PEOX group is a methoxy-terminated PEOX.

In some embodiments, the hydrophilic polymeric group comprises a polysarcosine group. In some embodiments, the polysarcosine groups have an average molecular weight of at least 750 Daltons, at least 1000 Daltons, or at least 1500 Daltons. In some embodiments, the hydrophilic polymeric groups comprise polysarcosine groups having an average molecular weight in the range of from 750 Daltons to 2500 Daltons, or from 1000 Daltons to 2000 Daltons.

The hydrophilic polymeric group may be attached to the outer building unit via any suitable means. In some embodiments, a linking group is used to attach the hydrophilic polymeric group to the outer building unit.

The hydrophilic polymeric groups are typically attached via use of a precursor which contains a reactive group that is reactive with an amine group, such as a reactive acyl group (which can form an amide bond), or an aldehyde (which can form an amine group under reductive amination conditions).

In some embodiments, the PEG group is covalently attached to a PEG linking group (L1) via an ether linkage formed between a carbon atom present in the PEG group and an oxygen atom present in the PEG linking group, and each PEG group is covalently attached to a building unit via an amide linkage formed between a nitrogen atom present in a building unit and the carbon atom of an acyl group present in the PEG linking group. In some embodiments, the L1-PEG groups are each

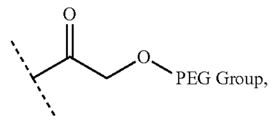

and wherein the PEG group is a methoxy-terminated PEG having an average molecular weight in the range of from about 500 to 2500 Daltons.

In some embodiments, the PEOX group is covalently attached to a PEOX linking group (L1') via a linkage formed between a nitrogen atom present in the PEOX group and a carbon atom present in the PEOX linking group, and each PEOX group is covalently attached to a building unit via an amide linkage formed between a nitrogen atom present in a building unit and the carbon atom of an acyl group present in the PEOX linking group. In some embodiments, the L1'-PEOX groups are each

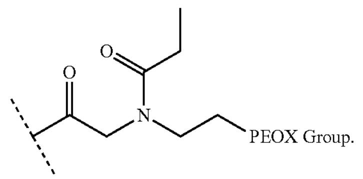

In some embodiments, the hydrophilic polymeric group comprises a polysarcosine group, i.e. a group comprising repeat units of the formula:

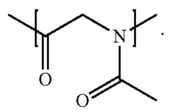

In some embodiments, the polysarcosine groups are attached to a building unit via an amide linkage formed between a nitrogen atom present in a building unit and the carbon atom of an acyl group present in the polysarcosine group In some embodiments, the hydrophilic polymeric groups comprise polysarcosine groups having an average molecular weight of at least 750 Daltons, at least 1000 Daltons, or at least 1500 Daltons. In some embodiments, the second terminal groups comprise polysarcosine groups having an average molecular weight in the range of from 750 Daltons to 2500 Daltons, or from 1000 Daltons to 2000 Daltons.

In many cases, a population of dendrimers which has been functionalised at the dendrimer surface contains a random stoichiometry and topology of functional groups. For example, reaction of a population of dendrimer-targeting agent conjugates containing, e.g. 64 reactive surface groups with one or more reactive functional groups may result in a diverse population of functionalised dendrimers, with some dendrimers containing higher numbers of functional groups than others. In cases where there are multiple different surface groups available for reaction with a reactive functional group, a wide distribution of dendrimers having different surface topologies may also be obtained.

The present dendrimer-targeting agent conjugates, intermediates, and processes, may allow for high loadings of therapeutic agent through covalent attachment to a surface building unit. Such dendrimer-targeting agent conjugates may also be considered to facilitate therapeutically effective levels of therapeutic agent to be released over an extended period of time following administration, and thus may decrease the frequency and/or number of administrations required. The present dendrimer-targeting agent conjugates may also allow for the targeted delivery of the therapeutic agent to its site of action. Consequently, such dendrimer-targeting moiety agent may reduce off-target activity, such as cytotoxic activity.

Internalisation of the Dendrimer-Targeting Agent Conjugates

The dendrimer-targeting agent conjugates provide targeted anti-cancer therapy. The beneficial properties of the conjugates is understood, at least in part, to be associated with the observed rapid internalisation of example conjugates containing an MMAE therapeutic agent into the target cell. In some embodiments, the dendrimer-targeting agent conjugate is internalised within a HER2-expressing cell.

As used herein, the term "internalisation" refers to the endocytosis of the dendrimer-targeting agent conjugate into a cell. The ability of the dendrimer-targeting agent conjugate to specifically seek out and bind to the HER2 receptor on the target HER2-expressing cancer cells and be internalised rapidly, means that a reduced amount of the conjugate is circulating in the blood plasma. As such, it follows that there should be reduced opportunity for therapeutic agents such as ultracytotoxic moieties like MMAE, to undergo undesired cleavage from the dendrimer-targeting agent conjugate at sites other than those where HER2 is overexpressed (e.g. tumour cells), and a reduced likelihood of side effects or toxicity associated with non-specific release of the therapeutic agent in the subject. In contrast, administration of an equivalent dose of a therapeutic agent, such as an ultracytotoxic moiety, may cause extreme toxicity to the point where the therapeutic agent cannot be safely administered alone. For example, it is understood that MMAE and MMAF are too toxic to be safely administered alone to a subject. Accordingly, the dendrimer-targeting agent conjugate is considered to provide a safer means for delivering therapeutic agent, such as ultracytotoxic agents, including MMAE and MMAF.

In some embodiments, the administration of the conjugate provides for reduced side effects in comparison to administration of an equivalent dose of free therapeutic agent. In some embodiments, the administration of the conjugate provides for at least 10%, at least 20%, at least 30%, at least 40%, at least 50%, at least 60%, at least 70%, at least 80%, or at least 90% reduction in the plasma concentration (e.g., Cmax, or concentration at a specified time point following administration (e.g., 1 h, 6 h, 12 h, 24 h, 48 h)) of therapeutic agent in comparison to administration of an equivalent dose of free therapeutic agent.

In some embodiments, the therapeutic agent is an ultracytotoxic (e.g. MMAE, MMAF), and the administration of the dendrimer-targeting agent conjugate provides for at least 10%, at least 20%, at least 30%, at least 40%, at least 50%, at least 60%, at least 70%, at least 80%, or at least 90% reduction in the plasma concentration (e.g., Cmax, or concentration at a specified time point following administration (e.g., 1 h, 6 h, 12 h, 24 h, 48 h)) of therapeutic agent in comparison to administration of an equivalent dose of free therapeutic agent.

Accordingly, there is also provided a method of killing a HER2-expressing cell, comprising: contacting a conjugate as defined herein with a HER2-expressing cell such that the conjugate is internalised within the cell, whereby the therapeutic agent kills the HER2-expressing cell. In some embodiments, the therapeutic agent is an ultracytotoxic (e.g. MMAE, MMAF). In some embodiments, the conjugate (e.g. an ultracytotoxic-containing conjugate) is internalised into the cell by way of endocytosis.

Conjugates of the present disclosure have been found to be effective in in vivo cancer studies, i.e. xenograft studies. It is considered that the comparatively small size (e.g. low molecular weight of the conjugates as a whole) assists in penetration into tumour tissue, and assists effectiveness of the therapy. Accordingly, in some embodiments, the molecular weight of the conjugates is in the range of up to about 120 kDa, or up to about 100 kDa, or up to about 80 kDa, or up to about 60 kDa, or up to about 50 kDa, or up to about 45 kDa, or up to about 40 kDa.

Compositions

In some embodiments, the dendrimer-targeting agent conjugates are presented as a composition, preferably a pharmaceutical composition.

It will be appreciated that there may be some variation in the molecular composition between the dendrimer-targeting agent conjugates present in a given composition, as a result of the nature of the synthetic process for producing the dendrimers. For example, as discussed above one or more synthetic steps used to produce a dendrimer-targeting agent conjugate may not proceed fully to completion, which may result in the presence of dendrimer-targeting agent conjugates that do not all comprise the same number of therapeutic agent moieties, targeting agents, or which contain incomplete generations of building units.

In one example, the composition comprises a plurality of dendrimers that do not all comprise the same number of therapeutic agent moieties. In one example, the composition comprises a plurality of dendrimers that do not all comprise the same number of targeting agents. In some embodiments, the composition comprises a plurality of dendrimer-targeting agent conjugates wherein the average number of targeting agents covalently linked to the dendrimer is 1. In some embodiments, the composition comprises a plurality of dendrimer-targeting agent conjugates wherein the average number of targeting agents covalently linked to the dendrimer is 1.2. In some embodiments, the composition comprises a plurality of dendrimer-targeting agent conjugates wherein the average number of targeting agents covalently linked to the dendrimer is between 1 and 1.5. In some embodiments, the composition comprises a plurality of dendrimer-targeting agent conjugates wherein the average number of targeting agents covalently linked to the dendrimer is between 0.5 and 5. In some embodiments, the composition comprises a plurality of dendrimer-targeting agent conjugates wherein the average number of targeting agents covalently linked to the dendrimer is between 1 and 4. In some embodiments, the composition comprises a plurality of dendrimer-targeting agent conjugates wherein the average number of targeting agents covalently linked to the dendrimer is between 1 and. In some embodiments, the composition comprises a plurality of dendrimer-targeting agent conjugates wherein the average number of targeting agents covalently linked to the dendrimer is between 1 and 1.5. Accordingly, there is provided a composition comprising a plurality of dendrimer-targeting agent conjugates or pharmaceutically acceptable salts thereof, wherein the dendrimer-targeting agent conjugates are as defined herein. In some embodiments, there is provided a composition for therapeutic use comprising a dendrimer-targeting agent conjugate and a therapeutically acceptable excipient. In some embodiments, the composition is formulated for parenteral delivery. In some embodiments, the composition is formulated for intravenous delivery. In some embodiments, the composition is formulated for subcutaneous delivery. In some embodiments, the composition is formulated for intramuscular injection.

The present disclosure also provides pharmaceutical formulations or compositions, both for veterinary and for human medical use, which comprise the conjugates of the present disclosure or a pharmaceutically acceptable salt thereof, with one or more pharmaceutically acceptable carriers, and optionally any other therapeutic ingredients, stabilisers, or the like.

Accordingly, there is also provided a composition for pharmaceutical use, comprising i) a conjugate as defined herein; and ii) a pharmaceutically acceptable excipient.

The excipient(s) must be pharmaceutically acceptable in the sense of being compatible with the other ingredients of the formulation/composition and not unduly deleterious to the recipient thereof.

In some embodiments, the composition comprises a pharmaceutically acceptable solvent, such as water for injection and/or a pharmaceutically acceptable organic solvent.

The compositions of the present disclosure may for example include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include diluents, buffers, citrate, trehalose, binders, disintegrants, thickeners, lubricants, preservatives (including antioxidants), inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the present disclosure are listed in “Remington: The Science & Practice of Pharmacy”, 19.sup.th ed., Williams & Williams, (1995), and in the “Physician’s Desk Reference”, 52.sup.nd ed., Medical Economics, Montvale, N.J. (1998), and in “Handbook of Pharmaceutical Excipients”, Third Ed., Ed. A. H. Kibbe, Pharmaceutical Press, 2000.

The dendrimer-targeting agent conjugates of the present disclosure may for example be formulated in compositions including those suitable for inhalation to the lung, by aerosol, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the dendrimer-targeting agent conjugate into association with a carrier that constitutes one or more accessory ingredients. In general, the compositions are prepared by bringing the dendrimer-targeting agent conjugate into association with a liquid carrier to form a solution or a suspension, or alternatively, bring the dendrimer-targeting agent conjugate into association with formulation components suitable for forming a solid, optionally a particulate product, and then, if warranted, shaping the product into a desired delivery form. Solid formulations of the present disclosure, when particulate, will typically comprise particles with sizes ranging from about 1 nanometer to about 500 microns. In general, for solid formulations intended for intravenous administration, particles will typically range from about 1 nm to about 10 microns in diameter. The composition may contain dendrimer-targeting moiety conjugates of the present disclosure that are nanoparticulate having a particulate diameter of below 1000 nm, for example, between 5 and 1000 nm, especially 5 and 500 nm, more especially 5 to 400 nm, such as 5 to 50 nm and especially between 5 and 20 nm. In one example, the composition contains dendrimer-targeting moiety conjugates with a mean size of between 5 and 20 nm. In some embodiments, the dendrimer-targeting moiety conjugate is polydispersed in the composition, with PDI of between 1.01 and 1.8, especially between 1.01 and 1.5, and more especially between 1.01 and 1.2. In one example, the dendrimer-targeting agent conjugate is monodispersed in the composition.

In some preferred embodiments, the composition is formulated for parenteral delivery. For example, in one embodiment, the formulation may be a sterile, lyophilized composition that is suitable for reconstitution in an aqueous vehicle prior to injection.

In some embodiments, a formulation suitable for parenteral administration conveniently comprises a sterile aqueous preparation of the dendrimer-targeting agent conjugate, which may for example be formulated to be isotonic with the blood of the recipient.

In some embodiments, the composition is formulated for parenteral infusion as part of a chemotherapy regimen.

In some embodiments, the composition is formulated for intraperitoneal delivery. Any suitable means of delivery may be used. For example, in some embodiments delivery may be by lavage or aerosol. In one embodiment the composition is formulated for intraperitoneal delivery, and is for treatment of cancers in the peritoneal cavity, which include malignant epithelial tumors (e.g., ovarian cancer), and peritoneal carcinomatosis (eg gastrointestinal especially colorectal, gastric, gynecologic cancers, and primary peritoneal neoplasms).

Pharmaceutical formulations are also provided which are suitable for administration as an aerosol, by inhalation. These formulations comprise a solution or suspension of the desired dendrimer or a salt thereof. The desired formulation may be placed in a small chamber and nebulized. Nebulization may be accomplished by compressed air or by ultrasonic energy to form a plurality of liquid droplets or solid particles comprising the dendrimers or salts thereof.

As discussed below, the dendrimer-targeting agent conjugates of the present disclosure may for example be administered in combination with one or more additional pharmaceutically active agents. For example, the dendrimer-targeting agent conjugate may be administered in a composition together with a further pharmaceutical active agent.
Examples of further pharmaceutically active agents include chemotherapeutic and cytotoxic agents, small molecule cytotoxics, tyrosine kinase inhibitors, checkpoint inhibitors, EGFR inhibitors, antibody therapies, taxanes and aromatase inhibitors.

Not only can the dendrimer-targeting agent conjugates of the present disclosure be administered with other chemotherapy drugs but may also be administered in a composition together with other medications as appropriate.

METHODS OF USE

Also provided herein is a method of treating cancer comprising administering to a subject in need thereof a therapeutically effective amount of a conjugate as defined herein, or a pharmaceutical composition comprising a conjugate as defined herein.

Also provided herein is use of a conjugate as defined herein, or of a composition as comprising a conjugate as defined herein, in the manufacture of a medicament for the treatment of cancer.

Also provided herein is a conjugate as defined herein, or a pharmaceutical composition comprising a conjugate as defined herein, for use in therapy. Also provided herein is a conjugate as defined herein, or a pharmaceutical composition comprising a conjugate as defined herein, for use in the treatment of cancer.

In some embodiments, the dendrimer-targeting agent conjugate is used in a method of treating or preventing cancer, for example for suppressing the growth of a tumour. In some embodiments the dendrimer-targeting agent conjugate is for use in the treatment of cancer.

In some embodiments, the cancer is a solid tumour. The cancer may be a primary or metastatic tumour. In some embodiments the cancer is a primary tumour. In some embodiments the cancer is a metastatic tumour.

In some embodiments, the cancer is characterised by an abnormal, or overexpression, of HER2 (also referred to as ERBB2). Such abnormal or overexpression of HER2 is known to occur in, for example, breast cancers, testicular cancers, ovarian cancers, stomach cancers, adenocarcinomas of the lung, gastric cancers, pancreatic cancers, salivary duct carcinomas, oesophageal cancers, and uterine cancers (e.g., uterine serious endometrial carcinoma). In some embodiments, the cancer is selected from the group consisting of breast cancers, testicular cancers, ovarian cancers, stomach cancers, adenocarcinomas of the lung, gastric cancers, pancreatic cancers, salivary duct carcinomas, oesophageal cancers, and uterine cancers (e.g., uterine serious endometrial carcinoma). In some embodiments, the cancer is breast cancer. In some embodiments, the cancer is testicular cancer. In some embodiments, the cancer is ovarian cancer. In some embodiments, the cancer is stomach cancer. In some embodiments, the cancer is adenocarcinoma of the lung. In some embodiments, the cancer is gastric cancer. In some embodiments, the cancer is pancreatic cancer. In some embodiments, the cancer is salivary duct carcinoma. In some embodiments, the cancer is oesophageal cancer. In some embodiments, the cancer is uterine cancer.

Accordingly, there is also provided a method, use, dendrimer-targeting agent conjugate, or composition for use, wherein the cancer is selected from the group consisting of ovarian cancer, breast cancer, stomach cancer, uterine cancer, or another cancer characterised by abnormal or overexpression expression of HER2 (i.e., ERBB2).

Combinations

Drugs are often administered in combination with other drugs, especially during chemotherapy. Accordingly, in some embodiments the dendrimer-targeting agent conjugate is administered in combination with one or more further pharmaceutically active agents, for example one or more further anti-cancer agents/drugs. The dendrimer-targeting agent conjugate and the one or more further pharmaceutically active agents may be administered simultaneously, subsequently or separately. For example, they may be administered as part of the same composition, or by administration of separate compositions. The one or more further pharmaceutically active agents may for example be anti-cancer agents for therapy of colorectal cancer, stomach cancer, pancreas cancer, prostate cancer or breast cancer. Examples of further pharmaceutically active agents include chemotherapeutic and cytotoxic agents, small molecule cytotoxics, tyrosine kinase inhibitors, checkpoint inhibitors, EGFR inhibitors, antibody therapies, taxanes and aromatase inhibitors.

Dose

It will be appreciated that the term "therapeutically effective amount" refers to a dendrimer-targeting agent conjugate being administered in an amount sufficient to alleviate or prevent to some extent one or more of the symptoms of the disorder or condition being treated. A therapeutically effective amount of dendrimer-targeting agent conjugate may be referred to based on, for example, the amount of dendrimer-targeting agent conjugate administered. Alternatively, it may be determined based on the amount of therapeutic agent which the dendrimer-targeting agent conjugate is theoretically capable of delivering, e.g. based on the loading of the therapeutic agent on the dendrimer-targeting agent conjugate.

The dendrimer-targeting agent conjugate may be administered by any suitable route, including for example, the dendrimer-targeting agent conjugate may be administered intravenously. In some embodiments, the dendrimer-targeting agent conjugate is delivered as an IV bolus. In some embodiments the dendrimer-targeting agent conjugate is administered IV over a time a period in the range of from 0.5 to 60 minutes, or in the range of from 0.5 to 15 minutes, or in the range of from 0.5 to 5 minutes. In another example, the dendrimer-targeting agent conjugate may be administered intraperitoneally. The route of administration may for example be targeted to the disease or disorder which the subject has. For example, in some embodiments the disease or disorder may be an intra-abdominal malignancy such as a gynecological or gastrointestinal cancer, and the dendrimer-targeting agent conjugate may be administered intraperitoneally. In some embodiments the dendrimer-targeting agent conjugate may be for treatment of a cancer of the peritoneal cavity, such as a malignant epithelial tumors (e.g., ovarian cancer) or peritoneal carcinomatosis (e.g. gastrointestinal especially colorectal, gastric, gynecologic cancers, and primary peritoneal neoplasms), and the dendrimer-targeting moiety conjugate is administered intraperitoneally.

In some embodiments, the amount of dendrimer-targeting agent conjugate administered is sufficient to deliver between 2 and 100 mg of active agent/$m^2$, between 2 and 50 mg of active agent/$m^2$, between 2 and 40 mg of active agent/$m^2$, between 2 and 30 mg of active agent/$m^2$, between 2 and 25 mg of active agent/$m^2$, between 2 and 20 mg of active agent/$m^2$, between 5 and 50 mg of active agent/$m^2$, between 10 to 40 mg of active agent/$m^2$ between 15 and 35 mg of active agent/$m^2$, between 10 and 20 mg/$m^2$, between 20 and 30 mg/$m^2$, or between 25 and 35 mg of active agent/$m^2$. A dose of active agent of 10 mg/kg in a mouse should be approximately equivalent to a human dose of 30 mg/$m^2$ (FDA guidance 2005). (To convert human mg/kg dose to mg/$m^2$, the figure may be multiplied by 37, FDA guidance 2005).

In some embodiments, a therapeutically effective amount of the dendrimer-targeting agent conjugate is administered to a subject in need thereof at a predetermined frequency. In some embodiments, the dendrimer-targeting agent conjugate is administered to a subject in need thereof according to a dosage regimen in which the dendrimer-targeting agent conjugate is administered once per one to four weeks. In some embodiments, the dendrimer-targeting agent conjugate is administered to a subject in need thereof according to a dosage regimen in which the dendrimer-targeting agent conjugate is administered once per three to four weeks.

The targeted conjugates of the present disclosure provide the therapeutic agent in a controlled manner. By controlling the release of the therapeutic agent from the conjugate, the levels of circulating therapeutic agent (e.g. ultracytotoxic) can also be controlled. For example, the maximum plasma concentration of the therapeutic agent may be considerably lower than that resulting from dosing an equivalent amount of free therapeutic agent. In some embodiments, administration of the conjugate results in at least a 10%, at least a 20%, at least a 30%, at least a 40%, at least a 50%, at least a 60%, at least a 70%, or at least an 80% reduction in the maximum plasma concentration of released therapeutic agent in comparison to administration of an equivalent dose of free therapeutic agent.

Preparation of Conjugates

The dendrimer-targeting agent may be prepared using any suitable synthetic route, such as those described in the Examples.

In some embodiments, the dendrimer-targeting agent conjugate is produced by a process comprising:

reacting a first intermediate comprising a HER2 targeting agent which is a peptidic moiety having a molecular weight of up to about 80 kDa and comprising an antigen-binding site, the targeting agent being covalently attached to a spacer precursor group, and the spacer precursor group comprising a first reactive group with a second intermediate which is a dendrimer comprising i) a core unit (C); and ii) building units (BU), each building unit being a lysine residue or an analogue thereof;

wherein the core unit is covalently attached to at least two building units via amide linkages, each amide linkage being formed between a nitrogen atom present in the core unit and a carbon atom of an acyl group present in a building unit;

a therapeutic agent which is covalently linked to a surface building unit of the dendrimer; and hydrophilic polymeric groups which are covalently linked to surface building units of the dendrimer, the second intermediate comprising a second reactive group wherein the first and second reactive groups are complementary such that they are suitable for reaction with each other so as to covalently link the HER2 targeting agent to the dendrimer.

The present disclosure also provides intermediates useful in the synthesis of the dendrimer-targeting agent conjugates. Thus, there is also provided an intermediate for preparation of a dendrimer-targeting agent conjugate comprising a HER2 targeting agent which is a peptidic moiety having a molecular weight of up to about 80 kDa and comprising an antigen-binding site, the targeting agent being covalently attached to a spacer precursor group, and the spacer precursor group comprising a reactive group suitable for reaction with a complementary reactive group present on a dendrimeric intermediate.

In some embodiments, the targeting agent is covalently attached to the spacer precursor group via an unnatural amino acid residue. In some embodiments, the targeting agent is covalently attached to the spacer precursor group via a triazole moiety (e.g. produced by reaction of an azido-containing unnatural amino acid such as azidophenylalanine, with an alkyne containing group such as DBCO [Dibenzylcyclooctyne]).

In some embodiments, the spacer precursor group comprises one or more oligomeric or polymeric groups, such as a PEG, PEOX or a polyamino acid (e.g. polysarcosine) group. For example, it may contain a PEG group, e.g. of from 2 to 100 —$CH_2CH_2O$— units.

In some embodiments, the reactive group present on the spacer precursor group is an alkene group, e.g. a reactive alkene which is suitable for reaction with a tetrazine-containing group. In some embodiments, the reactive group is a trans-cyclooctene group.

The present disclosure also relates to the following numbered clauses:

1. A dendrimer-targeting agent conjugate, comprising:

a) a dendrimer comprising i) a core unit (C); and ii) building units (BU), each building unit being a lysine residue or an analogue thereof;

wherein the core unit is covalently attached to at least two building units via amide linkages, each amide linkage being formed between a nitrogen atom present in the core unit and a carbon atom of an acyl group present in a building unit;

b) a HER2 targeting agent which is a peptidic moiety having a molecular weight of up to about 80 kDa and comprising an antigen-binding site, which is covalently linked to the dendrimer by a spacer group;

c) a therapeutic agent which is covalently linked to a surface building unit of the dendrimer; and d) PEG or PEOX groups which are covalently linked to surface building units of the dendrimer.

2. A conjugate according to clause 1, wherein the peptidic moiety is selected from: a heavy chain antibody, Fab, Fv, scFv or a single domain antibody.

3. A conjugate according to clause 1 or clause 2, wherein the peptidic moiety comprises or consists of a heavy chain variable ($V_H$) domain.

4. A conjugate according to any of clauses 1 to 3, wherein the peptidic moiety comprises or consists of a light chain variable ($V_L$) domain.

5. A conjugate according to any of clauses 1 to 4, wherein the targeting agent has a molecular weight of about 5 kDa to about 30 kDa.

6. A conjugate according to clause 5, wherein the targeting agent has a molecular weight of about 5 kDa to about 15 kDa.

7. A conjugate according to clause 6, wherein the targeting agent has a molecular weight of about 10 kDa to about 16 kDa.

8. A conjugate according to any of clauses 1 to 7, wherein the targeting agent comprises less than 120 amino acid residues.

9. A conjugate according to any of clauses 1 to 8, wherein the targeting agent comprises or consists of any of the amino acid sequences as defined herein.

10. A conjugate according to any of clauses 1 to 9, wherein the covalent linkage between the targeting agent and the spacer group has been formed by reaction between complementary reactive functional groups present on a targeting agent precursor and a spacer group precursor.

11. A conjugate according to clause 10, wherein the targeting agent precursor comprises an unnatural amino acid residue, the unnatural amino acid residue having a side-chain including a reactive functional group.

12. A conjugate according to clause 11, wherein the unnatural amino acid residue is a 4-azidophenylalanine residue.

13. A conjugate according to any of clauses 1 to 12, wherein the targeting agent is covalently linked to the spacer group via the C-terminus of the targeting agent.

14. A conjugate according to any of clauses 10 to 13, wherein the spacer group precursor comprises a reactive functional group which is an alkyne group.

15. A conjugate according to clause 14, wherein the alkyne group is a dibenzocyclooctyne group.

16. A conjugate according to any of clauses 1 to 15, wherein the therapeutic agent is an ultracytotoxic agent.

17. A conjugate according to clause 16, wherein the therapeutic agent is an auristatin or a maytansinoid.

18. A conjugate according to clause 17, wherein the therapeutic agent is monomethyl auristatin E.

19. A conjugate according to clause 17, wherein the therapeutic agent is monomethyl auristatin F.

20. A conjugate according to any of clauses 1 to 19, wherein the therapeutic agent is covalently linked to a surface building unit of the dendrimer via a linker.

21. A conjugate according to any of clauses 1 to 20, wherein the therapeutic agent is covalently linked to a surface building unit of the dendrimer via a cleavable linker.

22. A conjugate according to clause 21, wherein the cleavable linker comprises a Val-Cit-PAB group.

23. A conjugate according to any of clauses 1 to 22, wherein the conjugate comprises PEG groups which are covalently linked to surface building units of the dendrimer.

24. A conjugate according to clause 23, wherein the PEG groups have an average molecular weight in the range of from about 500 to about 2500 g/mole.

25. A conjugate according to any of clauses 1 to 24, wherein the spacer group comprises a PEG group.

26. A conjugate according to any of clauses 1 to 25, wherein the core unit comprises the structure:

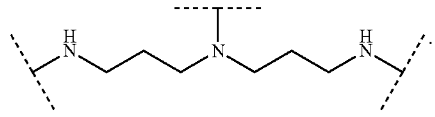

27. A conjugate according to any of clauses 1 to 26, wherein the dendrimer has from one to five generations of building units.

28. A conjugate according to clause 27, wherein the dendrimer has three generations of building units.

29. A conjugate according to any of clauses 1 to 28, wherein the building units are each:

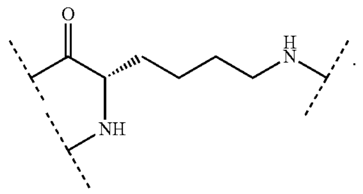

30. A conjugate according to any of clauses 1 to 29, for administration in combination with a further active agent.

31. A conjugate according to any of clauses 1 to 30, wherein the conjugate is internalised within a HER2-expressing cell.

32. A conjugate according to any of clauses 1 to 31, wherein administration of the conjugate results in reduced side effects in comparison to administration of an equivalent dose of free therapeutic agent.

33. A conjugate according to any of clauses 1 to 32, wherein administration of the conjugate results in at least a 50% reduction in the maximum plasma concentration of released therapeutic agent in comparison to administration of an equivalent dose of free therapeutic agent.

34. A composition comprising a plurality of conjugates as defined in any of clauses 1 to 33.

35. A pharmaceutical composition, comprising:

i) a conjugate according to any of clauses 1 to 34; and ii) a pharmaceutically acceptable excipient.

36. A composition according to clause 34 or 35, wherein the composition is formulated for parenteral delivery.

37. A conjugate according to any of clauses 1 to 33, or a composition according to any of clauses 34 to 36, for use in the treatment of cancer.

38. A method of treating cancer comprising administering to a subject in need thereof a therapeutically effective amount of a conjugate according to any of clauses 1 to 33 or a composition according to any of clauses 34 to 37.

39. Use of a conjugate according to any of clauses 1 to 33, or of a composition according to any of clauses 34 to 38, in the manufacture of a medicament for the treatment of cancer.

40. A method, use, or conjugate or composition for use, according to any of clauses 37 to 39, wherein the cancer is ovarian cancer, breast cancer, stomach cancer, uterine cancer, or another cancer characterised by abnormal expression of the ERBB2 gene.

41. A method of killing a HER2-expressing cell, comprising:

contacting a conjugate according to any of clauses 1 to 33 with a HER2-expressing cell such that the conjugate is internalised within the cell, whereby the therapeutic agent kills the HER2-expressing cell.

The present disclosure is further described by the following examples. It is to be understood that the following description is for the purpose of describing particular embodiments only and is not intended to be limiting with respect to the above description.

EXAMPLES

The following nomenclature is used herein in reference to dendrimer conjugate synthesis:

| Abbreviation | Name | Structure[1] |
|---|---|---|
| NEOEOEN | 2-[2-(2-aminoethoxy)ethoxy]-ethylamine | 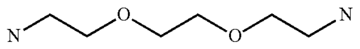 |
| [Boc] NEOEOEN | t-butoxycarbonylamino-3,6-oxa-8-aminooctane | 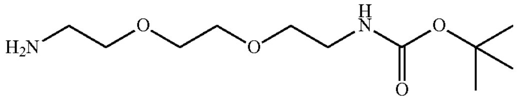 [SMILES: CC(C)(C)OC(=O)NCCOCCOCCN] |
| $Su(NPN)_2$ | | 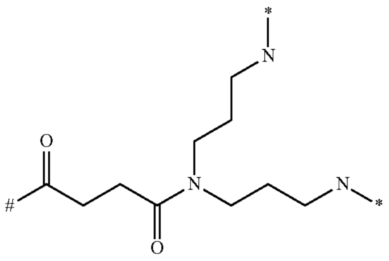 |
| Lys | Lysine | 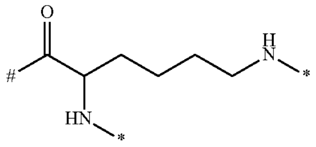 |
| DBL-oPNP | p-nitrophenyl active ester of di-Boc Lysine | 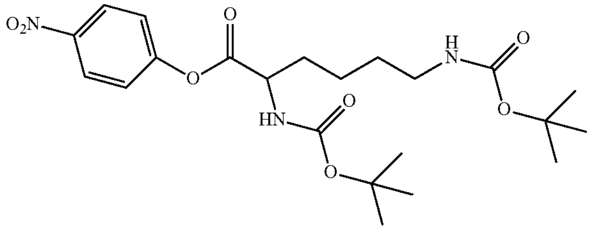 [SMILES: CC(C)(C)OC(=O)NCCCCC(NC(=O)OC(C)(C)C)C(=O)Oc1ccc([N+](=O)[O-])cc1] |
| $NH_2$•TFA | | Represents the surface amine groups of the deprotected molecule as the TFA salt |
| Boc | t-butyloxycarbonyl | 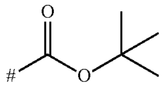 |

-continued
| Abbreviation | Name | Structure[1] |
| --- | --- | --- |
| $(NPN)_2$ $[Boc]_2$ | | 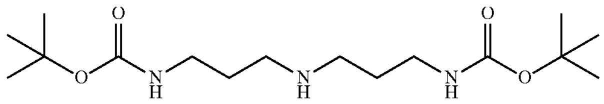 [SMILES: CC(C)(C)OC(=O)NCCCNCCCNC(=O)OC(C)(C)C] |
| HO-Su$(NPN)_2$ $[Boc]_2$ | | 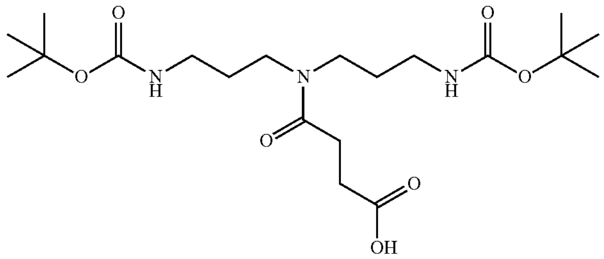 [SMILES: CC(C)(C)OC(=O)NCCCN(CCCNC(=O)OC(C)(C)C)C(=O)CCC(=O)O] |
| oPNPO-Su$(NPN)_2$ $[Boc]_2$ | | 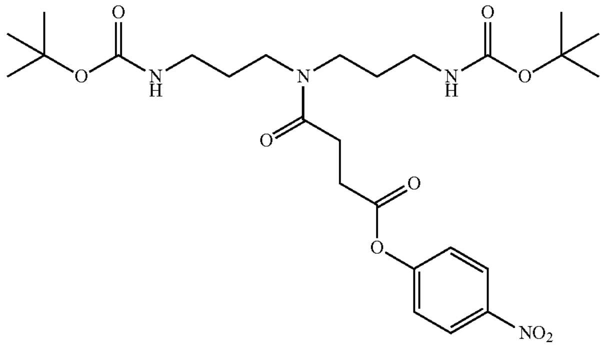 [SMILES: CC(C)(C)OC(=O)NCCCN(CCCNC(=O)OC(C)(C)C)C(=O)CCC(=O)Oc1ccc([N+](=O)[O-])cc1] |
| MeOGly•HCl | | 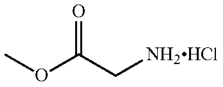 |

-continued
| Abbreviation | Name | Structure[1] |
|---|---|---|
| NHGlu-Val-Cit-PAB-MMAE Or NHGlu-vc-PAB- | | 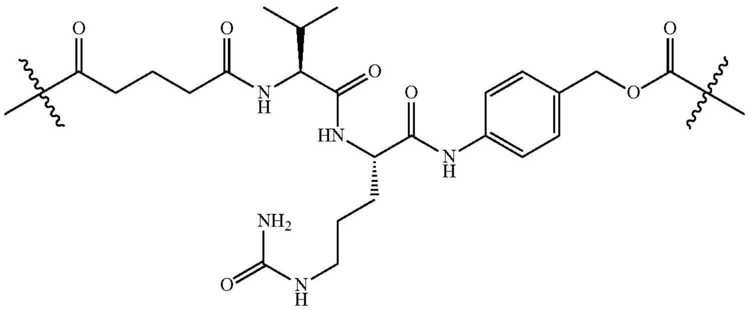 |
| Val-Ala-PAB-P-Trigger-NMeCO | | 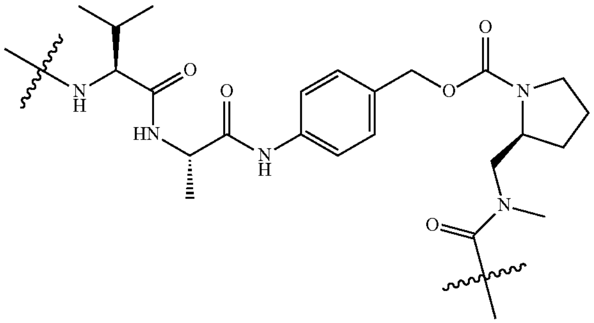 |
| DBCO-Glu-NHPEG$_{24}$CO-NHPEG$_3$-TCO/ DBCO-PEG$_{12}$-TCO | | 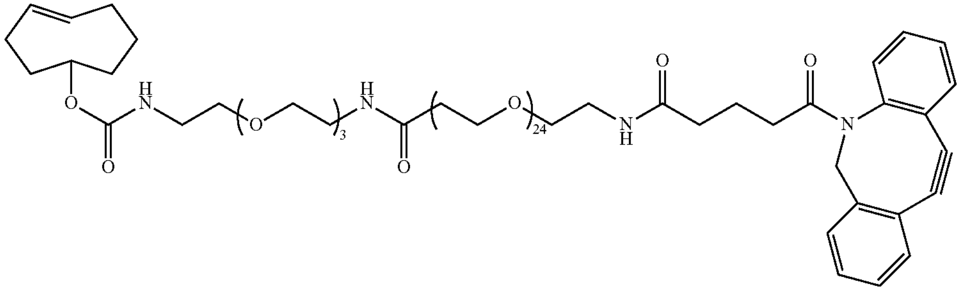 |

| | |
|---|---|
| MeCN | Acetonitrile |
| LCMS | Liquid chromatography mass spectrometry |
| ESI MS | Electrospray mass spectrometry |
| UPA | Unique point of linkage |
| Lys | Lysine |
| Boc | Benzyloxycarbonyl |
| PBS | Phosphate buffered saline |
| DIPEA | Diisopropylethylamine |
| PEG | Polyethylene glycol |
| NH-PEG Also known as NH-COPEG-OMe | NH-COPolyethylene glycol-OMe |
| PyBop | Benzotriazol-1-yl-oxytri-pyrrolidinophosphonium hexafluorophosphate |
| SEC | Size exclusion chromatography |
| TFA | Trifluoroacetic acid |
| NMM | N-methylmorpholine |
| HPLC | High Performance Liquid Chromatography |
| DMF | Dimethylformamide |
| DBL-oPNP | Di-Boc-(L)-lysine para-nitrophenyl ester |
| NHFmoc | NH-Fluorenylmethyloxycarbonyl |
| NHBoc | NH-tert-butyloxycarbonyl |
| MMAE | Mono-methyl Auristatin E |
| MMAF(OMe) | Mono-methyl Auristatin F (methyl ester) |
| $N(PNBoc)_2$ | diBoc dipropylenetriamine |
| TEA | Triethylamine |
| NMR | Nuclear Magnetic Resonance |
| $N_2$ | Nitrogen |
| $D_2O$ | Deuterium oxide |
| $CD_3OD$ | Deuterated methanol |
| Glu | Glutamic acid derivative |
| Val | Valine |
| Arg | Arginine |
| Ala | Alanine |
| Cit | Citrulline |
| PAB | Para-aminobenzylcarbamate |
| DGA | Diglycolic acid |
| $R_t$ | Retention time |
| DMAP | 4-(Dimethylamino)pyridine |
| NHS | N-hydroxysuccinimide |
| DCM | Dichloromethane |
| EtOAc | Ethyl acetate |
| THF | tetrahydrofuran |
| N3 | Azide |
| MAL | maleimide |
| BCN | Bicyclononyne containing linker |
| MAL-EDA-BCN | Maleimido-ethylenediamine-bicyclononyne |
| DBCO | dibenzylcyclooctyne containing linker |
| UPA | A dendrimer with a selected point of linkage at which a linker or targeting agent is or can be attached |
| BCNTriazolo | Bicyclo[6,1,0]nonyne-[1,2,3]triazolo |
| DBCOTriazolo | Dibenzocyclooctyne-[1,2,3]triazolo |
| MPED | N-(3-maleimidopropionic acid)-ethylene diamine |
| DTX | Docetaxel |
| t-BuOH | tertiary butanol |
| TBTA | Tris[(1-benzyl-1H-1,2,3-triazol-4-yl)methyl]amine |
| DFO | Deferoxamine |
| CTX | Cabazitaxel |
| SN-38 | 7-ethyl-10-hydroxycamptothecin |

HPLC MS (Mass Spectrometry) and NMR Equipment Details:

HPLC—Waters 2795 with 2996 Diode Array Detector (DAD)

MS—Waters ZQ4000 with ESI probe, inlet flow split to give around 50 μL/min to the MS.

Mass Spectra data was acquired in positive or negative electrospray ionisation mode as indicated. The raw data was deconvoluted using a Maximum Entropy algorithm (MaxEnt) as implemented in MassLynx software v4.0, supplied by Waters Corporation. The data reported in the experimental details corresponds to the observed value after deconvolution to a theoretical zero charge state.

NMR—300 MHz Bruker.

Preparation of carboxy reactive dendrimer scaffolds have been previously described in particular in WO2007/082331, WO2008/017125, WO2012/167309 and WO2015/184510. One skilled in the art can use or adapt these methods to prepare the various dendrimers outlined herein.

In the following examples [Lys] in a formula refers to the lysine building units on the surface layer of the dendrimer.

Example 1

General Procedure A. Boc Deprotection

To an ice-cooled, stirred suspension of Boc compound (1.0 equivalent) in water was added TFA (40-200 equivalents/Boc group). After 5 minutes, the ice-bath was removed and the reaction mixture left to stir at room temperature overnight. The volatiles were removed in vacuo and the remaining aqueous solution diluted further with water and lyophilised to give the deprotected product in quantitative yield.

General Procedure B. Addition of a Lysine Layer on Dendrimer Surface.

To a stirred solution of the TFA dendrimer (1.0 equivalent) in DMF under an atmosphere of nitrogen was added TEA (6.0 equivalents/$NH_2$), followed by DBL-oPNP (2.0 equivalents/$NH_2$). The ensuing reaction mixture was left to stir overnight at room temperature.

The volatiles were removed in vacuo and the resulting crude material purified using standard methods.

General Procedure C. Pegylation of the Dendrimer Surface Using HO-Lys-(α-NHBoc)(ε-NHPEG$_{1100}$) Wedge.

To a stirred solution of TFA dendrimer (1.0 equivalent) in DMF under an atmosphere of nitrogen was added PyBOP (2.0 equivalents/$NH_2$) and DIPEA (8.0 equivalents/$NH_2$). After 10 minutes a solution of HO-Lys-(α-NHBoc)(ε-NHPEG$_{1100}$) (1.35 equivalents/$NH_2$) in DMF was added and the ensuing reaction mixture stirred overnight at room temperature. The volatiles were removed in vacuo and the resulting crude material purified using standard methods.

General Procedure D. Capping of the Dendrimer Surface with HO-Lys-(α-NHBoc)(ε-NHFmoc) Wedge Followed by Fmoc Deprotection Step 1: To a stirred solution of HO-Lys-(α-NHBoc)(ε-NHFmoc) (1.5 eq/$NH_2$) and NMM (2.5 eq/$NH_2$) in DMF was added PyBOP (1.4 eq/$NH_2$). The ensuing reaction mixture was stirred at room temperature for 15 min then a solution of TFA-dendrimer (1.0 equivalent) and NMM (2.5 eq/$NH_2$) in DMF was added. The ensuing reaction mixture was left to stir at room temperature for 1 hour then slowly added to ice-cold MeCN and stirred for 15 mins The resulting solid was collected by filtration and washed with MeCN (3×) then lyophilised.

Step 2: To a solution of Fmoc/Boc dendrimer (1.0 equivalent) in DMF was added piperidine (21 eq/Fmoc). The solution was allowed to stir at room temperature for 90 minutes then slowly added to ice-cold $Et_2O$. After 15 mins, the precipitated solid was collected by filtration, washed with $Et_2O$, dissolved in $H_2O$ and lyophilised.

General Procedure E. Capping Dendrimer Surface with DGA-Doxorubicin or DGA-Nemorubicin DGA-3'-NH-Doxorubicin Step 1: A solution of DMAP (2.5 equivalents) in DMF was added to a stirred solution of Dox·HCl (1.0 equivalents) in DMF at room temperature. After 5 minutes, a solution of DGA (0.9 equivalents) in DMF was added. The reaction was complete in 3 hours.

Step 2: To the above reaction mixture was added PyBOP (2.0 equivalents/dendrimer $NH_2$), followed by the addition of a solution of TFA-dendrimer (azido-$PEG_{24}$-CO[N(PN)$_2$[Lys]$_4$[(α-$NH_2$·TFA)(ε-$NHPEG_{1100}$)]4 or azido-$PEG_{24}$-CO[N(PN)$_2$[Lys]$_8$[(α-$NH_2$·TFA)(ε-$NHPEG_{1100}$)]$_8$) (1.0 equivalent) and DIPEA (6.0 equivalents/dendrimer $NH_2$) in DMF. The ensuing reaction mixture was left to stir at room temperature overnight. The volatiles were removed in vacuo and the resulting crude material purified by SEC.

DGA-14-O-Nemorubicin

Step 1: A solution of DMAP (2.5 equivalents) in DMF was added to a stirred solution of Nemorubicin (1.0 equivalents) in DMF at room temperature. After 5 minutes, a solution of DGA (0.9 equivalents) in DMF was added. The reaction was complete in 3 hours.

Step 2: To the above reaction mixture was added PyBOP (2.0 equivalents/dendrimer $NH_2$), followed by the addition of a solution of TFA-dendrimer (azido-$PEG_{24}$-CO[N(PN)$_2$[Lys]$_2$[Lys]$_4$[(α-$NH_2$·TFA)(ε-$NHPEG_{1100}$)]4 or azido-$PEG_{24}$-CO[N(PN)$_2$[Lys]$_2$[Lys]$_4$[Lys]$_8$[(α-$NH_2$·TFA)(ε-$NHPEG_{1100}$)]$_8$) (1.0 equivalent) and DIPEA (6.0 equivalents/dendrimer $NH_2$) in DMF. The ensuing reaction mixture was left to stir at room temperature overnight. The volatiles were removed in vacuo and the resulting crude material purified by SEC.

General Procedure F. Capping Dendrimer Surface with Glu-Vc-PAB-MMAE or DGA-MMAF(OMe)

Azido-$PEG_{24}$-CO[N(PN)$_2$[Lys]$_8$[(α-$NH_2$·TFA)(ε-$NHPEG_{570/1100/2000}$)]$_8$ (1.0 equivalent) was dissolved in a mixture of DMF and NMM (5.0 equivalents/$NH_2$) at room temperature. This solution was added to HO-Glu-vc-PAB-MMAE or DGA-MMAF (OMe) (1.2 equivalents/$NH_2$) and PyBOP (2.0 equivalents/$NH_2$) and left at room temperature. The resulting crude material purified by SEC.

General Procedure G. Conjugation of Affibody to Dox/Pt (IV)-Acetate/MMAE/MMAF Dendrimer Step 1: A solution of Affibody protein (1.0 mg/mL PBS) was treated with TCEP (50 mM, 39.0 equivalents) and the reaction mixture shaken at 650 rpm for 2 hours at room temperature. The resulting solution was purified by SEC.

Step 2: The collected permeate was treated with a solution of maleimide-bicyclo[6.1.0]nonyne (Mal-BCN) (20.0 equivalents) in DMSO. The ensuing reaction mixture was shaken at 650 rpm for 2 hours at room temperature. The resulting solution was purified by SEC.

Step 3: The affibody-BCN solution was treated with a solution of azido-$PEG_{24}$-CO[N(PN)$_2$[Lys]$_4$[(α-DGA-3'-NH-Dox)(ε-$NHPEG_{1100}$)]4 in PBS (858 μM) or azido-$PEG_{24}$-CO[N(PN)$_2$[Lys]$_8$[(α-DGA-3'-NH-Dox)(ε-$NHPEG_{1100}$)]$_8$ (580 μM in PBS) or azido-$PEG_{24}$-CO[N(PN)$_2$][Lys]$_8$[(α-Pt(IV)-acetate)(ε-$NHPEG_{1100}$)]$_8$ (903 μM in PBS) or azido-$PEG_{24}$-CO[N(PN)$_2$[Lys]$_8$[(α-Glu-vc-PAB-MMAE)(ε-$NHPEG_{570/1100/2000}$)]$_8$ (240 μM in PBS) or azido-$PEG_{24}$-CO[N(PN)$_2$[Lys]$_8$[(α-DGA-MMAF (OMe))(ε-$NHPEG_{70/1100/2000}$)]$_8$ (365 μM in PBS) (1.3 equivalents affibody-BCN/dendrimer). The ensuing reaction mixture was shaken at 650 rpm overnight at room temperature and then treated with a 9.38 mM (30% EtOH/water) solution of DBCO agarose (5.0 equivalents/dendrimer). The ensuing suspension was shaken at 1200 rpm at room temperature overnight. The suspension was purified using SEC.

General Procedure H. Conjugation of Nanobody to MMAE Dendrimers

Step 1: A solution of linker (BCN-$PEG_2$NH-Glu-$NHPEG_{24}$CO-$NHPEG_3$-TCO or DBCO-Glu-$NHPEG_{24}$CO-$NHPEG_3$-TCO) was prepared by dissolving linker (1 mg) in 20:80 (DMSO/10 mM PBS, 1 mL).

Step 2: The TCO-linker solution (1 eq.) was added to a solution of the tetrazine functionalised dendrimer (e.g. Tz-MMAE-dendrimer or BHA-Tz-MMAE-dendrimer) (1.0 eq., 8 mg/mL) in PBS (1). Reaction mixture allowed to stand at room temperature for 30 min. Completion of the reaction was indicated by disappearance of the pink tetrazine colour. The reaction was monitored by HPLC.

Step 3: Once the reaction was complete, the contents were diluted with PBS (to a final volume of 0.5 mL) with PBS. A portion of the BCN/DBCO-MMAE-dendrimer (1.0 eq.) was added to a solution of Nanobody-azide (1.0 eq., 9.2 mg/ml) in Tris buffer (20 mM, 1 mL). The resulting solution was left to stand at RT for 7 h, then at 4° C. overnight. Purification of the Nanobody-dendrimer construct was carried out by anion exchange chromatography followed by SEC.

Example 1a Synthesis of Intermediates 1.1 Azido-$PEG_{24}$-CO[N(PNBoc)$_2$] Compound 1

To a stirred solution of azido-$PEG_{24}$-acid (2.00 g, 1.71 mmol) and PyBOP (1.33 g, 2.56 mmol) in DMF (20 mL) under an atmosphere of $N_2$ was added NMM (563 μL, 5.12 mmol). After 10 min, a solution of N(PNBoc)$_2$ (622 mg, 1.88 mmol) in DMF (5 mL) was added and the ensuing reaction mixture left to stir overnight at room temperature. The volatiles were removed in vacuo and the resulting oil dissolved in MeCN and purified by preparative HPLC (27-50-70% MeCN, $R_t$ 47-50 min) to give a pale yellow oily solid (1.37 g, 54%). $^1$H-NMR (300 MHz, $CD_3OD$) δ (ppm): 1.44 (m, 18H); 1.65-1.84 (m, 4H); 2.63 (t, J 6.3 Hz, 2H); 3.05 (dt, J 6.9 and 14.7 Hz, 4H); 3.36-3.41 (m, 6H); 3.60-3.78 (m, 98H). LCMS (philic method, formic acid buffer) $R_t$=9.32 min. ESI MS (+ve) 1486.3 $[M]^+$; calc. m/z for $C_{67}H_{132}N_6O_{29}$ $[M]^+$: 1486.8.

1.2 Azido-$PEG_{24}$-CO[N(PN$H_2$·TFA)$_2$], Compound 2

Prepared according to General Procedure A, using azido-$PEG_{24}$-CO[N(PNBoc)$_2$](1.37 g, 922 μmol). The lyophilised product was obtained as a pale yellow oil (1.67 g, 119%). $^1$H-NMR (300 MHz, $D_2O$) δ (ppm): 1.88-2.06 (m, 4H); 2.74 (t, J 6.0 Hz, 2H); 2.96 (t, J 7.2 Hz, 2H); 3.04 (apparent t, J 7.5 Hz, 2H); 3.42-3.52 (m, 6H); 3.67-3.95 (m, 93H). LCMS (philic method, TFA buffer) $R_t$=8.47 min, ESI MS (+ve) 1286.0 $[M]^+$; calc. m/z for $C_{57}H_{116}N_6O_{25}$ $[M]^+$=1286.6.

1.3 Azido-$PEG_{24}$-CO[N(PN)$_2$][Lys]$_2$[Boc]$_4$, G1, Compound 3

Prepared according to General Procedure B, using azido-$PEG_{24}$-CO[N(PN$H_2$·TFA)$_2$](186 mg, 145 μmol). The crude material was dissolved in MeCN and purified by preparative HPLC (30-80% MeCN, $R_t$ 33.5-36 min) to give a pale yellow oil (224 mg, 80%). $^1$H-NMR (300 MHz, $CD_3OD$) δ (ppm): 1.22-1.87 (m, 56H); 2.64 (t, J 6.0 Hz, 2H); 3.03 (t, J 6.6 Hz, 4H); 3.13-3.23 (m, 4H), 3.36-3.45 (m, 6H); 3.60-3.69 (m, 100H); 3.77 (t, J 6.0 Hz, 2H); 3.85-3.88 (m, 1H); 3.92-4.02 (m, 2H). LCMS (phobic method, formic buffer) $R_t$=6.74 min; ESI MS (+ve) 1942.4, $[M]^+$; calc. m/z for $C_{89}H_{72}N_{10}O_{35}^+$ $[M+H]^+$=1942.4.

1.4 Azido-$PEG_{24}$-CO[N(PN)$_2$][Lys]$_2$[$NH_2$·TFA]4, G1, Compound 4

Prepared according to General Procedure A, using azido-$PEG_{24}$-CO[N(PN)$_2$[Lys]$_2$[Boc]4 (220 mg, 113 μmol). The lyophilised product was obtained as a pale yellow oil (251 mg, 111%). LCMS (philic method, formic buffer) $R_t$=6.49 min, ESI MS (+ve) 1542.1 $[M]^+$; calc. m/z for $C_{69}H_{140}N_{10}O_{27}$ $[M]^+$=1541.90.

1.5 Azido-$PEG_{24}$-CO[N(PN)$_2$][Lys]$_4$[(α-Boc)(ε-$NHPEG_{1100}$)]$_4$, G2, Compound 5

Prepared according to General Procedure C, using azido-$PEG_{24}$-CO[N(PN)$_2$[Lys]$_2$[$NH_2$·TFA]$_4$ (120 mg, 60.1 μmol). The crude material was dissolved in MeCN/$H_2O$ (1:1) and purified by preparative HPLC (20-70% MeCN, $R_t$ 31-32.5 min) to give the product as a pale yellow oil (244 mg, 59%). $^1$H-NMR (300 MHz, $CD_3OD$) δ (ppm): 1.24-1.91 (m, 74H); 2.42-2.47 (m, 8H); 2.62-2.66 (m, 2H); 3.13-3.25 (m, 12H); 3.36 (s, 12H); 3.52-3.78 (m, 490H); 3.85-3.88 (m, 4H); 3.94-4.11 (m, 4H); 4.25-4.31 (m, 2H). LCMS (philic method, formic buffer) $R_t$=8.70 min; ESI MS (+ve) 1714.0 $[M+4H]^{4+}/4$, 1371.7 $[M+5H]^{5+}/5$; 1143.0 $[M+6H]^{6+}/6$, 980.0 $[M+7H]^{7+}/7$. Transforms to 6852.

1.6 Azido-$PEG_{24}$-CO[N(PN)$_2$][Lys]$_4$[(α-$NH_2$. TFA)(ε-NHPEG$_{1100}$)]$_4$, G2, Compound 6

Prepared according to General Procedure A, using azido-$PEG_{24}$-CO[N(PN)$_2$[Lys]$_4$[(α-Boc)(ε-NHPEG$_{1100}$)]$_4$ (244 mg, 35.6 μmol). The crude lyophilised material was redissolved in water and purified by preparative HPLC (22-70% MeCN, 0.01% TFA, $R_t$ 27 min) to give the product as a pale yellow sticky solid (173 mg, 67%). $^1$H-NMR (300 MHz, $D_2O$) δ (ppm): 1.31-1.98 (m, 40H); 2.51-2.56 (m, 8H); 2.72 (broad t, J 6.0 Hz, 2H); 3.16-3.30 (m, 16H); 3.40 (s, 12H); 3.46-3.53 (m, 4H); 3.62-3.97 (m, 490H); 4.03 (t, J 6.6 Hz, 2H); 4.24-4.29 (m, 2H). LCMS (philic method, TFA buffer) $R_t$=9.85 min; ESI MS (+ve) 1614.1 $[M+4H]^{4+}/4$, 1291.6 $[M+5H]^{5+}/5$; 1076.5 $[M+6H]^{6+}/6$. Transforms to 6452.

1.7 Azido-$PEG_{24}$-CO[N(PN)$_2$][Lys]$_4$[Boc]$_8$, G2, Compound 7

Prepared according to General Procedure B, using azido-$PEG_{24}$-CO[N(PN)$_2$][Lys]$_2$[$NH_2$·TFA]$_4$ (117 mg, 58.6 μmol). The crude material was obtained as a pale yellow oil (167 mg, 100%). LCMS (phobic method 4.1a, formic buffer) $R_t$=8.35 min; ESI MS (+ve) 1328.6 $[M+2H]^{2+}/2$-Boc; calc. m/z for $C_{133}H_{252}N_{18}O_{47}$ $[M]^+$=2855.6.

1.8 Azido-$PEG_{24}$-CO[N(PN)$_2$][Lys]$_4$[$NH_2$. TFA]$_8$, G2, Compound 8

Prepared according to General Procedure A, using azido-$PEG_{24}$-CO[N(PN)$_2$][Lys]$_4$[Boc]$_4$ (167 mg, 58.6 μmol). The crude aqueous solution was purified by preparative HPLC (10-60% MeCN, 0.1% TFA buffer; $R_t$ 27-29 min) to give the product as a very pale yellow sticky solid (124 mg, 71% over 2 steps). $^1$H-NMR (300 MHz, $D_2O$) δ (ppm): 1.30-1.96 (m, 42H); 2.71 (t, J 6.0 Hz, 2H); 2.98-3.04 (m, 8H); 3.13-3.30 (m, 8H); 3.36-3.53 (m, 7H); 3.68-3.84 (m, 100H); 3.93 (t, J 6.6 Hz, 2H); 4.04 (t, J 6.6 Hz, 2H); 4.25 (t, J 7.2 Hz, 2H). LCMS (philic method, TFA buffer) $R_t$=7.76 min, ESI MS (+ve) 1028.3 $[M+2H]^{2+}/2$, 685.9 $[M+3H]^{3+}/3$; calc. m/z for $C_{93}H_{190}N_{18}O_{31}^{2+}$ $[M+2H]^{2+}/2$: 1028.3, calc m/z for $C_{93}H_{191}N_{18}O_{31}^{3+}$ $[M+3H]^{3+}/3$: 685.9.

1.9 Azido-$PEG_{24}$-CO[N(PN)$_2$][Lys]$_8$[(α-Boc)(ε-NHPEG$_{1100}$)]S, G3, Compound 9

Prepared according to General Procedure C, using azido-$PEG_{24}$-CO[N(PN)$_2$][Lys]$_4$[$NH_2$·TFA]$_8$ (123 mg, 41.5 μmol) to give the crude material as a brown oil. LCMS (philic method, formic buffer) $R_t$=11.52 min, ESI MS (+ve) 2113 $[M+6H]^{6+}/6$, 1812 $[M+7H]^{7+}/7$, 1585 $[M+8H]^{8+}/8$, 1409 $[M+9H]^{9+}/9$, 1268 $[M+10H]^{10+}/10$, 1153 $[M+11H]^{11+}/11$, 1057 $[M+12H]^{12+}/12$. Transforms to 12 673.

1.10 Azido-$PEG_{24}$-CO[N(PN)$_2$][Lys]$_8$[(α-TFA)(ε-NHPEG$_{1100}$)]$_8$, G3, Compound 10

Prepared according to General Procedure A, using azido-$PEG_{24}$-CO[N(PN)$_2$][Lys]$_8$[(α-Boc)(ε-NHPEG$_{1100}$)]$_8$ (526 mg, 41.5 μmol). The crude aqueous solution was purified by preparative HPLC (3-60% MeCN, 0.1% TFA buffer; $R_t$ 38-39 min) to give the product as a pale yellow sticky solid (359 mg, 68% over 2 steps). LCMS (philic method, TFA buffer) $R_t$=10.27 min. Transforms to 11 880.

1.11 Azido-$PEG_{24}$-CO[N(PN)$_2$][Lys]$_8$[(α-Boc)(ε-Fmoc)]$_8$, G3, Compound 11

Prepared according to General Procedure D, using azido-$PEG_{24}$-CO[N(PN)$_2$][Lys]$_4$[$NH_2$·TFA]$_8$ (105 mg, 35.4 μmol). The product was obtained as a white solid (166 mg, 83%). $^1$H-NMR (300 MHz, $d_6$-DMSO) δ (ppm): 1.23-1.49 (m, 160H); 2.73-2.95 (m, 36H); 3.44-3.60 (m, 94H); 3.83 (m, 8H); 4.05-4.28 (m, 29H); 6.33-6.90 (m, 8H, NH); 7.24-7.87 (m, 84H).

1.12 Azido-$PEG_{24}$-CO[N(PN)$_2$][Lys]$_8$[(α-Boc)(ε-$NH_2$)$_8$, G3, Compound 12

Prepared according to General Procedure D, using azido-$PEG_{24}$-CO[N(PN)$_2$][Lys]$_8$[(α-Boc)(ε-Fmoc)]$_8$ (169 mg, 29.9 μmol) to give a fluffy solid (95 mg, 82%). $^1$H-NMR (300 MHz, $d_4$-MeOH) δ (ppm): 1.46-1.49 (m, 160H); 2.69 (brs, 14H); 3.09-3.19 (m, 18H); 3.38-3.41 (m, 8H); 3.55-3.78 (m, 96H), 3.89-4.33 (m, 14H).

1.13 Azido-$PEG_{24}$-CO[N(PN)$_2$][Lys]$_8$[(α-Boc)(ε-NHPEG$_{570}$)]$_8$, G3, Compound 13 and Azido-$PEG_{24}$-CO[N(PN)$_2$][Lys]$_8$[(α-$NH_2$. TFA)(ε-NHPEG$_{570}$)]$_8$, G3, Compound 14

To a solution of mPEG$_{570}$-$CO_2H$ (205 mg, 348 μmol), NMM (60 μL, 546 μmol) and PyBOP (171 mg, 329 μmol) in DMF (1.5 mL) was added azido-$PEG_{24}$-CO[N(PN)$_2$[Lys]$_8$[(α-Boc)(ε-$NH_2$)]$_8$ in DMF (0.5 mL). The ensuing reaction mixture was allowed to stir at room temperature overnight, then concentrated in vacuo, dissolved in water, treated with TFA and stirred overnight at room temperature. The mixture was concentrated and taken up in water then purified using a Millipore Centrifugation filtration units (3K MWCO regenerated cellulose) and freeze dried product (68% over 2 steps) as an off-white fluffy material. $^1$H-NMR (300 MHz, $D_2O$) δ (ppm): 1.33-1.90 (m, 88H); 2.51-2.55 (m, 16H); 2.67-2.75 (m, 4H), 3.16-3.23 (m, 32H); 3.40-3.53 (m, 32H), 3.62-4.03 (m, 470H); 4.21-4.39 (m, 7H). LCMS (philic method, formic acid buffer) $R_t$=7.50 min.

1.14 Azido-$PEG_{24}$-CO[N(PN)$_2$][Lys]$_8$[(α-Boc)(ε-NHPEG$_{2000}$)]$_8$, G3, Compound 15

To a stirred solution of azido-$PEG_{24}$-CO[N(PN)$_2$[Lys]$_8$[(α-Boc)(ε-$NH_2$)]$_8$ (95.0 mg, 24.5 μmol) in DMF (4 mL) was added DIPEA (85 μL, 488 μmol) followed by mPEG$_{2000}$-NHS (720 mg, 313 μmol). The ensuing reaction mixture was allowed to stir at room temperature overnight. The crude residue was dissolved in water and purified by ultrafiltration (5K, Pall PES membrane). The retentate was collected and freeze dried to give an off-white fluffy material (76%). $^1$H-NMR (300 MHz, $D_2O$) δ (ppm): 1.33-1.63 (m, 160H); 3.05-3.15 (m, 35H); 3.29 (s, 24H); 3.35-3.96 (m, 1370H); 4.13-4.19 (m, 6H). LCMS (philic method, formic acid buffer) $R_t$=11.24 min.

1.15 Azido-$PEG_{24}$-CO[N(PN)$_2$][Lys]$_8$[(α-$NH_2$·TFA)(ε-NHPEG$_{2000}$)]$_8$, G3, Compound 16

Prepared according to General Procedure A, using azido-$PEG_{24}$-CO[N(PN)$_2$][Lys]$_8$[(α-Boc)(ε-NHPEG$_{2000}$)]$_8$ (40.0 mg, 1.87 μmol) to give the product as an off-white fluffy material (35 mg, 88%). $^1$H-NMR (300 MHz, $D_2O$) δ (ppm): 1.28-1.79 (m, 88H); 2.51-2.58 (m, 4H); 3.04-3.18 (m, 35H); 3.28 (s, 24H); 3.35-3.97 (m, 1348H), 4.14-4.25 (m, 6H). LCMS (philic method, formic acid buffer) $R_t$=9.12 min.

1.16 (MeTzPh)-$PEG_{24}$-CO[N(PNBoc)$_2$] Compound 46

To a stirred solution of (MeTzPh)-$PEG_{24}$-$CO_2H$ (0.402 g, 0.305 mmol), PyBOP (0.205 g, 0.394 mmol) and NMM (130 μL, 1.18 mmol) in DMF (3 mL) was added NH(PNBoc)$_2$ (0.147 g, 0.444 mmol) under an atmosphere of $N_2$. The ensuing reaction mixture left to stir overnight at room temperature. The volatiles were removed in vacuo and the resulting oil was purified on silica chromatography (5% to 10% MeOH/DCM) to give the desired product Compound 106 as a red residue (0.474 g, 95%). $^1$HNMR (300 MHz, $CD_3OD$) δ (ppm): 1.43-1.44 (m, 18H); 1.64-1.80 (m, 4H); 2.63 (t, J 6.0 Hz, 2H); 3.00 (s, 3H); 3.02-3.09 (m, 4H); 3.34-3.40 (m, 4H), 3.58-3.77 (m, 99H); 3.88-3.91 (m, 2H); 4.25-4.28 (m, 2H); 7.15-7.20 (m, 2H); 8.46-8.51 (m, 2H). LCMS (phobic method, formic acid buffer) RT=6.20 min. ESI MS (+ve) 1631.0 $[M+H]^+$; calc. m/z for $C_{76}H_{140}N_7O_{30}$ $[M+H]^+$: 1631.0.

1.17 (MeTzPh)-$PEG_{24}$-CO[N($PNH_2$·HCl)$_2$] Compound 47

To (MeTzPh)-$PEG_{24}$-CO[N(PNBoc)$_2$] Compound 1 (0.420 g, 0.258 mmol) in ice/water bath, 1.25 M HCl/MeOH solution (8 mL, 10.0 mmol) was slowly added. After 5 min, the ice-bath was removed and the ensuing reaction mixture left to stir at room temperature overnight. The volatiles were removed in vacuo to give product Compound 107 as a red residue (0.388 g, 100%). $^1$HNMR (300 MHz, $CD_3OD$) δ (ppm): 1.91-2.07 (m, 4H); 2.68 (t, J 6.0 Hz, 2H); 2.94-3.09 (m, 7H); 3.53-3.80 (m, 108H); 3.88-3.91 (m, 2H); 4.25-4.28 (m, 2H); 7.16-7.20 (m, 2H); 8.47-8.51 (m, 2H). LCMS (philic method, formic acid buffer) RT=8.12 min. ESI MS (+ve) 1430.9 $[M+H]^+$; calc. m/z for $C_{66}H_{124}N_7O_{26}$ $[M+H]^+$: 1430.8.

1.18 (MeTzPh)-$PEG_4$CO—NH-$PEG_{24}$-CO[N($PNH_2$·HCl)$_2$] Compound 48

To a stirred solution of $H_2N$-$PEG_{24}$-CO[N(PNBoc)$_2$] (0.418 g, 0.286 mmol) in DMF (2.0 mL) was added (MeTzPh)-$PEG_4$-$CO_2H$ (0.15 g, 0.344 mmol), PyBOP (0.178 g, 0.342 mmol) and NMM (80 μL, 0.727 mmol). The ensuing reaction mixture left to stir overnight at room temperature. The volatiles were removed in vacuo and the resulting oil was cooled in ice/water bath then 1.25 M HCl/MeOH solution (10.0 mL, 12.5 mmol) was slowly added. After 5 min, the ice-bath was removed and the ensuing reaction mixture left to stir at room temperature overnight. The volatiles were removed in vacuo and the resulting oil was dissolved in MeCN/$H_2O$ (8 mL, 1:1) and purified by preparative HPLC (10-50% MeCN, 0.1% formic acid buffer, RT 35 min) to give red solid Compound 108 (1.37 g, 54%). $^1$HNMR (300 MHz, $CD_3OD$) δ (ppm): 1.91-2.04 (m, 4H); 2.43 (t, J 6.0 Hz, 2H); 2.68 (t, J 6.0 Hz, 2H); 2.94-3.07 (m, 4H); 3.00 (s, 3H); 3.35 (t, J 6.0 Hz, 2H); 3.51-3.80 (m, 119H); 3.88-3.91 (m, 2H); 4.25-4.28 (m, 2H); 7.16-7.20 (m, 2H); 8.46-8.51 (m, 2H). LCMS (philic method, formic acid buffer) RT=8.15 min. ESI MS (+ve) 1677.9 $[M+H]^+$; calc. m/z for $C_{77}H_{145}N_8O_{31}$ $[M+H]^+$: 1678.0.

1.19 (MeTzPh)-$PEG_4$CO-NH$PEG_{24}$-CO[N(PN)$_2$[Lys]$_2$ [NHBoC]$_4$ G1 Compound 49

To a stirred solution of (MeTzPh)-$PEG_4$CO-NH$PEG_{24}$-CO[N($PNH_2$·HCl)$_2$] Compound 48 (0.195 g, 0.111 mmol) and DBL-oPNP (0.146 g, 0.312 mmol) in DMF (3.0 mL) under an atmosphere of $N_2$ was added NMM (125 μL, 0.864 mmol). The ensuing reaction mixture was then left to stir overnight at room temperature. The volatiles were removed in vacuo and the resulting oily residue was purified by column chromatography on silica gel (5%-10%-15% MeOH/DCM) to give the desired product Compound 109 as a red oil (0.186 g, 72%). $^1$HNMR (300 MHz, $CD_3OD$) δ (ppm): 1.28-1.87 (m, 56H); 2.43 (t, J 6.0 Hz, 2H); 2.63 (t, J 6.0 Hz, 4H); 3.00 (s, 3H); 3.02-3.06 (m, 4H); 3.10-3.21 (m, 4H); 3.35-3.41 (m, 6H); 3.51-3.78 (m, 110H); 3.84-3.99 (m, 4H); 4.25-4.28 (m, 4H); 7.15-7.20 (m, 2H); 8.47-8.51 (m, 2H). LCMS (phobic method, formic buffer) RT=6.68 min; ESI MS (+ve) 2335.3, $[M+H]^+$; calc. m/z for $C_{109}H_{201}N_{12}O_{41}$+[M+H]$^+$=2335.4.

1.20 (MeTzPh)-$PEG_4$CO-NH$PEG_{24}$-CO[N(PN)$_2$[Lys]$_2$ [$NH_2$·HCl]$_4$ G1 Compound 50

To an ice-cooled (MeTzPh)-$PEG_4$CO-NH$PEG_{24}$-CO[N (PN)$_2$[Lys]$_2$[NHBoc]$_4$ Compound 49 (0.215 g, 0.0921 mmol), was slowly added a solution of 1.25 M HCl/MeOH (6.0 mL, 7.50 mmol). After 5 min, the ice-bath was removed and the ensuing reaction mixture left to stir at room temperature overnight. The volatiles were removed in vacuo to give the product Compound 110 as a red oil (0.208 g, 108%). %). $^1$HNMR (300 MHz, $CD_3OD$) δ (ppm): 1.51-1.99 (m, 20H); 2.47 (t, J 6.0 Hz, 2H); 2.67 (t, J 6.0 Hz, 4H); 2.90-3.04 (m, 7H); 3.35-3.41 (m, 7H); 3.51-3.78 (m, 106H); 4.25-4.28 (m, 2H); 7.17-7.20 (m, 2H); 8.47-8.51 (m, 2H); LCMS (philic method, formic buffer) RT=7.28 min, ESI MS (+ve) 1934.9 $[M+H]^+$; calc. m/z for $C_{89}H_{169}N_{12}O_{33}$ $[M]^+$=1935.2.

1.21 (MeTzPh)-$PEG_4$CO-NH$PEG_{24}$-CO[N(PN)$_2$][Lys]$_4$ [NHBoc]$_8$ G2 Compound 51

To a stirred solution of (MeTzPh)-$PEG_4$CO-NH$PEG_{24}$-CO[N(PN)$_2$[Lys]$_2$[$NH_2$·HCl]$_4$ Compound 50 (0.192 g, 0.0822 mmol) and DBL-oPNP (Ref.1) (0.215 g, 0.460 mmol) in DMF (3.0 mL) under an atmosphere of $N_2$ was added NMM (215 uL, 0.1.96 mmol). The ensuing reaction mixture was then left to stir overnight at room temperature. The volatiles were removed in vacuo and the resulting oily residue was purified on silica chromatography (5%-10%-15% MeOH/DCM) to give the desired product Compound 51 as a red oil (0.231 g, 87%). $^1$HNMR (300 MHz, $CD_3OD$) δ (ppm): 1.28-1.87 (m, 140H); 2.44 (t, J 6.0 Hz, 2H); 2.63 (t, J 6.0 Hz, 2H); 3.00 (s, 3H); 3.02-3.06 (m, 10H); 3.10-3.21 (m, 16 kH); 3.33-3.40 (m, 8 kH); 3.51-3.77 (m, 120H); 3.84-3.99 (m, 14H); 3.94-4.10 (m, 4H); 4.25-4.28 (m, 4H); 7.15-7.20 (m, 2H); 8.47-8.52 (m, 2H). LCMS (phobic method, formic buffer) RT=8.15 min; ESI MS (+ve) $[M+2]^+$=1624.5; [(M−3Boc)+3]=1016.6; calc. m/z for $C_{153}H_{281}N_{20}O_{53}$+[M+H]=3247.99.

1.22 (MeTzPh)-$PEG_4$CO-NH$PEG_{24}$-CO[N(PN)$_2$][Lys]$_4$ [$NH_2$·HCl]$_8$ G2 Compound 52

To an ice-cooled (MeTzPh)-$PEG_4$CO-NH$PEG_{24}$-CO[N (PN)$_2$][Lys]$_4$[NHBoc]$_8$ Compound 51 (0.231 g, 0.0711 mmol), was slowly added a solution of 1.25 M HCl/MeOH (9.0 mL, 11.3 mmol) was slowly added. After 5 min, the ice-bath was removed and the ensuing reaction mixture left to stir at room temperature overnight. The volatiles were removed in vacuo to give the product Compound 51 as a red oil (0.226 g, 100%). $^1$HNMR (300 MHz, $CD_3OD$) δ (ppm): 1.51-1.96 (m, 40H); 2.53 (t, J 6.0 Hz, 2H); 2.96-3.04 (m, 10H); 3.15-3.20 (m, 8H); 3.39-3.45 (m, 7H); 3.54-4.10 (m, 102H); 4.25-4.28 (m, 2H); 7.17-7.20 (m, 2H); 8.48-8.51 (m, 2H); LCMS (philic method, formic buffer) RT=6.38 min, ESI MS (+ve) 2447.6 $[M+H]^+$; calc. m/z for $C_{113}H_{217}N_{20}O_{37}$ $[M+H]^+$=2447.6.

1.23 (MeTzPh)-$PEG_4$CO-NH$PEG_{24}$-CO[N(PN)$_2$][Lys]$_8$ [(α-$NH_2$·HCl)(ε-NH-CO$PEG_{1100}$)]$_8$ G3 Compound 53

To a stirred solution of HO-Lys(α-NHBoc)(ε-NH-CO$PEG_{1100}$) (0.541 g, 0.402 mmol) and PyBOP (0.195 g, 0.375 mmol) in DMF (2 mL) under an atmosphere of $N_2$ was added NMM (225 μL, 2.96 mmol). After 10 min, that solution was added to (MeTzPh)-$PEG_4$CO-NH$PEG_{24}$-CO [N(PN)$_2$][Lys]$_4$[$NH_2$·HCl]$_8$ Compound 52 (0.109 g, 0.0398 mmol) in DMF (1 mL). The ensuing reaction mixture was left to stir overnight at room temperature. The volatiles were removed in vacuo and the resulting crude was cooled in ice/water bath. To the cooled residue, 1.25 M (8.0 mL, 10 mmol) was slowly added. After 10 min, the cold bath was removed and the reaction was left stirring at room temperature overnight. The volatiles were removed in vacuo then dissolved in $H_2O$ (16 mL). The solution was purified by centrifugation* using Millipore Amicon Ultra-15 Centrifugal Filter Units (4 units×10 kDa MWCO units). The retentate was freeze-dried overnight to give product Compound 53 (0.327 g, 65%) as a red solid. $^1$HNMR (300 MHz, $CD_3OD$) δ (ppm): 1.40-1.87 (m, 88H); 2.49-2.56 (m, 18H); 2.68-2.72 (m, 2H); 3.08 (s, 3H); 3.17-3.30 (m 30H); 3.37-3.51 (m, 10H); 3.41 (s, 24H); 3.59-4.01 (m, 816H); 4.25-4.40 (m, 8H); 7.29-7.33 (m, 2H); 8.44-8.49 (m, 2H); LCMS (philic method, TFA buffer) RT=10.28 min.

*[The units were pre-rinsed with $H_2O$ (5 mL) and spinning at 4000 rpm for 5 min. This process was repeated. The crude solution was filtered through 0.45 μm syringe filter then placed in the centrifugation units. The units were then spun at 4000 rpm for 15 min. The retentate was then diluted with $H_2O$ (4 mL) then spun again at 4000 rpm for 15 min. This process was repeated 8 times.]

1.24 (MeTzPh)-$PEG_4$CO-NH$PEG_{24}$-CO[N(PN)$_2$][Lys]$_8$[$NH_2$·HCl]$_{16}$ G3 Compound 54

To a stirred solution of (MeTzPh)-$PEG_4$CO-NH$PEG_{24}$-CO[N(PN)$_2$][Lys]$_4$[$NH_2$·HCl]$_8$ Compound 52 (0.098 g, 0.0358 mmol) and DBL-oPNP (0.207 g, 0.443 mmol) in DMF (2.0 mL) under an atmosphere of $N_2$ was added NMM (190 μL, 1.973 mmol). The ensuing reaction mixture was then left to stir overnight at room temperature. The volatiles were removed in vacuo and the resulting oily residue was purified on silica chromatography (5%-10%-15% MeOH/DCM) to give the Boc protected product as a red oil (0.128 g, 70%). The purified material was cooled in ice/water bath then a solution of 1.25 M HCl/MeOH (6.5 mL, 8.5 mmol) was slowly added. After 5 min, the ice-bath was removed and the ensuing reaction mixture left to stir at room temperature overnight. The volatiles were removed in vacuo to give the product Compound 54 as a red oil (0.107 g, 100%). LCMS (philic method, TFA buffer) RT=7.48 min, ESI MS (+ve) 3471 $[M+H]^+$; calc. m/z $[M+H]^+$=3472.

1.25 (MeTzPh)-$PEG_4$CO-NH$PEG_{24}$-CO[N(PN)$_2$][Lys]$_{16}$[(α-$NH_2$·HCl)(ε-NH—CO $PEG_{1100}$)]$_{16}$ G4 Compound 55

To a stirred solution of HO-Lys(α-NHBoc)(ε-NH-CO$PEG_{1100}$) (0.107 g, 0.132 mmol) and PyBOP (0.065 g, 0.125 mmol) in DMF (1.5 mL) under an atmosphere of $N_2$ was added NMM (50 μL, 0.455 mmol). After 10 min, that solution was added to (MeTzPh)-$PEG_4$-$PEG_{24}$-CO[N(PN)$_2$][Lys]$_8$[$NH_2$·HCl]$_{16}$ Compound 54 (0.0221 g, 0.00545 mmol). The ensuing reaction mixture was left to stir overnight at room temperature. The volatiles were removed in vacuo and the resulting crude was cooled in ice/water bath. To the cooled residue, 1.25 M HCl/MeOH (1.5 mL, 1.88 mmol) was slowly added. After 10 min, the cold bath was removed and the reaction was left stirring at room temperature overnight. The volatiles were removed in vacuo then dissolved in $H_2O$ (5 mL). The solution was purified by centrifugation using Millipore Amicon Ultra-15 Centrifugal Filter Unit (10 kDa MWCO). The retentate was freeze-dried overnight and further purified on Gilson [Single Gradient 60 min, 10>60% ACN (0.1% TFA buffer, RT 36 min] to give product Compound 55 (0.021 g, 25%) as red solid. $^1$HNMR (300 MHz, $CD_3OD$) δ (ppm): 1.28-1.87 (m, 184H); 2.42-249 (m, 35H); 3.00 (s, 3H); 3.12-3.23 (m 60H); 3.34-3.40 (m, 63H); 3.52-4.01 (m, 826H); 4.25-4.39 (m, 16H); 7.17-7.20 (m, 2H); 8.48-8.51 (m, 2H); LCMS (philic method, TFA buffer) RT=8.96 min. ESI MS (+ve) 2095 $[M+7H]^+$; 1834 $[M+8H]^+$; 1630 $[M+9H]^+$.

1.26 (MeTzPh)-$PEG_4$CO-NH$PEG_{24}$-CO[N(PN)$_2$][Lys]$_{16}$[$NH_2$·TFA]$_{32}$ G4 Compound 56

Prepared as per compound 54 and deprotected using TFA/AcOH to give Compound 56 (0.078 g, 78%) as a red solid. LCMS (philic method, TFA buffer) RT=7.74 min. ESI MS (+ve) 2095 $[M+7H]^+$; 1834 $[M+8H]^+$; 1630 $[M+9H]^+$.

1.27 (MeTzPh)-$PEG_4$CO-NH$PEG_{24}$-CO[N(PN)$_2$][Lys]$_{32}$[(α-$NH_2$. TFA)(ε-NH-CO$PEG_{1100}$)]32 G5 Compound 57

To a stirred solution of HO-Lys(α-NHBoc)(ε-NH-CO$PEG_{1100}$) (0.476 g, 0.354 mmol) and PyBOP (0.170 g, 0.327 mmol) in DMF (3.0 mL) under an atmosphere of $N_2$ was added NMM (180 μL, 0.500 mmol). After 10 min, that solution was added to (MeTzPh)-$PEG_4$CO—NH$PEG_{24}$-CO[N(PN)$_2$][Lys]$_{16}$[$NH_2$·TFA]$_{32}$ Compound 56 (0.078 g, 0.00850 mmol). The ensuing reaction mixture was left to stir overnight at room temperature. The volatiles were removed in vacuo and the resulting crude was dissolved in $H_2O$ (1.0 mL) and TFA (1.0 mL) was slowly added. The reaction was left stirring at room temperature overnight. The reaction was diluted with $H_2O$ (12 mL) and purified by centrifugation using Millipore Amicon Ultra-15 Centrifugal Filter Unit (10 kDa MWCO). The retentate was freeze-dried overnight to give product Compound 57 (0.374 g, 91%) as pink solid. 1HNMR (300 MHz, $D_2O$) δ (ppm): 1.41-1.87 (m, 376H); 2.52-2.56 (m, 64H); 3.09 (s, 3H); 3.17-3.24 (m, 126H); 3.41 (s, 93H) 3.48-3.98 (m, 2960H); 4.27-4.39 (m, 32H); 7.30-7.33 (m, 2H); 8.46-8.49 (m, 2H); HPLC Analysis (philic method, ammonium formate as buffer) RT=8.60 min.

1.28 (MeTzPh)$PEG_4$CO-NH$PEG_{24}$CO—[N(PN)$_2$][Lys]$_8$[((α-NHCy5)$_1$(α-NHAc)$_7$)(ε-NH-CO$PEG_{1100}$)$_8$], G3, Compound 37

A solution of Cy5-NHS ester (1.0 mL of a 1 mg/mL solution in DMF; 1.0 mg, 1.59 μmol) was added to vial containing (MeTzPh)$PEG_4$CO-NH$PEG_{24}$CO—[N(PN)$_2$][Lys]$_8$[((L-$NH_2$·HCl)$_8$)(ε-NH-CO$PEG_{1100}$)$_8$], Compound 53 (20 mg, 1.59 μmol) in DMF (0.5 mL). To this solution was added NMM (10 μL, 91.0 μmol) and the ensuing reaction mixture protected from light and stirred at RT. After 3.5 h acetic anhydride (20 μL, 212 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 19.3 mg (93%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.30.

1.29 (MeTzPh)$PEG_4$CO-NH$PEG_{24}$CO—[N(PN)$_2$][Lys]$_{16}$[((α-NHCy5)$_1$(α-NHAc)$_{15}$)(ε-NH-CO$PEG_{1100}$)$_{16}$], G4, Compound 38

A solution of Cy5-NHS ester (520 μL of a 1 mg/mL solution in DMF; 0.52 mg, 844 nmol) was added to vial containing (MeTzPh)$PEG_4$CO-NH$PEG_{24}$CO—[N(PN)$_2$][Lys]$_{16}$[((α-$NH_2$·HCl)$_{16}$)(ε-NH-CO$PEG_{1100}$)$_{16}$], Compound 55 (20 mg, 844 nmol) in DMF (1.0 mL). To this solution was added NMM (10 μL, 94.5 μmol) and the ensuing reaction mixture protected from light and stirred at RT. After 3.5 h acetic anhydride (20 μL, 230 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 19.9 mg (98%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.40

1.30 (MeTzPh)$PEG_4$CO-$NHPEG_{24}$CO—[N(PN)$_2$][Lys]$_{32}$ [((α-NHCy5)$_1$(α-NHAc)$_{31}$)(ε-NH-$COPEG_{1100}$)$_{32}$], G5, Compound 39

A solution of Cy5-NHS ester (300 μL of a 1 mg/mL solution in DMF; 0.30 mg, 487 nmol) was added to vial containing (MeTzPh)$PEG_4$CO-$NHPEG_{24}$CO—[N(PN)$_2$][Lys]$_{32}$[(α-$NH_2$·HCl)$_{32}$(ε-NH-$COPEG_{1100}$)$_{32}$], Compound 57 (20 mg, 435 nmol) in DMF (1.2 mL). To this solution was added NMM (11 uL, 97.5 μmol) and the ensuing reaction mixture protected from light and stirred at RT. After 3.5 h acetic anhydride (22 μL, 237 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 18.7 mg (91%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.50.

1.31 Cabazitaxel (CTX)-2'-OCOO-oPNP Ester, Compound 58

To a solution of Cabazitaxel (CTX, 111.0 mg, 0.132 mmol) in DMF (3 mL) were added Triethylamine (37.0 μL, 0.264 mmol), DMAP (1.64 mg, 0.013 mmol) and p-nitrophenyl chloroformate (24.0 mg, 0.12 mmol). The mixture was stirred for 2 h at room temperature. Solvent was removed under the reduced pressure and the residue obtained purified using column chromatography over silica gel using a gradient of 0:100 to 50:50 (Ethyl Acetate:Hexane) to give the title product as a white solid (28 mg, 21%). LCMS (philic method, TFA buffer) $R_t$=6.55 min. ESI MS (+ve) 1001 $[M]^+$; calc. m/z for $C_{52}H_{60}N_2O_{18}$ $[M]^+$: 1001

1.32 Fmoc-Val-Ala-PAB-P-Trigger-(NMeBoc), Compound 59

The compound may be obtained as described in Dal Corso et. al Angew. Chem Int. Ed. 2020, 59, 4176-4181. It may also be prepared as follows. Fmoc-Val-Ala-PAB-O-oPNP ester (Iris Biotech, 127.0 mg, 0.186 mmol) and (S)-tert-butyl methyl(pyrrolidine-2-ylmethyl)carbamate (Ascension Chemical, 42.0 mg, 0.195 mmol) were taken in a round bottom flask followed by addition of THE (5 mL). The reaction mixture stirred at room temperature for 2 h under inert atmosphere. LCMS analysis of the reaction mixture showed formation of the title compound. Solvent was removed under reduced pressure and the product obtained will be used in next reaction without purification. LCMS (philic method, TFA buffer), $R_t$=6.60 min. ESI MS (+ve) 756 $[M]^+1$; calc. m/z for $C_{42}H_{53}N_5O_8$ $[M]^+1$: 756]

1.33 TFA·$NH_2$-Val-Ala-PAB-P-Trigger-(NMeBoc), Compound 60

To a stirred solution of Compound 59 (141.0 mg, 0.186 mmol) in DMF (3 mL) was added piperidine (0.6 mL, 6.07 mmol) at 0° C. and the reaction mixture stirred for 1 h. Solvent was removed under recued pressure and the residue obtained dissolved in acetonitrile and purified using preparative HPLC (40-90% MeCN, 0.05% TFA buffer, RT~45 min) to give title compound as a colourless liquid after lyophilisation (63.0 mg, 52%). LCMS (philic method, TFA buffer) ESI MS (+ve) 556 [M]+Na; calc. m/z for $C_{27}H_{43}N_5O_6$ [M]+Na: 556; $^1$H-NMR (300 MHz, MeOD) δ (ppm): 7.62-7.51 (m, 2H), 7.44-7.25 (m, 2H), 5.18-4.98 (bs, 2H), 4.56 (q, J=9.0 Hz, 1H), 4.13 (bs, 1H), 3.72 (d, J=6.0 Hz, 1H), 3.51-3.36 (m, 2H), 2.89 (s, 1H), 2.73 (bs, 1H), 2.35-2.13 (m, 1H), 2.05-1.70 (m, 4H), 1.59-1.36 (m, 11H), 1.18-1.00 (m, 6H).

1.34 COOH-$PEG_9$-Val-Ala-PAB-P-Trigger-(NMeBoc), Compound 61

To a stirred solution of compound 60 (52.0 mg, 0.081 mmol) in acetonitrile (2 mL) was added DIPEA (87.2 μL, 0.50 mmol) and the reaction mixture cooled to 0° C. COOH-$PEG_9$-NHS ester (Iris Biotech; 86.0 mg, 0.139 mmol) added to the reaction mixture and the reaction mixture stirred at room temperature for 16 h. LCMS analysis of the reaction mixture showed formation of the product LCMS (philic method, TFA buffer; 5-60% acetonitrile over 15 mins), $R_t$=11.32 min. ESI MS (+ve) 1048 [M]+$H_2O$; calc. m/z for $C_{49}H_{83}N_5O_{18}$ $[M]^+H_2O$: 1048]. Solvent was removed under reduced pressure and the product obtained will be used in next reaction without purification.

1.35 COOH-$PEG_9$-Val-Ala-PAB-P-Trigger-(NMe·TFA), Compound 62

To a stirred solution of compound 61 (84.0 mg, 0.081 mmol) in dichloromethane (2 mL) was added TFA (0.5 mL, 6. mmol) at 0° C. and the reaction mixture stirred at room temperature for 1 h. Solvent was removed under recued pressure and the residue obtained dissolved in acetonitrile, purified using preparative HPLC (5-70% Acetonitrile, 0.05% TFA buffer, RT 32-33 min) to give title compound as a thick colourless liquid after lyophilisation (87.0 mg, 100%). LCMS (philic method, FA buffer) ESI MS (+ve) 930 $[M]^+1$; calc. m/z for $C_{45}H_{77}N_5O_{15}$ $[M]^+1$: 930; $^1$H-NMR (300 MHz, MeOD) δ (ppm): 7.64 (d, J=9.0 Hz, 2H), 7.37 (d, J=9.0 Hz, 2H), 5.13 (d, J=9.0 Hz, 1H), 4.61-4.40 (m, 2H), 4.19 (d, J=6.0 Hz, 1H), 3.85 (t, J=6.0 Hz, 1H), 3.79-3.69 (m, 4H), 3.69-3.51 (m, 35H), 3.17-3.05 (m, 2H), 2.85 (s, 1H), 2.76-2.68 (m, 3H), 2.92 (t, J=6.0 Hz, 1H), 2.62-2.45 (m, 4H), 2.27-1.84 (m, 4H), 1.46 (d, J=9.0 Hz, 2H), 1.08-0.92 (m, 6H).

1.36 COOH-$PEG_9$-Val-Ala-PAB-P-Trigger-NMeCO-CTX, Compound 63

To a solution of Compound 46 (28.0 mg, 0.027 mmol) in DMF (3 mL) were added DIPEA (9.40 μL, 0.54 mmol) and Compound 51 (27.3 mg, 0.027 mmol). The mixture was stirred for 16 h at room temperature. Solvent was removed under the reduced pressure and the residue obtained dissolved in acetonitrile (2 mL). This solution was purified by preparative HPLC (5-60% ACN, $R_t$ 32.2-34.3 min) to give the title product as a white solid (26 mg, 56%) after lyophilisation. LCMS (philic method, TFA buffer) $R_t$=5.57 min. ESI MS (+ve) 1792 $[M]^+$; calc. m/z for $C_{90}H_{130}N_6O_{31}$ $[M]^+$: 1792

Example 1b Synthesis of BCN and DBCO Linkers 1.37 BCN-$PEG_2$-Glu-CO-$NHPEG_{24}CO_2H$, Compound 31

To a solution of $NH_2$-$PEG_{24}$-COOH (93.7 mg, 0.082 mmol) in a mixture of water/THF (1:1, 4 mL) was added sodium bicarbonate (15.2 mg, 0.181 mmol). The mixture was stirred for 5 min. at room temperature before a solution of BCN-$PEG_2$-NHS ester (50 mg, 0.093 mmol) in THE (2 mL) was added. The resulting reaction mixture was stirred for 15 h at RT. The volatiles were then removed under reduced pressure and ACN (2.5 mL) was added to the resulting aqueous suspension. This solution was purified by preparative HPLC (5-60% ACN, Rf 32.2-34.3 min) to give the title product as a white solid (42 mg, 33%) after lyophilisation $^1$H-NMR (300 MHz, $D_2O$) δ (ppm): 0.85-0.92 (m, 2H); 1.25-1.35 (m, 1H); 1.43-1.57 (m, 2H); 1.73-1.83

(m, 2H); 2.09-2.25 (m, 9H); 2.39 (t, J=9.0 Hz, 2H); 3.21-3.31 (m, 6H); 3.35-3.85 (m, 106H); 4.10 (d, J=9.0 Hz, 2H). LCMS (philic method, formic buffer) $R_t$=10.28 min.; ESI MS (+ve) m/z 1566.7 $[M]^+$.

1.38 BCN-$PEG_2$-Glu-CO-$NHPEG_{24}$CO-$NHPEG_3$-TCO, Compound 32

To a stirred solution of BCN-$PEG_2$-Glu-CO-$NHPEG_{24}$-COOH Compound 31 (10.0 mg, 0.006 mmol) in DMF (3.0 mL) were added PyBOP (3.64 mg, 0.007 mmol), NMM (1.31 μL, 0.012 mmol) followed by TCO-$PEG_3$-$NH_2$ (2.41 mg, 0.007 mmol). The ensuing reaction mixture was stirred at room temperature overnight. The solvent was then removed under reduced pressure and the resulting residue dissolved in ACN (2 mL) then filtered through 0.45 μm filter. The collected filtrate was purified by preparative HPLC (30-50% ACN $R_t$ 40-42 min) and the product-containing fractions concentrated under reduced pressure to remove ACN. The remaining aqueous solution was lyophilized overnight to give the title product as a white solid (4.7 mg, 39%). $^1$H-NMR (300 MHz, $CD_3OD$) δ (ppm): 0.89-1.05 (m, 2H), 1.26-1.48 (m, 2H), 1.52-1.79 (m, 5H), 1.83-2.06 (m, 6H), 2.11-2.39 (m, 12H), 2.48 (t, 2H, J=6.0 Hz), 3.35-3.44 (m, 6H), 3.47-3.79 (m, 102H), 3.83-3.92 (m, 1H), 4.16 (d, 2H, J=6.0 Hz), 4.26-4.41 (m, 1H), 4.58 (bs, 10H), 5.39-5.74 (m, 3H). LCMS (philic method, formic acid buffer) $R_t$=11.0 min. ESI MS (+ve) 1894.0 $[M]^+$; calc. m/z for $C_{90}H_{165}N_5O_{36}$ $[M]^+$: 1894.2

1.39 DBCO-Glu-$NHPEG_{24}$CO-$NHPEG_3$-TCO, Compound 33

To a stirred solution of DBCO-Glu-$NHPEG_{24}$COOPFP (50.0 mg, 0.031 mmol) in DMF (3 mL) were added TCO-$PEG_3$-$NH_2$ (10.7 mg, 0.031 mmol) followed by NMM (4.08 μL, 0.037 mmol). The ensuing reaction mixture was stirred at room temperature for 3 hrs, then concentrated under reduced pressure. The resulting residue was dissolved in ACN (2 mL), filtered through 0.45 μm filter and the filtrate purified by preparative HPLC (40-70% ACN $R_t$ 27-29 min). The product-containing fractions were concentrated under reduced pressure to remove ACN and the remaining aqueous solution lyophilized overnight to give the title product as a viscous colourless liquid (25.0 mg, 42%). $^1$H-NMR (300 MHz, $CD_3OD$) δ (ppm): 1.31-1.62 (m, 4H), 1.60-1.83 (m, 6H), 1.92-2.16 (m, 4H), 2.25 (t, 2H, J=6.0 Hz), 2.91-3.03 (m, 4H), 3.12-3.58 (m, 78H), 3.59-3.69 (m, 1H), 4.01-4.18 (m, 1H), 4.92 (d, 2H, J=15H), 5.15-5.49 (m, 3H), 6.95-7.59 (m, 8H). LCMS (philic method, formic acid buffer) $R_t$=7.0 min. ESI MS (+ve) 1775.0.0 $[M]^+$; calc. m/z for $C_{88}H_{148}N_4O_{32}$ $[M]^+$: 1775.12

1.40 MeTzPh-$PEG_4PEG_{24}$-CO[N$(PN)_2$]$[Lys]_8$[(α-Cy5)$_1$(α-NHAc)$_7$(ε-$NHPEG_{1100}$)$_8$], G3, Compound 37

A solution of Cy5-NHS ester (1.0 mL of a 1 mg/mL solution in DMF; 1.0 mg, 1.59 μmol) was added to vial containing MeTzPh-$PEG_4PEG_{24}$-CO[N$(PN)_2$]$[Lys]_8$(α-$NH_2$)$_8$(ε-$NHPEG_{1100}$)$_8$], (20 mg, 1.59 μmol) in DMF (0.5 mL). To this solution was added NMM (10 μL, 91.0 μmol) and the ensuing reaction mixture protected from light and stirred at RT. After 3.5 h acetic anhydride (20 μL, 212 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 19.3 mg (93%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.30.

1.41 MeTzPh-$PEG_4PEG_{24}$-CO[N$(PN)_2$]$[Lys]_{16}$[(α-Cy5)$_1$(α-NHAc)$_{15}$(ε-$NHPEG_{1100}$)$_{16}$], G4, Compound 38

A solution of Cy5-NHS ester (520 μL of a 1 mg/mL solution in DMF; 0.52 mg, 844 nmol) was added to vial containing MeTzPh-$PEG_4PEG_{24}$-CO[N$(PN)_2$]$[Lys]_{16}$[(α-$NH_2$)$_{16}$(ε-$NHPEG_{1100}$)$_{16}$], (20 mg, 844 nmol) in DMF (1.0 mL). To this solution was added NMM (10 μL, 94.5 μmol) and the ensuing reaction mixture protected from light and stirred at RT. After 3.5 h acetic anhydride (20 μL, 230 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 19.9 mg (98%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.40.

1.42 MeTzPh-$PEG_4PEG_{24}$-CO[N$(PN)_2$]$[Lys]_{32}$[(α-Cy5)$_1$(α-NHAc)$_{31}$(ε-$NHPEG_{1100}$)$_{32}$], G5, Compound 39

A solution of Cy5-NHS ester (300 μL of a 1 mg/mL solution in DMF; 0.30 mg, 487 nmol) was added to vial containing MeTzPh-$PEG_4PEG_{24}$-CO[N$(PN)_2$]$[Lys]_{32}$[(α-$NH_2$)$_{32}$(ε-$NHPEG_{1100}$)$_{32}$], (20 mg, 435 nmol) in DMF (1.2 mL). To this solution was added NMM (11 μL, 97.5 μmol) and the ensuing reaction mixture protected from light and stirred at RT. After 3.5 h acetic anhydride (22 μL, 237 μmol) was added and the reaction mixture left to stir overnight. The reaction mixture was concentrated under reduced pressure then taken up in MQ water (5 mL) and divided in two for purification through two (pre-equilibrated) PD10 columns. Once the sample entered the column bed, the sample was eluted with 3.5 mL MQ water and the filtrate collected. The filtrates were combined and freeze dried overnight. Lyophilisation gave the title product as a bright blue powder, 18.7 mg (91%). HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.50.

1.43 BHA$[Lys]_4$[((α-NH-$COPEG_{24}$NH-$COPEG_4$(PhTzMe))$_{1-3}$(α-Lys(α-NHCy5)(ε-NHDFO))$_1$(α-$NH_2$)$_{0-2}$)(ε-NH-$COPEG_{1000}$)$_4$], G2, Compound 99

Prepared according to General Procedure C using BHA $[Lys]_4$[(α-NH-$COPEG_{24}$NH-$COPEG_4$(PhTzMe))$_{1-3}$(α-$NH_2$)$_{1-3}$)(ε-NH-$COPEG_{1000}$)$_4$], G2, Compound 107 (3.0 mg, 0.414 μmol) and HO-Lys[(α-Cy5)(ε-DFO)] Compound 108 (0.56 mg, 0.414 μmol) and purified by spin column (10 kDa MW cut off washing with 10×450 μL MQ water) to give the desired product Compound 99 (final concentration of 3.56 mg in 300 μL MQ water).

1.44 BHA$[Lys]_8$[((α-NH-$COPEG_{24}$NH-$COPEG_4$(PhTzMe))$_{1-4}$(α-Lys(α-NHCy5)(ε-NHDFO))$_1$(α-$NH_2$)$_{5-6}$)(ε-NH-$COPEG_{412}$)$_8$], G3, Compound 100

Prepared according to General Procedure C using BHA $[Lys]_8$[((α-$NHCOPEG_{24}$NH-$COPEG_4$(PhTzMe))$_{1-4}$(α-$NH_2$)$_{4-7}$))(ε-NH-$COPEG_{412}$)$_8$], G3, Compound 109 (2.97 mg, 0.452 μmol) and HO-Lys[(α-NHCy5)(ε-NHDFO)] Compound 40 (0.61 mg, 0.452 μmol) and purified by spin column (10 kDa MW cut off washing with 10×450 μL MQ water) to give the product Compound 100 at (final concentration of 3.60 mg in 300 μL MQ water).

1.45 BHA[Lys]$_8$[((α-NH-COPEG$_{24}$NH-COPEG$_4$(PhTzMe))$_1$(α-Lys(α-NHCy5)(ε-NHDFO))$_1$(α-NH$_2$)$_6$)(ε-NH-COPEG$_{1000}$)$_8$], G3, Compound 101

Prepared according to General Procedure C, using BHA[Lys]$_8$[((α-NHCOPEG$_{24}$NH-COPEG$_4$(PhTzMe))$_1$(α-NH$_2$)$_7$)(ε-NHCOPEG$_{1000}$)$_8$], G3, Compound 110 (3.14 mg, 0.234 μmol) and HO-Lys(α-NHCy5)(ε-NHDFO) Compound 108 (0.32 mg, 0.234 μmol) and purified by spin column (10 kDa MW cut off washing with 10×450 μL MQ water) and purified by spin column (10 kDa MW cut off washing with 10×450 μL MQ water) to give the product Compound 27 (final concentration of 3.45 mg in 300 μL MQ water).

1.46 BHA[Lys]$_{16}$[((α-NH-COPEG$_{24}$NH-COPEG$_4$(PhTzMe))$_1$(α-Lys(α-NHCy5)(ε-NHDFO))$_1$(α-NH$_2$)$_{14}$)(ε-NH-COPEG$_{1000}$)$_{16}$], G4, Compound 102

Prepared according to General Procedure C, using BHA[Lys]$_{16}$[((α-NH-COPEG$_{24}$NH-COPEG$_4$(PhTzMe))$_1$(α-NH$_2$)$_{15}$)(ε-NH-COPEG$_{1000}$)$_{16}$], G4, Compound 111 (11.8 mg, 0.454 μmol) and HO-Lys(α-NHCy5)(ε-NHDFO) Compound 108 (0.62 mg, 0.454 μmol) and purified by spin column (10 kDa MW cut off washing with 10×450 μL MQ water) to give 9.3 mg of Compound 28 as a blue solid (after lyophilisation).

1.47 BHA[Lys]$_{32}$[((α-NH-COPEG$_{24}$NH-COPEG$_4$(PhTzMe))$_{1-4}$(α-Lys(α-NHCy5)(ε-NHDFO))$_1$(α-NH$_2$)$_{27-30}$)(ε-NH-COPEG$_{1000}$)$_{32}$], G5, Compound 103

Prepared according to General Procedure C, using BHA[Lys]$_{16}$[((α-NH-COPEG$_{24}$NH-COPEG$_4$(PhTzMe))$_{1-4}$(α-NH$_2$)$_{27-30}$)(ε-NH-COPEG$_{1000}$)$_{32}$], G4, Compound 112 (12.9 mg, 0.271 μmol) and HO-Lys(α-Cy5)(ε-DFO) Compound 108 (0.37 mg, 0.271 μmol) and purified by spin column (10 kDa MW cut off washing with 10×450 μL MQ water) to give 8.4 mg of product Compound 103 as a blue solid after lyophilisation.

1.48 BHA[Lys]$_4$[((α-Lys(α-NHCy5)(α-NHDFO))$_1$(α-NH$_2$)$_3$)(ε-NH-COPEG$_{24}$NH-COPEG$_4$(PhTzMe)$_4$], G2, Compound 105

To a stirred solution of BHA[Lys]$_4$[(α-NH$_2$·HCl)$_4$(ε-NH-COPEG$_{24}$NH-COPEG$_4$(PhTzMe)$_4$], G2, Compound 113 (11.0 mg, 0.0015 mmol) at RT in DMF (3 mL) was added NMM (3.32 μL, 0.039 mmol), HO-Lys[(α-NHCy5)(ε-NHDFO)] Compound 108 (2.06 mg, 0.0015 mmol) and PyBOP (1.18 mg, 0.0022 mmol). After 18 h, the volatiles were removed under reduced pressure and the blue solid residue was dissolved in MQ water and the solution filtered (0.45 μm acrodisc syringe filter). The filtrate was concentrated by spin column (Amicon Ultra, 0.5 mL, 3 kDa MW cut off) and the retentate was washed repeatedly with MQ water (10×450 μL) to give Compound 24 (concentration 10 mg/mL in MQ water; 1.3 mL. LCMS (philic method, TFA buffer), Gradient: 20 to 90% Acetonitrile over 8 mins; $R_t$=5.64 mins; 1HNMR (300 MHz, $D_2O$) δ (ppm): 8.52 (d, 8H, J=9.0 Hz), 8.32 (s, 1H), 8.29-8.17 (m, 2H), 7.78-7.70 (m, 2H), 7.69-7.62 (m, 2H), 7.57-7.47 (m, 2H), 7.48-7.25 (m, 16H), 7.21 (d, 8H, J=9.9 Hz), 7.15-7.08 (m, 1H), 7.06-7.00 (m, 1H), 6.70-6.60 (m, 2H), 6.21-6.12 (m, 2H), 4.37-4.20 (m, 14H), 4.18-4.06 (m, 8H), 3.98-3.50 (m, 480H), 3.48-3.34 (m, 15H), 3.27-3.06 (m, 18H), 3.06-2.97 (m, 19H), 2.88 (s, 8H), 2.54-2.40 (m, 19H), 2.08-1.98 (m, 28H), 1.93-1.12 (m, 99H), 1.00-0.82 (m, 8H).

1.49 BHA[Lys]$_4$[((α-NH-COPEG$_{24}$NH-COPEG$_4$(PhTzMe))$_1$(α-NH$_2$)$_3$)(ε-NH-COPEG$_{1000}$)$_4$], G2, Compound 107

Prepared according to the General Procedure C using BHA[Lys]$_4$[(α-NH$_2$·TFA)$_4$(ε-NH-COPEG$_{1000}$)$_4$] (50.0 mg, 0.007 mmol) and HOOCPEG$_{24}$NH-COPEG$_4$(PhTzMe) (Click Chemistry Tools, 13.39 mg, 0.010 mmol) except the reaction vessel was wrapped in foil to exclude light and the residue was purified by SEC (Sephadex™ LH-20) using methanol as the eluent to give the product Compound 107 (44.00 mg, 77%); $^1$HNMR (300 MHz, $D_2O$) δ (ppm): 8.42-8.26 (m, 2H), 7.44-7.11 (m, 12H), 6.04 (bs, 1H), 4.44-4.07 (m, 8H), 4.07-3.37 (m, 556H), 3.33 (s, 12H), 3.25-2.90 (m, 17H), 2.62-2.43 (m, 2H), 1.96-0.97 (m, 48H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.08-9.01.

1.50 BHA[Lys]$_8$[((α-NH-COPEG$_{24}$NH-COPEG$_4$(PhTzMe))$_1$(α-NH$_2$)$_7$)(ε-NH-COPEG$_{412}$)$_8$], G3, Compound 109

Prepared according to the General Procedure C using BHA[Lys]$_8$[(α-NH$_2$·TFA)$_8$(ε-NH-COPEG$_{412}$)$_8$] (50.0 mg, 0.008 mmol) and HOOC-PEG$_{24}$NH-COPEG$_4$(PhTzMe) (Click Chemistry Tools; 11.2 mg, 0.008 mmol) except the reaction vessel was wrapped in foil to exclude light and the residue was purified by SEC (Sephadex™ LH-20) using methanol as the eluent to give the product Compound 109 (29 mg, 55%); $^1$HNMR (300 MHz, $D_2O$) δ (ppm): 8.43-8.20 (m, 2H), 7.50-7.09 (m, 10H), 6.03 (bs, 1H), 4.41-4.05 (m, 10H), 4.01-3.41 (m, 258H), 3.31 (s, 16H), 3.24-2.83 (m, 28H), 2.41 (bs, 13H), 2.00-0.98 (m, 75H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$=8.16-8.93 min.

1.51 BHA[Lys]$_8$[((α-NH-COPEG$_{24}$NH-COPEG$_4$(PhTzMe))$_1$(α-NH$_2$)$_7$)(ε-NH-COPEG$_{1000}$)$_8$], G3, Compound 110

Prepared according to the General Procedure C using BHA[Lys]$_8$[(α-NH$_2$·TFA)$_8$(ε-NH-COPEG$_{1000}$)$_8$] (100.0 mg, 0.007 mmol) and HOOCPEG$_{24}$NH-COPEG$_4$(PhTzMe) (Click Chemistry Tools; 15.97 mg, 0.010 mmol) except the reaction vessel was wrapped in foil to exclude light and the residue was purified by SEC (Sephadex™ LH-20) using methanol as the eluent to give the product Compound 19 (SPL-9248) (69 mg, 66%); $^1$HNMR (300 MHz, $D_2O$) δ (ppm): 8.45-8.25 (m, 2H), 7.47-7.07 (m, 12H), 6.07 (bs, 1H), 4.45-4.05 (m, 12H), 4.04-3.37 (m, 936H), 3.32 (s, 25H), 3.23-2.88 (m, 32H), 2.59-2.32 (m, 6H), 1.90-0.98 (m, 90H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$=8.21-9.15 min.

1.52 BHA[Lys]$_{16}$[((α-NH-COPEG$_{24}$NH-COPEG$_4$(PhTzMe))$_1$(α-NH$_2$)$_{15}$)(ε-NH-COPEG$_{1000}$)$_{16}$, G4, Compound 111

Prepared according to the General Procedure C using BHALys[Lys]$_2$[Lys]$_4$[Lys][Lys]$_{16}$[(α-NH$_2$·TFA)$_{16}$(ε-NH-COPEG$_{1000}$)$_{16}$] (Ref 1)(100.0 mg, 0.004 mmol) and HOOCPEG$_{24}$NH-COPEG$_4$(PhTzMe) (Click Chemistry Tools; 6.74 mg, 0.005 mmol) except the reaction vessel was wrapped in foil to exclude light and the residue was purified by SEC (Sephadex™ LH-20) using methanol as the eluent to give the product Compound 111 (63 mg, 65%); $^1$HNMR (300 MHz, $D_2O$) δ (ppm): 8.45-8.28 (m, 2H), 7.47-7.07 (m, 12H), 6.03 (bs, 1H), 4.40-4.08 (m, 23H), 4.06-3.38 (m, 1906H), 3.33 (s, 56H), 3.29-2.91 (m, 78H), 2.63-2.45 (m, 3H), 1.98-0.98 (m, 200H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 243 nm, 0.4 mL/min, $R_t$=8.51-9.02 min.

1.53 BHA$[Lys]_{32}[((\alpha$-NH-COPEG$_{24}$NH-COPEG$_4$(PhTzMe))$_{1-4}$($\alpha$-NH$_2$)$_{28-31}$)($\epsilon$-NH-COPEG$_{1000}$)$_{32}$], G5, Compound 112

Prepared according to the General Procedure C using BHA$[Lys]_{32}[(\alpha$-NH$_2$·TFA)$_{32}$($\epsilon$-NH-COPEG$_{1000}$)$_{32}$] (100.0 mg, 0.002 mmol) and HOOCPEG$_{24}$NH-COPEG$_4$(PhTzMe) (Click Chemistry Tools; 3.38 mg, 0.005 mmol) except the reaction vessel was wrapped in foil to exclude light and the residue was purified by SEC (Sephadex™ LH-20) using methanol as the eluent to give the product Compound 21 (68 mg, 72%); $^1$HNMR (300 MHz, $D_2O$) δ (ppm): 8.44-8.29 (m, 2H), 7.44-7.09 (m, 12H), 6.02 (bs, 1H), 4.37-4.11 (m, 31H), 4.08-3.37 (m, 2937H), 3.32 (s, 83H), 3.27-2.88 (m, 116H), 2.59-2.42 (m, 3H), 2.18-0.92 (m, 313H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$=8.77 min.

1.54 BHA$[Lys]_4[(\alpha$-NHBoc)$_4$($\epsilon$-NH-COPEG$_{24}$NH-COPEG$_4$(PhTzMe)$_4$], G2, Compound 113

To a stirred solution of BHA$[Lys]_4[(\alpha$-NHBoc)$_4$($\epsilon$-NH$_2$)$_4$] (46.0 mg, 0.031 mmol) in DMF at RT was added NMM (68.0 μL, 0.620 mmol), HOOCPEG$_{24}$NH-COPEG$_4$(PhTzMe) (Click Chemistry Tools; 43.0 mg, 0.155 mmol) and PyBOP (81.0 mg, 0.155 mmol). After 16 h, the reaction mixture was dissolved in ACN:MQ water (3 mL, 1:1 v/v) and the solution filtered (0.45 μm acrodisc syringe filter). The filtrate was purified by preparative HPLC; 30-80% ACN over 60 min, Mobile phase: MQ water and acetonitrile, $R_t$ 33.0-36.0 min. to give Compound 22 as a pink solid 52 mg (22%). LCMS (philic method, TFA buffer) $R_t$=5.66 min; $^1$HNMR (300 MHz, $D_2O$) δ (ppm): 8.52 (d, 8H, J=9.0 Hz), 7.40-7.26 (m, 10H), 7.20 (d, 8H, J=9.0 Hz), 6.23-6.17 (m, 1H), 4.36-4.21 (m, 10H), 3.99-3.83 (m, 13H), 3.82-3.46 (m, 487H), 3.46-3.32 (m, 22H), 3.27-3.02 (m, 15H), 3.02 (s, 12H), 2.54-2.38 (m, 17H), 1.92-1.14 (m, 89H).

1.55 BHA$[Lys]_4[(\alpha$-NH$_2$·HCl)$_4$($\epsilon$-NH-COPEG$_{24}$NH-COPEG$_4$(PhTzMe)$_4$], G2, Compound 114

To a stirred solution of BHA$[Lys]_4[(\alpha$-NHBoc)$_4$($\epsilon$-NH-COPEG$_{24}$NH-COPEG$_4$(PhTzMe)$_4$], G2, Compound 113 (48.0 mg) in methanol (2 mL) was added a solution of 3M HCl in methanol (2 mL) and the reaction mixture stirred at room temperature for 20 hrs. The volatiles were removed under reduced pressure to give BHALys$[Lys]_2[Lys]_4[(\alpha$-NH$_2$·HCl)$_4$($\epsilon$-NH-COPEG$_{24}$NH-COPEG$_4$(PhTzMe)$_4$], G2, Compound 23 as a pink solid 41.0 mg (91%). LCMS (philic method, TFA buffer), Gradient: 20 to 90% Acetonitrile over 8 mins; $R_t$=5.27 mins.

1.56 HO-Lys[($\alpha$-NHCy5)($\epsilon$-NHDFO)], Compound 108

To a stirred solution of Compound 115 (20.0 mg, 0.032 mmol) in DMSO (5 mL) was added DIPEA (32 μL, 0.224 mmol) followed byp-SCN-Deferoxamine (Macrocyclics, 24.0 mg, 0.032 mmol). The reaction mixture stirred at room temperature for 4 h and then concentrated by blowing a stream of nitrogen gas over the solution for several hours. The residue obtained was then purified by preparative HPLC: 30-60% ACN in MQ water+0.1% TFA (60 min, $R_t$ 39-42 min) to give the product Compound 108 as a blue solid 15 mg (34%). LCMS (philic method, TFA buffer) $R_t$=5.93 min; ESI MS (+ve) 1364 [M]$^+$; calc. m/z for $C_{71}H_{103}N_{12}O_{11}S_2$ [M]$^+$=1364 $^1$HNMR (300 MHz, $D_2O$) δ (ppm): 8.25 (t, 2H, J=12.0 Hz), 7.56-7.18 (m, 9H), 6.65 (t, 1H, J=12.0 Hz), 6.37-6.15 (m, 2H), 4.43-4.32 (m, 1H), 4.11 (t, 2H, J=6.0 Hz), 3.70-3.46 (m, 8H), 3.22-3.10 (m, 3H), 2.86-2.69 (m, 3H), 2.56-2.38 (m, 3H), 2.31 (t, 2H, J=6.0 Hz), 2.11 (s, 2H), 1.96-1.18 (m, 32H).

1.57 HO-Lys[($\alpha$-NHCy5) ($\epsilon$-NH$_2$)], Compound 115

To a stirred solution of Compound 116 (36 mg; 0.043 mmol) in DMF (4 mL) was added piperidine (1.5 mL) and the reaction mixture was stirred at room temperature for 1 h. The solvent was removed under reduced pressure and the residue was purified by preparative HPLC; 20-90% ACN in MQ water+0.1% formic acid (60 min. $R_t$ 32.0-33.0 min) to give the product Compound 59 as a blue solid 12 mg (44%). LCMS (philic method, TFA buffer) $R_t$=7.65 min; ESI MS (+ve) 611 [M]$^+$; calc. m/z for $C_{38}H_{51}N_4O_3$ [M]$^+$=611.

1.58 Synthesis of HO-Lys[($\alpha$-NHCy5)($\epsilon$-NHDFO)] wedge, Compound 116

To a stirred solution of HO-Lys[($\alpha$-NH$_2$·TFA)($\epsilon$-NHFmoc)] (57.0 mg, 0.118 mmol) in DMF (5 mL) was added NMM (52 μL, 0.472 mmol) and Cyanine5 NHS ester (Lumiprobes, 40.0 mg, 0.059 mmol). The reaction mixture was stirred at room temperature overnight whereupon the volatiles were removed in vacuo. The residue was dissolved in ACN:MQ water (3 mL 1:1 v/v) and the solution filtered (0.45 μm acrodisc syringe filter). The filtrate was purified by preparative HPLC; 20-90% ACN in MQ water+0.1% formic acid (60 min, $R_t$ 39.0-42.0 min) to give Compound 58 as a blue solid 33 mg (67%). LCMS (philic method, TFA buffer) $R_t$=10.54 min; ESI MS (+ve) 833 [M]$^+$; calc. m/z for $C_{53}H_{61}N_4O_5$ [M]$^+$=833.46 $^1$HNMR (300 MHz, $D_2O$) δ (ppm): 8.21 (t, 2H, J=15.0 Hz), 7.79 (d, 2H, J=6.0 Hz), 7.63 (d, 2H, J=6.0 Hz), 7.49-7.24 (m, 10H), 6.61 (t, 1H, J=12.0 Hz), 6.29-6.22 (m, 2H), 4.49-4.26 (m, 2H), 0.18 (t, 1H, J=6.0 Hz), 4.07 (t, 2H, J=6.0 Hz), 3.68-3.60 (m, 2H), 3.60 (s, 3H), 3.12 (t, 2H, J=6.0 Hz), 2.28 (t, 2H, J=6.0 Hz), 1.94-1.61 (m, 6H), 1.71 (s, 12H), 1.62-1.19 (m, 6H).

Example 2 Synthesis of Dendrimer Drug Conjugates 2.1 Azido-PEG$_{24}$-CO[N(PN)$_2$]$[Lys]_4[(\alpha$-NH-DGA-3'-NH-Dox)($\epsilon$-NH-COPEG$_{1100}$)]$_4$, G2, Compound 17

Prepared according to General Procedure E, using azido-PEG$_{24}$-CO[N(PN)$_2$]$[Lys]_4[(\alpha$-NH$_2$·TFA)($\epsilon$-NHPEG$_{1100}$)]$_4$ (50.0 mg, 7.24 μmol) to give a dark red oily solid (58 mg, 89%). $^1$H-NMR (300 MHz, $CD_3OD$) δ (ppm): 0.69-2.17 (m, 68H); 2.30-2.50 (m, 8H); 2.56-2.68 (m, 2H); 3.02-3.24 (m, 8H); 3.38-3.41 (m, 24H); 3.52-4.56 (m, 520H); 4.69-4.77 (m, 12H); 5.19-5.57 (m, 4H); 7.15-8.14 (m, 12H). LCMS (philic method, formic buffer)

$R_t$=11.23 min. ESI MS (+ve) transforms to 9016.

2.2 Azido-PEG$_{24}$CO—[N(PN)$_2$]$[Lys]_4[(\alpha$-NH-DGA-14-O-Nemo)($\epsilon$-NH-COPEG$_{1100}$)]$_4$, G2, Compound 64

Prepared according to General Procedure E, using Azido-PEG$_{24}$CO—[N(PN)$_2$]$[Lys]_4[(\alpha$-NH$_2$·TFA)($\epsilon$-NH-COPEG$_{1100}$)]$_4$ (50.0 mg, 7.24 μmol) to give a dark red oily solid (58 mg, 89%). $^1$H-NMR (300 MHz, $CD_3OD$) δ (ppm): 0.69-2.17 (m, 68H); 2.30-2.50 (m, 8H); 2.56-2.68 (m, 2H); 3.02-3.24 (m, 8H); 3.38-3.41 (m, 24H); 3.52-4.56 (m, 520H); 4.69-4.77 (m, 12H); 5.19-5.57 (m, 4H); 7.15-8.14 (m, 12H). LCMS (philic method, formic buffer) $R_t$=11.23 min. ESI MS (+ve) transforms to 9016.

2.3 Azido-PEG$_{24}$-CO[N(PN)$_2$]$[Lys]_8[(\alpha$-NH-DGA-3'-NH-Dox)($\epsilon$-NH-COPEG$_{1100}$)]$_8$, G3, Compound 18

Prepared according to General Procedure E, using azido-PEG$_{24}$-CO[N(PN)$_2$]$[Lys]_8[(\alpha$-NH$_2$·TFA)($\epsilon$-NHPEG$_{1100}$)]$_8$ (50.0 mg, 3.91 μmol) to give a dark red oily solid (50 mg, 75%). $^1$H-NMR (300 MHz, $CD_3OD$) δ (ppm): 0.88-1.93 (m, 120H); 2.33-2.51 (m, 16H); 2.58-2.72 (m, 2H); 3.04-3.24 (m, 8H); 3.35-3.41 (m, 76H); 3.52-4.61 (m, 964H); 5.27-5.45 (m, 8H); 7.13-8.13 (m, 24H). LCMS (philic method, formic buffer) $R_t$=11.30 min 2.4 Azido-$PEG_{24}CO$—$[N(PN)_2][Lys]_8[(\alpha$-NH-DGA-14-O-Nemo)($\varepsilon$-NH-$COPEG_{1100})]_8$, G3, Compound 65

Prepared according to General Procedure E, using azido-$PEG_{24}CO$—$[N(PN)_2][Lys]_8[(\alpha$-$NH_2$·TFA$)_8(\varepsilon$-NH-$COPEG_{1100})_8]$ (50.0 mg, 3.91 μmol) to give a dark red oily solid (50 mg, 75%). $^1$H-NMR (300 MHz, $CD_3OD$) δ (ppm): 0.88-1.93 (m, 120H); 2.33-2.51 (m, 16H); 2.58-2.72 (m, 2H); 3.04-3.24 (m, 8H); 3.35-3.41 (m, 76H); 3.52-4.61 (m, 964H); 5.27-5.45 (m, 8H); 7.13-8.13 (m, 24H). LCMS (philic method, formic buffer) $R_t$=11.30 min 2.5 Azido-$PEG_{24}CO$—$[N(PN)_2][Lys]_8[(\alpha$-NH-Glu-Val-Cit-PAB-MMAE$)_8(\varepsilon$-NH-$COPEG_{570})_8]$, G3, Compound 19

Prepared according to General Procedure F, using azido-$PEG_{24}CO$—$[N(PN)_2][Lys]_8[(\alpha$-$NH_2$·TFA$)_8(\varepsilon$-NH-$COPEG_{570})_8]$ (7.2 mg, 842 nmol) and HO-Glu-vc-PAB-MMAE (10.0 mg, 8.08 μmol) to give the product concentration of 14.6 mg/3.5 mL (240 μM).

2.6 Azido-$PEG_{24}CO$—$[N(PN)_2][Lys]_8[(\alpha$-NH-Glu-Val-Cit-PAB-MMAE$)_8(\varepsilon$-NH-$COPEG_{1100})_8]$, G3, Compound 20

Prepared according to General Procedure F, using azido-$PEG_{24}CO$—$[N(PN)_2][Lys]_8[(\alpha$-$NH_2$·TFA$)_8(\varepsilon$-NH-$COPEG_{1100})_8]$ (10.8 mg, 842 nmol) and HO-Glu-vc-PAB-MMAE (10.0 mg, 8.08 μmol) to give the product concentration of 18 mg/3.5 mL (240 μM).

2.7 Azido-$PEG_{24}CO$—$[N(PN)_2[Lys]_8[(\alpha$-NH-Glu-Val-Cit-PAB-MMAE$)_8(\varepsilon$-NH-$COPEG_{2000})_8]$, G3, Compound 21

Prepared according to General Procedure F, using azido-$PEG_{24}CO$—$[N(PN)_2][Lys]_2[Lys]_4[Lys]_8[(\alpha$-$NH_2$·TFA$)_8(\varepsilon$-NH-$COPEG_{2000})_8]$ (18.1 mg, 842 nmol) and HO-Glu-vc-PAB-MMAE (10.0 mg, 8.08 μmol) to give the product concentration of 25.5 mg/3.5 mL (240 μM).

2.8 Azido-$PEG_{24}CO$—$[N(PN)_2][Lys]_2[Lys]_4[Lys]_8[(\alpha$-NH-DGA-MMAF(OMe)$)_8(\varepsilon$-NH-$COPEG_{1100})_8]$, G3, Compound 22

Prepared according to General Procedure F, using Azido-$PEG_{24}CO$—$[N(PN)_2][Lys]_2[Lys]_4[Lys]_8[(\alpha$-$NH_2$·TFA)(s-$NH_0$-$COPEG_{1100})]_8$ (16.3 mg, 1.28 μmol) and DGA-MMAF (OMe) (10.6 mg, 12.3 μmol) to give the product concentration of 23.8 mg/3.5 mL (365 μM).

2.9 Azido-$PEG_{24}CO$—$[N(PN)_2][Lys]_8[(\alpha$-NH-DGA-Pt(IV) acetate))($\varepsilon$-NH-$COPEG_{1100})]_8$, G3, Compound 23

To a stirred solution of Azido-$PEG_{24}CO$—$[N(PN)_2][Lys]_8[(\alpha$-$NH_2$·TFA)($\varepsilon$-NH-$COPEG_{1100})]_8$ (SPL 19 and SPL 32) (22.4 mg, 1.75 μmol) in DMF (0.5 mL) was added NMM (7.4 μL, 67.3 μmol). The resulting solution was then added to a stirred solution of acetate-diglycolic acid-1R,2R-cyclohexane-1,2-diamine-oxalato platinum (IV) (10.4 mg, 17.7 μmol) and PyBOP (8.74 mg, 16.8 μmol) in DMF (0.5 mL). The ensuing reaction mixture was protected from light and stirred at room temperature overnight then purified by SEC to yield product as an off-white solid (24 mg, 86%). $^1$H-NMR (300 MHz, $CD_3OD$) δ (ppm): 1.28-1.89 (m, 128H), 2.07 (s, 23H), 2.24-3.01 (m, 57H), 3.12-3.26 (m, 22H), 3.37 (s, 25H), 3.39-3.90 (m, 768H), 4.04-4.69 (m, 80H). LCMS (philic method, TFA buffer) $R_t$=10.63 min. ICP-OES: Determined Pt % 9.0%, indicating there are 7 Pt containing moieties on the macromolecule. Actual molecular weight of conjugate is determined to be 16.1 kDa.

2.10 $BHA[Lys]_8[((\alpha$-NH-$COPEG_{24}$NH-$COPEG_4$(PhMeTz)$)_{1-4}(\alpha$-$NH_2)_{4-7})(\varepsilon$-NH-$COPEG_{1000})_8]$, G3, Compound 34

A stirred solution of $BHA[Lys]_8[(\alpha$-$NH_2$·TFA$)_8(\varepsilon$-NH-$COPEG_{1000})_8]$ (100 mg, 0.00786 mmol, 1.0 eq) in DMF (300 μL) was prepared at RT. To this was added (MeTzPh) $PEG_4CO$-$NHPEG_{24}CO_2H$ (Click Chemistry Tools; 16 mg, 0.01 mmol, 1.3 eq), PyBOP (8 mg, 0.013 mmol, 1.6 eq) and DMF (200 μL). The reaction mixture was stirred for 3 min before addition of NMM (40 mg, 50 μL, 0.38 mmol, 48 eq). The contents were protected from light and stirred overnight at RT. The reaction mixture was diluted with MQ water and lyophilized overnight. The lyophilized material was taken up in MeOH (1 mL) and purified by SEC (400 drops/tube, MeOH sephadex LH20, 35 drop/min). The product-containing fractions were checked by HPLC and collected in 2 different fractions. Each fraction was concentrated under reduced pressure, then the resulting residue taken up in MQ water, filtered (0.45 μm acrodisc filter) and freeze dried to yield the title product as a pink solid (69 mg, 66%).

HPLC (C8 Xbridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, Rf (min)=8.4 (broad peak). $^1$H-NMR (300 MHz, $D_2O$) δ (ppm): 1.00-2.00 (m, 90H), 2.51 (t, 3H), 2.60 (br s, 3H), 3.00-3.12 (m, 6H), 3.12-3.35 (br s, 27H), 3.35-3.45 (m, 26H), 3.45-4.15 (m, 937H), 4.15-4.45 (m, 12H), 6.12 (s, 1H), 7.15-7.50 (m, 12H), 8.40-8.50 (m, 2H).

2.11 $BHA[Lys]_8[((\alpha$-NH-$COPEG_{24}$NH-$COPEG_2$-BCN$)_{1-4}$ $(\alpha$-$NH_2)_{4-7})(\varepsilon$-NH-$COPEG_{1000})_8]$, G3, Compound 35

A stirred solution of BCN-$PEG_2CO$-$NHPEG_{24}$-$CO_2H$ Compound 31 (9.6 mg, 0.006 mmol, 1.3 eq) in DMF (200 μL) was prepared at RT. To this was added PyBOP (4 mg, 0.008 mmol, 1.6 eq) and NMM (23 mg, 25 μL, 0.226 mmol, 48 eq) and after 5 min $BHA[Lys]_8[(\alpha$-$NH_2$·TFA$)_8(\varepsilon$-NH-$COPEG_{1000})_8]$ (60 mg, 0.006 mmol, 1.0 eq) was added followed by DMF (200 μL). The contents were protected from light and stirred at overnight at RT. The reaction mixture was diluted with ACN (10 mL) then purified by SEC (400 drops/tube, ACN sephadex LH20, 35 drop/min). The product-containing fractions were checked by HPLC, collected, filtered (0.45 μm acrodisc filter), concentrated under reduced pressure and freeze dried overnight to give the title compound as a pale yellow solid (58 mg, yield 92%).

HPLC (C8 Xbridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, Rf (min)=8.43 (broad peak). $^1$H-NMR (300 MHz, MeOD) δ (ppm): 0.75-1.12 (m, 15H) 1.12-2.15 (m, 95H), 2.15-2.35 (m, 7H), 2.55 (br s, 3H), 3.00-3.35 (m, 90H), 3.35-3.38 (s, 17H), 3.38-4.09 (m, 592H), 4.13 (d, 2H), 4.18-4.63 (br s, 7H), 6.18 (s, 0.9H), 7.12-7.48 (m, 7H).

2.12 (MeTzPh)$PEG_4CO$-$NHPEG_{24}CO$—$[N(PN)_2][Lys]_8$ $[((\alpha$-NH-Cy5$)_{1-4}(\alpha$-NH-Glu-Val-Cit-PAB-MMAE$)_{4-7})(\varepsilon$-NH-$COPEG_{1100})_8]$, G3, Compound 36

A solution of Cy5-NHS (214 μL of a 4.2 mg/mL solution in DMF; 1.43 μmol, 1.0 eq.) was added to neat (MeTzPh) $PEG_4CO$-$NHPEG_{24}CO$—$[N(PN)_2][Lys]_8[(\alpha$-$NH_2$·HCl$)_8(\varepsilon$-NH-$COPEG_{1100})_8]$ Compound 8 (18 mg, 1.43 μmol). Once fully dissolved, NMM (10 μL, 91.0 μmol) was added and the ensuing reaction mixture stirred and protected from light. After 2 h, NMM (10 μL, 91.0 μmol) and PyBOP (7.3 mg, 14.0 μmol) were added to the dendrimer solution, followed by a solution of Glu-VC-PAB-MMAE in DMF (290 μL of a 60 mg/mL solution, 14.0 μmol, 9.8 eq.). The ensuing reaction mixture was protected from light and stirred at RT overnight.

The reaction mixture was diluted with PBS (2.0 mL) to make a final volume of 2.5 mL. The diluted solution was then passed through a PD10 de-salting column (pre-equilibrated with PBS). Once the entire solution had entered the bed of the column, PBS (3.5 mL) was added to elute the product (which appeared as a blue band). Final theoretical concentration of construct=8.7 mg/mL in PBS. Material stored frozen at −80° C. HPLC (C8 Xbridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=95-10 min (broad peak); 83% conjugate-related peak with 17% MMAE/MMAE-linker.

2.13 (MeTzPh)$PEG_4$CO-NH$PEG_{24}$CO—[N(PN)$_2$][Lys]$_2$ [$^3$H-Lys]$_4$[Lys]$_8$[(α-NH-Glu-Val-Cit-PAB-MMAE)$_8$(ε-NH-COPEG$_{1100}$)$_8$], G3, Compound 40

To a solution of (MeTzPh)$PEG_4$CO-NH$PEG_{24}$CO—[N(PN)$_2$][Lys]$_2$[$^3$H-Lys]$_4$[Lys]$_8$[(α-$NH_2$·HCl)$_8$(ε-NH-COPEG$_{1100}$)$_8$] (Prepared using the method used for the synthesis of Compound 53) (36.8 mg, 2.93 μmol) in NMM/DMF (7.8 μL/0.5 mL) was added solid PyBOP (24.7 mg, 47.5 μmol). Once fully dissolved, the dendrimer solution was added to a solution of HO-Glu-VC-PAB-MMAE (40 mg, 32.3 μmol) in NMM/DMF (7.8 μL/0.5 mL). The ensuing reaction mixture was protected from light and stirred at RT overnight.

The reaction mixture was diluted with PBS (4.0 mL) to make a final volume of 5 mL. The diluted solution was then passed through two PD10 de-salting columns (pre-equilibrated with PBS, 2.5 mL through each column). Once all solutions had entered the bed of the columns, PBS (3.5 mL) was added to each column to elute the product. The resulting crude mixtures were further purified using regenerated cellulose Amicon Ultra-0.5 mL centrifugation units (10K MWCO). Final theoretical concentration of construct=29-30 mg/mL in PBS. The material stored frozen at −20° C. HPLC (C8 Xbridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=9.5-12 min (broad peak); 91.4% conjugate-related peak with 8.6% MMAE/MMAE-linker related peaks.

2.14 (MeTzPh)$PEG_4$CO-NH$PEG_{24}$CO—[N(PN)$_2$][Lys]$_8$ [((α-NH-DFO)$_2$(α-NH-Glu-Val-Cit-PAB-MMAE)$_6$)(ε-NH-COPEG$_{1100}$)$_8$], G3 Compound 66

A stirred solution of p-SCN-Deferoxamine (2.1 mg, 2.79 μmol) in DMSO (100 μL) was prepared at RT. To this was added (MeTzPh)$PEG_4$CO-NH$PEG_{24}$CO[N(PN)$_2$][Lys]$_8$ [(α-$NH_2$·HCl)$_8$(ε-NH-COPEG$_{1100}$)$_8$] Compound 53 (17.0 mg, 1.35 μmol) in DMF (200 μL). The ensuing reaction mixture was stirred for 3 min before addition of NMM (10 μL, 91.0 μmol). The resulting solution was protected from light and stirred for 4 h at RT. PyBOP (7.0 mg, 13.5 μmol) was added and after 5 min the reaction mixture was added to neat HO-Glu-Val-Cit-PAB-MMAE (9.76 mg, 7.89 μmol). The ensuing reaction mixture was left to stand overnight. The reaction mixture was diluted with PBS buffer (4.5 mL) and divided across 4 Amicon Ultra centrifugal filters (10K MWCO) and the filters centrifuged (14K rcf, 15 min). The retentate was diafiltered against PBS (400 μL, 14K rcf, 15 min×10 times). The retentate was combined to give a pink coloured solution, approximate concentration of 16 mg of Compound 67 in 2 mL. HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=8.7-9.8 min (broad peak).

2.15 BHA[Lys]$_8$[((α-NH-COPEG$_{24}$NH-COPEG$_4$(PhMeTz))$_1$(α-NH-DFO)$_2$(α-NH-Glu-Val-Cit-PAB-MMAE)$_8$)(ε-NH-COPEG$_{1100}$)$_8$], G3, Compound 67

A stirred solution of p-SCN-Deferoxamine (2.0 mg, 2.66 μmol) in DMSO (100 μL) was prepared at RT. To this was added BHALys[Lys]$_8$[((α-NH-COPEG$_{24}$NH-COPEG$_4$(PhMeTz))$_1$(α-$NH_2$)$_7$)(ε-NHPEG$_{1100}$)$_8$] Compound 34 (17.0 mg, 1.27 μmol) in DMF (200 μL). The ensuing reaction mixture was stirred for 3 min before addition of NMM (10 μL, 91.0 μmol). The resulting solution was protected from light and stirred for 4 h at RT. PyBOP (7.0 mg, 13.5 μmol) was added and after 5 min the reaction mixture was added to neat HO-Glu-Val-Cit-PAB-MMAE (9.17 mg, 7.41 μmol). The ensuing reaction mixture was left to stand overnight. The reaction mixture was diluted with PBS buffer (4.5 mL) and divided across 4 Amicon Ultra centrifugal filters (10K MWCO) and the filters centrifuged (14K rcf, 15 min). The retentate was diafiltered against PBS (400 μL, 14K rcf, 15 min×10 times). The retentate was combined to give a pink coloured solution, approximate concentration of 16 mg of compound 68 in 2 mL. HPLC (C8 XBridge, 3×100 mm) gradient: 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$ (min)=9.3-9.7 min (broad peak).

2.16 (MeTzPh)$PEG_4$CO-NH$PEG_{24}$CO—[N(PN)$_2$][Lys]$_8$ [((α-NH-Cy5)$_1$(α-NH-Glu-SN38)$_7$)(ε-NH-COPEG$_{1100}$)$_8$], G3 Compound 68

To a stirred solution of (MeTzPh)$PEG_4$CO-NH$PEG_{24}$CO—[N(PN)$_2$][Lys]$_8$[((ca-$NH_2$·HCl)$_8$(ε-NH-COPEG$_{1100}$)$_8$] Compound 53 (10 mg, 0.75 μmol) in DMF (2 mL) were added NMM (4.0 μL, 36.0 μmmol) and Sulfo Cy5 NHS ester (0.58 mg, 0.75 μmol). The reaction mixture stirred at room temperature for 2 h. SN38-Glu-COOH (WO2020/102852) (3.94 mg, 7.8 μmmol) and PyBOP (4.05 mg, 7.8 μmmol) were added to the reaction mixture and the reaction mixture stirred for another 20 h at room temperature. The solvent was removed under reduced pressure and the residue obtained purified using Size Exclusion Chromatography (Sephadex LH 20), using acetonitrile as mobile phase to give title compound as a blue solid (6.0 mg). UPLC-TOF analysis of the reaction mixture confirms the random addition of sulfo Cy5 NHS ester and SN-38-Glu-COOH on the dendrimer. UPLC-TOF (philic method, TFA buffer) $R_t$=84.80-5.80 min.

2.17 BHA[Lys]$_{32}$[((α-NH-COPEG$_{24}$NH-COPEG$_4$(PhMeTz))$_{1-4}$(α-$NH_2$)$_{28-31}$(ε-NH-COPEG$_{1100}$)$_{32}$], G5, Compound 69

Prepared according to the General Procedure C using BHALys[Lys]$_{32}$[(α-$NH_2$·TFA)$_{32}$(ε-NH-COPEG$_{1000}$)$_{32}$] (100.0 mg, 0.002 mmol) and HOOCPEG$_{24}$NH-COPEG$_4$(PhTzMe) (Click Chemistry Tools; 3.38 mg, 0.005 mmol) except the reaction vessel was wrapped in foil to exclude light and the residue was purified by SEC (Sephadex™ LH-20) using methanol as the eluent to give the product Compound 69 (68 mg, 72%); $^1$HNMR (300 MHz, $D_2O$) δ (ppm): 8.44-8.29 (m, 2H), 7.44-7.09 (m, 12H), 6.02 (bs, 1H), 4.37-4.11 (m, 31H), 4.08-3.37 (m, 2937H), 3.32 (s, 83H), 3.27-2.88 (m, 116H), 2.59-2.42 (m, 3H), 2.18-0.92 (m, 313H); HPLC (C8 XBridge, 3×100 mm) gradient (formate buffer): 5% ACN/$H_2O$ (0-1 min), 5-80% ACN (1-7 min), 80% ACN (7-12 min), 80-5% ACN (12-13 min), 5% ACN (13-15 min), 214 nm, 0.4 mL/min, $R_t$=8.77 min.

2.18 BHA[Lys]$_{32}$[((α-NH-COPEG$_{24}$NH-COPEG$_4$(PhMeTz))$_{1-4}$(α-NHCy5)$_1$(α-NH-COPEG$_9$-Val-Ala-PAB-P-Trigger-NMeCO-CTX)$_{22}$) (α-$NH_2$)$_{5-8}$(ε-NH-COPEG$_{1100}$)$_{32}$], G5, Compound 70

To a stirred solution of BHA[Lys]$_{32}$[((α-NH-COPEG$_{24}$NH-COPEG$_4$(PhMeTz))$_{1-4}$((α-$NH_2$)$_{28-31}$(ε-NH-COPEG$_{1100}$)$_{32}$] Compound 69 (20.0 mg, 0.4 μmol) in DMF were added NMM (8.0 μL, 72 μmol) followed by Cy5-NHS ester (0.26 mg, 0.4 μmol) and the reaction mixture stirred at room temperature overnight. Compound 63 (25.7 mg, 14.4 μmol) and PyBOP were added to the reaction mixture and the mixture stirred at room temperature for another 20 h. Solvent was removed under reduced pressure and the crude residue dissolved in acetonitrile (2 mL) and solution obtained filtered through 0.45 μM filter. The filtrate was collected and purified using Size Exclusion Chromatography (Sephadex LH20), using acetonitrile as a solvent to give the title compound as a blue solid (27 mg; 75%). $^1$HNMR (300 MHz, MeOD) δ (ppm): 8.52 (d, 2H, J=9.0 Hz), 8.25-7.05 (m, 329H), 6.39-5.89 (m, 23H), 5.73-4.94 (m, 141H), 4.64-4.05 (m, 161H), 4.05-3.36 (m, 4026H), 3.18-2.22 (m, 323H), 2.18-0.56 (m, 1362H); HPLC (C8 XBridge, 3×100 mm) gradient (formate buffer): 75% ACN/$H_2O$ (0-1 min), 75-90% ACN (1-7 min), 90% ACN (7-12 min), 90-75% ACN (12-13 min), 75% ACN (13-15 min), 214 nm, 0.4 mL/min, $R_t$ (min)=8.90-9.10.

Example 3 Synthesis of Targeted Dendrimer Conjugates 3.1 Affibody-MPED-BCN-triazolo-$PEG_{24}$-CO[N(PN)$_2$][Lys]$_4$[(α-NH-DGA-3'NH-Dox)$_{1-4}$(ε-NH-COPEG$_{1100}$)]$_4$, G2, Compound 24

Prepared according to General Procedure G, using affibody-BCN (900 μL) and azido-$PEG_{24}$-CO[N(PN)$_2$][Lys]$_4$[(α-NH-DGA-3'-NH-Dox)-4(ε-NH-COPEG$_{1100}$)]$_4$ (300 μL of a 858 μM solution) (molar ratio Affibody-BCN:DGA-Dox dendrimer; 1:3). SDS-PAGE analysis showed band corresponding to affibody-dendrimer conjugate around 19 kDa (700 nm).

3.2 Affibody-BCN/$N_3$-$PEG_{24}$CO—[N(PN)$_2$][Lys]$_4$[(α-NH-DGA-14-O-Nemo)(ε-NH-COPEG$_{1100}$)]$_4$, G2, Compound 71

Prepared according to General Procedure G, using affibody-BCN (900 μL) and azido-$PEG_{24}$CO—[N(PN)$_2$][Lys]$_4$[(α-NH-14-O-DGA-Nemo)(ε-NH-COPEG$_{1100}$)]$_4$ (300 μL of a 858 μM solution) (molar ratio Affibody-BCN:DGA-Nemo dendrimer; 1:3). SDS-PAGE analysis showed band corresponding to affibody-dendrimer conjugate around 19 kDa (700 nm).

3.3 Affibody-MPED-BCN-triazolo-$PEG_{24}$-CO[N(PN)$_2$][Lys]$_8$[(α-NH-DGA-3'-NH-Dox)(ε-NH-COPEG$_{1100}$)]$_8$, G3, Compound 25

Prepared according to General Procedure G, using affibody-BCN (105 μL) and azido-$PEG_{24}$-CO[N(PN)$_2$][Lys]$_8$[(α-NH-DGA-3'-NH-Dox)(ε-NH-COPEG$_{1100}$)]$_8$ (35 μL of a 580 μM solution) (molar ratio Affibody-BCN:DGA-Dox dendrimer; 1:1). SDS-PAGE analysis showed band corresponding to affibody-dendrimer conjugate around 27 kDa (700 nm). The conjugation yield was estimated to be 80%, this was calculated by addition of azide IR Dye 800CW and measurement of fluorescence at 800 nm.

3.4 Affibody-BCN/$N_3$-$PEG_{24}$CO—[N(PN)$_2$][Lys]$_8$[(α-NH-DGA-14-O-Nemo)(ε-NH-COPEG$_{1100}$)]$_8$, G3, Compound 72

Prepared according to General Procedure G, using affibody-BCN (105 μL) and azido-$PEG_{24}$CO—[N(PN)$_2$][Lys]$_8$[(α-NH-DGA-14-O-Nemo)(ε-NH-COPEG$_{1100}$)]$_8$ (35 μL of a 580 μM solution) (molar ratio Affibody-BCN:DGA-Nemo dendrimer; 1:1). SDS-PAGE analysis showed band corresponding to affibody-dendrimer conjugate around 27 kDa (700 nm). The conjugation yield was estimated to be 80%, this was calculated by addition of azide IR Dye 800CW and measurement of fluorescence at 800 nm.

3.5 Affibody-BCN/$N_3$-$PEG_{24}$CO—[N(PN)$_2$][Lys]$_8$[(α-NH-Glu-Val-Cit-PAB-MMAE)$_8$(ε-NH-COPEG$_{1100}$)$_8$], G3, Compound 26

Prepared according to General Procedure G, using affibody BCN (2.0 mg, 286 nmol at 1.0 mg/mL PBS) and azido-$PEG_{24}$CO—[N(PN)$_2$][Lys]$_8$[(α-NH-Glu-vc-PAB-MMAE)(ε-NH-COPEG$_{1100}$)]$_8$ (1.0 mL of a 240 μM solution). Lyophilisation of the purified material gave a white fluffy powder (2.19 mg, 31%). SDS-PAGE analysis showed band corresponding to affibody-dendrimer conjugate around 30 kDa (700 nm).

3.6 Affibody-BCN/$N_3$-$PEG_{24}$CO—[N(PN)$_2$][Lys]$_8$[(α-NH-Glu-Val-Cit-PAB-MMAE)$_8$(ε-NH-COPEG$_{2000}$)$_8$], G3, Compound 27 (Compound 78 in SPL 40)

Prepared according to General Procedure G, using affibody BCN (1.0 mg, 143 nmol at 1.0 mg/mL PBS) and azido-$PEG_{24}$CO—[N(PN)$_2$][Lys]$_8$[(α-NH-Glu-vc-PAB-MMAE)(ε-NH-COPEG$_{2000}$)]$_8$ (250 μL of a 233 μM solution). SDS-PAGE analysis showed band corresponding to affibody-dendrimer conjugate around 40 kDa (700 nm).

3.7 Affibody-BCN/$N_3$-$PEG_{24}$CO—[N(PN)$_2$][Lys]$_8$[(α-NH-DGA-Pt(IV)-acetate)(ε-NH-COPEG$_{1100}$)]$_8$, G3, Compound 28

Prepared according to General Procedure G, using affibody BCN (5.0 mg, 715 nmol at 1.0 mg/mL PBS) and azido-$PEG_{24}$CO—[N(PN)$_2$][Lys]$_8$[(α-NH-DGA-Pt(IV)-acetate)(ε-NH-COPEG$_{1100}$)]$_8$ (600 μL of a 903 μM solution). Lyophilisation of the purified material gave a white fluffy powder (5.90 mg, 47%). SDS-PAGE analysis showed a band corresponding to affibody-dendrimer conjugate around 30 kDa (700 nm).

3.8 Fab-triazoloDBCO-$PEG_{24}$-CO[N(PN)$_2$[Lys]$_4$[(α-DGA-3'-NH-Dox)(ε-NHPEG$_{1100}$)]$_4$ G2-Dox PEG$_{1100}$ dendrimer, Compound 29

A solution of azido-$PEG_{24}$-CO[N(PN)$_2$[Lys]$_4$[(α-NH-DGA-3'-NH-Dox)(ε-NH-COPEG$_{1100}$)]$_4$ (10 μL of a 500 μM solution in PBS) was added to a solution of Fab-DBCO* (40 μL of a 13.4 μM solution in HEPES buffer). The ensuing reaction mixture was shaken (650 rpm) at room temperature overnight to produce Fab-azido-$PEG_{24}$-CO[N(PN)$_2$[Lys]$_4$[(α-NH-DGA-3'NH-Dox)(ε-NH-COPEG$_{1100}$)]$_4$. SDS-PAGE analysis was conducted and scanned at 700 nm and 800 nm using an Odyssey scanner. The SDS-PAGE when scanned at 700 nm showed the DBCO-Fab band corresponding to 50 kDa and the expected Fab-[dendrimer-Dox/PEG$_{1100}$]$_2$, compound 30, at around 65 kDa.

3.9 Fab-DBCO/$N_3$-$PEG_{24}$CO—[N(PN)$_2$[Lys]$_4$[(α-NH-DGA-14-O-Nemo)(ε-NH-COPEG$_{1100}$)]$_4$, Compound 73

A solution of azido-$PEG_{24}$CO—[N(PN)$_2$[Lys]$_4$[(α-NH-DGA-14-O-Nemo)(ε-NH-COPEG$_{1100}$)]$_4$ (10 μL of a 500 μM solution in PBS) was added to a solution of Fab-DBCO* (40 μL of a 13.4 μM solution in HEPES buffer). The ensuing reaction mixture was shaken (650 rpm) at room temperature overnight to produce Fab-DBCO/$N_3$-$PEG_{24}$CO—[N(PN)$_2$[Lys]$_4$[(α-NH-DGA-14-O-Nemo)(ε-NH-COPEG$_{1100}$)]$_4$. SDS-PAGE analysis was conducted and scanned at 700 nm and 800 nm using an Odyssey scanner. The SDS-PAGE when scanned at 700 nm showed the DBCO-Fab band corresponding to 50 kDa and the expected Fab-[dendrimer-Nemo/PEG$_{1100}$]$_2$, compound 30, at around 65 kDa.

3.10 Affibody-BCN/$N_3$-$PEG_{24}$CO—[N(PN)$_2$][Lys]$_2$[Lys]$_4$[Lys]$_8$[(α-NH-DGA-MMAF(OMe)$_8$(ε-NH-COPEG$_{1100}$)$_8$], G3, Compound 30

Prepared according to General Procedure G, using affibody BCN (2.0 mg, 286 nmol at 1.0 mg/mL PBS) and azido-$PEG_{24}$CO—[N(PN)$_2$][Lys]$_8$[(α-NH-DGA-MMAF(OMe))(ε-NH-COPEG$_{1100}$)]$_8$ (600 μL of a 365 μM solution). Lyophilisation of the purified material gave a white fluffy powder (2.06 mg, 33%). SDS-PAGE analysis showed a band corresponding to affibody-dendrimer conjugate around 30 kDa (700 nm).

3.11 Nanobody-$PEG_2$-TCO-MePhTz-$PEG_4$-$PEG_{24}$-CO[N(PN)$_2$][Lys]$_8$[(α-NH-Cy5)$_1$(α-NH-Glu-VC-PAB-MMAE)$_7$(ε-NH-COPEG$_{1100}$)$_8$], Compound 41

The nanobody construct was prepared using DBCO-$PEG_{12}$-TCO and Nanobody 2D3 N-terminal tag, TEV, C-terminal azide in accordance with Example 4 below.

3.12 Nanobody-$PEG_2$-TCO-MePhTz-$PEG_4$-$PEG_{24}$-CO[N$(PN)_2$][Lys]$_8$[(α-NH-Cy5)$_1$(α-NH-Glu-VC-PAB-MMAE)$_7$(ε-NH-COPEG$_{1100}$)$_8$], Compound 42

The nanobody construct was prepared using DBCO-$PEG_{12}$-TCO and Nanobody 2D3 N-terminal tag, TEV, C-terminal azide in accordance with Example 4 below.

3.13 Nanobody-$PEG_2$-TCO-MeTzPh-$PEG_4PEG_{24}$-CO[N$(PN)_2$][Lys]$_{16}$[(α-NH-Cy5)$_1$(α-NHAc)$_{15}$ (ε-NH-COPEG$_{1100}$)$_{16}$], Compound 43

The nanobody construct was prepared using DBCO-$PEG_{12}$-TCO and Nanobody 2D3 N-terminal tag, TEV, C-terminal azide in accordance with Example 4 below 3.14 Nanobody-$PEG_2$-TCO-MeTzPh-$PEG_4PEG_{24}$-CO[N$(PN)_2$][Lys]$_{32}$[(α-NH-Cy5)$_1$(α-NHAC)$_{31}$(ε-NH-COPEG$_{1100}$)$_{32}$], Compound 44

The nanobody construct was prepared using DBCO-$PEG_{12}$-TCO and Nanobody 2D3 N-terminal tag, TEV, C-terminal azide in accordance with Example 4 below 3.15 Nanobody-$PEG_2$-TCO-MeTzPh-$PEG_4PEG_{24}$-CO[N$(PN)_2$][$^3$H-Lys]$_4$[Lys(α-NH-Glu-VC-PAB-MMAE)$_8$(ε-NH-COPEG$_{1100}$)$_8$], Compound 45

The nanobody construct was prepared using DBCO-$PEG_{12}$-TCO and Nanobody 2D3 N-terminal tag, TEV, C-terminal azide in accordance with Example 4 below 3.16 Nanobody-$N_3$/DBCO-Glu-NHPEG$_{24}$CO-NHPEG$_3$-TCO (MeTzPh)PEG$_4$CO-NHPEG$_{24}$CO—[N$(PN)_2$][Lys]$_8$[((α-NH-DFO)$_2$(α-NH-Glu-Val-Cit-PAB-MMAE)$_6$)(ε-NH-COPEG$_{1100}$)$_8$], Compound 74

Prepared using General Procedure H using DBCO-Glu-NHPEG$_{24}$CO-NHPEG$_3$-TCO linker Compound 33 (1 eq.), tetrazine dendrimer (MeTzPh)PEG$_4$CO-NHPEG$_{24}$CO—[N$(PN)_2$] [Lys]$_4$ [Lys]$_8$[((α-NH-DFO)$_2$(α-NH-Glu-Val-Cit-PAB-MMAE)$_6$)(ε-NH-COPEG$_{1100}$)$_8$], Compound 66 (1 eq.) and Nanobody-$N_3$ ("Nanobody-N3-C-terminal Tag") (1 eq.) SDS-PAGE analysis showed a band corresponding to nanobody-dendrimer conjugate ~37 kDa (FIG. 1).

3.17 Nanobody-$N_3$/BCN-NHPEG$_2$-Glu-NHPEG$_{24}$CO-NHPEG$_3$-TCO (MeTzPh)PEG$_4$CO—NHPEG$_{24}$CO—[N$(PN)_2$][Lys]$_8$[((α-NH-DFO)$_2$(α-NH-Glu-Val-Cit-PAB-MMAE)$_6$)(ε-NH-COPEG$_{1100}$)$_8$], Compound 75

Prepared using General Procedure H using BCN-NHPEG$_2$-Glu-NHPEG$_{24}$CONHPEG$_3$-TCO linker Compound 32 (1 eq.), tetrazine dendrimer (MeTzPh)PEG$_4$CO-NHPEG$_{24}$CO—[N$(PN)_2$][Lys]$_4$[Lys]$_8$[((α-NH-DFO)$_2$(α-NH-Glu-Val-Cit-PAB-MMAE)$_6$)(ε-NH-COPEG$_{1100}$)$_8$], Compound 66 (1 eq.) and Nanobody-$N_3$ ("Nanobody-N3-C-terminal Tag") (1 eq.) SDS-PAGE analysis showed a band corresponding to nanobody-dendrimer conjugate ~37 kDa (FIG. 1).

3.18 BHA[Lys]$_8$[((α-NH-COPEG$_{24}$NH-COPEG$_4$(PhMeTz) TCO-PEG$_3$NH-COPEG$_{24}$NH-Glu-DBCO $N_3$-Nanobody)$_1$(α-NH-DFO)$_2$(α-NH-Glu-Val-Cit-PAB-MMAE)$_5$)(ε-NH-COPEG$_{1100}$)$_8$], G3, Compound 76

Prepared using General Procedure H using DBCO-Glu-NHPEG$_{24}$CO-NHPEG$_3$-TCO linker Compound 33 (1 eq.), tetrazine dendrimer BHA[Lys]$_8$[((α-NH-COPEG$_{24}$NH-COPEG$_4$(PhMeTz))$_1$(α-NH-DFO)$_2$(α-NH-Glu-Val-Cit-PAB-MMAE)$_5$)(ε-NH-COPEG$_{1100}$)$_8$], Compound 67 (1 eq.) and Nanobody-$N_3$ ("Nanobody-N3-C-terminal Tag") (1 eq.) SDS-PAGE analysis showed a band corresponding to nanobody-dendrimer conjugate ~37 kDa (FIG. 1).

3.19 Nanobody-$N_3$/DBCO-Glu-NHPEG$_{24}$CO-NHPEG$_3$-TCO (MeTzPh)PEG$_4$CO—NHPEG$_{24}$CO—[N$(PN)_2$][Lys]$_8$[((α-NH-Cy5)$_1$(α-NH-Glu-10-O-SN38)$_7$) (ε-NH-COPEG$_{1100}$)$_8$], Compound 77

Figure 2:
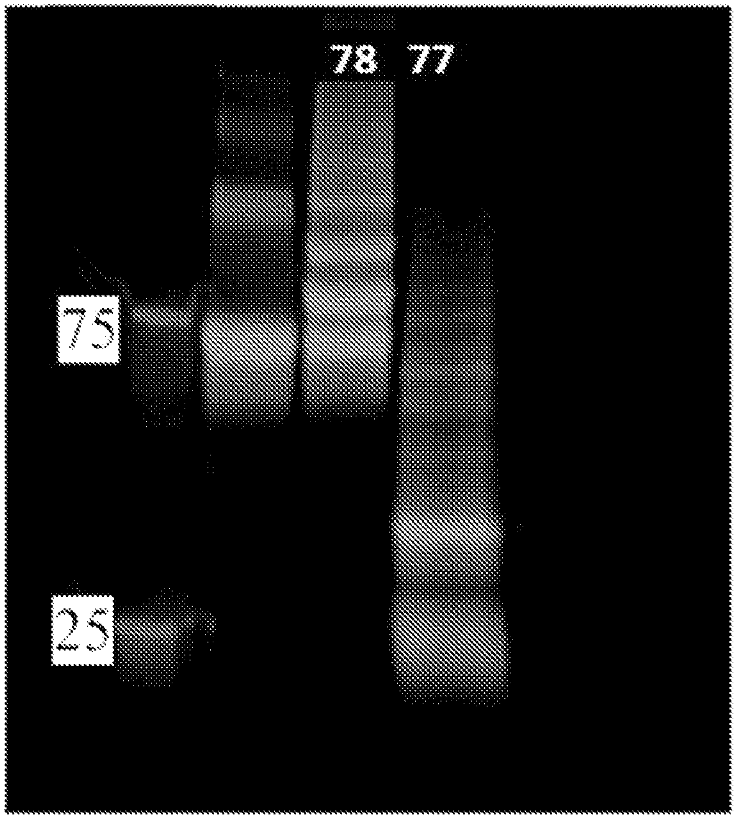
FIG. 2 shows SDS Page and fluorescent imaging analysis of compound 77 and 78.

Prepared using General Procedure H using DBCO-Glu-NHPEG$_{24}$CO-NHPEG$_3$-TCO linker Compound 33 (1 eq.), tetrazine dendrimer (MeTzPh)PEG$_4$CO-NHPEG$_{24}$CO—[N$(PN)_2$][Lys]$_8$[((α-NH-Cy5)$_1$(α-NH-Glu-10-O-SN38)$_7$)(ε-NH-COPEG$_{1100}$)$_8$], Compound 68 (1 eq.) and Nanobody-$N_3$ ("Nanobody-N3-C-terminal Tag") (1 eq.) SDS-PAGE analysis showed a band corresponding to nanobody-dendrimer conjugate ~37 kDa (FIG. 2).

3.20 BHA[Lys]$_{32}$[((α-NH-COPEG$_{24}$NH-COPEG$_4$(PhMeTz) TCO-PEG$_3$NH-COPEG$_{24}$NH-Glu-DBCO/$N_3$-Nanobody)$_{1-4}$(α-NHCy5)$_1$(α-NH-COPEG$_9$-Val-Ala-PAB-P-Trigger-NMeCO-CTX)$_{22}$) (α-$NH_2$)$_5$-8 (ε-NH-COPEG$_{1100}$)$_{32}$], G5, Compound 78

Prepared using General Procedure H using DBCO-Glu-NHPEG$_{24}$CO-NHPEG$_3$-TCO linker Compound 33 (1 eq.), tetrazine dendrimer BHA[Lys]$_2$[Lys]$_4$[Lys]$_8$[Lys]$_{16}$[Lys]$_{32}$[((α-NH-COPEG$_{24}$NH-COPEG$_4$(PhMeTz))$_{1-4}$(α-NHCy5)$_1$(α-NH-COPEG$_9$-Val-Ala-PAB-P-Trigger-NMeCO-CTX)$_{22}$($NH_2$)$_{5-8}$(ε-NH-COPEG$_{1100}$)$_{32}$], Compound 70 (1 eq.) and Nanobody-$N_3$ ("Nanobody-N3-C-terminal Tag") (1 eq.) SDS-PAGE analysis showed a band corresponding to nanobody-dendrimer conjugate ~95 kDa (FIG. 2)

3.21 BHA[Lys]$_4$[((α-NH-COPEG$_{24}$NH-COPEG$_4$(PhMeTz) TCO-PEG$_3$NH-COPEG$_{24}$NH-Glu-DBCO $N_3$-Nanobody)$_1$(α-Lys(α-NHCy5)(ε-NHDFO))$_1$(α-$NH_2$)$_2$)(ε-NH-COPEG$_{1000}$)$_4$, G2, Compound 86 and BHA[Lys]$_4$[((α-NH-COPEG$_{24}$NH-COPEG$_4$(PhMeTz) TCO-PEG$_3$NH-COPEG$_{24}$NH-Glu-DBCO/$N_3$-Nanobody)$_{2-3}$(α-Lys(α-NHCy5)(ε-NHDFO))$_1$(α-$NH_2$))$_{0-1}$(ε-NHCOPEG$_{1000}$)$_4$], G2, Compound 87

Prepared according to General Procedure H using BHA[Lys]$_4$[((α-NH-COPEG$_{24}$NH-COPEG$_4$(PhMeTz))$_1$(α-Lys(α-NHCy5)(ε-NHDFO))$_1$(α-$NH_2$)$_1$)(ε-NH-COPEG$_{1000}$)$_4$], G2, Compound 99 except:

Step 1: The TCO linker solution 80 was prepared in neat DMSO

Step 2: The dendrimer was dissolved in Tris buffer at pH 8 and, upon complete reaction of the TCO linker with the dendrimer (UPLC or LCMS), the reaction mixture was diluted with Tris buffer such that the final concentration of DMSO was <5% (v/v) and purified by centrifugal ultrafiltration (Amicon, 0.5 mL regenerated cellulose membrane, 10 kDa MWCO).

Purification method same as method used for the purification of Compound 74 and 76. to give the nanobody-dendrimer conjugates Compound 86 (232 μg; 0.45 μg/μL in HEPES buffer at pH 8) and the nanobody-dendrimer conjugate Compound 87 (60 μg; 0.30 μg/μL in HEPES buffer at pH 8.

3.22 BHA[Lys]$_8$[((α-NH-COPEG$_{24}$NH-COPEG$_4$(PhMeTz) TCO-PEG$_3$NH-COPEG$_{24}$NH-Glu-DBCO/$N_3$-Nanobody)$_1$(α-Lys(α-NHCy5)(ε-NHDFO))$_1$(α-$NH_2$)$_6$)(ε-NH-COPEG$_{412}$)$_8$], G3, Compound 88 and BHA[Lys]$_8$[((α-NH-COPEG$_{24}$NH-COPEG$_4$(PhMeTz) TCO-PEG$_3$NH-COPEG$_{24}$NH-Glu-DBCO $N_3$-Nanobody)$_{2-4}$(α-Lys(α-NHCy5)(ε-NHDFO))$_1$(α-$NH_2$)$_{3-5}$(ε-NH-COPEG$_{412}$)$_8$], G3 Compound 88a Prepared according to General Procedure H using BHA[Lys]$_8$[((α-NH-COPEG$_{24}$NH-COPEG$_4$(PhMeTz))$_{1-4}$(α-Lys(α-NHCy5)(ε-NHDFO))$_1$(α-$NH_2$)$_{3-6}$)(ε-NH-COPEG$_{412}$)$_8$], G3, Compound 100 except:

Step 1: The TCO linker Compound 80 solution was prepared in neat DMSO

Step 2: The dendrimer was dissolved in Tris buffer at pH 8 and, upon complete reaction of the TCO linker with the dendrimer (UPLC or LCMS), the reaction mixture was diluted with Tris buffer such that the final concentration of DMSO was <5% (v/v) and purified by centrifugal ultrafiltration (Amicon, 0.5 mL regenerated cellulose membrane, 10 kDa MWCO)

Purification method same as method used for the purification of Compound 74 and 76 to give the nanobody-dendrimer conjugates Compound 88 (140 μg; 1.48 μg/μL in HEPES buffer at pH 8) and Compound 88a (not pure).

3.23 BHA[Lys]$_8$[((α-NH-COPEG$_{24}$NH-COPEG$_4$(PhMeTz) TCO-PEG$_3$NH-COPEG$_{24}$NH-Glu-DBCO/N$_3$-Nanobody)$_1$ (α-Lys(α-NHCy5)(ε-NHDFO))$_1$(α-NH$_2$)$_6$)(ε-NH-COPEG$_{1000}$)$_8$], G3, Compound 89 qnd BHA[Lys]$_8$[((α-NH-COPEG$_{24}$NH-COPEG$_4$(PhMeTz) TCO-PEG$_3$NH-COPEG$_{24}$NH-Glu-DBCO N$_3$-Nanobody)$_{2-4}$(α-Lys(α-NHCy5)(ε-NHDFO))$_1$(α-NH$_2$)$_{3-5}$)(ε-NH-COPEG$_{1000}$)$_8$], G3, Compound 89a Prepared according to General Procedure H using BHA [Lys]$_8$[((α-NH-COPEG$_{24}$NH-COPEG$_4$(PhMeTz))$_{1-4}$(α-Lys (α-NHCy5)(ε-NHDFO))$_1$(α-NH$_2$)$_{3-6}$)(ε-NH-COPEG$_{1000}$)$_8$], G3, Compound 101 except:

Step 1: The TCO linker (Compound 80) solution was prepared in neat DMSO

Step 2: The dendrimer was dissolved in Tris buffer at pH 8 and, upon complete reaction of the TCO linker with the dendrimer (UPLC or LCMS), the reaction mixture was diluted with Tris buffer such that the final concentration of DMSO was <5% (v/v) and purified by centrifugal ultrafiltration (Amicon, 0.5 mL regenerated cellulose membrane, 10 kDa MWCO)

Purification method same as method used for the purification of Compound 74 and 76 to give the nanobody-dendrimer conjugates Compound 89 (249 μg; 2.68 μg/μL in HEPES buffer at pH 8) and Compound 89a (not pure).

3.24 BHA[Lys]$_{16}$[((α-NH-COPEG$_{24}$NH-COPEG$_4$ (PhMeTz) TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_{14}$(ε-NH-COPEG$_{1000}$)$_{16}$], G4, Compound 90 and BHA[Lys]$_{16}$ [((α-NH-COPEG$_{24}$NH-COPEG$_4$(PhMeTz) TCO-PEG$_3$NH-COPEG$_{24}$NH-Glu-DBCO N$_3$-Nanobody)$_{2-4}$(α-Lys(α-NHCy5)(ε-NHDFO))$_1$(α-NH$_2$)$_{11-13}$(ε-NHCOPEG$_{1000}$)$_{16}$], G4, Compound 91

Prepared according to General Procedure H using BHA [Lys]$_{16}$[((α-NH-COPEG$_{24}$NH-COPEG$_4$(PhMeTz)$_1$(α-Lys (α-NHCy5)(ε-NHDFO))$_1$(α-NH$_2$)$_{14}$(ε-NH-COPEG$_{1000}$)$_{16}$], G4, Compound 102 except:

Step 1: The TCO linker (Compound 80) solution was prepared in neat DMSO

Step 2: The dendrimer was dissolved in Tris buffer at pH 8 and, upon complete reaction of the TCO linker with the dendrimer (UPLC or LCMS), the reaction mixture was diluted with Tris buffer such that the final concentration of DMSO was <5% (v/v) and purified by centrifugal ultrafiltration (Amicon, 0.5 mL regenerated cellulose membrane, 10 kDa MWCO)

Purification method same as method used for the purification of Compound 74 and 76 to give nanobody-dendrimer conjugates Compound 90 (203 μg; 0.975 μg/μL and 0.556 μg/μL in HEPES buffer at pH 8) and Compound 91 (101 μg; 0.34 μg/μL in HEPES buffer at pH 8).

3.25 BHA[Lys]$_{32}$[((α-NH-COPEG$_{24}$NH-COPEG$_4$ (PhMeTz) TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_{30}$(ε-NH-COPEG$_{1100}$)$_{32}$], G5, Compound 92 and BHA[Lys]$_{32}$ [((α-NH-COPEG$_{24}$NH-COPEG$_4$(PhMeTz) TCO-PEG$_3$NH-COPEG$_{24}$NH-Glu-DBCO N$_3$-Nanobody)$_{2-4}$[α-Lys(α-NHCy5)(ε-NHDFO))$_1$(α-NH$_2$)$_{27-29}$(ε-NH-COPEG$_{1000}$)$_{32}$], G5, Compound 93

Prepared according to General Procedure H using BHA [Lys]$_{32}$[((α-NH-COPEG$_{24}$NH-COPEG$_4$(PhMeTz))$_{1-4}$(α-Lys(α-NHCy5)(ε-NHDFO))$_1$(α-NH$_2$)$_{27-30}$)(ε-NH-COPEG$_{1000}$)$_{32}$], G5, Compound 103 except:

Step 1: The TCO linker Compound 80 solution was prepared in neat DMSO

Step 2: The dendrimer was dissolved in Tris buffer at pH 8 and, upon complete reaction of the TCO linker with the dendrimer (UPLC or LCMS), the reaction mixture was diluted with Tris buffer such that the final concentration of DMSO was <5% (v/v) and purified by centrifugal ultrafiltration (Amicon, 0.5 mL regenerated cellulose membrane, 10 kDa MWCO)

Purification method same as method used for the purification of Compound 74 and 76 to give the nanobody-dendrimer conjugates Compound 92 (370 μg; 3.66 μg/μL in HEPES buffer at pH 8) and product Compound 93 (177 μg; 1.72 μg/μL in HEPES buffer at pH 8).

3.26 BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz))$_2$)(ε-NH-COPEG$_{24}$NH-COPEG$_4$(PhMeTz)) TCO-PEG$_3$NH-COPEG$_{24}$NH-Glu-DBCO N$_3$-Nanobody)$_2$], G2, Compound 94a, BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz))$_1$(ε-NH-COPEG$_{24}$NH-COPEG$_4$(PhMeTz) TCO-PEG$_3$NH-COPEG$_{24}$NH-Glu-DBCO N$_3$-Nanobody)$_3$], G2, Compound 94, and BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz) TCO-PEG$_3$NH-COPEG$_{24}$NH-Glu-DBCO/N$_3$-Nanobody)$_4$], G2, Compound 95

Prepared according to General Procedure H using BHA [Lys]$_4$[(α-Lys(α-NHCy5)(ε-NHDFO))$_1$(α-NH$_2$)$_3$)(ε-NH-COPEG$_{24}$NH-COPEG$_4$(PhMeTz))$_4$], G2 dendrimer, Compound 24 except:

Step 1: The TCO linker Compound 51 solution was prepared in water

Step 2: The dendrimer was dissolved in MQ water.

Purification method was the same as used for the purification of Compound 74 and 76 to give the nanobody-dendrimer conjugates Compound 95 and Compound 94 as an inseparable mixture (final concentration of 294 ug in HEPES buffer at pH 8).

Also prepared by adding a solution of DBCO-Glu-NHPEG$_{24}$CO-NHPEG$_3$-TCO

Compound 80 (57 μL of a 10 mg/mL solution in MQ water, 0.322 μmol) to a solution of the Nanobody-N$_3$ ("Nanobody-N3-C-terminal Tag") (2.5 mg, 0.161 μmol, in 900 μL of Tris buffer at pH 8. The reaction mixture was left at RT for 2 d whereupon the reaction mixture was then purified by centrifugal ultrafiltration using Tris buffer pH 8 (Amicon, 0.5 mL regenerated cellulose membrane, 10 kDa MWCO; 10×450 μL) a. To this solution was added a solution of Compound 105 (230.0 μg in 500 μL MQ water; 0.026 μmol) and the reaction mixture was left to stand at RT overnight. Purification method same as method used for the purification of Compound 74 and 76 to give gave the nanobody-dendrimer Compound 95, Compound 94a and Compound 94 as an inseparable mixture (final concentration of 124 μg in HEPES buffer at pH 8).

3.27 BHA[Lys]$_4$[((α-NH-COPEG$_{24}$NH-COPEG$_4$(PhTzMe) TCO-PEG$_8$-Nanobody)$_1$(α-Lys(α-NHCy5)$_1$(ε-NHDFO)$_1$)$_1$ (α-NH$_2$)$_2$)(ε-NH-COPEG$_{1000}$)$_4$], G2, Compound 97

A solution of the di-bromo maleimide linker Compound 106 was prepared by dissolving 2.0 mg in 1 mL DMSO (1.0 mL). A solution of TCEP (0.5 M in PBS pH 7) (2.3 μL, 1.174 μmmol) was added to a solution of the nanobody ("Nanobody-N3-C-terminal Tag") (Compound 79) (1.0 mg, 0.058 μmmol in 715 μL of Tris buffer at pH 8). The reaction mixture was heated at 37° C. for 1 h whereupon DMSO was added (673 μL) followed by a solution of the linker Compound 57 (93.0 μg, 0.117 μmmol) in DMSO (47.0 μL). After 1.5 h, the reaction mixture was cooled to RT and centrifuged whereupon a solution of Compound 99 (100 μg, 17 μL, 1.78 mg in 300 μL MQ water) was added to the precipitate and the solution left at 4° C. overnight. Purification method same as the method used for the purification of Compound 74 and 76 to give gave Compound 97 (29 μg) as a solution in Tris buffer at pH 8 (final concentration=1.78 mg/mL).

3.28 BHA[Lys]$_4$[((α-NH-COPEG$_{24}$-NH-COPEG$_4$ (PhTzMe) TCO-PEG$_3$-Nanobody)$_{1-3}$(α-Lys(α-NHCy5)$_1$(ε-NHDFO)$_1$)$_1$(α-NH$_2$)$_{0-2}$)(ε-NH-COPEG$_{1000}$)$_4$], G2, Compound 98

A solution of TCO-PEG$_3$-aldehyde (Conju-Probe) linker solution (0.7 mg, 1.46 μmol) in DMSO (50 μL) was added to a solution of the nanobody ("Nanobody-N3-C-terminal Tag") (Compound 79) (931 μL of a 1.07 mg/mL stock solution in PBS buffer at pH 6.5) followed by the addition of solution of NaBH$_3$CN (0.09 mg, 1.5 μmol) in water (19 μL). The reaction mixture was cooled to 4° C. and the reaction monitored by UPLC analysis. After 16 h, the reaction mixture was diluted with PBS buffer (pH 6.5) to a total volume of 2.0 mL and then purified by centrifugal ultrafiltration using PBS buffer pH 6.5 (Amicon, 0.5 mL regenerated cellulose membrane, 10 kDa MWCO; 14×450 μL) UPLC: 5-20-30 ACN % over 15 mins using 0.01% TFA buffer; Nanobody (Compound 79) $R_t$=8.46 mins with m/z 13802; Product: 9.99 mins with m/z 14263. To the nanobody-PEG$_3$-TCO solution (500 μL PBS pH 6.5) was added a solution of the G2 dendrimer Compound 107 (179 μg, 0.020 μmol) in MQ water (15 μL). After standing at 4° C. overnight, the reaction mixture was purified using same method used for the purification of Compound 74 and 764 to give Compound 99 (12 μg; as shown in FIG. 1*i*, Lane 1) as a solution in Tris buffer at pH 8 (final concentration=575 ug/mL).

TABLE 1

Table of Compounds Prepared

| Compound # | Compound Description |
|---|---|
| 1 | Azido-PEG$_{24}$-CO[N(PNBoc)$_2$] |
| 2 | Azido-PEG$_{24}$-CO[N(PNH$_2$•TFA)$_2$] |
| 3 | Azido-PEG$_{24}$-CO[N(PN)$_2$][Lys]$_2$[Boc]$_4$ |
| 4 | Azido-PEG$_{24}$-CO[N(PN)$_2$][Lys]$_2$[NH$_2$•TFA]$_4$ |
| 5 | Azido-PEG$_{24}$-CO[N(PN)$_2$][Lys]$_4$[(α-Boc)(ε-NHPEG$_{1100}$)]$_4$ |
| 6 | Azido-PEG$_{24}$-CO[N(PN)$_2$][Lys]$_4$[(α-NH$_2$•TFA)(ε-NHPEG$_{1100}$)]$_4$ |
| 7 | Azido-PEG$_{24}$-CO[N(PN)$_2$][Lys]$_4$[Boc]$_8$ |
| 8 | Azido-PEG$_{24}$-CO[N(PN)$_2$][Lys]$_4$[NH$_2$•TFA]$_8$ |
| 9 | Azido-PEG$_{24}$-CO[N(PN)$_2$][Lys]$_8$[(α-Boc)(ε-NHPEG$_{1100}$)]$_8$ |
| 10 | Azido-PEG$_{24}$-CO[N(PN)$_2$][Lys]$_8$[(α-NH$_2$•TFA)(ε-NHPEG$_{1100}$)]$_8$ |
| 11 | Azido-PEG$_{24}$-CO[N(PN)$_2$][Lys]$_8$[(α-Boc)(ε-Fmoc)]$_8$ |
| 12 | Azido-PEG$_{24}$-CO[N(PN)$_2$][Lys]$_8$[(α-Boc)(ε-NH$_2$)]$_8$ |
| 13 | Azido-PEG$_{24}$-CO[N(PN)$_2$][Lys]$_8$[(α-Boc)(ε-NHPEG$_{570}$)]$_8$ |
| 14 | Azido-PEG$_{24}$-CO[N(PN)$_2$][Lys]$_8$[(α-NH$_2$•TFA)(ε-NHPEG$_{570}$)]$_8$ |
| 15 | Azido-PEG$_{24}$-CO[N(PN)$_2$][Lys]$_8$[(α-Boc)(ε-NHPEG$_{2000}$)]$_8$ |
| 16 | Azido-PEG$_{24}$-CO[N(PN)$_2$][Lys]$_8$[(α-NH$_2$•TFA)(ε-NHPEG$_{2000}$)]$_8$ |
| 17 | Azido-PEG$_{24}$-CO[N(PN)$_2$][Lys]$_4$[(α-NH-DGA-3'-NH-Dox)(ε-NH-COPEG$_{1100}$)]$_4$/<br>Azido-PEG$_{24}$-CO[N(PN)$_2$][Lys]$_4$[(α-DGA-Dox)(ε-NHPEG$_{1100}$)]$_4$ G2 |
| 18 | Azido-PEG$_{24}$CO-[N(PN)$_2$][Lys]$_4$[(α-NH-DGA-14-O-Nemo)(ε-NH-COPEG$_{1100}$)]$_4$/<br>Azido-PEG$_{24}$-CO[N(PN)$_2$][Lys]$_8$[(α-DGA-Nemo)(ε-NHPEG$_{1100}$)]$_8$ G3 |
| 19 | Azido-PEG$_{24}$CO-[N(PN)$_2$][Lys]$_2$[Lys]$_4$[Lys]$_8$[(α-NHGlu-Val-Cit-PAB-MMAE)$_8$(ε-NH-COPEG$_{570}$)$_8$], G3/<br>Azido-PEG$_{24}$-CO[N(PN)$_2$][Lys]$_8$[(α-Glu-vc-PAB-MMAE)(ε-NHPEG$_{570}$)]$_8$ G3 |
| 20 | Azido-PEG$_{24}$CO-[N(PN)$_2$][Lys]$_8$[α-NHGlu-Val-Cit--PAB-MMAE)$_8$(ε-NH-COPEG$_{1100}$)$_8$]/<br>Azido-PEG$_{24}$-CO[N(PN)$_2$][Lys]$_8$[(α-Glu-vc-PAB-MMAE)(ε-NHPEG$_{1100}$)]$_8$ G3 |
| 21 | Azido-PEG$_{24}$CO-[N(PN)$_2$[Lys]$_8$[(α-NHGlu-Val-Cit-PAB-MMAE)$_8$(ε-NH-COPEG$_{2000}$)$_8$]/<br>Azido-PEG$_{24}$-CO[N(PN)$_2$][Lys]$_8$[(α-Glu-vc-PAB-MMAE)(ε-NHPEG$_{2000}$)]$_8$ G3 |
| 22 | Azido-PEG$_{24}$CO-[N(PN)$_2$][Lys]$_2$[Lys]$_4$[Lys]$_8$[(α-NHDGA-MMAF(OMe))$_8$(ε-NH-COPEG$_{1100}$)$_8$]/<br>Azido-PEG$_{24}$-CO[N(PN)$_2$][Lys]$_8$[(α-DGA-MMAF(OMe))(ε-NHPEG$_{1100}$)]$_8$ G3 |
| 23 | Azido-PEG$_{24}$CO-[N(PN)$_2$][Lys]$_8$[(α-NHDGA-Pt(IV) acetate))(ε-NH-COPEG$_{1100}$)]$_8$, G3,/<br>Azido-PEG$_{24}$-CO[N(PN)$_2$][Lys]$_8$[(α-Pt(IV)-acetate)(ε-NHPEG$_{1100}$)]$_8$ G3 |
| 24 | Affibody-MPED-BCN-triazolo-PEG$_{24}$-CO[N(PN)$_2$][Lys]$_4$[(α-DGA-3'-NH-Dox)$_{1-4}$(ε-NHPEG$_{1100}$)]$_4$/<br>Affibody-G2-DGA-Dox/PEG$_{1100}$ dendrimer conjugate |
| 25 | Affibody-MPED-BCN-triazolo-PEG$_{24}$-CO[N(PN)$_2$][Lys]$_8$[(α-DGA-3'-NH-Dox)(ε-NHPEG$_{1100}$)]$_8$, G3/<br>Affibody-G3-DGA-Dox/PEG$_{1100}$ dendrimer conjugate |
| 26 | Affibody-BCN/N$_3$-PEG$_{24}$CO-[N(PN)$_2$][Lys]$_8$[(α-NH-Glu-Val-Cit-PAB-MMAE)$_8$(ε-NH-COPEG$_{1100}$)$_8$]/<br>Affibody-G3-MMAE/PEG$_{1100}$ dendrimer conjugate |

TABLE 1-continued

Table of Compounds Prepared

| Compound # | Compound Description |
|---|---|
| 27 | Affibody-BCN/N$_3$-PEG$_{24}$CO-[N(PN)$_2$][Lys]$_8$[(α-NH-Glu-Val-Cit-PAB-MMAE)$_8$(ε-NH-COPEG$_{2000}$)$_8$]/ Affibody-G3-MMAE/PEG$_{2000}$ dendrimer conjugate |
| 28 | Affibody-BCN/N$_3$-PEG$_{24}$CO-[N(PN)$_2$][Lys]$_8$[(α-NH-DGA-Pt(IV)-acetate)(ε-NH-COPEG$_{1100}$)]$_8$ , G3/ Affibody-G3-Pt(IV)-acetate/PEG$_{1100}$ dendrimer conjugate |
| 29 | Fab-triazoloDBCO-PEG$_{24}$-CO[N(PN)$_2$[Lys]$_4$[(α-DGA-3'-NH-Dox)(ε-NHPEG$_{1100}$)]$_4$ G2-Dox/PEG1100 dendrimer/ Fab-G2-Doxorubicin/PEG$_{1100}$ dendrimer conjugate |
| 30 | Affibody-BCN/N$_3$-PEG$_{24}$CO-[N(PN)$_2$][Lys]$_2$[Lys]$_4$[Lys]$_8$[(α-NHDGA-MMAF(OMe)$_8$(ε-NH-COPEG$_{1100}$)$_8$]/ Affibody-G3-MMAF/PEG$_{1100}$ dendrimer conjugate |
| 31 | BCN-PEG$_2$-Glu-CO-NHPEG$_{24}$CO$_2$H/BCN-PEG$_2$-Glu-PEG$_{24}$-CO$_2$H |
| 32 | BCN-PEG$_2$-Glu-CO-NHPEG$_{24}$CO-NHPEG$_3$-TCO/BCN-PEG$_2$-Glu-PEG$_{24}$-PEG$_3$-TCO |
| 33 | DBCO-Glu-NHPEG$_{24}$CO-NHPEG$_3$-TCO/DBCO-Glu-PEG$_{24}$-PEG$_3$-TCO |
| 34 | BHA[Lys]$_8$[((α-NH-COPEG$_{24}$NH-COPEG$_4$(PhMeTz))$_{1-4}$(α-NH$_2$)$_{4-7}$)(ε-NH-COPEG$_{1100}$)$_8$], G3/ BHA-[Lys]$_8$[(α-(MeTzPh-PEG$_4$-PEG$_{24}$)$_1$(α-NH$_2$)$_7$(ε-NHPEG$_{1000}$)$_8$] |
| 35 | BHA[Lys]$_8$[((α-NH-COPEG$_{24}$NH-COPEG$_2$-BCN)$_{1-4}$(α-NH$_2$)$_{4-7}$)(ε-NH-COPEG$_{1000}$)$_8$], G3/ BHA-[Lys]$_8$[(α-(BCN-PEG$_3$-Glu-PEG$_{24}$)$_1$(α-NH$_2$)$_7$(ε-NHPEG$_{1000}$)$_8$] |
| 36 | (MeTzPh)PEG$_4$CO-NHPEG$_{24}$CO-[N(PN)$_2$][Lys]$_8$[((α-NH-Cy5)$_{1-4}$(α-NH-Glu-Val-Cit-PAB-MMAE)$_{4-7}$)(ε-NH-COPEG$_{1100}$)$_8$]/ MePhTz-PEG$_4$-PEG$_{24}$-CO[N(PN)$_2$][Lys]$_8$[(α-(Cy5)$_1$(α-Glu-VC-PAB-MMAE)$_7$(ε-NHPEG$_{1100}$)$_8$] |
| 37 | MeTzPh-PEG$_4$PEG$_{24}$-CO[N(PN)$_2$][Lys]$_8$[(α-Cy5)$_1$(α-NHAc)$_7$(ε-NHPEG$_{1100}$)$_8$]/ MeTzPh-PEG$_4$PEG$_{24}$-CO[N(PN)$_2$][Lys]$_8$[(α-Cy5)$_1$(α-NHAc)$_7$(ε-NHPEG$_{1100}$)$_8$] |
| 38 | (MeTzPh)PEG$_4$CO-NHPEG$_{24}$CO-[N(PN)$_2$][Lys]$_{16}$[((α-NHCy5)$_1$(α-NHAc)$_{15}$)(ε-NH-COPEG$_{1100}$)$_{16}$]/ MeTzPh-PEG$_4$PEG$_{24}$-CO[N(PN)$_2$][Lys]$_{16}$[(α-Cy5)$_1$(α-NHAc)$_{15}$(ε-NHPEG$_{1100}$)$_{16}$] |
| 39 | (MeTzPh)PEG$_4$CO-NHPEG$_{24}$CO-[N(PN)$_2$][Lys]$_{32}$[((α-NHCy5)$_1$(α-NHAc)$_{31}$)(ε-NH-COPEG$_{1100}$)$_{32}$]/ MeTzPh-PEG$_4$PEG$_{24}$-CO[N(PN)$_2$][Lys]$_{32}$[(α-Cy5)$_1$(α-NHAc)$_{31}$(ε-NHPEG$_{1100}$)$_{32}$] |
| 40 | (MeTzPh)PEG$_4$CO-NHPEG$_{24}$CO-[N(PN)$_2$][Lys]$_2$[$^3$H-Lys]$_4$[Lys]$_8$[(α-NH-Glu-Val-Cit-PAB-MMAE)$_8$(ε-NH-COPEG$_{1100}$)$_8$]/ MeTzPh-PEG$_4$PEG$_{24}$-CO[N(PN)$_2$][3H-Lys]$_4$[Lys(α-Glu-VC-PAB-MMAE)$_8$(ε-NHPEG$_{1100}$)$_8$] |
| 41 | Nanobody-PEG$_{12}$-TCO-MePhTz-PEG$_4$-PEG$_{24}$-CO[N(PN)$_2$][Lys]$_8$[(α-(Cy5)$_1$(α-Glu-VC-PAB-MMAE)$_7$(ε-NHPEG$_{1100}$)$_8$] |
| 42 | Nanobody-PEG$_{12}$-TCO-MePhTz-PEG$_4$-PEG$_{24}$-CO[N(PN)$_2$][Lys]$_8$[(α-(Cy5)$_1$(α-Glu-VC-PAB-MMAE)$_7$(ε-NHPEG$_{1100}$)$_8$ |
| 43 | Nanobody-PEG$_{12}$-TCO-MeTzPh-PEG$_4$PEG$_{24}$-CO[N(PN)$_2$][Lys]$_{16}$[(α-Cy5)$_1$(α-NHAc)$_{15}$ (ε-NHPEG$_{1100}$)$_{16}$] |
| 44 | Nanobody-PEG$_{12}$-TCO MeTzPh-PEG$_4$PEG$_{24}$-CO[N(PN)$_2$][Lys]$_{32}$[(α-Cy5)$_1$(α-NHAc)$_{31}$(ε-NHPEG$_{1100}$)$_{32}$ |
| 45 | Nanobody-PEG$_{12}$-TCO MeTzPh-PEG$_4$PEG$_{24}$-CO[N(PN)$_2$][3H-Lys]$_4$[Lys(α-Glu-VC-PAB-MMAE)$_8$(ε-NHPEG$_{1100}$)$_8$] |
| 46 | (MeTzPh)-PEG$_{24}$-CO[N(PNBoc)$_2$] |
| 47 | (MeTzPh)-PEG$_{24}$-CO[N(PNH$_2$•HCl)$_2$] |
| 48 | (MeTzPh)-PEG$_4$CO-NHPEG$_{24}$-CO[N(PNH$_2$•HCl)$_2$] |
| 49 | ((MeTzPh)-PEG$_4$CO-NHPEG$_{24}$-CO[N(PN)$_2$[Lys]$_2$[NHBoc]$_4$ |
| 50 | ((MeTzPh)-PEG$_4$CO-NHPEG$_{24}$-CO[N(PN)$_2$[Lys]$_2$[NH$_2$•HCl]$_4$ |
| 51 | (MeTzPh)-PEG$_4$CO-NHPEG$_{24}$-CO[N(PN)$_2$][Lys]$_4$[NHBoc]$_8$ |
| 52 | (MeTzPh)-PEG$_4$CO-NHPEG$_{24}$-CO[N(PN)$_2$][Lys]$_4$[NH$_2$•HCl]$_8$ |
| 53 | (MeTzPh)-PEG$_4$CO-NHPEG$_{24}$-CO[N(PN)$_2$][Lys]$_8$[(α-NH$_2$•HCl)(ε-NH-COPEG$_{1100}$)]$_8$ |
| 54 | (MeTzPh)-PEG$_4$CO-NHPEG$_{24}$-CO[N(PN)$_2$][Lys]$_8$[NH$_2$•HCl]$_{16}$ |
| 55 | (MeTzPh)-PEG$_4$CO-NHPEG$_{24}$-CO[N(PN)$_2$][Lys]$_{16}$[(α-NH$_2$•HCl)(ε-NH-CO PEG$_{1100}$)]$_{16}$ |
| 56 | (MeTzPh)-PEG$_4$CO-NHPEG$_{24}$-CO[N(PN)$_2$][Lys]$_{16}$[NH$_2$•TFA]$_{32}$ |
| 57 | (MeTzPh)-PEG$_4$CO-NHPEG$_{24}$-CO[N(PN)$_2$][Lys]$_{32}$[(α-NH$_2$•TFA)(ε-NH-COPEG$_{1100}$)]$_{32}$ |
| 58 | Cabazitaxel (CTX)-2'-OCOO-oPNP ester |
| 59 | Fmoc-Val-Ala-PAB-P-Trigger-(NMeBoc) |
| 60 | TFA•NH$_2$-Val-Ala-PAB-P-Trigger-(NMeBoc) |
| 61 | COOH-PEG$_9$-Val-Ala-PAB-P-Trigger-(NMeBoc) |
| 62 | COOH-PEG$_9$-Val-Ala-PAB-P-Trigger-(NMe•TFA) |
| 63 | COOH-PEG$_9$-Val-Arg-PAB-P-Trigger-NMeCO-CTX |
| 46 | Azido-PEG$_{24}$CO-[N(PN)$_2$][Lys]$_4$[(α-NHDGA-14-O-Nemo)(ε-NH-COPEG$_{1100}$)]$_4$ |
| 65 | Azido-PEG$_{24}$CO-[N(PN)$_2$][Lys]$_8$[(α-NH-DGA-14-O-Nemo)(ε-NH-COPEG$_{1100}$)]$_8$ |
| 66 | (MeTzPh)PEG$_4$CO-NHPEG$_{24}$CO-[N(PN)$_2$][Lys]$_4$[Lys]$_8$[((α-NHDFO)$_2$(α-NHGlu-Val-Cit-PAB-MMAE)$_6$)(ε-NH-COPEG$_{1100}$)$_8$] |

TABLE 1-continued

Table of Compounds Prepared

| Compound # | Compound Description |
|---|---|
| 67 | BHA[Lys]$_8$[((α-NH-COPEG$_{24}$NH-COPEG$_4$(PhMeTz))$_1$(α-NHDFO)$_2$(α-NHGlu-Val-Cit-PAB-MMAE)$_5$)(ε-NH-COPEG$_{1100}$)$_8$] |
| 68 | (MeTzPh)PEG$_4$CO-NHPEG$_{24}$CO-[N(PN)$_2$][Lys]$_4$[Lys]$_8$[((α-NHCy5)$_1$(α-NHGlu-SN38)$_7$)(ε-NH-COPEG$_{1100}$)$_8$] |
| 69 | BHA[Lys]$_{32}$[((α-NH-COPEG$_{24}$NH-COPEG$_4$(PhMeTz))$_{1-4}$(α-NH$_2$)$_{28-31}$(ε-NH-COPEG$_{1100}$)$_{32}$] |
| 70 | BHA[Lys]$_{32}$[((α-NH-COPEG$_{24}$NH-COPEG$_4$(PhMeTz))$_{1-4}$(α-NHCy5)$_1$(α-NH-COPEG$_9$-Val-Arg-PAB-P-Trigger-NHCO-CTX)$_{22}$) (α-NH$_2$)$_{5-8}$ (ε-NH-COPEG$_{1100}$)$_{32}$] |
| 71 | Affibody-BCN/N$_3$-PEG$_{24}$CO-[N(PN)$_2$][Lys]$_4$[(α-NHDGA-14-O-Nemo)(ε-NH-COPEG$_{1100}$)]$_4$ |
| 72 | Affibody-BCN/N$_3$-PEG$_{24}$CO-[N(PN)$_2$][Lys]$_8$[(α-NH-DGA-14-O-Nemo)(ε-NH-COPEG$_{1100}$)]$_8$ |
| 73 | Fab-DBCO/N$_3$-PEG$_{24}$CO-[N(PN)$_2$[Lys]$_4$[(α-NHDGA-14-O-Nemo)(ε-NH-COPEG$_{1100}$)]/G2-Nemo/PEG1100 dendrimer |
| 74 | Nanobody-N$_3$/DBCO-Glu-NHPEG$_{24}$CO-NHPEG$_3$-TCO/(MeTzPh)PEG$_4$CO-NHPEG$_{24}$CO-[N(PN)$_2$][Lys]$_8$[((α-NHDFO)$_2$ (α-NHGlu-Val-Cit-PAB-MMAE)$_6$)(ε-NH-COPEG$_{1100}$)$_8$] |
| 75 | Nanobody-N$_3$/BCN-NHPEG$_2$-Glu-NHPEG$_{24}$CO-NHPEG$_3$-TCO/(MeTzPh)PEG$_4$CO-NHPEG$_{24}$CO-[N(PN)$_2$][Lys]$_8$[((α-NHDFO)$_2$ (α-NHGlu-Val-Cit-PAB-MMAE)$_6$)(ε-NH-COPEG$_{1100}$)$_8$] |
| 76 | BHA[Lys]$_8$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-NHDFO)$_2$ (α-NHGlu-Val-Cit-PAB-MMAE)$_5$)(ε-NH-COPEG$_{1100}$)$_8$] |
| 77 | Nanobody-N$_3$/DBCO-Glu-NHPEG$_{24}$CO-NHPEG$_3$-TCO/(MeTzPh)PEG$_4$CO-NHPEG$_{24}$CO-[N(PN)$_2$][Lys]$_8$[((α-NHCy5)$_1$(α-NHGlu-SN38)$_7$)(ε-NH-COPEG$_{1100}$)$_8$] |
| 78 | BHA[Lys]$_2$[Lys]$_4$[Lys]$_8$[Lys]$_{16}$[Lys]$_{32}$[((α-NH-COPEG$_{24}$NH-COPEG$_4$(PhMeTz)/TCO-PEG$_3$NH-COPEG$_{24}$NH-Glu-DBCO/N$_3$-Nanobody)$_{1-4}$(α-NHCy5)$_1$(α-NH-COPEG$_9$-Val-Arg-PAB-P-Trigger-NHCO-CTX)$_{22}$) (α-NH$_2$)$_{5-8}$ (ε-NH-COPEG$_{1100}$)$_{32}$] |
| 79 | Nanobody (plain)<br>GGSHHHHHHGMASMTGGQQMGRDLYENLYFQG EVQLVESGGSLVQPGGSLRLSCA ASGFTFDDYAMSWVRQVPGKGLEWVSSINWSGTHTDYADSVKGRFTISRNNANNTLY LQMNSLKSEDTAVYYCAKNWRDAGTTWFEKSGSAGQGTQVTVSS |
| 80 | DBCO-Glu-NHPEG$_{24}$CO-NHPEG$_3$-TCO/DBCO-PEG$_{12}$-TCO |
| 81 | BHALys[Lys]$_2$[Lys]$_4$[Lys]$_8$[((α-NH-COPEG$_{24}$NH-COPEG$_4$(PhTzMe)/TCO-PEG$_3$NH-COPEG$_{24}$NH-Glu-DBCO)$_1$(α-Lys(α-NHCy5)(ε-NHDFO))$_1$(α-NH$_2$)$_6$)(ε-NH-COPEG$_{412}$)$_8$], G3 |
| 82 | BHALys[Lys]$_2$[Lys]$_4$[((α-NH-COPEG$_{24}$NH-COPEG$_4$(PhTzMe/TCO-PEG$_3$NH-COPEG$_{24}$NH-Glu-DBCO))$_1$(α-Lys(α-NHCy5)(ε-NHDFO))$_1$(α-NH$_2$)$_2$)(ε-NH-COPEG$_{1000}$)$_4$], G2 |
| 83 | BHALys[Lys]$_2$[Lys]$_4$[Lys]$_8$[((α-NH-COPEG$_{24}$NH-COPEG$_4$(PhTzMe)/TCO-PEG$_3$NH-COPEG$_{24}$NH-Glu-DBCO)$_1$(α-Lys(α-NHCy5)(ε-NHDFO))$_1$(α-NH$_2$)$_6$)(ε-NH-COPEG$_{1000}$)$_8$], G3 |
| 84 | BHALys[Lys]$_2$[Lys]$_4$[Lys]$_8$[Lys]$_{16}$[((α-NH-COPEG$_{24}$NH-COPEG$_4$(PhTzMe)/TCO-PEG$_3$NH-COPEG$_{24}$NH-Glu-DBCO)$_1$(α-Lys(α-NHCy5)(ε-NHDFO))$_1$(α-NH$_2$)$_{14}$)(ε-NH-COPEG$_{1000}$)$_{16}$], G4 |
| 85 | BHALys[Lys]$_2$[Lys]$_4$[Lys]$_8$[Lys]$_{16}$[Lys]$_{32}$[((α-NH-COPEG$_{24}$NH-COPEG$_4$(PhTzMe)/TCO-PEG$_3$NH-COPEG$_{24}$NH-Glu-DBCO)$_1$(α-Lys(α-NHCy5)(ε-NHDFO))$_1$(α-NH$_2$)$_{30}$)(ε-NH-COPEG$_{1000}$)$_{32}$], G5 |
| 86 | BHALys[Lys]$_2$[Lys]$_4$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_2$)(ε-NH-COPEG$_{1000}$)$_4$], G2<br>(using “Nanobody-N3-C-terminal Tag”) |
| 87 | BHALys[Lys]$_2$[Lys]$_4$[((α-NH-COPEG$_{24}$NH-COPEG$_4$(PhMeTz)/TCO-PEG$_3$NH-COPEG$_{24}$NH-Glu-DBCO/N$_3$-Nanobody)$_{2-3}$(α-Lys(α-NHCy5)(ε-NHDFO))$_1$(α-NH$_2$))$_{0-1}$ (ε-NHCOPEG$_{1000}$)$_4$], G2<br>(using “Nanobody-N3-C-terminal Tag”) |
| 88 | BHALys[Lys]$_2$[Lys]$_4$[Lys]$_8$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_6$)(ε-NH-COPEG$_{412}$)$_8$], G3<br>(using “Nanobody-N3-C-terminal Tag”) |
| 88a | BHA[Lys]$_8$[((α-NH-COPEG$_{24}$NH-COPEG$_4$(PhMeTz)/TCO-PEG$_3$NH-COPEG$_{24}$NH-Glu-DBCO/N$_3$-Nanobody)$_{2-4}$(α-Lys(α-NHCy5)(ε-NHDFO))$_1$(α-NH$_2$)$_{3-5}$)(ε-NH-COPEG$_{412}$)$_8$], G3 |
| 89 | BHA[Lys]$_8$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_6$)(ε-NH-COPEG$_{1000}$)$_8$], G3 |
| 89a | BHA[Lys]$_8$[((α-NH-COPEG$_{24}$NH-COPEG$_4$(PhMeTz)/TCO-PEG$_3$NH-COPEG$_{24}$NH-Glu-DBCO/N$_3$-Nanobody)$_{2-4}$(α-Lys(α-NHCy5)(ε-NHDFO))$_1$(α-NH$_2$)$_{3-5}$)(ε-NH-COPEG$_{1000}$)$_8$], G3, Compound 89a |
| 90 | BHA[Lys]$_{16}$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_{14}$)(ε-NH-COPEG$_{1000}$)$_{16}$], G4 |
| 91 | BHA[Lys]$_{16}$[((α-NH-COPEG$_{24}$NH-COPEG$_4$(PhMeTz)/TCO-PEG$_3$NH-COPEG$_{24}$NH-Glu-DBCO/N$_3$-Nanobody)$_{2-4}$(α-Lys(α-NHCy5)(ε-NHDFO))$_1$(α-NH$_2$)$_{11-13}$(ε-NHCOPEG$_{1000}$)$_{16}$], G4 |

TABLE 1-continued

Table of Compounds Prepared

| Compound # | Compound Description |
|---|---|
| 92 | BHA[Lys]$_{32}$[((α-NH-COPEG$_{24}$NH-COPEG$_4$(PhMeTz)/TCO-PEG$_3$NH-COPEG$_{24}$NH-Glu-DBCO/N$_3$-Nanobody)$_1$(α-Lys(α-NHCy5)(ε-NHDFO))$_1$(α-NH$_2$)$_{30}$(ε-NH-COPEG$_{1000}$)$_{32}$], G5 |
| 93 | BHA[Lys]$_{32}$[((α-NH-COPEG$_{24}$NH-COPEG$_4$(PhMeTz)/TCO-PEG$_3$NH-COPEG$_{24}$NH-Glu-DBCO/N$_3$-Nanobody)$_{2-4}$[α-Lys(α-NHCy5)(ε-NHDFO)]$_1$(α-NH$_2$)$_{27-29}$(ε-NH-COPEG$_{1000}$)$_{32}$], G5 |
| 94 | BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz))$_1$(ε-NH-COPEG$_{24}$NH-COPEG$_4$(PhMeTz)/TCO-PEG$_3$NH-COPEG$_{24}$NH-Glu-DBCO/N$_3$-Nanobody)$_3$], G2 |
| 94a | BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz))$_2$)(ε-NH-COPEG$_{24}$NH-COPEG$_4$(PhMeTz))/TCO-PEG$_3$NH-COPEG$_{24}$NH-Glu-DBCO/N$_3$-Nanobody)$_2$], G2, |
| 95 | BHA[Lys]$_4$[(α-Lys(α-NHCy5)(ε-NHDFO))$_1$(α-NH$_2$)$_3$)(ε-NH-COPEG$_{24}$NH-COPEG$_4$(PhMeTz)/TCO-PEG$_3$NH-COPEG$_{24}$NH-Glu-DBCO/N$_3$-Nanobody)$_4$], G2 |
| 96 | DBCO-Glu-NHPEG$_{24}$CO-NHPEG$_3$-TCO/DBCO-PEG$_{12}$-TCO |
| 97 | BHA[Lys]$_4$[((α-NH-COPEG$_{24}$NH-COPEG$_4$(PhTzMe)/TCO-PEG$_8$-Nanobody)$_1$(α-Lys(α-NHCy5)$_1$(ε-NHDFO)$_1$)$_1$(α-NH$_2$)$_2$)(ε-NH-COPEG$_{1000}$)$_4$], G2 |
| 98 | BHA[Lys]$_4$[((α-NH-COPEG$_{24}$-NH-COPEG$_4$(PhTzMe)/TCO-PEG$_3$-Nanobody)$_{1-3}$(α-Lys(α-NHCy5)$_1$(ε-NHDFO)$_1$)$_1$(α-NH$_2$)$_{0-2}$)(ε-NH-COPEG$_{1000}$)$_4$], G2 |
| 99 | BHA[Lys]$_4$[((α-NH-COPEG$_{24}$NH-COPEG$_4$(PhTzMe))$_{1-3}$(α-Lys(α-NHCy5)(ε-NHDFO))$_1$(α-NH$_2$)$_{0-2}$)(ε-NH-COPEG$_{1000}$)$_4$], G2 |
| 100 | BHA[Lys]$_8$[((α-NH-COPEG$_{24}$NH-COPEG$_4$(PhTzMe))$_{1-4}$(α-Lys(α-NHCy5)(ε-NHDFO))$_1$(α-NH$_2$)$_{3-6}$)(ε-NH-COPEG$_{412}$)$_8$], G3 |
| 101 | BHA[Lys]$_8$[((α-NH-COPEG$_{24}$NH-COPEG$_4$(PhTzMe))$_1$(α-Lys(α-NHCy5)(ε-NHDFO))1(α-NH$_2$)$_6$)(ε-NH-COPEG$_{1000}$)$_8$], G3 |
| 102 | BHA[Lys]$_{16}$[((α-NH-COPEG$_{24}$NH-COPEG$_4$(PhTzMe))$_1$(α-Lys(α-NHCy5)(ε-NHDFO))$_1$(α-NH$_2$)$_{14}$)(ε-NH-COPEG$_{1000}$)$_{16}$], G4 |
| 103 | BHA[Lys]$_{32}$[((α-NH-COPEG$_{24}$NH-COPEG$_4$(PhTzMe))$_{1-4}$(α-Lys(α-NHCy5)(ε-NHDFO))$_1$(α-NH$_2$)$_{27-30}$)(ε-NH-COPEG$_{1000}$)$_{32}$], G5 |
| 104 | Nanobody-N3-C-terminal Tag/DBCO-DFO |
| 105 | BHA[Lys]$_4$[((α-Lys(α-NHCy5)(α-NHDFO))$_1$(α-NH$_2$)$_3$)(ε-NH-COPEG$_{24}$NH-COPEG$_4$(PhTzMe)$_4$], G2 |
| 106 | BHA[Lys]$_4$[((α-Lys(α-NHCy5)(α-NHDFO))$_1$(α-NH$_2$)$_3$)(ε-NH-COPEG$_{24}$NH-COPEG$_4$(PhTzMe)$_4$], G2 |
| 107 | BHA[Lys]$_4$[((α-NH-COPEG$_{24}$NH-COPEG$_4$(PhTzMe))$_1$(α-NH$_2$)$_3$)(ε-NH-COPEG$_{1000}$)$_4$], G2 |
| 108 | HO-Lys[(α-NHCy5)(ε-NHDFO)] |
| 109 | BHA[Lys]$_8$[((α-NH-COPEG$_{24}$NH-COPEG$_4$(PhTzMe))$_1$(α-NH$_2$)$_7$)(ε-NH-COPEG$_{412}$)$_8$], G3 |
| 110 | BHA[Lys]$_8$[((α-NH-COPEG$_{24}$NH-COPEG$_4$(PhTzMe))$_1$(α-NH$_2$)$_7$)(ε-NH-COPEG$_{1000}$)$_8$], G3 |
| 111 | BHA[Lys]$_{16}$[((α-NH-COPEG$_{24}$NH-COPEG$_4$(PhTzMe))$_1$(α-NH$_2$)$_{15}$)(ε-NH-COPEG$_{1000}$)$_{16}$], G4 |
| 112 | BHA[Lys]$_{32}$[((α-NH-COPEG$_{24}$NH-COPEG$_4$(PhTzMe))$_{1-4}$(α-NH$_2$)$_{28-31}$)(ε-NH-COPEG$_{1000}$)$_{32}$], G5 |
| 113 | BHA[Lys]$_4$[(α-NHBoc)$_4$(ε-NH-COPEG$_{24}$NH-COPEG$_4$(PhTzMe)$_4$], G2 |
| 114 | BHA[Lys]$_4$[(α-NH$_2$•HCl)$_4$(ε-NH-COPEG$_{24}$NH-COPEG$_4$(PhTzMe)$_4$], G2 |
| 115 | HO-Lys[(α-NHCy5) (ε-NH$_2$)] |
| 116 | HO-Lys[(α-NHCy5)(ε-NHDFO)] wedge |

Example 4 Synthesis of HER2-Targeted Dendrimer Conjugates a) Nanobody Sequence Information

```
Nanobody 2D3 sequence Compound 79
EVQLVESGGSLVQPGGSLRLSCAASGFTFDDYAMSWVRQVPGKGLEWVSS

INWSGTHTDYADSVKGRFTISRNNANNTLYLQMNSLKSEDTAVYYCAKNW

RDAGTTWFEKSGSAGQGTQVTVSS

Nanobody 2D3 N-terminal tag, TEV, C-terminal azide
("N-terminal Tag-Nanobody-N3")
GGSHHHHHHGMASMTGGQQMGRDLYENLYFQGEVQLVESGGSLVQPGGSL

RLSCAASGFTFDDYAMSWVRQVPGKGLEWVSSINWSGTHTDYADSVKGRF

TISRNNANNTLYLQMNSLKSEDTAVYYCAKNWRDAGTTWFEKSGSAGQGT

QVTVSS#
```

-continued

```
Nanobody 2D3, with C-terminal tag, TEV, azide
("Nanobody-N3-C-terminal Tag")
EVQLVESGGSLVQPGGSLRLSCAASGFTFDDYAMSWVRQVPGKGLEWVSS

INWSGTHTDYADSVKGRFTISRNNANNTLYLQMNSLKSEDTAVYYCAKNW

RDAGTTWFEKSGSAGQGTQVTVSS#ENLYFQGHHHHHH
Where # = unnatural amino acid.
```

b) Nanobody-N$_3$ Expression Plasmid

The coding sequence of anti-HER2 nanobody clone 2D3 (US20110028695A1 SEQ ID NO: 1986) was inserted into the expression plasmid pET-His6-TEV-1B (Addgene plasmid 29653) using standard molecular biology techniques. *E. coli* K12 codon optimised DNA sequences were synthesised and then cloned into plasmid pET-His6-TEV-1B.

For incorporation of unnatural amino acids into the recombinant protein, the amber stop codon (TAG) was inserted in-frame at the last position of the nanobody coding sequence, followed then by an ochre (TAA) or opal (TGA) stop codon for translational termination. Where a C-terminal his6 tag was used, the amber stop codon (TAG) was inserted in-frame at the last position of the nanobody coding sequence, and the sequence encoding the TEV protease cleavage site and 6his tag followed by an ochre (TAA) or opal (TGA) stop codon for translational termination was then appended to this sequence.

c) Expression and Purification of Nanobody-$N_3$

Anti-HER2 nanobody 2D3 expression was performed in *E. coli* strain B95(DE3) (Mukai et al., Scientific Reports (2015), 5, 9699) transformed with nanobody expression plasmid and orthogonal pair expression plasmid pEVOL-pAcFRS.2.tl (Amiram et al., Nat. Biotechnol (2015), 33 (12). Cells were cultured in Terrific broth (25 g/L tryptone, 30 g/L yeast and 5 g/L glycerol, 0.017 M $KH_2PO_4$, 0.072 M $K_2HPO_4$) contained in baffled shake flasks at 37° C. until a cell density of $OD_{600}$ 0.7-1.0 was reached. Recombinant protein expression was induced by addition of 1.5 mM IPTG and 0.05% w/v L-(+)-arabinose with addition of 1.5 mM p-azido-phenylalanine, and allowed to proceed for 20 hours at 25° C. Bacteria were harvested by centrifugation and a cell lysate generated by high pressure homogenisation followed by addition of a protease inhibitor cocktail, lysozyme and DNAse treatment. The insoluble material can be dissolved in refolding buffer (6 M Guanidine HCl, 50 mM $NaH_2PO_4$, 300 mM NaCl, 20 mM Imidazole, pH 8). Following clarification by high speed centrifugation and filtration through a 0.45 M membrane filter, his6-tagged nanobody was purified by immobilised metal affinity chromatography (IMAC) using nickel-charged nitrilotriacetic acid-agarose. On-column refolding was achieved by first washing the bound protein with a column volume of 3 M Guanidine HCl, 50 mM $NaH_2PO_4$, 300 mM NaCl, 20 mM Imidazole, pH 8, followed by two column volumes of 50 mM $NaH_2PO_4$, 300 mM NaCl, 20 mM Imidazole, pH 8. Bound proteins were eluted with 2 column volumes of 50 mM $NaH_2PO_4$, 300 mM NaCl, 250 mM Imidazole, pH 8. Following IMAC, -nanobody-$N_3$ was further purified by anion exchange chromatography using a HiTrap Q HP column (GE Healthcare, catalogue 17115301). Binding and washing steps were performed using Tris buffer (20 mM, pH 8) and elution performed using a gradient of 0% to 50% of 1 M NaCl buffer (1M NaCl, 20 mM Tris, pH 8). Relevant nanobody fractions obtained were buffer exchanged into 20 mM Tris, pH 8 using Amicon 10k MWCO filter units (Merck, catalogue UFC901008).

d) Conjugation of Nanobody-N3-C-terminal Tag to dendrimers

Nanobody-N3-C-terminal Tag was conjugated to the dendrimers Compounds 81-85 using bio-orthogonal click chemistry to generate Compounds 86-95 according to the procedure described for Compounds 74 and 76 except that the linker DBCO-Glu-$NHPEG_{24}CO$-$NHPEG_3$-TCO (Compound 51, Click Chemistry Tools) was used.

Figure 3:
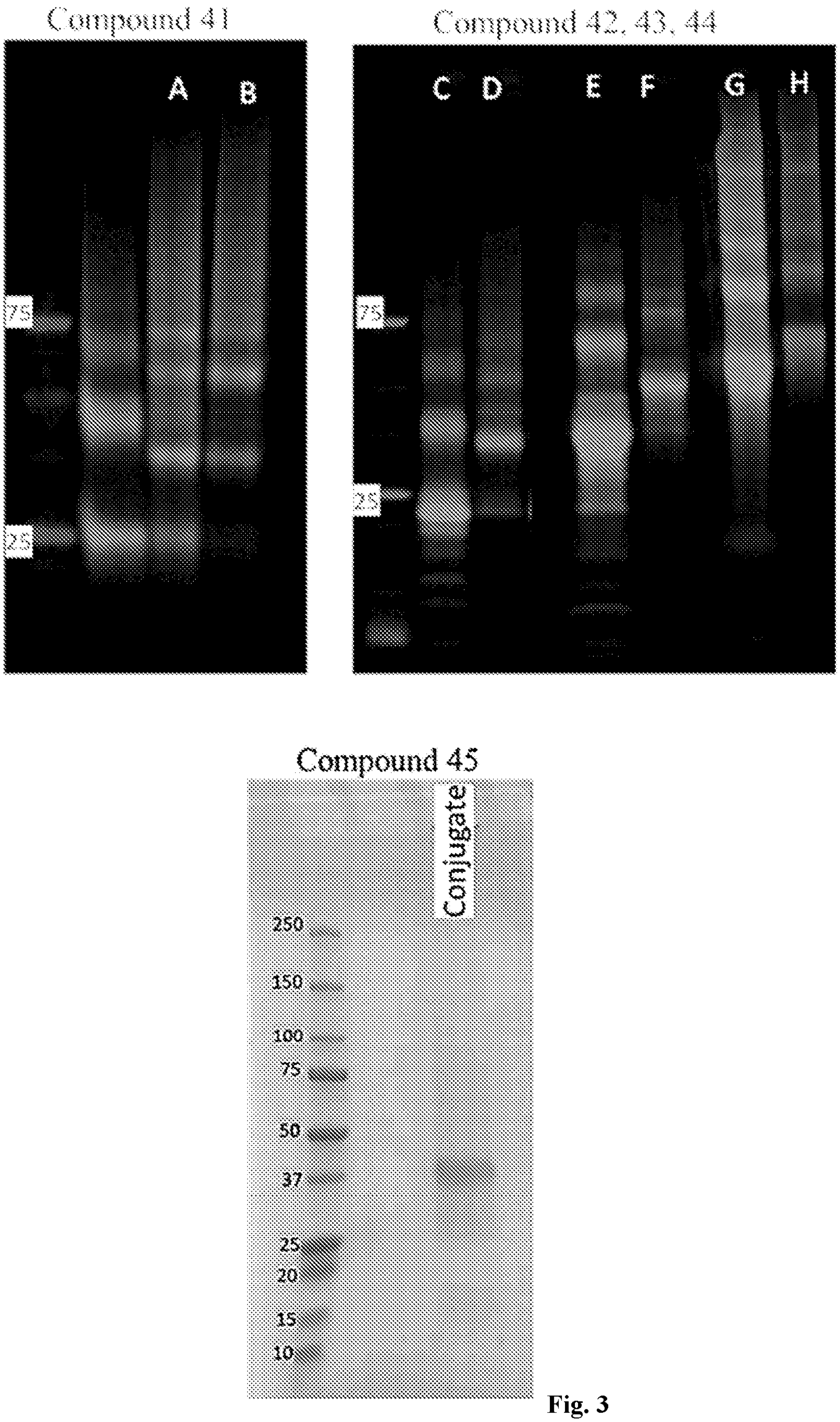
FIG. 3 shows SDS Page and fluorescent imaging analysis of compound 41 (Lane A: Crude mixture; Lane B: Purified conjugate), 42 (Lane C: Crude mixture; Lane D: Purified conjugate), 43 (Lane E: Crude mixture; Lane F: Purified conjugate), 44 (Lane G: Crude mixture; Lane H: Purified conjugate) and 45 (Purified conjugate).

Gels were run for compounds 41 to 45, which showed bands at the appropriate MW for the nanobody-dendrimer conjugates. The purity of each nanobody-dendrimer conjugate was confirmed using non-reducing sodium dodecyl sulfate-polyacrylamide gel electrophoresis (SDS-PAGE) (FIG. 3). Following electrophoretic separation on a 4-15% polyacrylamide gel (Bio-rad, catalogue 4561086), the nanobody-dendrimer conjugates appear as fluorescent bands corresponding approximately to the size of the dendrimer plus the additional mass of the nanobodies when imaged using a Typhoon Biomolecular Imager (GE Healthcare). Subsequent staining with Coomassie Brilliant Blue (CBB) revealed the presence of nanobody at the same locations. No other bands were revealed by CBB indicating the absence of unreacted nanobody and the purity of the preparation.

Example 5 SPR Binding Studies of Affibody-MMAE Dendrimers with Erb2 ECD

Direct Immobilization of ErbB2-ECD

Using a ProteOn XPR36 instrument, ErbB2-ECD was immobilized at 25° C. onto a GLC sensor chip surface (Bio-Rad), with HBS-P+ running buffer (10 mM HEPES, pH 7.4, 150 mM NaCl, 0.05% Tween 20). Standard amine coupling methodology described in Bio-Rad's amine coupling kit was utilized for this immobilization. Lane 1 was activated with a 50:50 mixture of EDC (0.5 mM) and sulfo-NHS (0.125 mM). ErbB2 protein was diluted to 2 mg/mL in 10 mM sodium acetate, pH 5.0 and injected over the activated surface channel. Any remaining activated sites were blocked with 1 M ethanolamine-HCl, pH 8.5. Protein coupling at average response levels of approximately 590 RU (1 RU=1 μg of protein/$mm^2$) was observed.

SPR Experimental Analysis

All SPR binding experiments were performed at 25° C. using HBS-EP+/BSA (10 mM HEPES, pH 7.4, 150 mM NaCl, 3 mM EDTA, 0.05% Tween20, 0.1 mg/ml BSA) as the instrument running buffer (RB). Following immobilization procedures, various concentrations of anti-ErbB2 affibodies and their MMAE-dendrimer conjugates were injected at 60 μl/min over immobilized ErbB2 proteins and their association monitored for 90 sec. Running buffer was subsequently injected over bound Ab-ErbB2 complexes and dissociation monitored for up to 60 min. Herceptin and Affibody controls failed to dissociate from the chip surface in the running buffer in a reasonable timeframe (<60 min). All binding measurements were performed in triplicate.

SPR Data Processing and Analysis

Collected experimental data were processed using Scrubber-Pro software (www.biologic.com.au). Kinetic parameters (ka=association and kd=dissociation rate constants) and equilibrium dissociation constant ($K_D$=$k_d$/$k_a$) were derived by fitting each set of experimental data to a Langmuir 1:1 binding model. All binding parameters were reported as averaged values+/−standard deviation.

SPR Results

Affibody-MMAE-dendrimer conjugates bound specifically to ErbB2 proteins in a process yielding classic kinetic binding profiles. Kinetic binding analyses of Affibody-MMAE-dendrimer conjugates were subsequently performed using dose response methodology. Kinetic rate and affinity parameters derived from SPR sensorgrams are summarized below. Note that the affibody is dimeric and so its binding constant is lower than would be observed for the monomeric affibody used in the dendrimer conjugate. No binding was observed for Compounds 20 and 21. The results clearly indicate nanomolar specific binding for the affibody-dendrimer targets albeit at a reduced amount compared to native affibody.

TABLE 2

SPR Binding Studies

| | $k_a$ ($M^{-1}s^{-1}$) × $10^4$ | $k_d$ ($s^{-1}$) × $10^4$ | $K_D$ |
|---|---|---|---|
| Herceptin | 230 ± 10 | 0.1 ± 0.0 | 4.3 ± 0.1 (pM) |
| Affibody | 190 ± 30 | 5.1 ± 0.2 | 266 ± 46 (pM) |
| Compound 26 (Affibody-MMAE-PEG 1100) | 2.5 ± 0.2 | 13.0 ± 00.1 | 50 ± 5 (nM) |
| Compound 27 | 3.2 ± 0.2 | 11.4 ± 00.3 | 36 ± 3 |

TABLE 2-continued

| SPR Binding Studies | | | |
|---|---|---|---|
| | $k_a$ ($M^{-1}s^{-1}$) × $10^4$ | $k_d$ ($s^{-1}$) × $10^4$ | $K_D$ |
| (Affibody-MMAE-PEG 2000) | | | (nM) |
| Compound 20 | — | — | — |
| (G3-MMAE-PEG 1100) | | | |
| Compound 21 | — | — | — |
| (G3-MMAE-PEG 2000) | | | |

Example 6 Cell Growth Inhibition (SRB Assay) by Affibody-MMAE Dendrimers

Cell growth inhibition in $HER2^-$ (ES2) and HER2+ (SKOV3) cell lines was determined using the Sulforhodamine B (SRB) assay [Voigt W. "Sulforhodamine B assay and chemosensitivity" Methods Mol. Med. 2005, 110, 39-48.] against various cancer cell lines after 72 hours with each experiment run in duplicate. GI50 is the concentration required to inhibit total cell growth by 50%, as per NCI standard protocols.

All compounds were tested based on equivalent drug loading. Results show that the PEG 1100 targeted dendrimer conjugate was more effective at inhibiting cell growth than the dendrimer with a PEG 2000 surface. Affibody alone was ineffective in this assay in either HER2+ or HER2− cell lines.

TABLE 3

Cell Growth Inhibition in $HER2^-$ (ES2) and $HER2^+$ (SKOV3) Cells

| Compound tested | Solvent used | ES2 Cell line $GI_{50}$ (nM) | SKOV3 Cell line $GI_{50}$ (nM) |
|---|---|---|---|
| MMAE | DMSO | <5, 2 | <5, 0.6 |
| MMAE-Cit-Val-PAB | DMSO | 320, >500 | 201, 330 |
| Affibody | PBS | >500, >500 | >500, >500 |
| Compound 26 | PBS | 248, 250 | 4, 5 |
| Compound 27 | PBS | >100 | >500 |

Example 7 Tolerability of Affibody-MMAE Dendrimers In Vivo

Groups of mice were administered an intravenous injection of dendrimer (0.1-0.3 ml solution in PBS) once weekly for 3 weeks (day 1, 8 and 15). Mice were weighed daily and watched for signs of toxicity. Animals were monitored for up to 10 days following the final drug dose. Any mice exceeding ethical endpoints (>2000 body weight loss, poor general health) were immediately sacrificed and observations were noted.

Compound 26 at 1 mg/kg was well tolerated in both nude SCID and balb/c mice with no animal needing to be sacrificed for poor health.

Example 8 In Vitro Efficacy of Conjugates

Description of Cell Lines Used:

| Cell Line | Cancer Type | Her2 Status | Reported Her2 receptor density per cell | EGFR (Her1) Density | Her 3 Status |
|---|---|---|---|---|---|
| MDA-MB-231 | Breast | 1+ | | 200,000 | Low/Mid |
| SKOV-3 | Ovarian | 2+/3+ | 3-700,000 | 50,000 | Low |
| SK-BR-3 | Breast | 3+ | ~1,500,000 | | Mid |
| NCI-N87 | Gastric | 3+ | ~1,300,000 | | Low |
| OE19 | Oesophageal | 3+ | >1,000,000 | | |

$GI_{50}$ Results:

The cytotoxicity of Herceptin®, Kadcyla®, Lapatinib, compound 36 (control) and 2D33 nanobody targeted dendrimer (compound 41) toward MDA-MB-231, SKOV-3, SK-Br-3, NCI-N87 and OE-19 cells were evaluated using an MTT assay. Cells were seeded at a density of 5×103, in 96 well plates and incubated overnight. Cells were then treated with 1 log unit serial dilutions of test compositions for 72 h (or six days for Herceptin). 10% media volume of MTT (Thiazolyl Blue Tetrazolium Bromide (Merck, Cat #M5655, 5 mg/ml sterile solution) was added during the final 2 h of incubation. Reduction of MTT in living cells yields an insoluble purple formazan metabolite. After incubation for 2 h all media was removed from the assay plate, 100 μl of DMSO added and the plate immediately read for absorbance at 570 nm. $GI_{50}$ is defined as the concentration inhibiting the growth/proliferation of cells by 50%. Cell viability and subsequent $GI_{50}$ values were was determined from the blank corrected dose-response curves, with 4-parameter nonlinear curve fit, in GraphPad Prism 7.02. The results demonstrate that example conjugates of the present disclosure have potent cytotoxic effects, particularly against cell lines which overexpress HER2, such as SK-BR-3, NCI-N87 and OE19.

IC 50 Results

| | Herceptin (n = 3) % growth inhibition | Kadcyla* (n = 3) $GI_{50}$ nM | Lapatinib (n = 2) $GI_{50}$ nM | Compound 41 (n = 2) $GI_{50}$ nM | Compound 36 (n = 2) $GI_{50}$ nM |
|---|---|---|---|---|---|
| MDA-MB-231 | 1.7 | 22.9 | 112,000 | 172 | 12,470 |
| SKOV-3 | 10 | 50.7 | 7,200 | 13.1 | 1600 |
| SK-BR-3 | 51 | 0.04 | 138 | 0.83 | 948 |
| NCI-N87 | 52 | 0.10 | 8.1 | 0.61 | 2040 |
| OE19 | 62 | 0.06 | 200 | 1.67 | 6120 |

*Based on estimated weight ADC;
Based on MMAE drug equivalents

Generation of HER2+ MDA-MB-231 Breast Cancer Cell Line for Paired Hi/Lo HER2 Cell Lines MDA-MB-231 breast cancer cells were transfected with plasmid HER2 WT Addgene, 16257) using Lipofectamine 3000 according to manufacturer's instructions. After passaging in the presence of 500 ug/ml Geneticin (Thermo Fisher, catalogue 10131035), cells with stable overexpression of HER2 WT were isolated by fluorescence activated single cell sorting using a MoFlo Astrios (Beckman Coulter). A clonal cell population isolated from this process was further passaged in Geneticin before a second round of cell sorting and screening for transgene expression. A selected clone was then further expanded and stocks of this cell line, referred to as MDA-MB-231/HER2, were cryopreserved to generate a master stock of stably transduced cells.

IC50 Results in Lo/Hi Expressing MDA-MB-231 Model:

The cytotoxicity of compound 36 (control) and compound 41 (targeted) toward MDA-MB-231, and MDA-MB-231/HER2 transfected cells were evaluated via alamarBlue assays. Cells were seeded at a density of $5\times10^3$, in 96 well plates and incubated overnight. Cells were then treated with indicated concentrations of test compositions for 48 h. alamarBlue (Thermo Fisher, DAL1025) was added during the final 4 h of incubation. Reduction of alamarBlue in living cells yields a red fluorescent metabolite that can be read on a plate reader (560 nm excitation/610 nm emission). Cell viability and subsequent $IC_{50}$ was determined from the blank corrected dose-response curves, with 4-parameter nonlinear nonlinear curve fit, variable slope (four parameters) in GraphPad Prism 7.02. The table below shows the $IC_{50}$ values of compound 36 (control) and compound 41 (targeted) with MDA-MB-231 and MDA-MB-231/HER2 cells. The $IC_{50}$ values of MDA-MB-231/HER2 with compound 36 (control) and compound 41 (targeted) were 2.842 μM and 13.55 nM, respectively. Compound 41 (targeted) is approximately 140-fold increase in MDA-MB-231/HER2 cell growth inhibition compared to compound 36 (control).

The dose response curve and $IC_{50}$ value for MDA-MB-231 and MDA-MB-231/HER2 of compound 36 (control) at different MMAE concentrations is provided below. Values are mean±standard deviation (sd; n=4):

| MMAE | Compound 36 (Cell viability %) | |
|---|---|---|
| Concentration (M) | MDA-MB-231 | MDA-MB-231/HER2 |
| $5\times10^{-5}$ | 81.1 ± 5.4 | 49.9 ± 15.0 |
| $1\times10^{-5}$ | 94.2 ± 12.1 | 61.6 ± 3.1 |
| $1\times10^{-6}$ | 94.4 ± 8.2 | 78.2 ± 9.1 |
| $1\times10^{-7}$ | 94.2 ± 12.5 | 96.1 ± 3.6 |
| $1\times10^{-8}$ | 96.6 ± 11.7 | 95.4 ± 7.6 |
| $IC_{50}$ | Ambiguous | 2.842 μM |

The dose response curve and $IC_{50}$ value for MDA-MB-231 and MDA-MB-231/HER2 of compound 41 (targeted) at different MMAE concentrations. Values are mean standard deviation (sd; n=4):

| MMAE | Compound 41 (Cell viability %) | |
|---|---|---|
| Concentration (M) | MDA-MB-231 | MDA-MB-231/HER2 |
| $1\times10^{-6}$ | — | 5.25 ± 1.24 |
| $1\times10^{-7}$ | — | 10.9 ± 2.4 |
| $2.5\times10^{-8}$ | 49.7 ± 2.7 | 27.4 ± 1.3 |
| $1\times10^{-8}$ | 67.2 ± 3.0 | 57.8 ± 2.3 |
| $1\times10^{-9}$ | 81.0 ± 1.8 | 80.0 ± 3.3 |
| $1\times10^{-10}$ | 87.6 ± 4.2 | 91.1 ± 2.5 |
| $1\times10^{-11}$ | 96.1 ± 5.6 | 90.0 ± 3.0 |
| $IC_{50}$ | Ambiguous | 13.55 nM |

Example 9 Binding of 2D3-Dendrimer Conjugates to HER2+ Cells

Different sized nanobody-dendrimer conjugates labeled with Cyanine 5 (Cy5), compounds 42, 43 and 44 were used to demonstrate binding to HER2+ human cell lines, against untargeted compounds 37, 38 and 39 (G3, G4, and G5). The HER2-expressing human metastatic carcinoma cell line MDA-MB-453 (ATCC HTB-131) and the HER2-negative epithelial adenocarcinoma cell line MDA-MB-231 (ATCC HTB-26) were maintained in Dulbecco's Modified Eagle's Medium (DMEM) containing 10% FBS and penicillin-streptomycin (100 U/mL) at 37° C. under a 5% $CO_2$ humidified atmosphere and subcultured prior to confluence using trypsin. Human adenocarcinoma ovary cell line SKOV-3 (ATCC® HTB-77) cells were maintained in RPMI media with the addition of 10% (v/v) FBS and penicillin-streptomycin (100 U/mL) at 37° C. in a 5% $CO_2$ humidified atmosphere and subcultured prior to confluence.

For measurement of cell association by fluorescence microscopy, cells were seeded at $1\times10^5$ cells per well in an 8 well chamber slide and allowed to adhere overnight. The following day, Unconjugated dendrimer compounds 37, 38 and 39 (control) or nanobody dendrimer compounds 42, 43 and 44 were added to the media to a final concentration of 0.5 ug/ml and incubated on ice for 1 hour. Cells were stained to visualise plasma membrane (wheat germ agglutinin-alexa fluor 488) and nucleus (Hoechst 33342). Cells were washed three times with 400 ul of chilled Fluorobrite media supplemented with 10% FBS. Cells were imaged using an Olympus IX83 microscope with a 40×0.9 NA air objective with a standard "Pinkel" DAPI/FITC/CY5 filter set.

For measurement of cell association by flow cytometry, cells in suspension were added at $1\times10^5$ cells per well to a 96 well assay plate. Following incubation with nanobody-dendrimer or unconjugated dendrimer for 1 hour on ice, cells were washed three times with 200 ul of DMEM containing 10% FBS to remove unbound dendrimer. Cells were then resuspended in chilled Fluorobrite media supplemented with 10% FBS and Cy5 fluorescence measured using 642 nm excitation and emission collected between 661-691 nm. To measure internalisation kinetics, nanobody-dendrimer was incubated with cells for 24, 4, 1, 0.5 and 0.1 hours at 37° C. before unbound nanobody-dendrimer was removed by washing and analysed by flow cytometry.

In Vitro Association Studies

MDA-MB-231, MDA-MB-231/HER2 (HER2 knock in) (as described above), or SKOV-3 cells were seeded in a 24-well plate ($1\times10^5$ cells per well) in 500 μL of appropriate growth media with the addition of 10% (v/v) fetal bovine serum (FBS) and incubated with compound 36 or 41 at 3.33 nM, with incubation time varied from 1 to 24 h at 37° C. in a 5% $CO_2$ humidified atmosphere. After incubation, non-binding/non-associating particles were removed from adherent cells by gently washing with DPBS three times (300 μL/well). Cells were removed from plates by treatment with TrypLE™ Express Enzyme (1×), no phenol red (150 μL/well) for 5-10 min at room temperature. The plates were then placed on ice. Cellular binding and association of sample were then determined through flow cytometry by the acquisition of the signal from Cy5.

Flow Cytometry:

Results show that the nanobody-dendrimer compounds 42, 43 and 44 bind to HER2-positive MDA-MB-453 cells. Unconjugated dendrimer compounds 37, 38 and 39 did not bind to MDA-MB-453 cells. Data shown is the mean MFI of cells treated in triplicate wells, with standard deviation. An ANOVA with Dunnett's multiple comparisons test was used for statistical analysis.

Mean Fluorescence Intensity (Cy5) of Cells Incubated with Dendrimers:

| Compound tested | MFI | ANOVA |
|---|---|---|
| Cells only | 3.047 ± 0.02 | — |
| 37 | 3.097 ± 0.01 | NS |
| 38 | 6.827 ± 0.07 | NS |

-continued

| Compound tested | MFI | ANOVA |
|---|---|---|
| 39 | 4.349 ± 0.08 | NS |
| 42 | 50.83 ± 14.98 | <0.0001 |
| 43 | 158.4 ± 6.611 | <0.0001 |
| 44 | 176.9 ± 4.041 | <0.0001 |

Flow Cytometry Results

Figure 4:
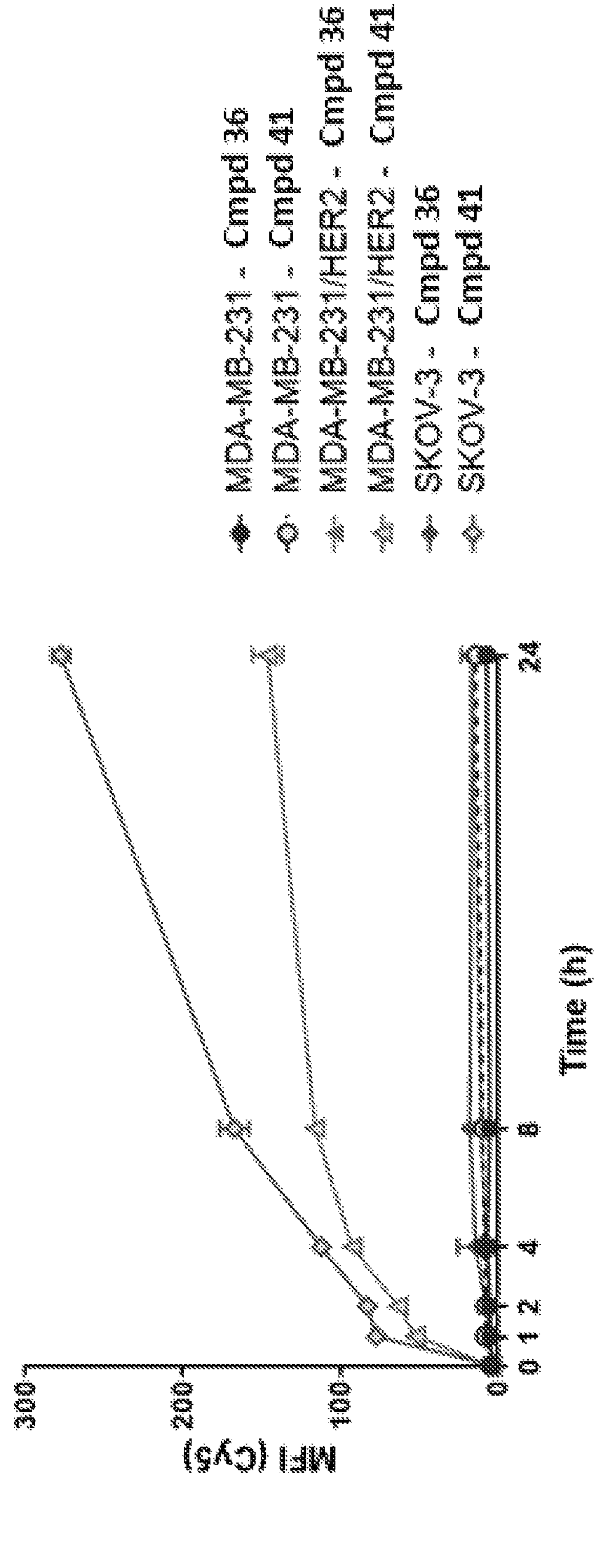
FIG. 4 shows mean fluorescence intensity value of Compound 36 (control) and Compound 41 (targeted) with MDA-MB-231, MDA-MB-231/HER2 and SKOV-3 cells over 24 h. At least 10,000 cells were counted per measurement. Values are mean±standard deviation (SD; n=3).

The results clearly indicate minimal binding of compound 36 (control) towards all three cell lines over 24 h. Compound 41 (targeted) showed increasing binding in relation to the level of HER2 receptor expression of cell line. By 24 h, flow cytometry revealed that MDA-MB-231/HER2 cells treated with compound 41 (146.1±9.6) displayed approximately 9-fold stronger fluorescence compared to the cells treated with compound 36 (16.05±1.89). Also, SKOV-3 cells treated with compound 41 (277.5±5.9) displayed approximately 16-fold stronger fluorescence compared to the cells treated with compound 36 (16.4±6.86). The results are shown in FIG. 4.

Dendrimer Size G3 to G5:

Additional dendrimer generations were tested: compounds 37 and 42 (G3), compounds 38 and 43 (G4) and compounds 39 and 44 (G5), unconjugated and conjugated to 2D3 respectively. Unconjugated control dendrimers compounds 37, 38 and 39 had significantly lower association with MDA-MB-231 (HER2 negative) and MDA-MB-231/HER2 (HER2 positive). 2D3-conjugated dendrimers 42, 43 and 44 have significant association with MDA-MB-231/HER2 over 24 h, with compound 44 (G5) having the highest percent of cellular association (73.47%±0.92), second being compound 42 (G3, 60.73±0.21) and compound 43 (G4, 56.27±1.02). Regardless of dendrimer generation, 2D3 HER2-nanobody conjugated with dendrimer substantially improves binding towards cells which overexpress HER2 receptors.

Percent of cellular association value of compound 42 (G3), compound 43 (G4) and compound 44 (G5) with MDA-MB-231 and MIDA-MB-231/BER2 cells over 24 h. Values are mean±standard deviation (SD; n=3):

| MDA-MB-231/HER2 | | | | | | | |
|---|---|---|---|---|---|---|---|
| Time (h) | Compound 42 | Compound 43 | Compound 44 | Compound 86 | Compound 89 | Compound 90 | Compound 92 |
| 0.25 | 0.67 ± 0.12 | 0.57 ± 0.12 | 0.43 ± 0.40 | — | — | — | — |
| 0.5 | 0.60 ± 0.0 | 0.67 ± 0.15 | 0.70 ± 0.10 | 189.7 ± 9.074 | 218.3 ± 16.5 | 157.3 ± 7.02 | 165.3 ± 31.5 |
| 0.75 | — | — | — | — | — | — | — |
| 1 | 2.57 ± 0.64 | 0.77 ± 0.15 | 2.80 ± 0.61 | — | — | — | — |
| 2 | 17.43 ± 4.15 | 6.13 ± 2.60 | 17.97 ± 2.20 | — | — | — | — |
| 4 | 50.63 ± 0.15 | 36.03 ± 2.36 | 59.77 ± 4.13 | — | — | — | — |
| 24 | 60.73 ± 0.21 | 56.27 ± 1.02 | 73.47 ± 0.92 | — | — | — | — |

| MDA-MB-231/HER2 | | | | | | |
|---|---|---|---|---|---|---|
| Time (h) | Compound 97 | Compound 98 | Compound 82 | Compound 83 | Compound 84 | Compound 185 |
| 0.25 | — | — | — | — | — | — |
| 0.5 | — | — | 14.83 ± 1.60 | 43.23 ± 3.48 | 16.7 ± 2.48 | 25.6 ± 0.43 |
| 0.75 | 14.97 ± 0.7 | 82.5 | — | — | — | — |
| 1 | — | — | — | — | — | — |
| 2 | — | — | — | — | — | — |
| 4 | — | — | — | — | — | — |
| 24 | — | — | — | — | — | — |

| MDA-MB-231 | | | | | | | |
|---|---|---|---|---|---|---|---|
| Time (h) | Compound 42 | Compound 43 | Compound 44 | Compound 86 | Compound 89 | Compound 90 | Compound 92 |
| 0.25 | 1.07 ± 0.38 | 0.87 ± 0.25 | 0.53 ± 0.50 | — | — | — | — |
| 0.5 | 0.87 ± 0.12 | 0.53 ± 0.15 | 1.03 ± 0.32 | 30.77 ± 0.50 | 25.07 ± 3.91 | 20.03 ± 2.73 | 17.47 ± 1.62 |
| 0.75 | — | — | — | — | — | — | — |
| 1 | 0.80 ± 0.20 | 1.00 ± 0.44 | 1.37 ± 0.59 | — | — | — | — |
| 2 | 1.13 ± 0.21 | 0.77 ± 0.31 | 0.73 ± 0.49 | — | — | — | — |
| 4 | 0.93 ± 0.45 | 0.83 ± 0.21 | 0.67 ± 0.25 | — | — | — | — |
| 24 | 0.83 ± 0.06 | 0.87 ± 0.06 | 0.80 ± 0.10 | — | — | — | — |

| | MDA-MB-231 | | | | | |
|---|---|---|---|---|---|---|
| Time (h) | Compound 97 | Compound 98 | Compound 82 | Compound 83 | Compound 84 | Compound 85 |
| 0.25 | — | — | — | — | — | — |
| 0.5 | — | — | 23.3 ± 3.98 | 42.8 ± 2.78 | 20.23 ± 0.63 | 33.23 ± 2.2 |
| 0.75 | 13.36 ± 2.82 | 0.15 ± 0.07 | | | | |
| 1 | — | — | — | — | — | — |
| 2 | — | — | — | — | — | — |
| 4 | — | — | — | — | — | — |
| 24 | — | — | — | — | — | — |

Percent of cellular association value of compound 37 (G3), compound 38 (G4) and compound 39 (G5) with MDA-MB-231 and MIDA-MB-231/BER2 cells over 24 h. Values are mean±standard deviation (SD; n=3):

| Time | MDA-MB-231/HER2 | | |
|---|---|---|---|
| (h) | Compound 37 | Compound 38 | Compound 39 |
| 1 | 2.47 ± 0.81 | 0.90 ± 0.35 | 1.07 ± 0.35 |
| 2 | 1.00 ± 0.26 | 0.50 ± 0.10 | 0.83 ± 0.31 |
| 4 | 1.07 ± 0.64 | 0.50 ± 0.35 | 0.47 ± 0.21 |
| 24 | 0.60 ± 0.17 | 0.37 ± 0.15 | 0.53 ± 0.49 |

| Time | MDA-MB-231 | | |
|---|---|---|---|
| (h) | Compound 37 | Compound 38 | Compound 39 |
| 1 | 1.10 ± 0.35 | 0.80 ± 0.10 | 0.97 ± 0.12 |
| 2 | 1.23 ± 0.47 | 0.77 ± 0.06 | 1.07 ± 0.21 |
| 4 | 0.83 ± 0.15 | 0.60 ± 0.10 | 0.87 ± 0.15 |
| 24 | 0.73 ± 0.06 | 0.60 ± 0.17 | 0.57 ± 0.06 |

Mean fluorescence intensity value of compound 42 (G3), compound 43 (G4) and compound 44 (G5) with MDA-MB-231 and MDA-MB-231/HER2 cells over 24 h. Values are mean±standard deviation (SD; n=3):

| | MDA-MB-2315 | | |
|---|---|---|---|
| Time (h) | 2D3-Compound 42 | 2D3-Compound 43 | 2D3-Compound 44 |
| 0.25 | 245.7 ± 17.5 | 227.3 ± 14.0 | 194.7 ± 95.8 |
| 0.5 | 228.0 ± 4.6 | 222.7 ± 2.1 | 245.0 ± 4.0 |
| 1 | 237.0 ± 9.2 | 229.7 ± 6.4 | 253.7 ± 12.9 |
| 2 | 241.0 ± 18.2 | 235.7 ± 4.0 | 233.3 ± 9.7 |
| 4 | 250.0 ± 5.8 | 246.3 ± 5.5 | 247.0 ± 10.6 |
| 24 | 224.3 ± 5.1 | 219.0 ± 4.6 | 223.0 ± 4.4 |

| | MDA-MB-231/HER2 | | |
|---|---|---|---|
| Time (h) | 2D3-Compound 42 | 2D3-Compound 43 | 2D3-Compound 44 |
| 0.25 | 235.0 ± 7.0 | 215.3 ± 14.0 | 207.0 ± 51.6 |
| 0.5 | 226.3 ± 8.7 | 224.3 ± 2.9 | 237.0 ± 9.5 |
| 1 | 294.3 ± 15.6 | 241.0 ± 11.5 | 295.0 ± 4.0 |
| 2 | 445.0 ± 33.2 | 342.3 ± 22.2 | 435.7 ± 16.3 |
| 4 | 799.7 ± 18.0 | 611.3 ± 35.2 | 1,038 ± 127.6 |
| 24 | 1,110 ± 27.8 | 1,012 ± 45.6 | 2,749 ± 88.1 |

Mean fluorescence intensity value of compound 37 (G3), compound 38 (G4) and compound 39 (G5) with MDA-MB-231 and MDA-MB-231/HER2 cells over 24 h. Values are mean±standard deviation (SD; n=3):

| Time | MDA-MB-231/HER2 | | |
|---|---|---|---|
| (h) | Compound 37 | Compound 38 | Compound 39 |
| 1 | 293.0 ± 8.5 | 269.0 ± 19.8 | 257.5 ± 12.0 |
| 2 | 268.0 ± 11.3 | 225.0 ± 5.7 | 249.0 ± 15.6 |
| 4 | 241.5 ± 17.7 | 198.0 ± 2.8 | 207.0 ± 2.8 |
| 24 | 206.0 ± 2.8 | 175.5 ± 0.7 | 207.5 ± 40.3 |

| Time | MDA-MB-231 | | |
|---|---|---|---|
| (h) | Compound 37 | Compound 38 | Compound 39 |
| 1 | 258.3 ± 19.6 | 239.3 ± 1.2 | 252.0 ± 6.0 |
| 2 | 256.7 ± 24.8 | 230.7 ± 2.3 | 249.0 ± 8.7 |
| 4 | 221.3 ± 3.5 | 217.3 ± 3.2 | 247.3 ± 7.2 |
| 24 | 215.3 ± 4.9 | 195.7 ± 0.6 | 196.3 ± 3.1 |

Figure 5:
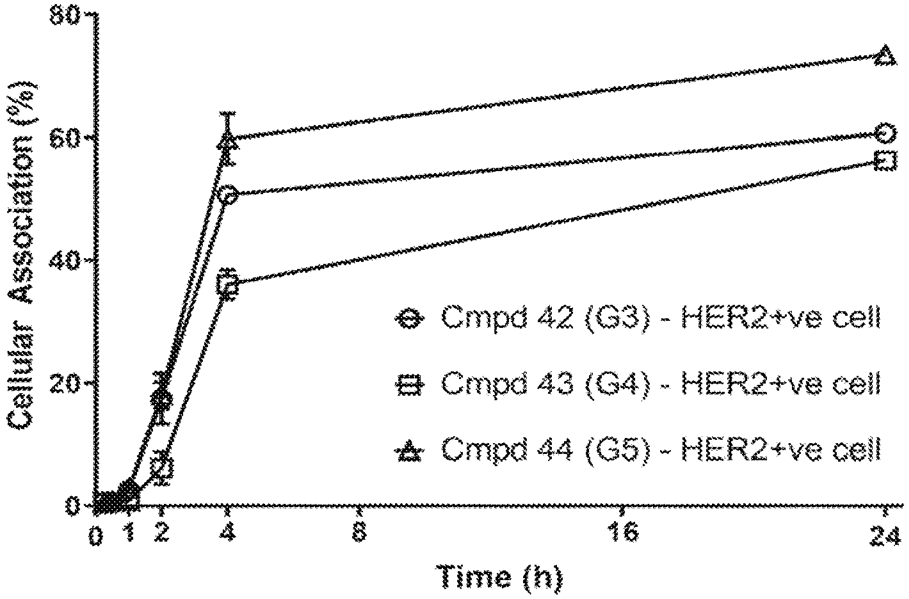
FIG. 5 shows flow cytometry analysis of dendrimers incubated with HER2 positive cell (MDA-MB-231/HER2) and HER2 negative cell (MDA-MB-231), at 3.33 nM over 24 h incubation at 37° C. At least 10,000 cells were counted per measurement. Values are mean standard deviation (SD; n=3).
Figure 5:
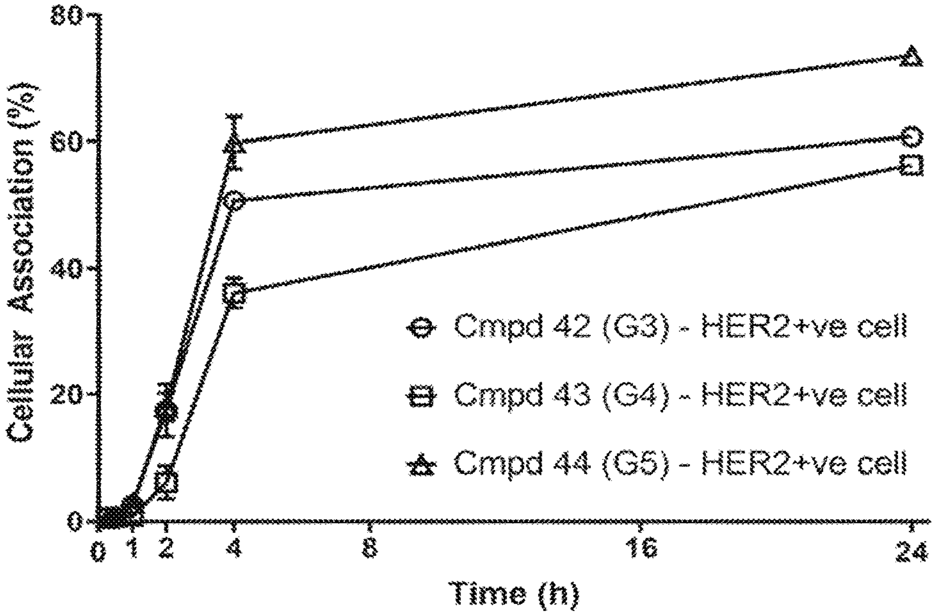
Figure 5:
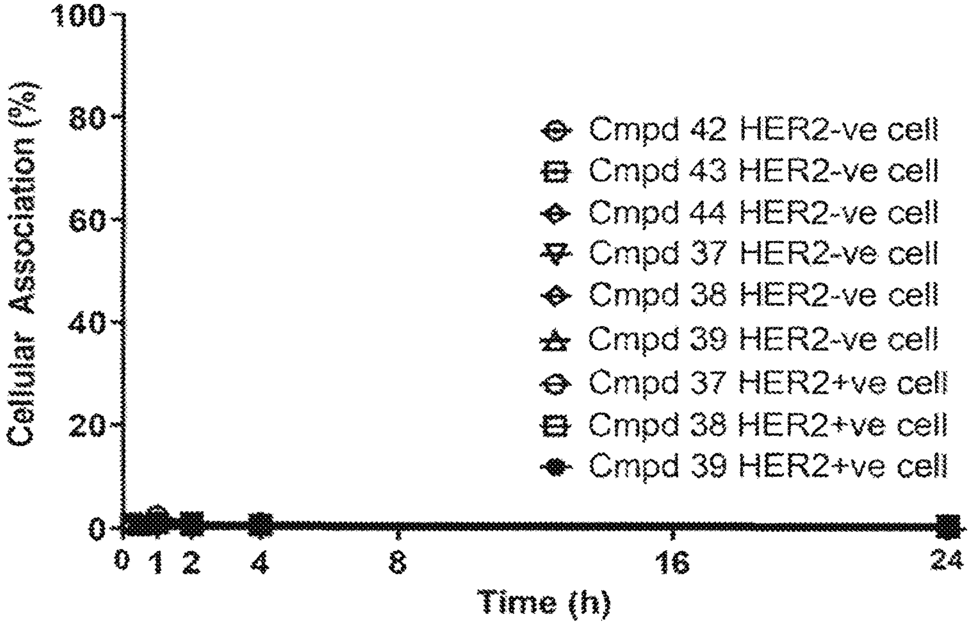
Figure 5:
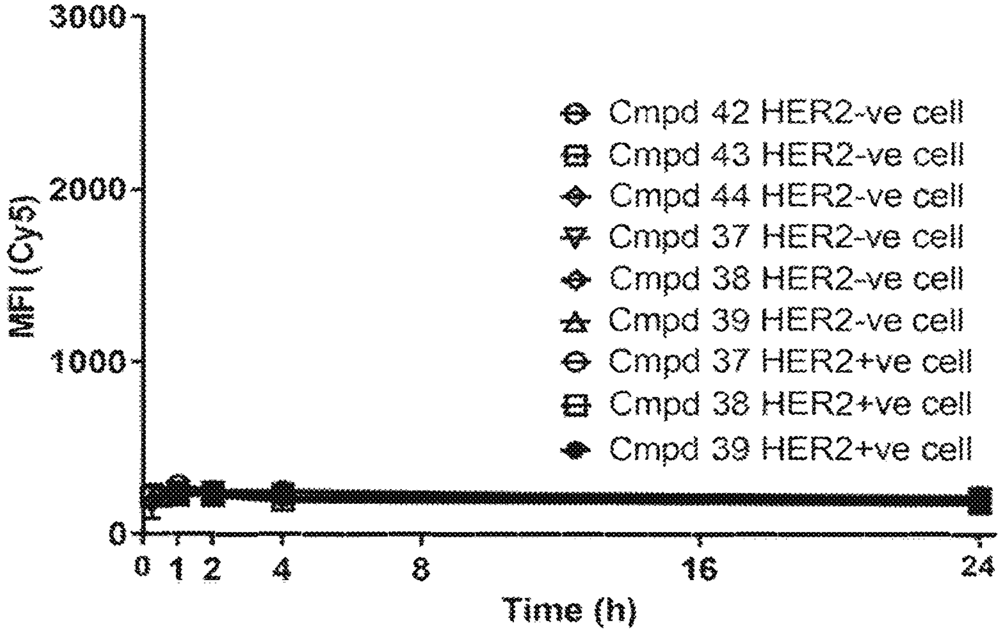

Flow cytometry results for the conjugates are shown in FIG. 5.

Example 10 Studies Demonstrating Internalisation of Conjugates into HER2-Overexpressing Cells

Confocal Cellular Uptake

MDA-MB-231, MDA-MB-231/HER2 and SKOV-3 cells were plated at $1.0\times10^4$ cells per well into μ-slide 8 well chambered coverslip (ibidi) and allowed to adhere overnight at 37° C., 5% $CO_2$. compounds 36 and 41 (3.33 nM) were then added and allowed to incubate for 1, 3, 6 and 24 hrs. The cells were washed and then fixed with 1% paraformaldehyde for 20 min at room temperature. The cell membrane was stained with Alexa Fluor 488-wheat germ agglutinin (AF488-WGA, 5 μg $mL^{-1}$) in DPBS at room temperature for 10 min. The cell nuclei were counterstained with 4',6-diamidino-2-phenylindole (DAPI, 2 μg $mL^{-1}$) in DPBS at room temperature for 10 min. Fluorescence images and optical sections were collected using a confocal microscope (Leica SP8). Images were processed with Fiji (Image J 1.52n).

Figure 6:
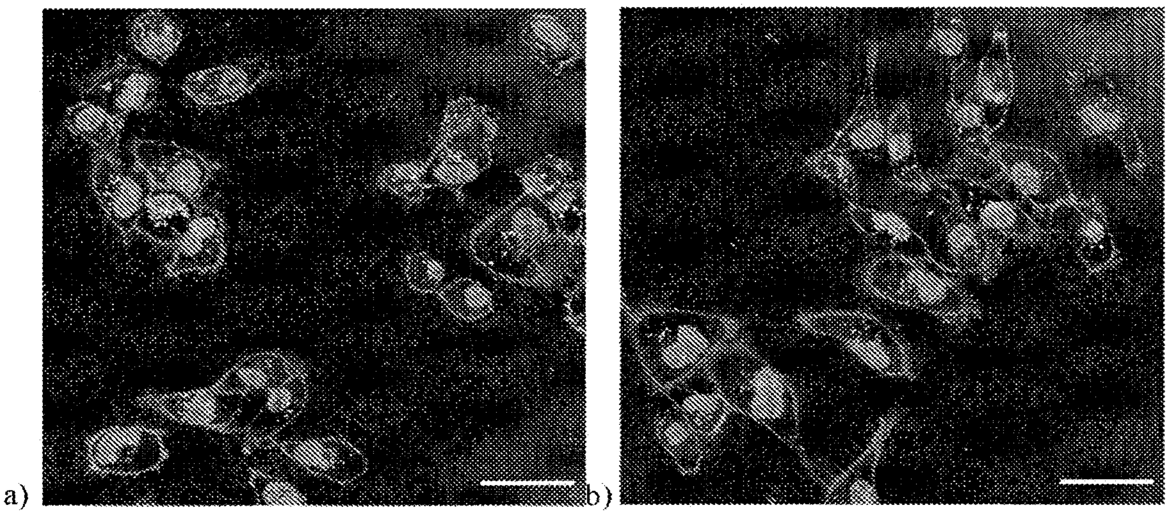
FIG. 6 shows confocal microscopy images of MDA-MB-231 cells treated with a) compound 36 (control) or b) compound 41 (targeted) at a concentration of 3.33 nM for 24 h. Green, blue and red fluorescence represent cell membrane stained with AF-488-WGA, nucleus stained with DAPI, and dendrimer labeled with Cy5, respectively. Scale bar=50 μm.
Figure 7:
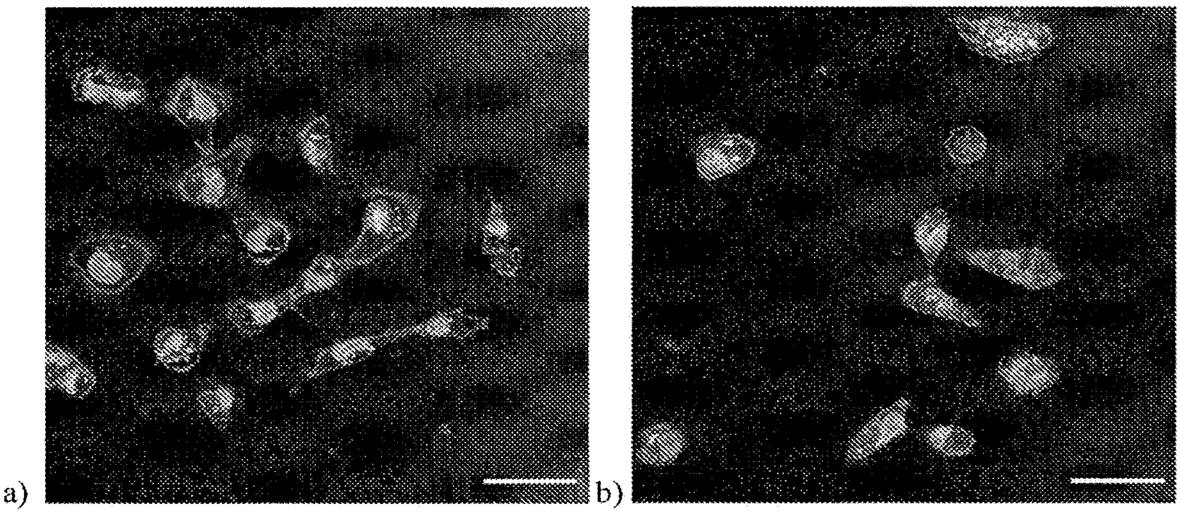
FIG. 7 shows confocal microscopy images of MDA-MB-231/HER2 cells treated with a) compound 36 (control) or b) compound 41 (targeted) at a concentration of 3.33 nM for 24 h. Green, blue and red fluorescence represent cell membrane stained with AF-488-WGA, nucleus stained with DAPI, and dendrimer labeled with Cy5, respectively. Scale bar=50 μm.
Figure 8:
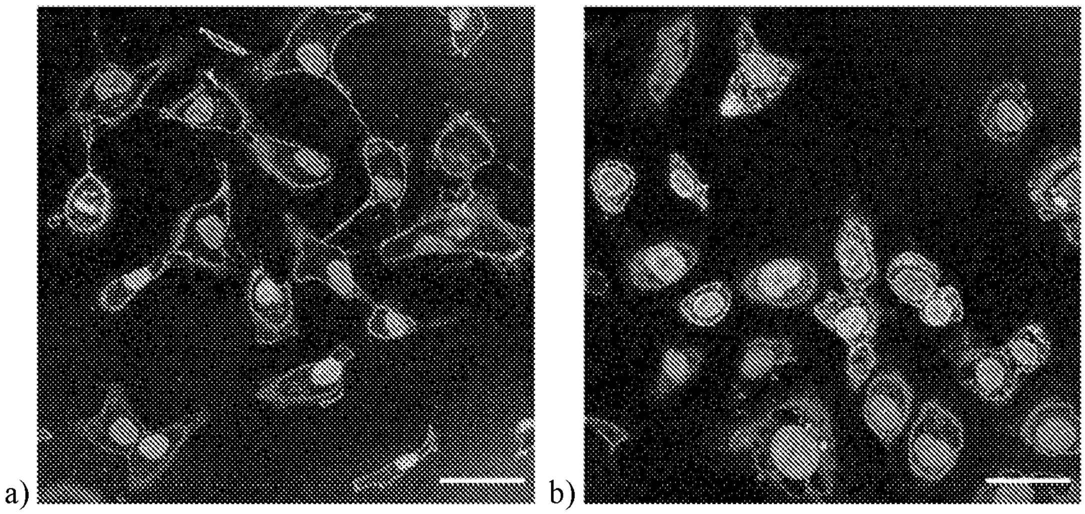
FIG. 8 shows confocal microscopy images of SKOV-3 cells treated with a) compound 36 (control) or b) compound 41 (targeted) at a concentration of 3.33 nM for 24 h. Green, blue and red fluorescence represent cell membrane stained with AF-488-WGA, nucleus stained with DAPI, and dendrimer labeled with Cy5, respectively. Scale bar=50 μm.

Confocal microscopy images are shown in FIGS. 6 to 8. The confocal images show little of either FIG. 6 *a*) compounds 36 and FIG. 6 *b*) 41 associated with MDA-MB-231 after 24 h of incubation. Whereas, targeted compound 41 was internalised by MDA-MB-231/HER2 and SKOV-3 cells after 24 h of incubation, (FIGS. 7*a* and 8*a*), compound 36 was not (FIGS. 7*b* and 8*b*).

Example 11 Tumour Distribution of Tritium-Labeled MMAE-Conjugated Dendrimers (Compounds 40 and 45)

MDA-MB-231/HER2 cells ($5\times10^6$ cells in 50 μL of PBS:Matrigel) were transplanted into the $4^{th}$ mammary fat pad of female NOD/SCID mice (5-7 weeks old) subcutaneously. Solid tumours were allowed to grow to 100 $mm^3$ (approximately 3-4 weeks). The mice were divided into two different groups, consisting of six mice in each group. compound 40 (control group) or compound 45 (targeted group) (0.5 μCi in 100 μL, PBS pH 7) was then injected via tail vein under isoflurane sedation. The mice were anaesthetised with isoflurane 48 h later, and blood collected via cardiac puncture immediately prior to cervical dislocation. Selected organs (including tumour, liver, spleen, kidney, pancreas, lung, heart and brain) were subsequently removed, weighed and processed for tritium (H) biodistribution.

Figure 9:
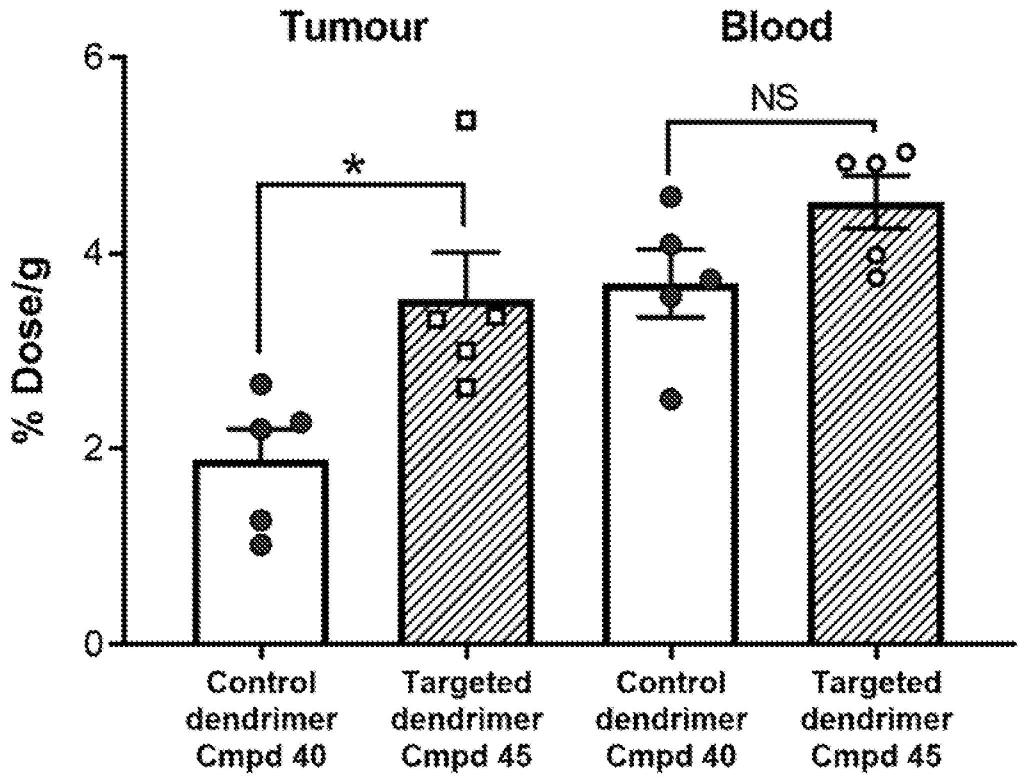
FIG. 9 shows tumour and blood distribution data of 3H-labeled compound 40 and compound 45 dendrimers after sacrifice at 48 h. All data was normalised by tissue mass. All data represents the mean±SEM (n=5); (NS=not significant; *=p-value<0.05).

The results are shown in FIG. 9. Targeted dendrimer compound 45 accumulated in HER2 positive tumours (3.53% dose/g±0.43) to a greater extent than the unconjugated control compound 40 (1.88% dose/g±0.28), which equates to an increase in tumour uptake by approximately 80% ($p<0.05$). The differences in blood concentration were insignificant between the targeted and control dendrimer, 4.52% dose/g±0.24 and 3.69% dose/g±0.31, respectively. As the differences in pharmacokinetics are unlikely to be affecting tumour retention, 2D3 HER2-nanobody targeting improved dendrimer retention.

Example 12 Efficacy and Confocal Imaging of Tumour Uptake of Cy5 Labelled-MMAE-Conjugated Dendrimers (Compounds 36 and 41) in SKOV3 Tumour Model Female NOD SCID mice (Age 8 weeks) were inoculated subcutaneously on the flank with $3\times10^6$ SKOV3 cells in PBS:Matrigel (1:1). Solid tumours were allowed to grow to 200 $mm^3$ (approximately 3 weeks). The mice were divided into five different groups, Compound 36 (control group) or compound 41 (targeted group) (0.5 mg/kg MMAE equivalents in 250 μL, PBS pH 7), Kadcyla® 40 mg/kg and Herceptin® (40 mg/kg), was then injected via tail vein under isoflurane sedation.

(a) Confocal Imaging

Figure 10:
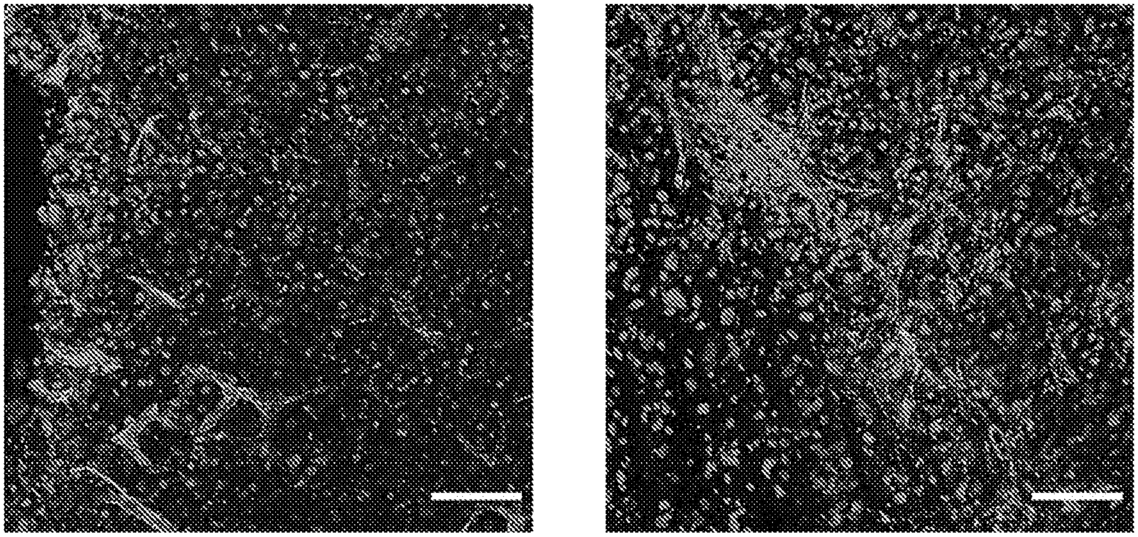
FIG. 10 shows representative ex-vivo tumour distribution of compounds 36 and 41 after sacrifice at 48 h. Data represents a typical field of view for (a) untargeted dendrimer (compound 36) and (b) targeted dendrimer (compound 41).
Figure 11:
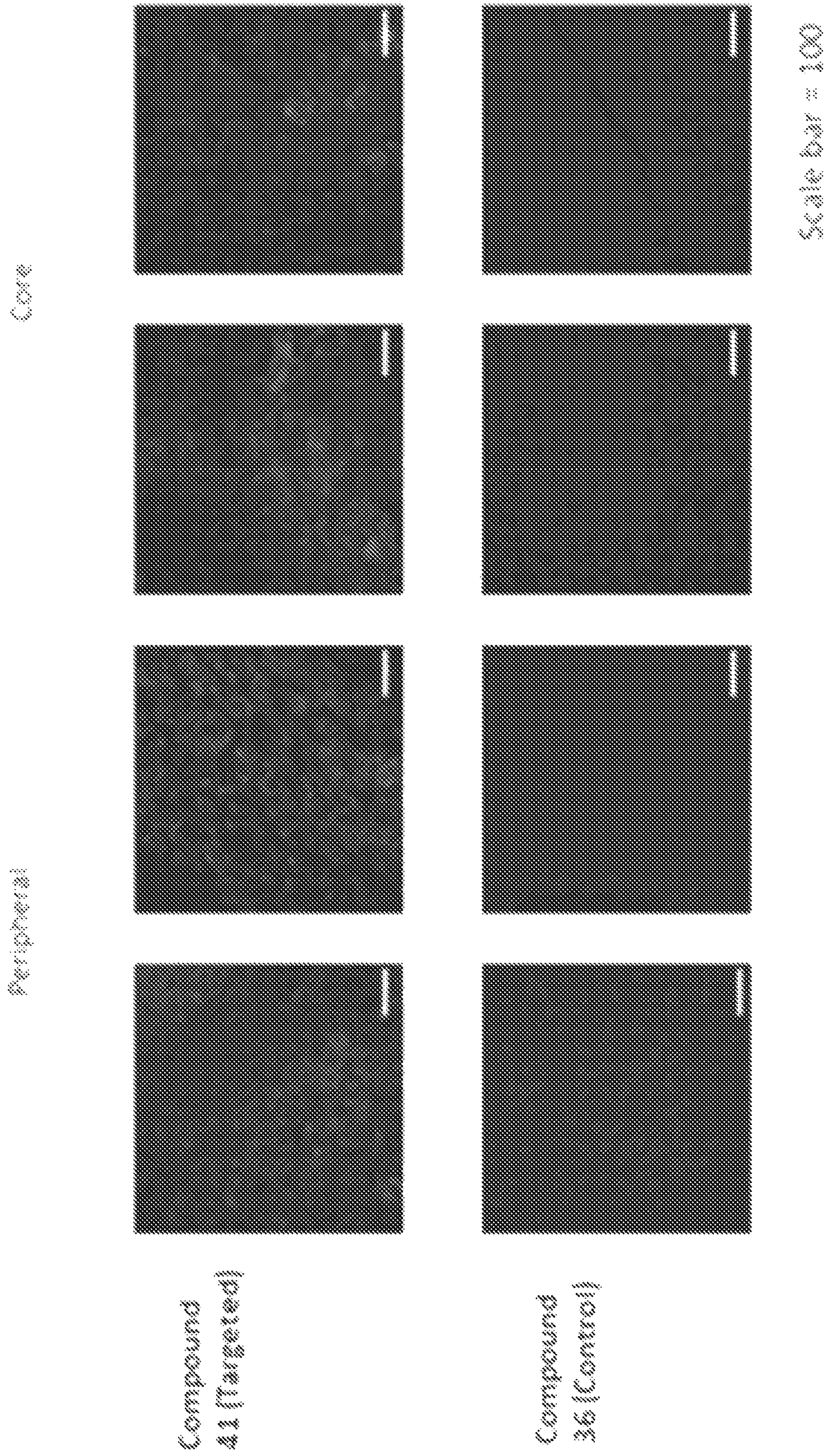
FIG. 11 shows images showing that targeted dendrimer (compound 41) was uptaken into the core and peripheral regions of a tumour, and showing that control compound 36 was not.

The mice were anaesthetised with isoflurane 48 h later, and blood collected via cardiac puncture immediately prior to cervical dislocation (n=2/group). Tumours were subsequently removed, fixed in 4% paraformaldehyde overnight, washed in PBS and embedded in agarose. Tumours were then vibratome sectioned to 100 μm, with sections stained for nuclei (DAPI, conc, time, supplier) and blood vessels (CD31, conc, time, supplier). Fluorescence images and optical sections were collected using a confocal microscope (Leica SP8). The results are shown in FIGS. 10 and 11. Targeted Dendrimer (compound 41) showed uptake in core and peripheral regions of the tumour, Compound 36 did not.

(b) Efficacy of Conjugate

Figure 12:
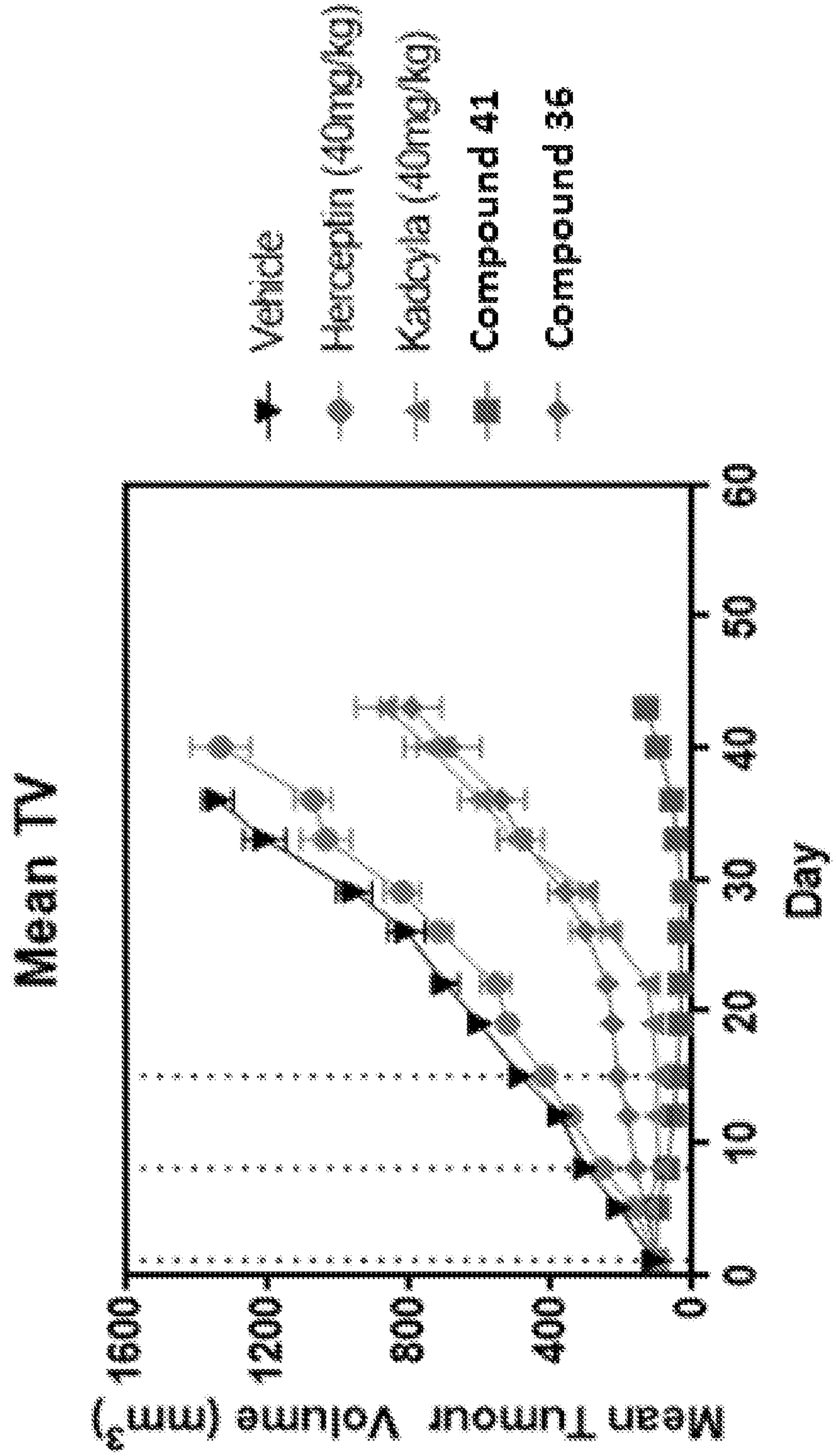
FIG. 12 shows a plot of mean tumour volume over time for mice inoculated with SKOV3 cells following treatment with vehicle, control compound 36, targeted conjugate 41, Kadcyla®, or Herceptin®.
Figure 13:
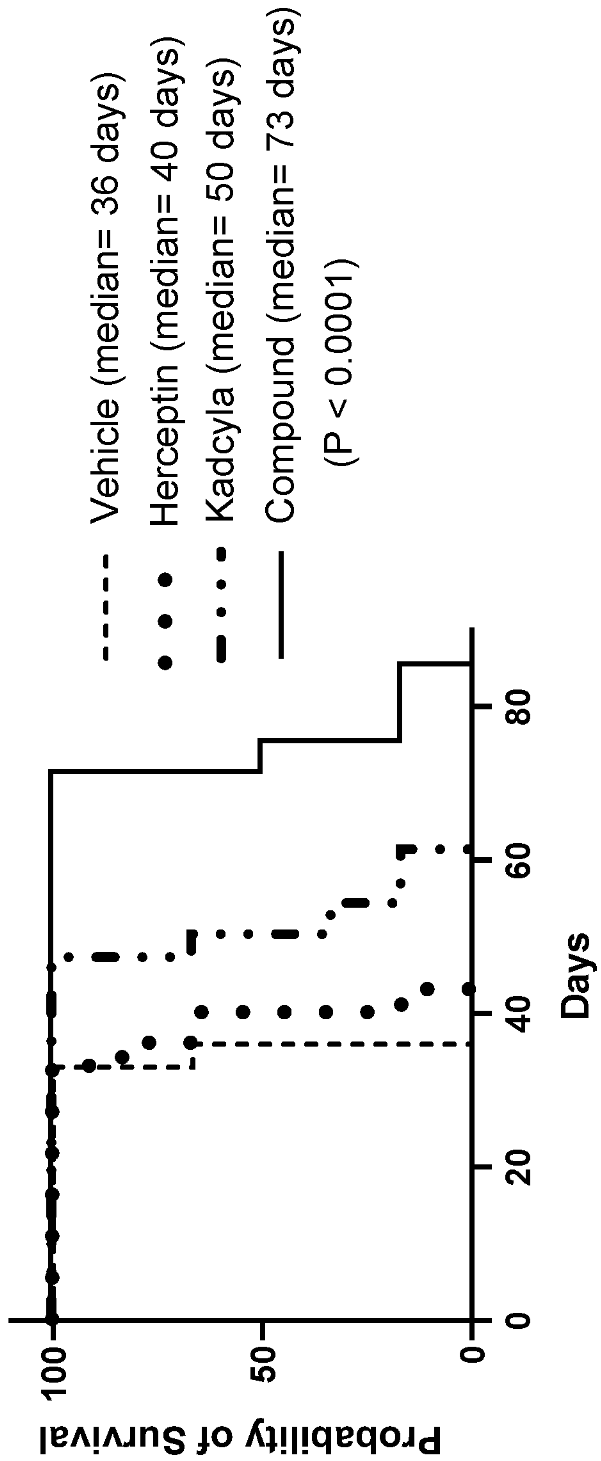
FIG. 13 shows percentage survival over time for mice inoculated with SKOV3 cells following treatment with vehicle, control compound 36, targeted conjugate 41, Kadcyla®, or Herceptin®.
Figure 14:
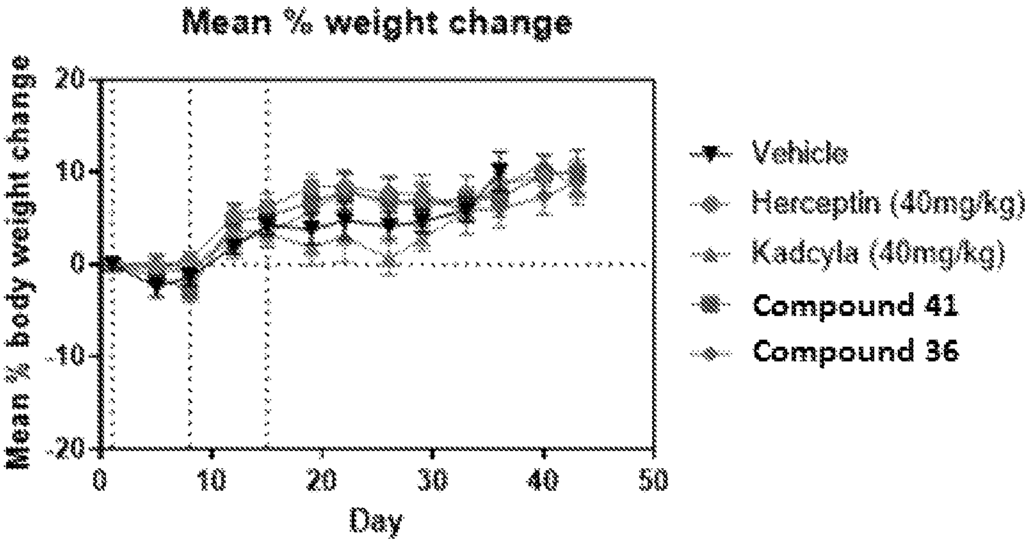
FIG. 14 shows mean % weight change over time for mice inoculated with SKOV3 cells following treatment with vehicle, control compound 36, targeted conjugate 41, Kadcyla®, or Herceptin®.

Tumour measurements were taken at regular intervals (n=6/group), until ethical endpoints were met. The results are shown in FIG. 12 (a plot of mean tumour volume over time), FIG. 13 (a plot of survival over time) and FIG. 14 (a plot of mean weight change over time). Targeted dendrimer compound 41 showed total tumour regression compared to compound 36, Herceptin® and Kadcyla®.

Example 13 Kinetics of Generation 4 Multi-Nanobody Dendrimer Internalisation in MDA-MB-231/HER2+ Cell Line Generation 4, Cy5-labeled nanobody-dendrimer conjugates with siderophore-derived chelator desferrioxamine (DFO) that were conjugated to either 1 (single nanobody) or from 2 to 4 (multiple nanobody) anti-HER2 2D3 nanobodies, compounds 90 and 91, separated as described above, were used to compare binding to HER2+ human cell lines where different numbers of nanobody are attached per dendrimer.

The epithelial adenocarcinoma cell line with HER2 knock-in, MDA-MB-231/HER2 (as described above) were maintained in Dulbecco's Modified Eagle's Medium (DMEM) containing 10% FBS and penicillin-streptomycin (100 U $mL^{-1}$) at 37° C. under a 5% $CO_2$ humidified atmosphere.

For measurement of cell binding by flow cytometry, 20,000 cells per well were plated overnight into 96 well culture plates in DMEM media supplemented with 10% FBS. Single or multiple nanobody dendrimers were added to cells at 3, 6, 12 and 30 nM and incubated for 0.5, 1, 2, 4 and 6 hours at 37 C. Control cells prepared in the same manner were pre-chilled and incubated with 30 nM single and multiple nanobody dendrimers for 6 hours on ice.

Figure 15:
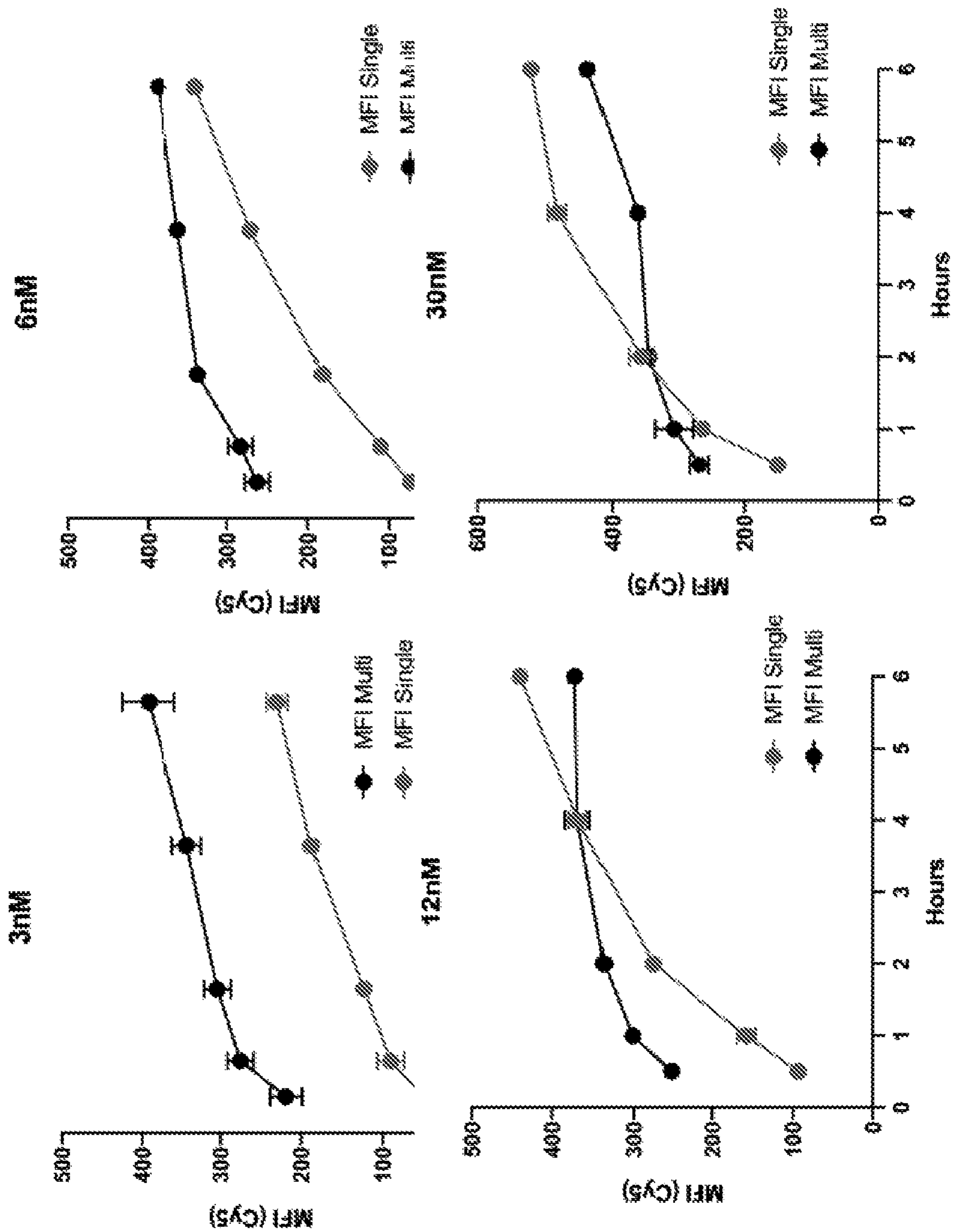
FIG. 15 shows internalisation kinetics of Generation 4 dendrimer with single (Compound 90; MFI Single) or multiple (Compound 91; MFI Multi) conjugated anti-HER2 nanobodies.

Following incubation with nanobody-conjugated dendrimers cells were washed three times with ice cold PBS supplemented with 1% Bovine serum albumin to remove unbound dendrimer and liberated from plates using TrypLE™ Express Enzyme (1×), no phenol red (Gibco, 12604013). Cells were resuspended in chilled DPBS for analysis by flow cytometry (Stratedigm S1000EON, California), with the presence of dendrimer measured by the acquisition of the signal from Cy5. To estimate the amount of internalised dendrimer at each concentration and time point, the Cy5 signal of cells incubated with dendrimer on ice was taken as the maximal surface bound dendrimer where no internalisation is assumed. This signal was subtracted from the signal measured in the cells incubated at 37 C, which represents surface bound and internalised dendrimer, to isolate the signal from internalised dendrimer only (see FIG. 15).

Multiple (Compound 91) conjugated anti-HER2 nanobody dendrimers internalise faster at low concentrations than with single (Compound 90). At higher concentration the Compound 90 shows greater levels of internalisation than compound 91 after about 2 hours.

Example 14 Confocal Imaging of Conjugates with Single and Multiple Nanobody in HER2 Hi Cell Lines HER2 hi, SKOV-3 cells were plated at $1.0\times10^4$ cells per well into μ-slide 8 well chambered coverslip (ibidi) and allowed to adhere overnight at 37° C., 5% $CO_2$. Compound 91 (multiple 2D3-dendrimer conjugate) and compound 90 (single 2D3-dendrimer conjugate) (3.33 nM) were then added and allowed to incubate for 1, 3, 6, and 24 hrs. The cells were washed with DPBS and then fixed with 1% paraformaldehyde for 20 min at room temperature. The cell membrane was stained with Alexa Fluor 488@ conjugate of wheat germ agglutinin (AF488-WGA, 5 μg $mL^{-1}$) in DPBS at room temperature for 10 min. The cell nuclei were counterstained with Hoechst 33342 (2 μg $mL^{-1}$) in PBS at room temperature for 10 min. Fluorescence images and optical sections were collected using a confocal microscope (Leica SP8). Images were processed with Fiji (ImageJ 1.52p).

Figure 16:
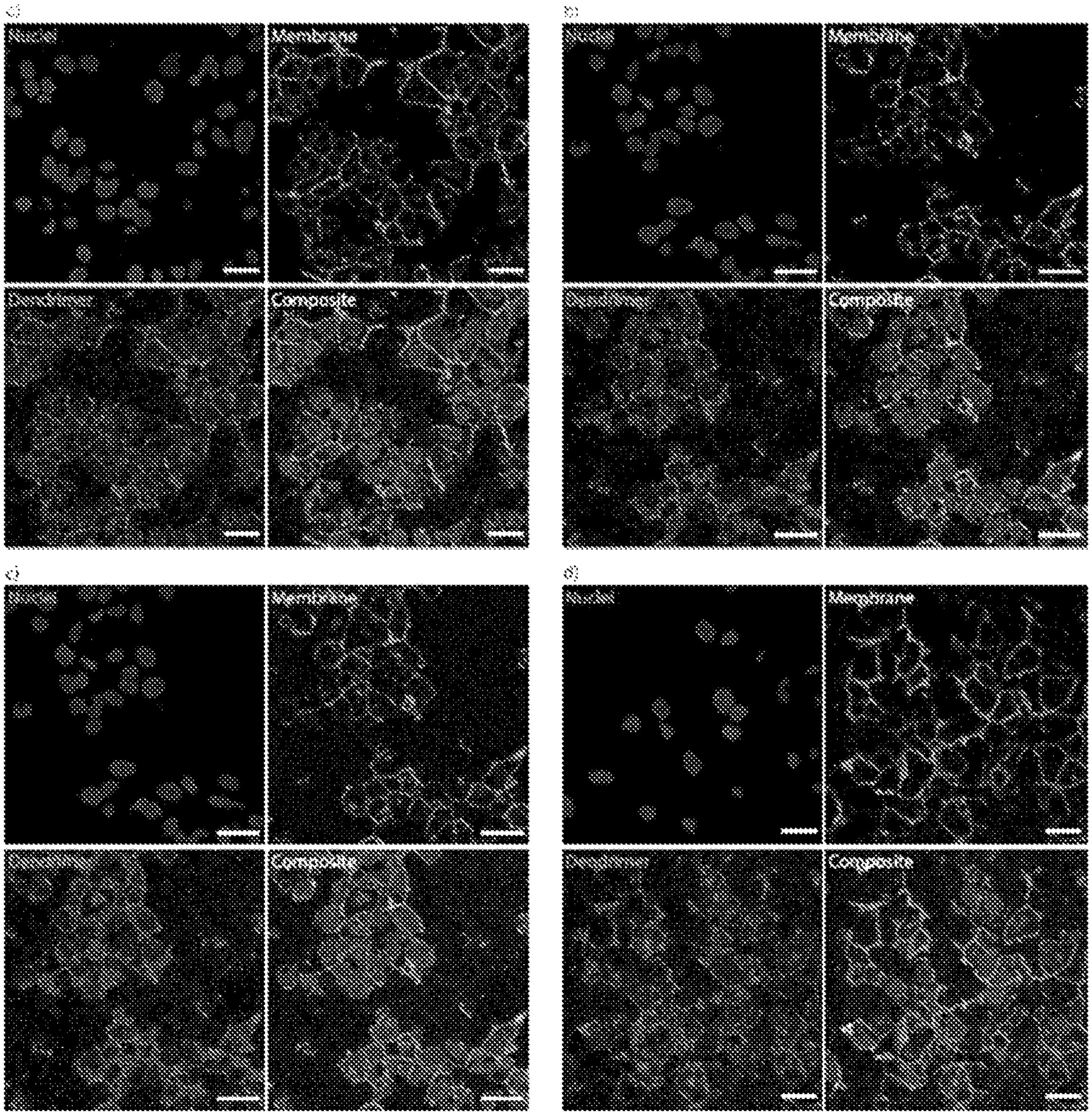
FIG. 16 shows confocal microscopy images of SKOV-3 cells after incubation with compound 91 (multiple 2D3-dendrimer conjugate) at 37° C. for a) 1 h, b) 3 h, c) 6 h, or d) 24 h. Compound 91 is labeled with Cy5 (magenta), cell membrane is stained with AF488-WGA (Green), and the nucleus is labeled with Hoechst 33342 (blue). Scale bar=30 μM.
Figure 17:
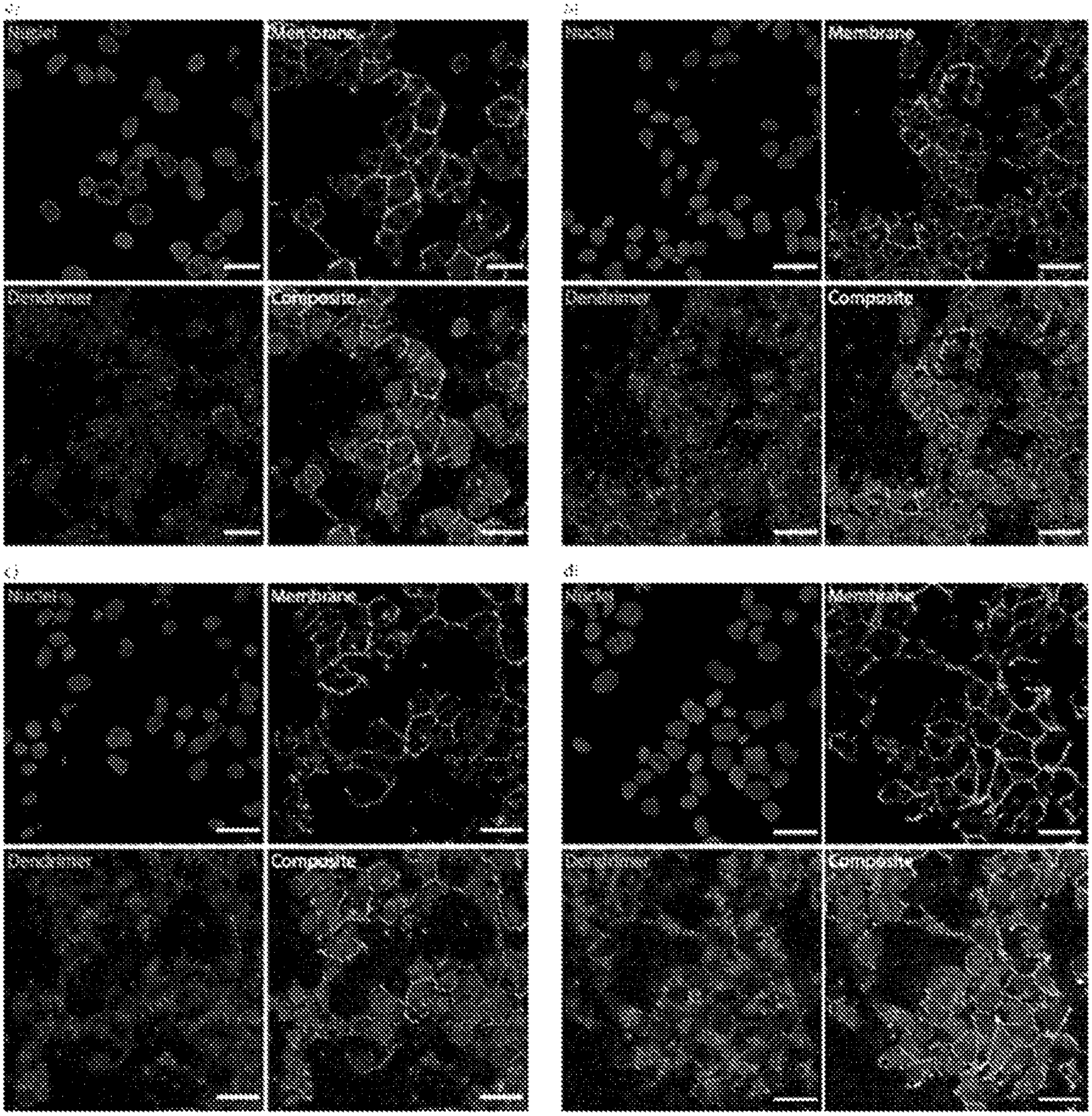
FIG. 17 shows confocal microscopy images of SKOV-3 cells after incubation with compound 90 (single 2D3-dendrimer conjugate) at 37° C. for a) 1 h, b) 3 h, c) 6 h, or d) 24 h. Compound 91 is labeled with Cy5 (magenta), cell membrane is stained with AF488-WGA (Green), and the nucleus is labeled with Hoechst 33342 (blue). Scale bar=30 μM.

Confocal microscopy images are shown in FIGS. 16 and 17. Both compound 90 and 91 bind and internalise with SKOV-3 cells after 24 h of incubation. Noticeably, compound 91 displays a greater extent of binding and internalisation at the 3 and 6 h time point compared to compound 90.

Multiple (Compound 91) conjugated anti-HER2 nanobody G4 dendrimers internalise faster than single nanobody G4 dendrimers (Compound 90) at this concentration and a difference can be seen up to 6 hours, but by 24 hours, they do not appear different.

Example 15 Imaging Study with Targeted Zr Radionuclide-Containing Dendrimers—SKOV3 Breast Cancer Xenograft The accumulation of 89Zr-labeled HER2 targeted and untargeted dendrimer constructs in a SKOV3 murine xenograft model of ovarian cancer was investigated. The biodistribution was measured by PET-CT out to 9 days post-injection and validated by ex vivo gamma scintillation imaging of excised organs at day 2 and 9 (where available). The study was conducted in 3 parts.

Tumour Initiation and Growth $5\times10^6$ SKOV3 cells (in 50 µL of 50:50 matrigel:PBS) were injected SC into the right flank of healthy female NOD-SCID (~20 g) 8 week old mice. Tumours were allowed to grow for 4 weeks prior to injection of imaging compounds.

All tumours were palpable at the time of imaging, with sizes ~3-5 mm at the time of the imaging experiment.

Study Compounds

The compounds in the table below were labeled as described below.

TABLE

| Study Compounds | | | |
|---|---|---|---|
| Compound No. | Untargeted | Compound No. | Targeted |
| | | 104 | DFO-NB |
| 99 | BHA-G2-$PEG_{1000}$ | 86 | BHA-G2-$PEG_{1000}$ + NB |
| | | 86 | BHA-G3-$PEG_{1000}$ + NB + lysine preload control |
| 100 | BHA-G3-$PEG_{412}$ | 88 | BHA-G3-$PEG_{412}$ + NB |
| 101 | BHA-G3-$PEG_{1000}$ | 89 | BHA-G3-$PEG_{1000}$ + NB |
| 102 | BHA-G4-$PEG_{1000}$ | 90 | BHA-G4-$PEG_{1000}$ + NB |
| 102 | BHA-G4-$PEG_{1000}$ | 90 | BHA-G4-$PEG_{1000}$ + NB |
| 103 | BHA-G5-$PEG_{1000}$ | 92 | BHA-G5-$PEG_{1000}$ + NB |

# = repeat

Radiolabeling of Study Compounds with Zr-89 and RadioTLC Analysis

Figure 18:
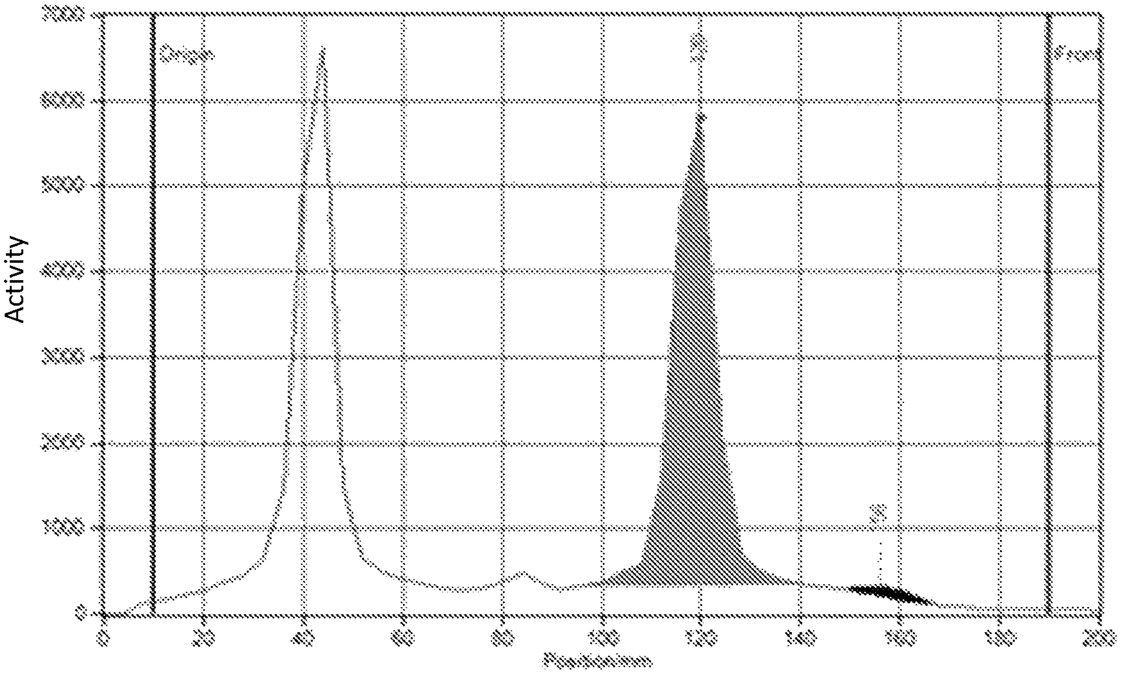
FIG. 18 is a radio TLC image for a compound of the disclosure showing that $^{89}Zr$ was bound to the dendrimer.

All constructs (pre-treated for Iron removal as needed: http://jnm.snmjournals.org/content/44/8/1271.long) were incubated with $^{89}Zr$ at an excess of dendrimer (see Table 1 for excess) in 0.1 M pH 7.4 HEPES buffer for 45 minutes at 37° C. Samples of each solution were taken and mixed 1:1 with 50 mM DTPA. 5 µL of each solution was spotted on TLC paper (Agilent iTLC-SG Glass microfiber chromatography paper impregnated with silica gel) and run with 50:50 $H_2O$:Ethanol. Plates were then imaged on a Eckert & Ziegler Mini-Scan and Flow-Count iTLC Reader. Where necessary, unbound zirconium was removed by purification using 7 K MWCO Zeba Spin Columns (Thermo Scientific) as per manufacturers protocols. All samples showed >95% labelling. Control experiments were conducted to monitor the elution behaviour of free $^{89}Zr$ and $^{89}Zr$ bound to DTPA for quality control, as well as each sample also run with and without DTPA to check for any unbound chelator labeled with $^{89}Zr$. A representative RadioTLC image is shown in FIG. 18 showing that all $^{89}Zr$ was bound to the dendrimer and there was no free $^{89}Zr$. RadioTLC is included below:

| Identifier | Area | % Peaks | Max. mm | Start mm | End mm | Maximum | % Total | Rf | Centroid mm |
|---|---|---|---|---|---|---|---|---|---|
| Compound | 55460 | 97.76 | 120 | 96 | 140 | 5815 | 33.5 | 0.61 | 118.44 |
| Zr89 | 1272 | 2.24 | 156 | 148 | 168 | 318 | 77 | 0.81 | 156.1 |

Study Injection Details

For the in vivo imaging experiments, study compounds were injected in 100 µL via the tail vein (29 G needle; approx. 1.5 to 3.5 MBq) into two mice to monitor tumour accumulation and biodistribution at various timepoints. Quantitation was performed ex vivo by gamma counting to determine organ distribution 9 days post-injection. For the biodistribution experiments, constructs were injected into two mice to monitor tumour accumulation and biodistribution ex vivo at 48 h post-injection by gamma counting.

Results

PET-CT Imaging

Figure 19:
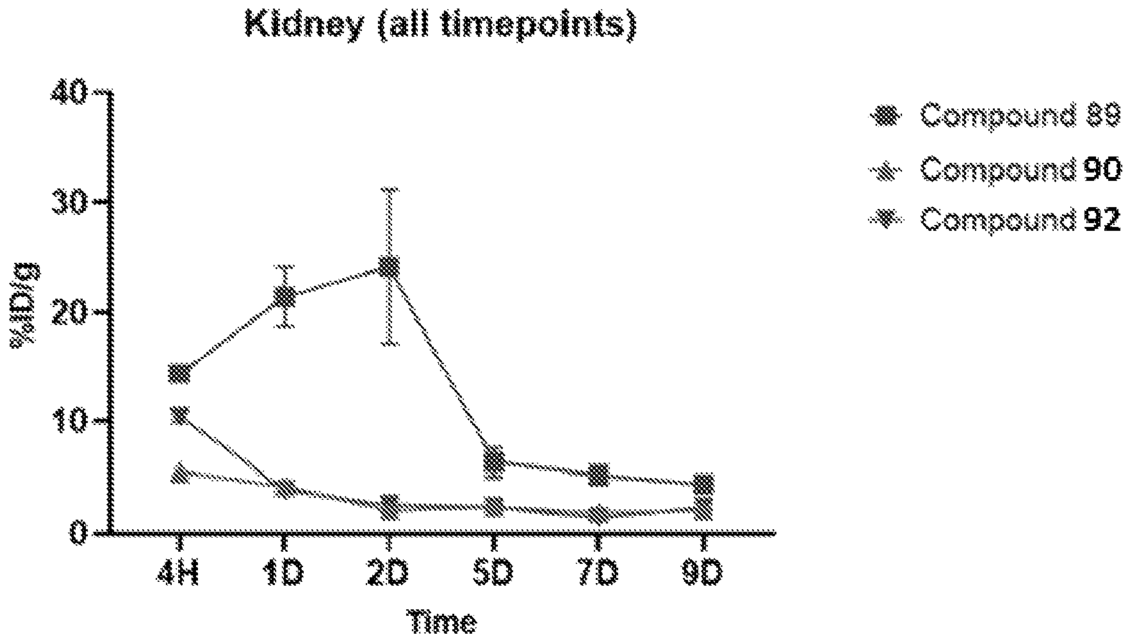
FIG. 19 shows graphs of percentage injected zirconium dose per gram in (a) kidney, (b) liver and (c) tumor over 9 days for compounds 89, 90, and 92.
Figure 19:
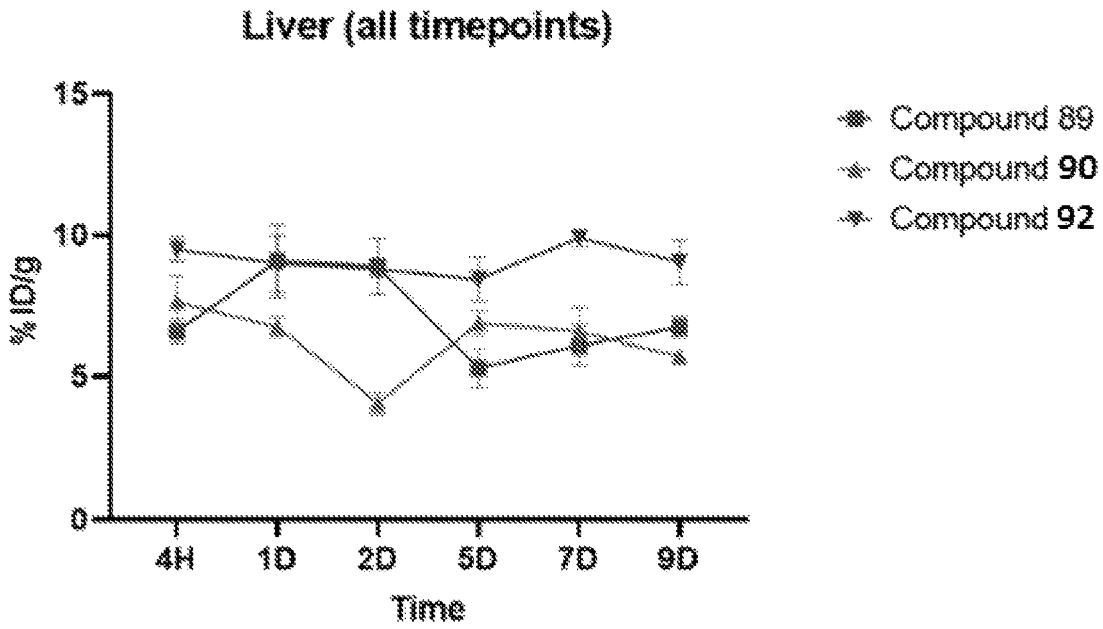
Figure 19:
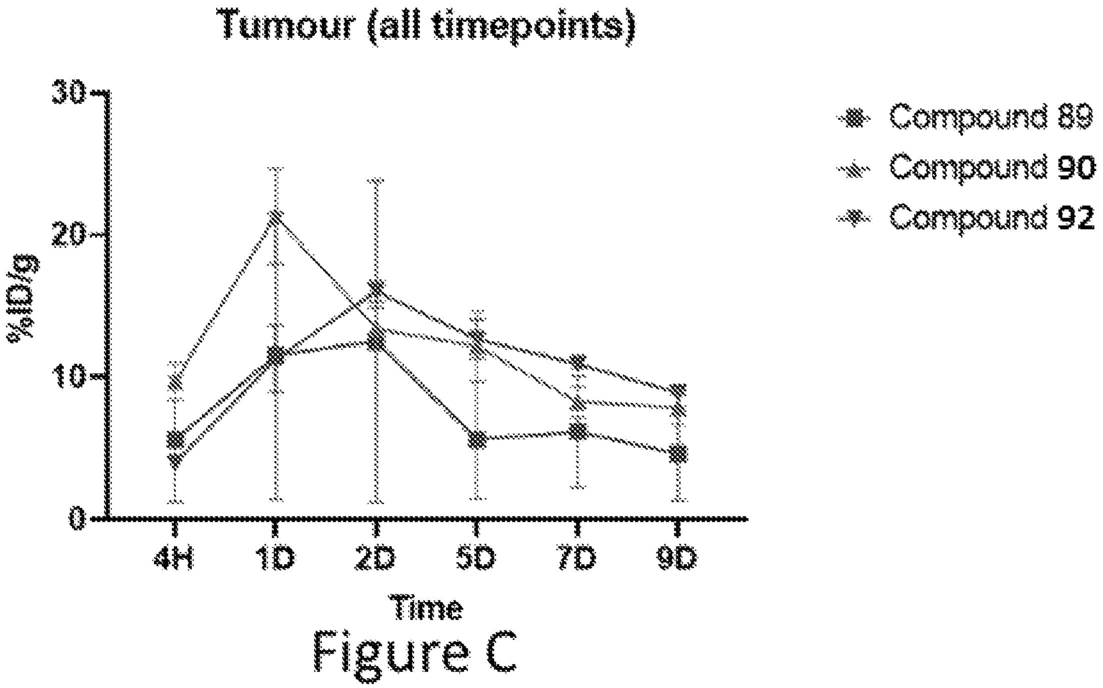
Figure 20:
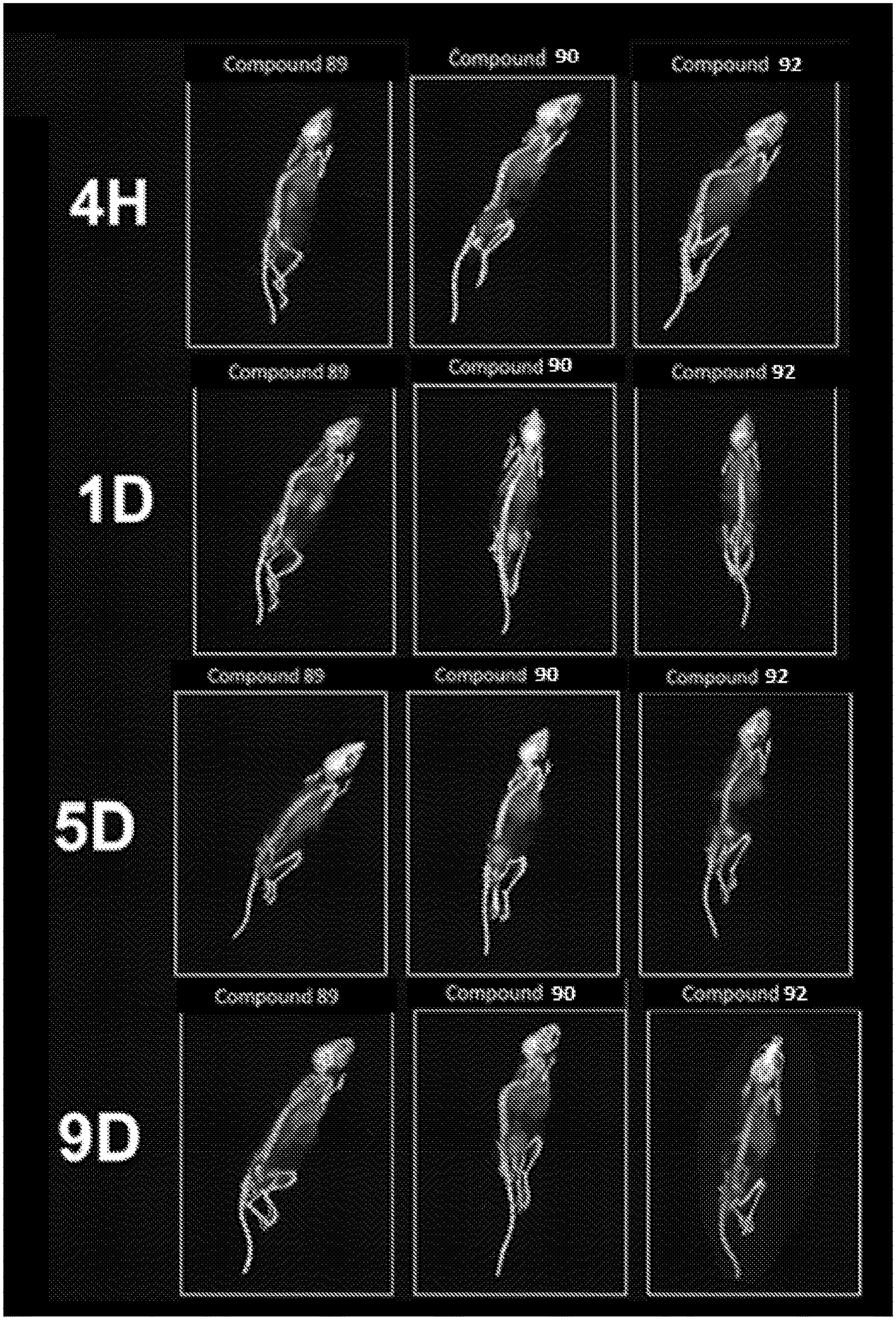
FIG. 20 shows representative maximum intensity projections of radiolabeled conjugates PET images of animals at 4 hours to 9 days. Data is represented in Becquerel per voxel (cm3) and have been thresholded to highlight tumour uptake.

Images were taken at 4 h, 24 h, 48 h, 5 d, 7 d, and 9 d post-injection using 30-90 minute static acquisitions. The PET Images were reconstructed using an ordered-subset expectation maximization (OSEM2D) algorithm and analysed using the Inveon Research Workplace software (IRW 4.1) (Siemens) which allows fusion of CT and PET images and definition of regions of interest (ROIs). CT and PET datasets of each individual animal were aligned using IRW software (Siemens) to ensure good overlap of the organs of interest. Activity per voxel was converted to nci/cc using a conversion factor obtained by scanning a cylindrical phantom filled with a known activity of 89Zr to account for PET scanner efficiency. Activity concentrations were then expressed as percent of the decay-corrected injected activity per $cm^3$ of tissue that can be approximate as percentage injected dose/g (% ID/g). Results are shown in FIG. 19 as graphs of percentage injected Zirconium dose per gram in (a) kidney, (b) liver and (c) tumour over 9 days for compounds 89, 90, and 92. Representative PET images are shown in FIG. 20. Representative maximum intensity projections of radiolabeled conjugates. All PET data is represented in Becquerel per voxel (cm3) and have been thresholded to highlight tumour uptake.

At 2 and 9 days post-injection, the organs were removed and signal intensity quantified by ex vivo gamma analysis and imaged. In addition, n=2 per cohort were culled at 48 hrs and evaluated for biodistribution by gamma analysis. Ex Vivo biodistribution results are shown in the table of FIG. 21, which provides the tumour:organ ratio of ex vivo signal of injected dose/g at days 2 and 9.

The results show higher tumour:blood ratio for the targeted compared to non targeted in particular the at day 2 in compound 88 (small G3 dendrimers). BY day 9, tumour: blood ratio for the targeted compared to non targeted is better, and in particular for compound 90 and 92 (the larger G4 and G5 dendrimers).

The percentage injected Zr dose/gram in ex vivo tumour and organs is also shown in the table of FIG. 22.

The results show higher signal in the tumour for the targeted compared to non targeted in particular for compound 90 and 92 (the larger G4 and G5 dendrimers) at day 2 and also at day 9 for compound 89 (G3 dendrimer).

CONCLUSION

1. The larger the dendrimer, the better tumour accumulation. 2D3 showed rapid clearance and low accumulation.
2. Targeted therapies lead to higher tumour accumulation than untargeted dendrimers.
3. Compound 88 (G3 1K– nanobody) shows a significantly enhanced signal in tumour compared to the other small dendrimers.
4. Compound 90 and 92 (G4 and G5 nanobody) showed >12% ID/g in tumour at 48 hrs, and >4% and >8% respectively at 9 days.
5. Small nanobody containing dendrimers and the nanobody alone have a higher kidney retention. No unusual accumulation in clearance organs was observed, with the liver and spleen signal showing expected concentration ranges as typically observed for similar systems.

Example 16 In Vitro Association Studies of G5, $PEG_{1000}$ Dendrimer, with or without Cabazitaxel MDA-MB-231, MDA-MB-231/HER2 (HER2 knock in), or SKOV-3 cells were seeded in a 24-well plate ($1\times10^5$ cells per well) in 500 μL of appropriate growth media with the addition of 10% (v/v) fetal bovine serum (FBS) and 1% (v/v) penicillin-streptomycin, and incubated with compound 70 (G5, $PEG_{1000}$, CTX) or 78 (2D3, G5, $PEG_{1000}$, CTX) at 3.33 nM, with incubation time varied from 1 to 24 h at 37° C. in a 5% $CO_2$ humidified atmosphere. After incubation, non-binding/non-associating particles were removed from adherent cells by gently washing with DPBS three times (300 μL/well). Cells were removed from plates by treatment with TrypLE™ Express Enzyme (1×), no phenol red (150 μL/well) for 5-10 min at room temperature. The plates were then placed on ice. Cellular binding and association of sample were then determined through flow cytometry by the acquisition of the signal from Cy5.

Flow Cytometry Results

Figure 23:
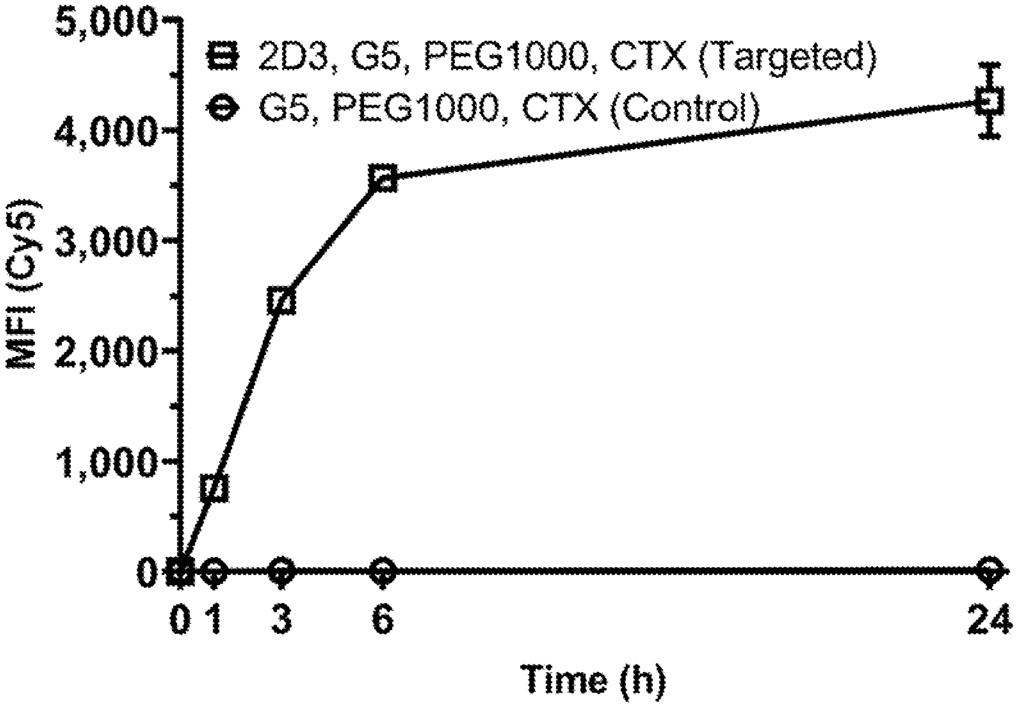
FIG. 23 shows flow cytometry analysis and mean fluorescence intensity value of Compound 70 (control) and Compound 78 (targeted) with MDA-MB-231/HER2 cells over 24 h.
Figure 24:
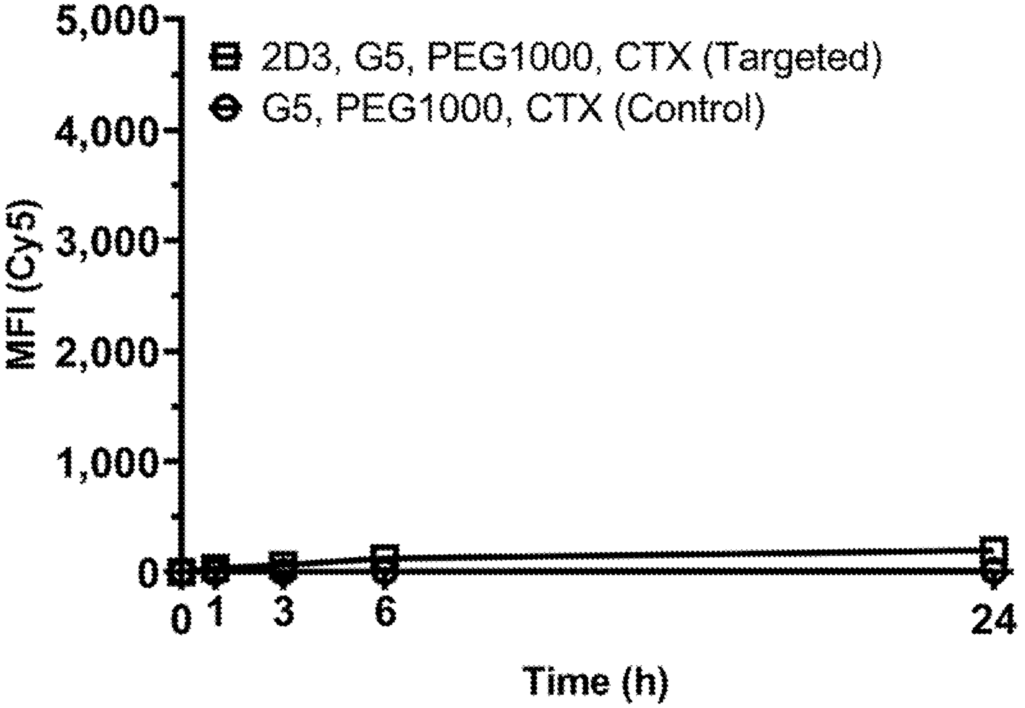
FIG. 24 shows flow cytometry analysis and mean fluorescence intensity value of Compound 70 (control) and Compound 78 (targeted) with MDA-MB-231 cells over 24 h.
Figure 25:
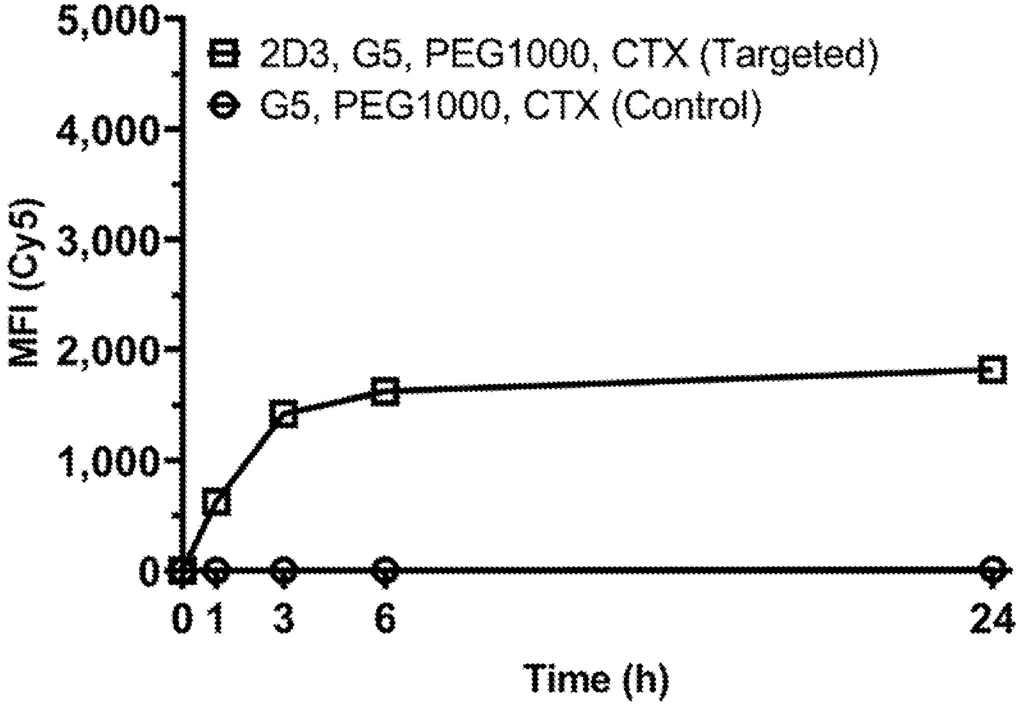
FIG. 25 shows flow cytometry analysis and mean fluorescence intensity value of Compound 70 (control) and Compound 78 (targeted) with SKOV-3 cells over 24 h.

The results clearly indicate minimal binding of compound 70 (control) towards all three cell lines over 24 h. Compound 78 (targeted) showed increasing binding in relation to the level of HER2 receptor expression of cell line. By 24 h, flow cytometry revealed that MDA-MB-231/HER2 cells treated with compound 78 (targeted) (4,269±322) displayed approximately 340-fold stronger fluorescence compared to the cells treated with compound 70 (control) (12.4±0.64). Also, SKOV-3 cells treated with compound 78 (targeted) (1,817±60.8) displayed approximately 160-fold stronger fluorescence compared to the cells treated with compound 70 (control) (11.4±0.42). The results are shown in FIGS. 23-25.

Mean fluorescence intensity (MFI) value of compound 70 (control), and compound 78 (targeted) with MDA-IVB-231, MDA-IVB-231/HER2 and SKOV-3 cells over 24 h. Values are mean±standard deviation (SD; n=2):

| | MDA-MB-231 | |
|---|---|---|
| Time (h) | Compound 70 (Control) | Compound 78 (Targeted) |
| 1 | 1.00 ± 0.14 | 36.7 ± 0.85 |
| 3 | 4.10 ± 0.71 | 64.8 ± 31.5 |
| 6 | 5.65 ± 0.64 | 125 ± 2.12 |
| 24 | 13.4 ± 0.07 | 197 ± 0.71 |

| | MDA-MB-231/HER2 (HER2 knock-in) | |
|---|---|---|
| Time (h) | Compound 70 (Control) | Compound 78 (Targeted) |
| 1 | 0.77 ± 0.06 | 755.7 ± 3.54 |
| 3 | 7.72 ± 4.17 | 2,460 ± 17.7 |
| 6 | 5.82 ± 0.07 | 3,567 ± 33.2 |
| 24 | 12.4 ± 0.64 | 4,269 ± 322 |

| | SKOV-3 | |
|---|---|---|
| Time (h) | Compound 70 (Control) | Compound 78 (Targeted) |
| 1 | 1.00 ± 0.29 | 625.8 ± 0.71 |
| 3 | 3.46 ± 0.69 | 1,422 ± 0.71 |
| 6 | 3.90 ± 0.10 | 1,621 ± 1.41 |
| 24 | 11.4 ± 0.42 | 1,817 ± 60.8 |

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

Abdollahpour-Alitappeh et al (2017) Novelty in Biomedicine 4: 145-151.

Al-Lazikani et al. (1997) J Mol Biol 273: 927-948.

Arezumand et al. (2017) Front Immunol 8:1746.

Bethesda, Md., 1987 and 1991.

Chetterjee et al. (2013) Biochemistry 52(10).

Chothia and Lesk (1987) J Mol Biol 196: 901-917.

Chothia et al. (1989) Nature 342: 877-883.

Giudicelli et al. (1997) Nucleic Acids Res 25: 206-211.

Honnegher and Pltkthun (2001) J Mol Biol 309: 657-670.

Hussack et al. (2018) BMC Res notes 11(1):866.

Kabat Sequences of Proteins of Immunological Interest, National Institutes of Health, Messerer et al. (2004) Clin. Cancer Res 10(19): 6638-6649.

Milla et al. (2012) Current Drug Metabolism 13(1): 105-119.

Mukai et al. (2015) Scientific Reports 5: 9699.

Nord et al. (1995) Protein Eng 8:601-608.

Oroudjev et al. (2010) Mol Can Thera 9:2700-2713.

Owen et al. (2011) WO2012167309.

Padlan et al. (1995) FASEB J Off Publ Fed Am Soc Exp Biol 9: 133-9.
Pohlmann et al. (2009) Clin Cancer Research 15(24): 7479-7491.
Pruszynski et al. (2013) Nucl Med Biol 40(1): 52-59.
Revets et al. (2011) US Application No. 20110028695
Vaneycken et al. (2011) FASEB J 25(7): 2433-2446.
Verel et al. (2003) J Nucl Med 44(8): 1271-1281.
Voigt (2015) Methods Mol Med 110: 39-48.
Wu et al. (2018) Translational Oncology 11(2): 366-373.

The invention claimed is:

1. A dendrimer-targeting agent conjugate, comprising:

a) a dendrimer comprising i) a core unit (C), wherein the core unit is

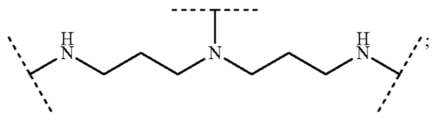

and ii) three to five generations of building units (BU), each building unit being a lysine residue having the structure

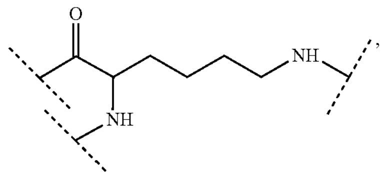

wherein the two amino nitrogen atoms of each building unit provide an attachment point for bonding to a subsequent generation of building units, therapeutic agent or a hydrophilic polymeric group, and the acyl group of each building unit provides an attachment point for bonding to a previous generation of building units or the core unit;

wherein the core unit is covalently attached to two building units via amide linkages, each amide linkage being formed between a nitrogen atom present in the core unit and a carbon atom of the acyl group present in a building unit;

b) a HER2 targeting agent which is a single domain antibody having a molecular weight of from 10 kDa to 16 kDa, and comprising an antigen-binding site, and wherein the HER2 targeting agent has three complementarity determining regions (CDRs) 1, 2 and 3 having the amino acid sequences GFTFD-DYAMS, SINWSGTHTD, and NWRDAGTTWFEKSGS, respectively, from the amino acid sequence of SEQ ID NO. 1, the HER2 targeting agent being covalently linked to a nitrogen atom in the core unit of the dendrimer by a spacer group comprising a polyethylene glycol (PEG) chain having from 2 to 60 ethyleneoxy repeat units;

c) a therapeutic agent which is covalently linked to a surface building unit of the dendrimer via a cleavable linker, wherein the therapeutic agent is an auristatin, a maytansinoid, an anti-microtubule agent or a topoisomerase inhibitor; and d) a hydrophilic polymeric group that is covalently linked to a surface building unit of the dendrimer, wherein the hydrophilic polymeric group is a polyethylene glycol (PEG) group having a mean molecular weight in the range of from 900 to 2300 g/mole.

2. The conjugate as claimed in claim 1, wherein the HER2 targeting agent comprises an amino acid sequence as depicted in SEQ ID NO.: 1, SEQ ID NO.: 2 or SEQ ID NO.: 3.

3. The conjugate as claimed in claim 1, wherein the covalent linkage between the targeting agent and the spacer group has been formed by reaction between complementary reactive functional groups present on a targeting agent precursor and a spacer group precursor.

4. The conjugate as claimed in claim 3, wherein the targeting agent precursor comprises an unnatural amino acid residue, the unnatural amino acid residue having a side-chain including a reactive functional group.

5. The conjugate as claimed in claim 4, wherein the unnatural amino acid residue is a residue of

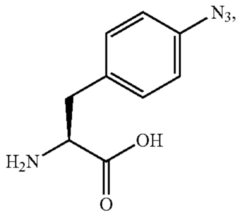

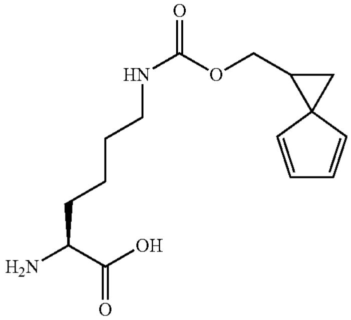

or

-continued

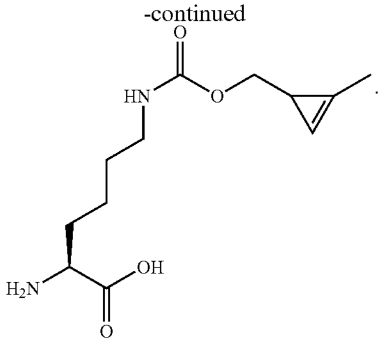

6. The conjugate as claimed in claim 1, wherein the targeting agent is covalently linked to the spacer group via the C-terminus of the targeting agent.

7. The conjugate as claimed in claim 4, wherein the spacer group precursor comprises a reactive functional group which is an alkyne group.

8. The conjugate as claimed in claim 1, wherein the therapeutic agent is a cytotoxic agent.

9. The conjugate as claimed in claim 1, wherein the dendrimer has from three to four generations of building units.

10. A pharmaceutical composition, comprising:

i) the conjugate as claimed in claim 1; and ii) a pharmaceutically acceptable excipient.

11. A method of treating cancer comprising administering to a subject in need thereof a therapeutically effective amount of a conjugate as claimed in claim 1.

12. The method of claim 11, wherein the cancer is ovarian cancer, breast cancer, stomach cancer, uterine cancer, or another cancer characterised by abnormal expression of the ERBB2 gene.

13. The conjugate as claimed in claim 1, wherein the therapeutic agent is an auristatin or a topoisomerase inhibitor.

14. The conjugate as claimed in claim 1, wherein the therapeutic agent is covalently linked to a surface building unit of the dendrimer via a cleavable linker which comprises a Val-Cit-PAB group, a Val-Ala-PAB group, a Val-Arg-PAB group, a Val-Ala-PAB-P-Trigger group or a Val-Arg-PAB-P-Trigger group.

15. The conjugate as claimed in claim 1, wherein the lysine residue is an L-lysine residue having the structure

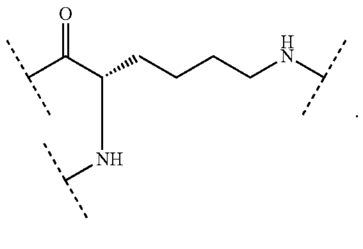

* * * * *

SEQUENCE LISTING

<160> NUMBER OF SEQ ID NOS: 3

<210> SEQ ID NO 1
<211> LENGTH: 124
<212> TYPE: PRT
<213> ORGANISM: Artificial Sequence
<220> FEATURE:
<223> OTHER INFORMATION: Nanobody 2D3 sequence

<400> SEQUENCE: 1

Glu Val Gln Leu Val Glu Ser Gly Gly Ser Leu Val Gln Pro Gly Gly
1 5 10 15

Ser Leu Arg Leu Ser Cys Ala Ala Ser Gly Phe Thr Phe Asp Asp Tyr
20 25 30

Ala Met Ser Trp Val Arg Gln Val Pro Gly Lys Gly Leu Glu Trp Val
35 40 45

Ser Ser Ile Asn Trp Ser Gly Thr His Thr Asp Tyr Ala Asp Ser Val
50 55 60

Lys Gly Arg Phe Thr Ile Ser Arg Asn Asn Ala Asn Asn Thr Leu Tyr
65 70 75 80

Leu Gln Met Asn Ser Leu Lys Ser Glu Asp Thr Ala Val Tyr Tyr Cys
85 90 95

Ala Lys Asn Trp Arg Asp Ala Gly Thr Thr Trp Phe Glu Lys Ser Gly
100 105 110

Ser Ala Gly Gln Gly Thr Gln Val Thr Val Ser Ser
115 120

<210> SEQ ID NO 2
<211> LENGTH: 157
<212> TYPE: PRT
<213> ORGANISM: Artificial Sequence
<220> FEATURE:
<223> OTHER INFORMATION: Nanobody 2D3 N-terminal tag, TEV, C-terminal azide
<220> FEATURE:
<221> NAME/KEY: X
<222> LOCATION: (157)..(157)
<223> OTHER INFORMATION: is unnatural amino acid

<400> SEQUENCE: 2

Gly Gly Ser His His His His His His Gly Met Ala Ser Met Thr Gly
1 5 10 15

Gly Gln Gln Met Gly Arg Asp Leu Tyr Glu Asn Leu Tyr Phe Gln Gly
20 25 30

Glu Val Gln Leu Val Glu Ser Gly Gly Ser Leu Val Gln Pro Gly Gly
35 40 45

Ser Leu Arg Leu Ser Cys Ala Ala Ser Gly Phe Thr Phe Asp Asp Tyr
50 55 60

Ala Met Ser Trp Val Arg Gln Val Pro Gly Lys Gly Leu Glu Trp Val
65 70 75 80

Ser Ser Ile Asn Trp Ser Gly Thr His Thr Asp Tyr Ala Asp Ser Val
85 90 95

Lys Gly Arg Phe Thr Ile Ser Arg Asn Asn Ala Asn Asn Thr Leu Tyr
100 105 110

-continued

Leu Gln Met Asn Ser Leu Lys Ser Glu Asp Thr Ala Val Tyr Tyr Cys
115 120 125

Ala Lys Asn Trp Arg Asp Ala Gly Thr Thr Trp Phe Glu Lys Ser Gly
130 135 140

Ser Ala Gly Gln Gly Thr Gln Val Thr Val Ser Ser Xaa
145 150 155

<210> SEQ ID NO 3
<211> LENGTH: 138
<212> TYPE: PRT
<213> ORGANISM: Artificial Sequence
<220> FEATURE:
<223> OTHER INFORMATION: Nanobody 2D3, with C-terminal tag, TEV, azide
<220> FEATURE:
<221> NAME/KEY: X
<222> LOCATION: (125)..(125)
<223> OTHER INFORMATION: is unnatural amino acid

<400> SEQUENCE: 3

Glu Val Gln Leu Val Glu Ser Gly Gly Ser Leu Val Gln Pro Gly Gly
1 5 10 15

Ser Leu Arg Leu Ser Cys Ala Ala Ser Gly Phe Thr Phe Asp Asp Tyr
20 25 30

Ala Met Ser Trp Val Arg Gln Val Pro Gly Lys Gly Leu Glu Trp Val
35 40 45

Ser Ser Ile Asn Trp Ser Gly Thr His Thr Asp Tyr Ala Asp Ser Val
50 55 60

Lys Gly Arg Phe Thr Ile Ser Arg Asn Asn Ala Asn Asn Thr Leu Tyr
65 70 75 80

Leu Gln Met Asn Ser Leu Lys Ser Glu Asp Thr Ala Val Tyr Tyr Cys
85 90 95

Ala Lys Asn Trp Arg Asp Ala Gly Thr Thr Trp Phe Glu Lys Ser Gly
100 105 110

Ser Ala Gly Gln Gly Thr Gln Val Thr Val Ser Ser Xaa Glu Asn Leu
115 120 125

Tyr Phe Gln Gly His His His His His His
130 135